(12) United States Patent
Alig et al.

(10) Patent No.: US 9,981,940 B2
(45) Date of Patent: May 29, 2018

(54) ARYL SULFIDE DERIVATIVES AND ARYL SULFOXIDE DERIVATIVES AS ACARICIDES AND INSECTICIDES

(71) Applicant: BAYER CROPSCIENCE AKTIENGESELLSCHAFT, Monheim am Rhein (DE)

(72) Inventors: Bernd Alig, Koenigswinter (DE); Silvia Cerezo-Galvez, Langenfeld (DE); Reiner Fischer, Monheim (DE); Adeline Koehler, Langenfeld (DE); Julia Johanna Hahn, Duesseldorf (DE); Angela Becker, Duesseldorf (DE); Kerstin Ilg, Cologne (DE); Arnd Voerste, Cologne (DE); Daniela Portz, Vettweiss (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 61 days.

(21) Appl. No.: 14/899,259

(22) PCT Filed: Jun. 16, 2014

(86) PCT No.: PCT/EP2014/062521
§ 371 (c)(1),
(2) Date: Dec. 17, 2015

(87) PCT Pub. No.: WO2014/202510
PCT Pub. Date: Dec. 24, 2014

(65) Prior Publication Data
US 2016/0145235 A1    May 26, 2016

(30) Foreign Application Priority Data

Jun. 20, 2013 (EP) ..................... 13172990

(51) Int. Cl.
| | | |
|---|---|---|
| C07D 207/273 | (2006.01) |
| C07D 207/38 | (2006.01) |
| C07D 207/408 | (2006.01) |
| C07D 249/12 | (2006.01) |
| C07D 257/04 | (2006.01) |
| C07D 271/113 | (2006.01) |
| C07D 277/40 | (2006.01) |
| C07D 277/42 | (2006.01) |
| C07D 233/70 | (2006.01) |
| C07D 401/04 | (2006.01) |
| C07D 405/04 | (2006.01) |
| A01N 25/00 | (2006.01) |
| A01N 43/36 | (2006.01) |
| A01N 43/50 | (2006.01) |
| A01N 43/653 | (2006.01) |
| A01N 43/713 | (2006.01) |
| A01N 43/78 | (2006.01) |
| A01N 43/82 | (2006.01) |

(52) U.S. Cl.
CPC ........... *C07D 401/04* (2013.01); *A01N 25/00* (2013.01); *A01N 43/36* (2013.01); *A01N 43/50* (2013.01); *A01N 43/653* (2013.01); *A01N 43/713* (2013.01); *A01N 43/78* (2013.01); *A01N 43/82* (2013.01); *C07D 207/273* (2013.01); *C07D 207/38* (2013.01); *C07D 207/408* (2013.01); *C07D 233/70* (2013.01); *C07D 249/12* (2013.01); *C07D 257/04* (2013.01); *C07D 271/113* (2013.01); *C07D 277/40* (2013.01); *C07D 277/42* (2013.01); *C07D 405/04* (2013.01)

(58) Field of Classification Search
None
See application file for complete search history.

(56) References Cited

FOREIGN PATENT DOCUMENTS

| | | | |
|---|---|---|---|
| EP | 0597360 A1 | 5/1994 | |
| EP | 1076053 A1 | 2/2001 | |
| EP | 2202226 A1 | 6/2010 | |
| JP | 201142611 | 3/2011 | |
| WO | 1999055668 A1 | 11/1999 | |
| WO | WO 2006/043635 * | 4/2006 | ........... C07D 249/14 |
| WO | 2007131680 A1 | 11/2007 | |
| WO | 2010100189 A1 | 9/2010 | |

OTHER PUBLICATIONS

International Search Report from corresponding PCT/EP2014/062521, dated Jul. 30, 2014.

* cited by examiner

*Primary Examiner* — Alicia L Otton
(74) *Attorney, Agent, or Firm* — McBee Moore Woodward & Vanik IP, LLC

(57) ABSTRACT

The present invention relates to aryl sulphide and aryl sulphoxide derivatives, to the use thereof as acaricides and insecticides for controlling animal pests and to processes and intermediates for preparation thereof. The aryl sulphide and aryl sulphoxide derivatives have the general structure (I)

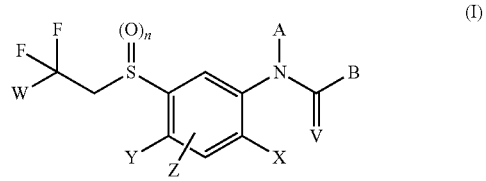

in which the respective radicals are as defined in the description.

23 Claims, No Drawings

ARYL SULFIDE DERIVATIVES AND ARYL SULFOXIDE DERIVATIVES AS ACARICIDES AND INSECTICIDES

CROSS REFERENCE TO RELATED APPLICATIONS

This application is a § 371 National Stage Application of PCT/EP2014/062521, filed 16 Jun. 2014, which claims priority to EP 13172990.7, filed 20 Jun. 2013.

BACKGROUND

Field of the Invention

The present invention relates to aryl sulphide and aryl sulphoxide derivatives, to the use thereof as acaricides and insecticides for controlling animal pests and to processes and intermediates for preparation thereof.

Description of Related Art

Various aryl sulphides and aryl sulphoxides and the insecticidal and acaricidal action thereof are already known from WO 1999/055668, WO 2007/131680 A, WO 2010/100189 A and JP 2011/42611.

The active ingredients already known from the publications cited above have disadvantages on application, for example in that they may have only inadequate insecticidal and/or acaricidal activity, if any, against animal pests, especially at relatively low application rates.

SUMMARY

It is therefore an object of the present invention to provide aryl sulphide and aryl sulphoxide derivatives which can be used as insecticides and/or acaricides with satisfactory insecticidal and/or acaricidal action against animal pests, especially at relatively low application rates, with high selectivity and improved compatibility in crops of useful plants.

Novel Compounds of the Formula (I)

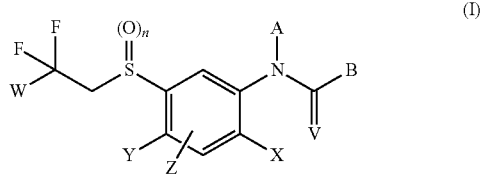

have now been found,
in which
A and B together with the atoms to which they are bonded are an optionally substituted five-membered ring which contains a double bond and may optionally be interrupted by a further carbonyl group, a further thiocarbonyl group, an optionally substituted imino group and/or by one or more heteroatoms;
V is oxygen, sulphur or an optionally substituted nitrogen;
W is hydrogen or halogen;
X, Y and Z, each independently
are hydrogen, halogen, hydroxyl, amino, cyano, nitro, OCN, SCN, $SF_5$; or
are trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulphinyl, haloalkylsulphinyl, alkoxyalkylsulphinyl, alkylsulphinylalkyl, alkylsulphonyl, haloalkylsulphonyl, alkoxyalkylsulphonyl, alkylsulphonylalkyl, alkylsulphonyloxy, alkylcarbonyl, haloalkylcarbonyl, carboxyl, alkylcarbonyloxy, alkoxycarbonyl, haloalkoxycarbonyl, aminocarbonyl, alkylaminocarbonyl, dialkylaminocarbonyl, alkenylaminocarbonyl, dialkenylaminocarbonyl, cycloalkylaminocarbonyl, alkylsulphonylamino, aminosulphonyl, alkylaminosulphonyl, dialkylaminosulphonyl, alkylsulphoximino, aminothiocarbonyl, alkylaminothiocarbonyl or dialkylaminothiocarbonyl, where all the aforementioned radicals may optionally be substituted; or
are phenylalkyl, phenoxy, phenylalkyloxy, phenoxyalkyl, phenylthio, phenylthioalkyl, phenylsulphinyl, phenylsulphonyl, hetarylalkyl, hetaryloxy, hetarylalkyloxy, hetarylthio, hetarylsulphinyl or hetarylsulphonyl, where all the aforementioned radicals may optionally be substituted; or
are cycloalkylalkyl, cycloalkyloxy, cycloalkylalkoxy, cycloalkylthio, cycloalkylalkylthio, cycloalkylsulphinyl, cycloalkylalkylsulphinyl, cycloalkylsulphonyl, cycloalkylalkylsulphonyl or cycloalkenyl, where all the aforementioned radicals may each optionally be substituted; or
are NR'R"
where R' and R" each independently
are hydrogen, cyano, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl; or
R' and R" together with the nitrogen atom to which they are bonded may form an optionally substituted, saturated or unsaturated five- to eight-membered ring optionally interrupted by one or more heteroatoms which are selected independently from the group consisting of O, S and N; or
are a 3- to 6-membered saturated, partly saturated or aromatic ring which may optionally contain one to three heteroatoms which are selected independently from the group consisting of O, S and N, and which may optionally be substituted;
or X and Z, or Y and Z, together with the carbon atoms to which they are bonded, form a 5- or 6-membered ring which is optionally substituted and optionally interrupted by one or more heteroatoms which are selected independently from the group consisting of O, S, N and CO;
n is the number 0, 1 or 2.

DETAILED DESCRIPTION OF A PREFERRED EMBODIMENT

If appropriate, the compounds of the formula (I) may be present in various polymorphic forms or as a mixture of various polymorphic forms. Both the pure polymorphs and the polymorph mixtures are provided by the invention and can be used in accordance with the invention.

Preferably, the double bond shown in formula (I), formed between the carbon atom in the α position to the nitrogen and V, is a double bond which is not within the five-membered ring formed by A and B. This double bond is therefore preferably exocyclic in relation to the ring formed by A and B. More particularly, through the presence of this double bond as an exocyclic double bond, the intention is that corresponding tautomers having an endocyclic double bond in relation to the five-membered ring formed by A and B are not included in the compounds encompassed by formula (I). However, this exclusion of the tautomers preferably relates exclusively to tautomers of the double bond present in formula (I) between the carbon atom in the α position to the nitrogen and V, and therefore does not include tautomeric double bonds that occur anywhere else in the molecule.

The compounds of the formula (I) include any diastereomers or enantiomers.

The inventive compounds are defined in general terms by the formula (I).

In a preferred embodiment of the present invention, the compounds have a structure of the general formula (I) in which A and B together with the atoms to which they are bonded are a substructure selected from the group consisting of

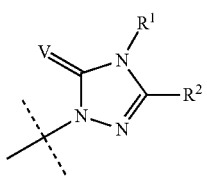
(I-A)

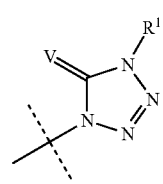
(I-B)

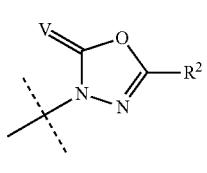
(I-C)

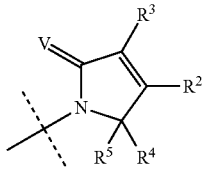
(I-D)

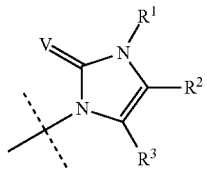
(I-E)

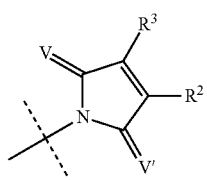
(I-F)

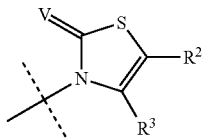
(I-G)

where
$R^1$ is hydrogen, cyano or nitro; or
is alkyl, cycloalkylalkyl, haloalkyl, cyanoalkyl, hydroxyalkyl, alkoxyalkyl, aminoalkyl, alkoxycarbonylalkyl, alkylsulphanylalkyl, alkylsulphinylalkyl, alkylsulphonylalkyl, haloalkylsulphanylalkyl, haloalkylsulphinylalkyl, haloalkylsulphonylalkyl, alkoxyalkylsulphanylalkyl, alkoxyalkylsulphinylalkyl, alkoxyalkylsulphonylalkyl, phenylalkyl, phenoxyalkyl, phenylsulphanylalkyl, phenylsulphinylalkyl, phenylsulphonylalkyl, hetarylalkyl, hetaryloxyalkyl, hetarylthioalkyl, where the aforementioned radicals may each be saturated or unsaturated and/or optionally substituted; or
is optionally substituted saturated or unsaturated cycloalkyl which may optionally be interrupted by one or more heteroatoms; or
is alkylcarbonyl, haloalkylcarbonyl, hydroxyalkylcarbonyl, alkoxyalkylcarbonyl, phenylcarbonyl, hetarylcarbonyl, alkoxycarbonyl, haloalkoxycarbonyl, aryloxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl(aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or is carbonyl or carboxyl; or
is optionally substituted phenyl or optionally substituted hetaryl; or
is alkoxy, haloalkoxy, cycloalkyloxy, aryloxy, arylalkyloxy or carbonyloxy, where the aforementioned radicals may optionally be substituted, or is hydroxyl; or
is alkylamino, haloalkylamino, dihaloalkylamino, dialkylamino, cycloalkylamino, dicycloalkylamino, cycloalkyl(alkyl)amino, arylamino, diarylamino, hetarylamino, dihetarylamino, alkyl(aryl)amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulphonylamino, or arylsulphonylamino, where the aforementioned radicals may each be saturated or unsaturated and/or optionally substituted, or is amino; or
is alkylsulphanyl, alkylsulphinyl, alkylsulphonyl, haloalkylsulphanyl, haloalkylsulphinyl, haloalkylsulphanyl, cycloalkylsulphanyl, cycloalkylsulphinyl, cycloalkylsulphonyl, cycloalkylalkylsulphanyl, cycloalkylalkylsulphinyl, cycloalkylalkylsulphonyl, arylsulphanyl, arylsulphinyl, arylsulphonyl, arylalkylsulphanyl, arylalkylsulphinyl, arylalkylsulphonyl, aminosulphonyl, alkylaminosulphonyl, dialkylaminosulphonyl or arylaminosulphonyl, where the aforementioned radicals may each be saturated or unsaturated and/or optionally substituted, or is sulphanyl; and $R^2$, $R^3$, $R^4$ and $R^5$ each independently
- are hydrogen, cyano, halogen or nitro; or
- are alkyl, cycloalkylalkyl, haloalkyl, cyanoalkyl, hydroxyalkyl, alkoxyalkyl, aminoalkyl, alkoxycarbonylalkyl, alkylsulphanylalkyl, alkylsulphinylalkyl, alkylsulphonylalkyl, haloalkylsulphanylalkyl, haloalkylsulphinylalkyl, haloalkylsulphonylalkyl, alkoxyalkylsulphanylalkyl, alkoxyalkylsulphinylalkyl, alkoxyalkylsulphonylalkyl, phenylalkyl, phenoxyalkyl, phenylsulphanylalkyl, phenylsulphinylalkyl, phenylsulphonylalkyl, hetarylalkyl, hetaryloxyalkyl, hetarylthioalkyl, where the aforementioned radicals may each be saturated or unsaturated and/or optionally substituted; or
- are optionally substituted saturated or unsaturated cycloalkyl which may optionally be interrupted by one or more heteroatoms; or
- are alkylcarbonyl, haloalkylcarbonyl, hydroxyalkylcarbonyl, alkoxyalkylcarbonyl, phenylcarbonyl, hetarylcarbonyl, alkoxycarbonyl, haloalkoxycarbonyl, aryloxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl(aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or are carbonyl or carboxyl; or
- are optionally substituted phenyl or optionally substituted hetaryl; or
- are alkoxy, haloalkoxy, alkoxyalkoxy, aryloxy, arylalkyloxy, cycloalkyloxy, cycloalkylalkyloxy or carbonyloxy, where the aforementioned radicals may be saturated or unsaturated and/or optionally substituted, or are hydroxyl; or
- are alkylamino, dialkylamino, haloalkylamino, dihaloalkylamino, cycloalkylamino, dicycloalkylamino, cycloalkyl(alkyl)amino, arylamino, diarylamino, hetarylamino, dihetarylamino, alkyl(aryl)amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulphonylamino, or arylsulphonylamino, where the aforementioned radicals may each be saturated or unsaturated and/or optionally substituted, or are amino; or
- are alkylsulphanyl, alkylsulphinyl, alkylsulphonyl, haloalkylsulphanyl, haloalkylsulphinyl, haloalkylsulphonyl, cycloalkylsulphanyl, cycloalkylsulphinyl, cycloalkylsulphonyl, cycloalkylalkylsulphanyl, cycloalkylalkylsulphinyl, cycloalkylalkylsulphonyl, arylsulphanyl, arylsulphinyl, arylsulphonyl, arylalkylsulphanyl, arylalkylsulphinyl, arylalkylsulphonyl, aminosulphonyl, alkylaminosulphonyl, dialkylaminosulphonyl or arylaminosulphonyl, where the aforementioned radicals may each be saturated or unsaturated and/or optionally substituted, or are sulphanyl; or $R^4$ and $R^5$ together with the atom to which they are bonded may form an optionally substituted, saturated or unsaturated three- to eight membered ring optionally interrupted by one or more heteroatoms which are selected independently from the group consisting of O, S and N; or $R^2$ is a saturated or unsaturated cycle optionally interrupted by one or more heteroatoms which are each selected from the group consisting of O, S and N, which may optionally be substituted;

W is hydrogen or halogen;

V and V' are each independently oxygen, sulphur or an optionally substituted nitrogen;

X, Y and Z are each independently as defined above; and n is the number 0 or 1.

Inventive compounds in which $R^1$ to $R^5$ are hydrogen may be present in tautomeric forms, all of which are encompassed by the present invention.

In a particularly preferred embodiment of the present invention, the compounds have a structure of the general formula (I) in which A and B together with the atoms to which they are bonded are a substructure selected from the group consisting of I-A to I-G;

$R^1$ is hydrogen, cyano or nitro; or
- is $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylsulphanyl$(C_1-C_6)$alkyl, hetarylsulphinyl$(C_1-C_6)$alkyl, hetarylsulphonyl$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or
- is optionally substituted saturated or unsaturated $(C_3-C_6)$cycloalkyl which may optionally be interrupted by one or more heteroatoms; or
- is $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$(C_1-C_6)$alkylaminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or
- is optionally substituted phenyl or optionally substituted hetaryl; or
- is $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or is hydroxyl; or
- is $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$(C_1-C_6)$alkylamino, arylamino, diarylamino, hetarylamino, dihetarylamino, $(C_1-C_6)$alkyl(aryl)

amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$ alkylcarbamoylamino, arylcarbamoylamino, $(C_1-C_6)$ alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or is $(C_1-C_6)$alkylsulphanyl, $(C_1-C_6)$alkylsulphinyl, $(C_1-C_6)$ alkylsulphonyl, halo$(C_1-C_6)$alkylsulphanyl, halo$(C_1-C_6)$alkylsulphinyl, halo$(C_1-C_6)$alkylsulphanyl, $(C_3-C_6)$ cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$ alkylsulphanyl, $(C_3-C_6)$cycloalkyl$(C_1-C_6)$ alkylsulphinyl, $(C_3-C_6)$cycloalkyl$(C_1-C_6)$ alkylsulphonyl, arylsulphanyl, arylsulphinyl, arylsulphonyl, aryl$(C_1-C_6)$alkylsulphanyl, aryl$(C_1-C_6)$ alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; and $R^2$, $R^3$, $R^4$ and $R^5$ each independently are hydrogen, cyano, halogen or nitro; or are $(C_1-C_6)$alkyl, $(C_3-C_6)$cycloalkyl$(C_1-C_6)$alkyl, halo $(C_1-C_6)$alkyl, cyano$(C_1-C_6)$alkyl, hydroxy$(C_1-C_6)$ alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$ alkyl, $(C_1-C_6)$alkylsulphonyl$(C_1-C_6)$alkyl, halo$(C_1-C_6)$ alkylsulphanyl$(C_1-C_6)$alkyl, halo$(C_1-C_6)$alkylsulphinyl $(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl $(C_1-C_6)$alkyl, phenoxy$(C_1-C_6)$alkyl, phenylsulphanyl $(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylthio$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or are optionally substituted saturated or unsaturated $(C_3-C_6)$cycloalkyl which may optionally be interrupted by one or more heteroatoms; or are $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$ alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$ alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$(C_1-C_6)$alkylaminocarbonyl, arylaminocarbonyl, diarylaminocarbonyl, $(C_1-C_6)$alkyl(aryl)aminocarbonyl, $(C_3-C_6)$cycloalkyl (aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or are carbonyl or carboxyl; or are optionally substituted phenyl or optionally substituted hetaryl; or are $(C_1-C_6)$alkoxy, halo$(C_1-C_6)$alkoxy, $(C_1-C_6)$alkoxy $(C_1-C_6)$alkoxy, aryloxy, aryl$(C_1-C_6)$alkyloxy, $(C_3-C_6)$ cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or are hydroxyl; or are $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl) amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$ alkylcarbamoylamino, arylcarbamoylamino, $(C_1-C_6)$ alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or are amino; or are $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$ alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$ cycloalkylsulphonyl, $(C_3-C_6)$cycloalkyl$(C_1-C_6)$ alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$ alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or are sulphanyl; or $R^4$ and $R^5$ together with the atom to which they are bonded are an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$ alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo $(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N; or $R^2$ is an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo $(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$ alkylsulphonyl- or optionally substituted $(C_3-C_6)$ cycloalkyl-substituted, saturated or unsaturated three- to six-membered ring optionally interrupted by heteroatoms from the group of O, S and N;

W is hydrogen or halogen;

V and V' are each independently oxygen, sulphur or an optionally substituted nitrogen;

X, Y and Z are each independently as defined above; and
n is the number 0 or 1.

In this preferred embodiment, it is particularly preferred that

X, Y and Z, each independently

- are hydrogen, halogen, hydroxyl, amino, cyano, nitro, OCN, SCN, SF$_5$; or
- are tri($C_1$-$C_6$)alkylsilyl, ($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxycarbonyl($C_1$-$C_6$)alkyl, ($C_1$-$C_6$)alkoxy($C_1$-$C_6$)alkyl, ($C_2$-$C_6$)alkenyl, halo($C_2$-$C_6$)alkenyl, cyano($C_2$-$C_6$)alkenyl, ($C_2$-$C_6$)alkynyl, halo($C_2$-$C_6$)alkynyl, cyano($C_2$-$C_6$)alkynyl, ($C_1$-$C_6$)alkoxy, halo($C_1$-$C_6$)alkoxy, cyano($C_1$-$C_6$)alkoxy, hydroxycarbonyl($C_1$-$C_6$)alkoxy, ($C_1$-$C_6$)alkoxycarbonyl($C_1$-$C_6$)alkoxy, ($C_1$-$C_6$)alkoxy($C_1$-$C_6$)alkoxy, ($C_1$-$C_6$)alkylhydroxyimino, ($C_1$-$C_6$)alkoxyimino, ($C_1$-$C_6$)alkyl($C_1$-$C_6$)alkoxyimino, halo($C_1$-$C_6$)alkyl($C_1$-$C_6$)alkoxyimino, ($C_1$-$C_6$)alkylthio, halo($C_1$-$C_6$)alkylthio, ($C_1$-$C_6$)alkoxy($C_1$-$C_6$)alkylthio, ($C_1$-$C_6$)alkylthio($C_1$-$C_6$)alkyl, ($C_1$-$C_6$)alkylsulphinyl, halo($C_1$-$C_6$)alkylsulphinyl, ($C_1$-$C_6$)alkoxy($C_1$-$C_6$)alkylsulphinyl, ($C_1$-$C_6$)alkylsulphinyl($C_1$-$C_6$)alkyl, ($C_1$-$C_6$)alkylsulphonyl, halo($C_1$-$C_6$)alkylsulphonyl, ($C_1$-$C_6$)alkoxy($C_1$-$C_6$)alkylsulphonyl, ($C_1$-$C_6$)alkylsulphonyl($C_1$-$C_6$)alkyl, ($C_1$-$C_6$)alkylsulphonyloxy, ($C_1$-$C_6$)alkylcarbonyl, halo($C_1$-$C_6$)alkylcarbonyl, carboxyl, ($C_1$-$C_6$)alkylcarbonyloxy, ($C_1$-$C_6$)alkoxycarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_6$)cycloalkylaminocarbonyl, ($C_1$-$C_6$)alkylsulphonylamino, aminosulphonyl, ($C_1$-$C_6$)alkylaminosulphonyl, di($C_1$-$C_6$)alkylaminosulphonyl, ($C_1$-$C_6$)alkylsulphoximino, aminothiocarbonyl, ($C_1$-$C_6$)alkylaminothiocarbonyl or di($C_1$-$C_6$)alkylaminothiocarbonyl, where all the aforementioned radicals may optionally be substituted by halogen; or
- are phenyl($C_1$-$C_3$)alkyl, phenoxy, phenyl($C_1$-$C_3$)alkyloxy, phenoxy($C_1$-$C_3$)alkyl, phenylthio, phenylthio($C_1$-$C_3$)alkyl, phenylsulphinyl, phenylsulphonyl, hetaryl($C_1$-$C_3$)alkyl, hetaryloxy, hetaryl($C_1$-$C_3$)alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or
- are ($C_3$-$C_6$)cycloalkyl($C_1$-$C_3$)alkyl, ($C_3$-$C_6$)cycloalkyloxy, ($C_3$-$C_6$)cycloalkyl($C_1$-$C_3$)alkoxy, ($C_3$-$C_6$)cycloalkylthio, ($C_3$-$C_6$)cycloalkyl($C_1$-$C_3$)alkylthio, ($C_3$-$C_6$)cycloalkylsulphinyl, ($C_3$-$C_6$)cycloalkyl($C_1$-$C_3$)alkylsulphinyl, ($C_3$-$C_6$)cycloalkylsulphonyl, ($C_3$-$C_6$)cycloalkyl($C_1$-$C_3$)alkylsulphonyl or ($C_3$-$C_8$)cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or
- are NR'R" where R' and R" each independently
  - are hydrogen, cyano, ($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, ($C_1$-$C_6$)alkylthio($C_1$-$C_6$)alkyl, ($C_2$-$C_6$)alkenyl, halo($C_2$-$C_6$)alkenyl, cyano($C_2$-$C_6$)alkenyl, ($C_2$-$C_6$)alkynyl, halo($C_2$-$C_6$)alkynyl, cyano($C_2$-$C_6$)alkynyl, acyl or ($C_1$-$C_6$)alkoxycarbonyl; or
- R' and R" together with the nitrogen atom to which they are bonded may form an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or
- are a ($C_3$-$C_6$)cycloalkyl, oxetanyl, oxolanyl, oxanyl, ($C_3$-$C_8$)cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;
- or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

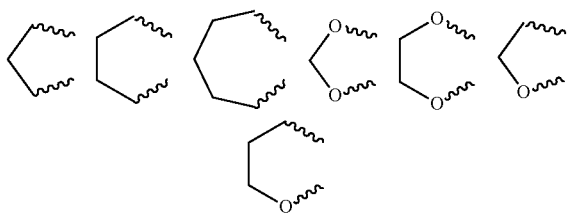

- or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

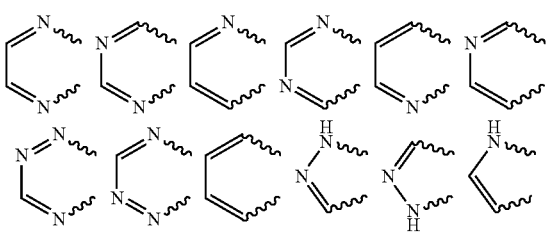

-continued

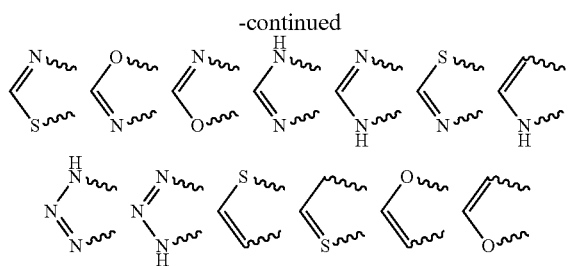

Further preferred isolated embodiments are described in more detail below:

First Embodiment (I-A):

In a first embodiment of the present invention, the inventive compounds have a structure of the general formula (I) in which A and B together with the atoms to which they are bonded are a substructure of the formula (I-A)

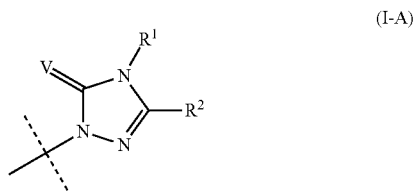

(I-A)

where $R^1$ is hydrogen, cyano or nitro; or is $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylsulphanyl$(C_1-C_6)$alkyl, hetarylsulphinyl$(C_1-C_6)$alkyl, hetarylsulphonyl$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or is optionally substituted saturated or unsaturated $(C_3-C_6)$ cycloalkyl which may optionally be interrupted by one or more heteroatoms; or is $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl) aminocarbonyl, arylaminocarbonyl, diarylaminocarbonyl, $(C_1-C_6)$alkyl(aryl)aminocarbonyl, $(C_3-C_6)$ cycloalkyl(aryl)aminocarbonyl, $(C_1-C_6)$ alkylaminothiocarbonyl, di$(C_1-C_6)$ alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or is optionally substituted phenyl or optionally substituted hetaryl; or is $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or is hydroxyl; or is $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or is $(C_1-C_6)$alkylsulphanyl, $(C_1-C_6)$alkylsulphinyl, $(C_1-C_6)$ alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$ cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$ alkylsulphanyl, $(C_3-C_6)$cycloalkyl$(C_1-C_6)$ alkylsulphinyl, $(C_3-C_6)$cycloalkyl$(C_1-C_6)$ alkylsulphonyl, arylsulphanyl, arylsulphinyl, arylsulphonyl, aryl$(C_1-C_6)$alkylsulphanyl, aryl$(C_1-C_6)$ alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; and $R^2$ is hydrogen, cyano, halogen or nitro; or is $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylthio$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or is optionally substituted saturated or unsaturated ($C_3$-$C_6$) cycloalkyl which may optionally be interrupted by one or more heteroatoms; or is ($C_1$-$C_6$)alkylcarbonyl, halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, ($C_1$-$C_6$)alkoxycarbonyl, halo($C_1$-$C_6$)alkoxycarbonyl, aryloxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or is optionally substituted phenyl or optionally substituted hetaryl; or is ($C_1$-$C_6$)alkoxy, halo($C_1$-$C_6$)alkoxy, ($C_1$-$C_6$)alkoxy($C_1$-$C_6$)alkoxy, aryloxy, aryl($C_1$-$C_6$)alkyloxy, ($C_3$-$C_6$)cycloalkyloxy, ($C_3$-$C_6$)cycloalkyl($C_1$-$C_6$)alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or is hydroxyl; or is ($C_1$-$C_6$)alkylamino, di($C_1$-$C_6$)alkylamino, halo($C_1$-$C_6$)alkylamino, dihalo($C_1$-$C_6$)alkylamino, ($C_3$-$C_6$)cycloalkylamino, di($C_3$-$C_6$)cycloalkylamino, ($C_3$-$C_6$)cycloalkyl(($C_1$-$C_6$)alkyl)amino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or is ($C_1$-$C_6$)alkylsulphanyl, ($C_1$-$C_6$)alkylsulphinyl, ($C_1$-$C_6$)alkylsulphonyl, halo($C_1$-$C_6$)alkylsulphanyl, halo($C_1$-$C_6$)alkylsulphinyl, halo($C_1$-$C_6$)alkylsulphonyl, ($C_3$-$C_6$)cycloalkylsulphanyl, ($C_3$-$C_6$)cycloalkylsulphinyl, ($C_3$-$C_6$)cycloalkylsulphonyl, ($C_3$-$C_6$)cycloalkyl($C_1$-$C_6$)alkylsulphanyl, ($C_3$-$C_6$)cycloalkyl($C_1$-$C_6$)alkylsulphinyl, ($C_3$-$C_6$)cycloalkyl($C_1$-$C_6$)alkylsulphonyl, arylsulphanyl, arylsulphinyl, arylsulphonyl, aryl($C_1$-$C_6$)alkylsulphanyl, aryl($C_1$-$C_6$)alkylsulphinyl, aryl($C_1$-$C_6$)alkylsulphonyl, aminosulphonyl, ($C_1$-$C_6$)alkylaminosulphonyl, di($C_1$-$C_6$)alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; or is an optionally singly or multiply, identically or differently halogen-, cyano-, nitro-, hydroxyl-, amino-, ($C_1$-$C_6$)alkyl-, halo($C_1$-$C_6$)alkyl-, ($C_1$-$C_6$)alkoxy-, halo($C_1$-$C_6$)alkoxy-, ($C_1$-$C_6$)alkylsulphinyl-, ($C_1$-$C_6$)alkylsulphanyl-, ($C_1$-$C_6$)alkylsulphonyl-, halo($C_1$-$C_6$)alkylsulphinyl-, halo($C_1$-$C_6$)alkylsulphanyl-, halo($C_1$-$C_6$)alkylsulphonyl- or optionally substituted ($C_3$-$C_6$)cycloalkyl-substituted, saturated or unsaturated three- to six-membered ring optionally interrupted by heteroatoms from the group of O, S and N;

W is hydrogen or halogen;

V is oxygen, sulphur or an optionally substituted nitrogen;

X, Y and Z each independently are hydrogen, halogen, hydroxyl, amino, cyano, nitro, OCN, SCN, $SF_5$; or are tri($C_1$-$C_6$)alkylsilyl, ($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxycarbonyl($C_1$-$C_6$)alkyl, ($C_1$-$C_6$)alkoxy($C_1$-$C_6$)alkyl, ($C_2$-$C_6$)alkenyl, halo($C_2$-$C_6$)alkenyl, cyano($C_2$-$C_6$)alkenyl, ($C_2$-$C_6$)alkynyl, halo($C_2$-$C_6$)alkynyl, cyano($C_2$-$C_6$)alkynyl, ($C_1$-$C_6$)alkoxy, halo($C_1$-$C_6$)alkoxy, cyano($C_1$-$C_6$)alkoxy, hydroxycarbonyl($C_1$-$C_6$)alkoxy, ($C_1$-$C_6$)alkoxycarbonyl($C_1$-$C_6$)alkoxy, ($C_1$-$C_6$)alkoxy($C_1$-$C_6$)alkoxy, ($C_1$-$C_6$)alkylhydroxyimino, ($C_1$-$C_6$)alkoxyimino, ($C_1$-$C_6$)alkyl($C_1$-$C_6$)alkoxyimino, halo($C_1$-$C_6$)alkyl($C_1$-$C_6$)alkoxyimino, ($C_1$-$C_6$)alkylthio, halo($C_1$-$C_6$)alkylthio, ($C_1$-$C_6$)alkoxy($C_1$-$C_6$)alkylthio, ($C_1$-$C_6$)alkylthio($C_1$-$C_6$)alkyl, ($C_1$-$C_6$)alkylsulphinyl, halo($C_1$-$C_6$)alkylsulphinyl, ($C_1$-$C_6$)alkoxy($C_1$-$C_6$)alkylsulphinyl, ($C_1$-$C_6$)alkylsulphinyl($C_1$-$C_6$)alkyl, ($C_1$-$C_6$)alkylsulphonyl, halo($C_1$-$C_6$)alkylsulphonyl, ($C_1$-$C_6$)alkoxy($C_1$-$C_6$)alkylsulphonyl, ($C_1$-$C_6$)alkylsulphonyl($C_1$-$C_6$)alkyl, ($C_1$-$C_6$)alkylsulphonyloxy, ($C_1$-$C_6$)alkylcarbonyl, halo($C_1$-$C_6$)alkylcarbonyl, carboxyl, ($C_1$-$C_6$)alkylcarbonyloxy, ($C_1$-$C_6$)alkoxycarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_6$)cyclo($C_1$-$C_6$)alkylaminocarbonyl, ($C_1$-$C_6$)alkylsulphonylamino, aminosulphonyl, ($C_1$-$C_6$)alkylaminosulphonyl, di($C_1$-$C_6$)alkylaminosulphonyl, ($C_1$-$C_6$)alkylsulphoximino, aminothiocarbonyl, ($C_1$-$C_6$)alkylaminothiocarbonyl or di($C_1$-$C_6$)alkylaminothiocarbonyl, where all the aforementioned radicals may optionally be substituted by halogen; or are phenyl($C_1$-$C_3$)alkyl, phenoxy, phenyl($C_1$-$C_3$)alkyloxy, phenoxy($C_1$-$C_3$)alkyl, phenylthio, phenylthio($C_1$-$C_3$)alkyl, phenylsulphinyl, phenylsulphonyl, hetaryl($C_1$-$C_3$)alkyl, hetaryloxy, hetaryl($C_1$-$C_3$)alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are ($C_3$-$C_6$)cycloalkyl($C_1$-$C_3$)alkyl, ($C_3$-$C_6$)cycloalkyloxy, ($C_3$-$C_6$)cycloalkyl($C_1$-$C_3$)alkoxy, ($C_3$-$C_6$)cycloalkylthio, ($C_3$-$C_6$)cycloalkyl($C_1$-$C_3$)alkylthio, ($C_3$-$C_6$)cycloalkylsulphinyl, ($C_3$-$C_6$)cycloalkyl($C_1$-$C_3$)alkylsulphinyl, ($C_3$-$C_6$)cycloalkylsulphonyl, ($C_3$-$C_6$)cycloalkyl($C_1$-$C_3$)alkylsulphonyl or ($C_3$-$C_8$)cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"
where R' and R" each independently
are hydrogen, cyano, ($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)

alkoxy(C$_1$-C$_6$)alkyl, (C$_1$-C$_6$)alkylthio(C$_1$-C$_6$)alkyl, (C$_2$-C$_6$)alkenyl, halo(C$_2$-C$_6$)alkenyl, cyano(C$_2$-C$_6$)alkenyl, (C$_2$-C$_6$)alkynyl, halo(C$_2$-C$_6$)alkynyl, cyano(C$_2$-C$_6$)alkynyl, acyl or (C$_1$-C$_6$)alkoxycarbonyl; or R' and R" together with the nitrogen atom to which they are bonded may form an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a (C$_3$-C$_6$)cycloalkyl, oxetanyl, oxolanyl, oxanyl, (C$_3$-C$_8$)cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

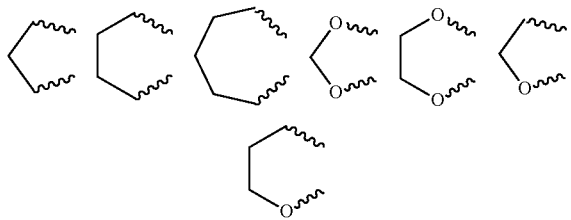

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

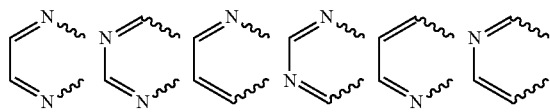

and n is the number 0 or 1.

At the same time, it is preferable that

R$^1$ is hydrogen; or is (C$_1$-C$_6$)alkyl, (C$_3$-C$_6$)cycloalkyl(C$_1$-C$_6$)alkyl, halo(C$_2$-C$_6$)alkyl, cyano(C$_1$-C$_6$)alkyl, (C$_1$-C$_6$)alkoxy(C$_1$-C$_6$)alkyl, (C$_1$-C$_6$)alkoxycarbonyl(C$_1$-C$_6$)alkyl, phenyl(C$_1$-C$_6$)alkyl, hetaryl(C$_1$-C$_6$)alkyl, (C$_2$-C$_6$)alkenyl, halo(C$_2$-C$_6$)alkenyl, (C$_3$-C$_6$)cycloalkenyl(C$_1$-C$_6$)alkyl, (C$_2$-C$_6$)alkynyl, where the aforementioned radicals may optionally be substituted; or is optionally substituted (C$_3$-C$_6$)cycloalkyl, (C$_3$-C$_6$)cycloalkenyl, which may optionally be interrupted by one or more heteroatoms from the group of O, S and N; or is (C$_1$-C$_6$)alkylcarbonyl, halo(C$_1$-C$_6$)alkylcarbonyl, (C$_1$-C$_6$)alkoxy(C$_1$-C$_6$)alkylcarbonyl, (C$_1$-C$_6$)alkoxycarbonyl, halo(C$_1$-C$_6$)alkoxycarbonyl, aminocarbonyl, (C$_1$-C$_6$)alkylaminocarbonyl, di(C$_1$-C$_6$)alkylaminocarbonyl, (C$_3$-C$_6$)cycloalkylaminocarbonyl, (C$_1$-C$_6$)alkylaminothiocarbonyl, di(C$_1$-C$_6$)alkylaminothiocarbonyl, (C$_2$-C$_6$)alkenylcarbonyl, (C$_3$-C$_6$)cycloalkenyl(C$_1$-C$_6$)alkylcarbonyl, (C$_2$-C$_6$)alkynylcarbonyl or aminothiocarbonyl, where the aforementioned radicals may each optionally be substituted, or is carbonyl or carboxyl; or is a phenyl or hetaryl ring which is optionally mono- or polysubstituted identically or differently by halogen, cyano, nitro, hydroxyl, amino, (C$_1$-C$_6$)alkyl, halo(C$_1$-C$_6$)alkyl, (C$_1$-C$_6$)alkoxy, halo(C$_1$-C$_6$)alkoxy, (C$_1$-C$_6$)alkylsulphinyl, (C$_1$-C$_6$)alkylsulphanyl, (C$_1$-C$_6$)alkylsulphonyl, halo(C$_1$-C$_6$)alkylsulphinyl, halo(C$_1$-C$_6$)alkylsulphanyl, halo(C$_1$-C$_6$)alkylsulphonyl or optionally substituted (C$_3$-C$_6$)cycloalkyl; or is (C$_1$-C$_6$)alkoxy, halo(C$_1$-C$_6$)alkoxy, (C$_3$-C$_6$)cycloalkyloxy, or carbonyloxy, where the aforementioned radicals may each optionally be substituted, or is hydroxyl; or is (C$_1$-C$_6$)alkylamino, halo(C$_1$-C$_6$)alkylamino, dihalo(C$_1$-C$_6$)alkylamino, di(C$_1$-C$_6$)alkylamino, (C$_3$-C$_6$)cycloalkylamino, di(C$_3$-C$_6$)cycloalkylamino, (C$_1$-C$_6$)alkylcarbonylamino, (C$_1$-C$_6$)alkoxycarbonylamino, (C$_1$-C$_6$)alkylcarbamoylamino, (C$_1$-C$_6$)alkylsulphonylamino, (C$_2$-C$_6$)alkenylamino, (C$_3$-C$_6$)cycloalkenyl(C$_1$-C$_6$)alkylamino, (C$_2$-C$_6$)alkynylamino, where the aforementioned radicals may each optionally be substituted, or is amino; or is (C$_1$-C$_6$)alkylsulphanyl, (C$_1$-C$_6$)alkylsulphinyl, (C$_1$-C$_6$)alkylsulphonyl, halo(C$_1$-C$_6$)alkylsulphinyl, halo(C$_1$-C$_6$)alkylsulphanyl, halo(C$_1$-C$_6$)alkylsulphanyl, (C$_3$-C$_6$)cycloalkyl(C$_1$-C$_6$)alkylsulphanyl, (C$_3$-C$_6$)cycloalkyl(C$_1$-C$_6$)alkylsulphinyl, (C$_3$-C$_6$)cycloalkyl(C$_1$-C$_6$)

alkylsulphonyl, aminosulphonyl, (C₁-C₆) alkylaminosulphonyl, di(C₁-C₆)alkylaminosulphonyl or arylaminosulphonyl, where the aforementioned radicals may each optionally be substituted, or is sulphanyl; and R² is hydrogen, cyano, halogen or nitro; or is (C₁-C₆)alkyl, (C₃-C₆)cycloalkyl(C₁-C₆)alkyl, halo(C₁-C₆)alkyl, cyano(C₁-C₆)alkyl, (C₁-C₆)alkoxy(C₁-C₆)alkyl, (C₁-C₆)alkoxycarbonyl(C₁-C₆)alkyl, (C₁-C₆)alkylsulphanyl(C₁-C₆)alkyl, (C₁-C₆)alkylsulphinyl(C₁-C₆)alkyl, phenyl(C₁-C₆)alkyl, hetaryl(C₁-C₆)alkyl, (C₂-C₆)alkenyl, halo(C₂-C₆)alkenyl, (C₃-C₆)cycloalkenyl(C₁-C₆)alkyl, (C₂-C₆)alkynyl, where the aforementioned radicals may each optionally be substituted; or is optionally substituted (C₃-C₆)cycloalkyl, (C₃-C₆)cycloalkenyl, which may optionally be interrupted by one or more heteroatoms form the group of O, S, and N; or is (C₁-C₆)alkylcarbonyl, halo(C₁-C₆)alkylcarbonyl, (C₁-C₆)alkoxy(C₁-C₆)alkylcarbonyl, (C₁-C₆)alkoxycarbonyl, halo(C₁-C₆)alkoxycarbonyl, aminocarbonyl, (C₁-C₆)alkylaminocarbonyl, di(C₁-C₆)alkylaminocarbonyl, (C₃-C₆)cycloalkylaminocarbonyl, (C₁-C₆)alkylaminothiocarbonyl, di(C₁-C₆)alkylaminothiocarbonyl, (C₂-C₆)alkenylcarbonyl, (C₃-C₆)cycloalkenyl(C₁-C₆)alkylcarbonyl, (C₂-C₆)alkynylcarbonyl or aminothiocarbonyl, where the aforementioned radicals may each optionally be substituted, or is carbonyl or carboxyl; or is a phenyl or hetaryl ring which is optionally mono- or polysubstituted identically or differently by halogen, cyano, nitro, hydroxyl, amino, (C₁-C₆)alkyl, halo(C₁-C₆)alkyl, (C₁-C₆)alkoxy, halo(C₁-C₆)alkoxy, (C₁-C₆)alkylsulphinyl, (C₁-C₆)alkylsulphanyl, (C₁-C₆)alkylsulphonyl, halo(C₁-C₆)alkylsulphinyl, halo(C₁-C₆)alkylsulphanyl, halo(C₁-C₆)alkylsulphonyl or optionally substituted (C₃-C₆)cycloalkyl; or is (C₁-C₆)alkoxy, halo(C₁-C₆)alkoxy, (C₁-C₆)alkoxy(C₁-C₆)alkoxy, (C₃-C₆)cycloalkyloxy, (C₃-C₆)cycloalkyl(C₁-C₆)alkyloxy, (C₂-C₆)alkenyloxy, (C₃-C₆)cycloalkenyl(C₁-C₆)alkoxy, (C₂-C₆)alkynyloxy or carbonyloxy, where the aforementioned radicals may each optionally be substituted, or is hydroxyl; or is (C₁-C₆)alkylamino, halo(C₁-C₆)alkylamino, dihalo(C₁-C₆)alkylamino, di(C₁-C₆)alkylamino, (C₃-C₆)cycloalkylamino, di(C₃-C₆)cycloalkylamino, (C₁-C₆)alkylcarbonylamino, (C₁-C₆)alkoxycarbonylamino, (C₁-C₆)alkylcarbamoylamino, (C₁-C₆)alkylsulphonylamino, (C₂-C₆)alkenylamino, (C₃-C₆)cycloalkenyl(C₁-C₆)alkylamino, (C₂-C₆)alkynylamino, where the aforementioned radicals may each optionally be substituted, or is amino; or is (C₁-C₆)alkylsulphanyl, (C₁-C₆)alkylsulphinyl, (C₁-C₆)alkylsulphonyl, halo(C₁-C₆)alkylsulphanyl, halo(C₁-C₆)alkylsulphinyl, halo(C₁-C₆)alkylsulphanyl, (C₃-C₆)cycloalkyl(C₁-C₆)alkylsulphanyl, (C₃-C₆)cycloalkyl(C₁-C₆)alkylsulphinyl, (C₃-C₆)cycloalkyl(C₁-C₆)alkylsulphonyl, aminosulphonyl, (C₁-C₆)alkylaminosulphonyl, di(C₁-C₆)alkylaminosulphonyl or arylaminosulphonyl, where the aforementioned radicals may each optionally be substituted, or is sulphanyl; or is an optionally identically or differently halogen-, cyano-nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated three- to six-membered ring optionally interrupted by heteroatoms from the group of O, S and N;

W is hydrogen or halogen, especially fluorine and chlorine;

V is oxygen, sulphur or an optionally substituted nitrogen;

X, Y and Z are each independently as defined above; and n is the number 0 or 1.

In a preferred configuration of this first embodiment, the substructure of the formula (I-A) is a substructure which is selected from the group consisting of

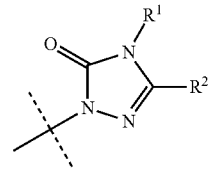
(I-A-1)

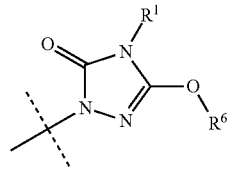
(I-A-2)

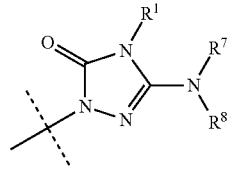
(I-A-3)

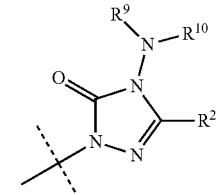
(I-A-4)

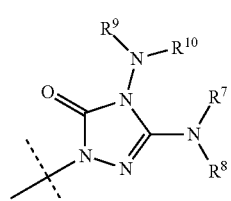
(I-A-5)

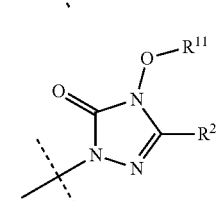
(I-A-6)

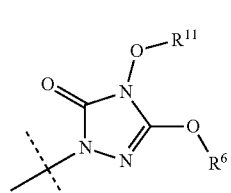
(I-A-7)

-continued (I-A-8)
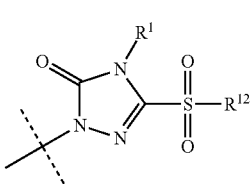

(I-A-9)
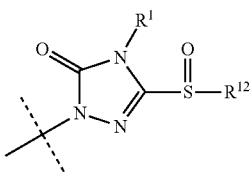

(I-A-10)
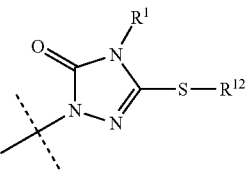

(I-A-11)
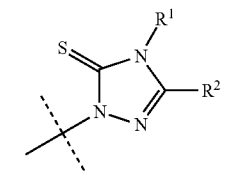

(I-A-12)
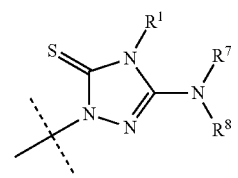

(I-A-13)
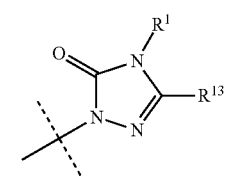

where
$R^1$ is hydrogen; or
is $(C_1-C_6)$alkyl, $(C_3-C_5)$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is $(C_3-C_6)$cycloalkyl, $(C_3-C_6)$cycloalkenyl, oxetanyl, oxolanyl, oxanyl, phenyl, pyrimidyl, pyridazinyl, pyrazinyl, triazinyl, thiazolyl, thiazadiazolyl, oxazolyl, oxadiazolyl, pyrazolyl or triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo $(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

$R^2$ is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo $(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is carboxyl;

$R^6$ is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo $(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

$R^7$ and $R^8$ are each independently hydrogen, $(C_1-C_6)$alkyl, halo$(C_2-C_6)$alkyl, cyano$(C_1-C_6)$alkyl or $(C_3-C_6)$cycloalkyl, where the aforementioned radicals may optionally each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo ($C_1$-$C_6$)alkylsulphonyl or optionally methyl-, fluorine-, chlorine-, cyano- or cyclopropyl-substituted cyclopropyl;

or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^9$ and $R^{10}$ are each independently hydrogen, ($C_1$-$C_6$)alkyl, halo($C_2$-$C_6$)alkyl, cyano($C_1$-$C_6$)alkyl, ($C_3$-$C_6$)cycloalkyl, or together are ($C_2$-$C_6$)alkylidene, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano- or cyclopropyl-substituted cyclopropyl;

or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^{11}$ is hydrogen; or is ($C_1$-$C_6$)alkyl, ($C_3$-$C_6$)cycloalkyl($C_1$-$C_3$)alkyl, ($C_2$-$C_6$)alkenyl, ($C_2$-$C_6$)alkynyl, halo($C_1$-$C_6$)alkyl, cyano($C_1$-$C_6$)alkyl, ($C_1$-$C_6$)alkoxy($C_1$-$C_6$)alkyl or phenyl($C_1$-$C_3$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl; or is ($C_3$-$C_6$)cycloalkyl, ($C_3$-$C_6$)cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;

$R^{12}$ is ($C_1$-$C_6$)alkyl, ($C_3$-$C_6$)cycloalkyl, ($C_2$-$C_6$)alkenyl, halo($C_1$-$C_6$)alkyl, cyano($C_1$-$C_6$)alkyl, phenyl($C_1$-$C_3$)alkyl or ($C_3$-$C_6$)cycloalkyl($C_1$-$C_6$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;

$R^{13}$ is halogen;

W is hydrogen or halogen (especially fluorine or chlorine);

X, Y and Z are each independently hydrogen, fluorine, chlorine, bromine, cyano, nitro, amino, hydroxyl, ($C_1$-$C_4$)alkyl, ($C_1$-$C_4$)haloalkyl, ($C_2$-$C_4$)alkenyl, ($C_2$-$C_4$)alkynyl, ($C_1$-$C_4$)alkoxy, ($C_1$-$C_4$)haloalkoxy or aminothiocarbonyl;

or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and n is the number 0 or 1.

In a likewise preferred configuration of this first embodiment, the substructure of the formula (I-A) is a substructure which is selected from the group consisting of

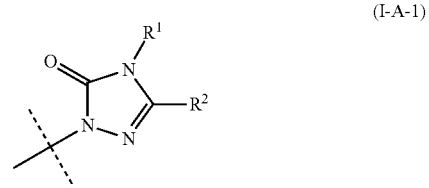
(I-A-1)

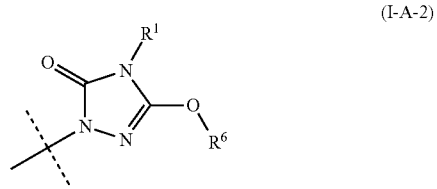
(I-A-2)

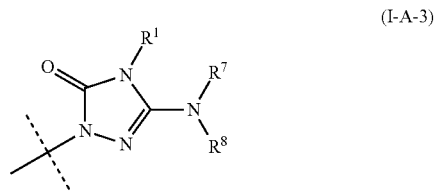
(I-A-3)

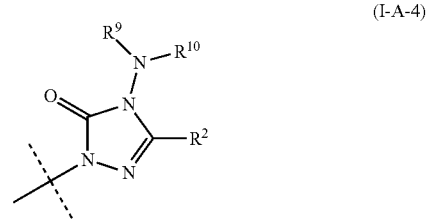
(I-A-4)

-continued (I-A-5)
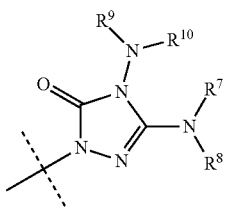

(I-A-6)
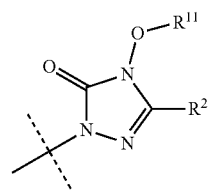

(I-A-7)
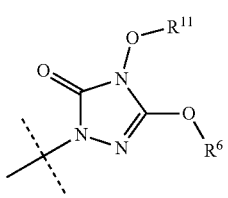

(I-A-8)
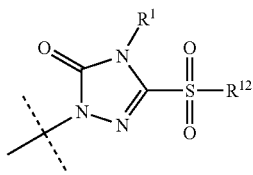

(I-A-9)
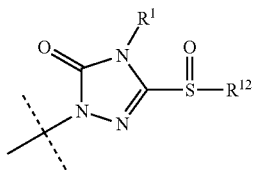

(I-A-10)
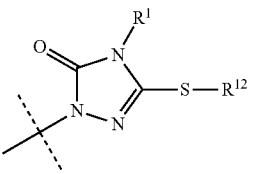

(I-A-11)
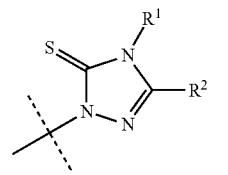

(I-A-12)
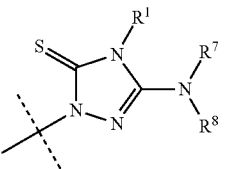

-continued (I-A-13)
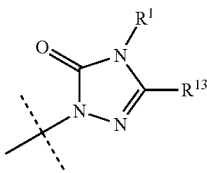

where
$R^1$ is hydrogen; or
is $(C_1-C_6)$alkyl, $(C_3-C_5)$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is $(C_3-C_6)$cycloalkyl, $(C_3-C_6)$cycloalkenyl, oxetanyl, oxolanyl, oxanyl, phenyl, pyridyl, pyrimidyl, pyridazinyl, pyrazinyl, triazinyl, thiazolyl, thiazadiazolyl, oxazolyl, oxadiazolyl, pyrazolyl or triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;
$R^2$ is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is carboxyl;
$R^6$ is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$ alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

$R^7$ and $R^8$ are each independently hydrogen, $(C_1-C_6)$alkyl, halo$(C_2-C_6)$alkyl, cyano$(C_1-C_6)$alkyl or $(C_3-C_6)$cycloalkyl, where the aforementioned radicals may optionally each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano- or cyclopropyl-substituted cyclopropyl;

or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^9$ and $R^{10}$ are each independently hydrogen, $(C_1-C_6)$alkyl, halo$(C_2-C_6)$alkyl, cyano$(C_1-C_6)$alkyl, $(C_3-C_6)$cycloalkyl, or together are $(C_2-C_6)$alkylidene, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano- or cyclopropyl-substituted cyclopropyl;

or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^{11}$ is hydrogen; or is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

$R^{12}$ is $(C_1-C_6)$alkyl, $(C_3-C_6)$cycloalkyl, $(C_2-C_6)$alkenyl, halo$(C_1-C_6)$alkyl, cyano$(C_1-C_6)$alkyl, phenyl$(C_1-C_3)$alkyl or $(C_3-C_6)$cycloalkyl$(C_1-C_6)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

$R^{13}$ is halogen;

W is hydrogen or halogen (especially fluorine or chlorine);

X, Y and Z are each independently hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;

or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and n is the number 0 or 1.

Preferably, the substructure of the formula (I-A) is a substructure which is selected from the group consisting of

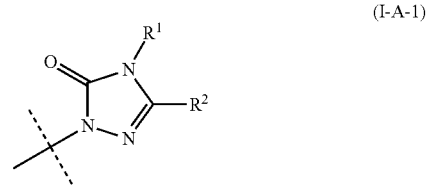

(I-A-1)

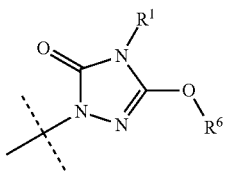 (I-A-2)

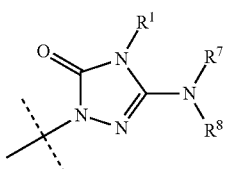 (I-A-3)

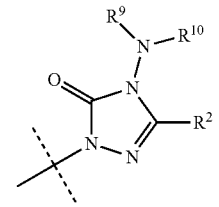 (I-A-4)

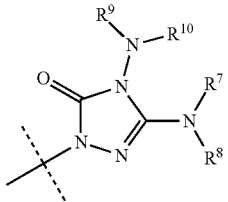 (I-A-5)

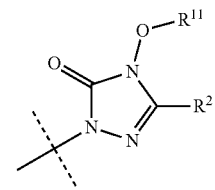 (I-A-6)

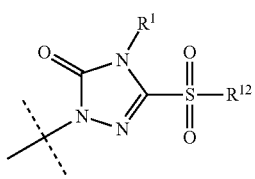 (I-A-8)

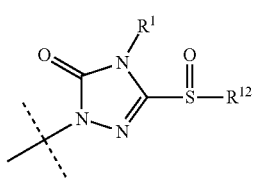 (I-A-9)

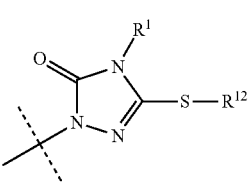 (I-A-10)

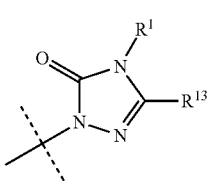 (I-A-13)

where
R$^1$ is hydrogen; or
is (C$_1$-C$_6$)alkyl, (C$_3$-C$_6$)cycloalkyl(C$_1$-C$_3$)alkyl, (C$_2$-C$_6$)alkenyl, (C$_2$-C$_6$)alkynyl, halo(C$_2$-C$_6$)alkyl, cyano(C$_1$-C$_6$)alkyl, (C$_1$-C$_6$)alkoxy(C$_1$-C$_6$)alkyl or phenyl(C$_1$-C$_3$)alkyl, where the aforementioned radicals may each optionally be mono- to trisubstituted by halogen, cyano, nitro, hydroxyl, amino, (C$_1$-C$_6$)alkyl, halo(C$_1$-C$_6$)alkyl, (C$_1$-C$_6$)alkoxy, halo(C$_1$-C$_6$)alkoxy, (C$_1$-C$_6$)alkylsulphinyl, (C$_1$-C$_6$)alkylsulphanyl, (C$_1$-C$_6$)alkylsulphonyl, halo(C$_1$-C$_6$)alkylsulphinyl, halo(C$_1$-C$_6$)alkylsulphanyl, halo(C$_1$-C$_6$)alkylsulphonyl or optionally methyl-, fluorine-, chlorine-, cyano-substituted cyclopropyl; or
is (C$_3$-C$_6$)cycloalkyl, (C$_3$-C$_6$)cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl or triazolyl, where the aforementioned radicals may each be mono- to trisubstituted by halogen, cyano, nitro, hydroxyl, amino, (C$_1$-C$_6$)alkyl, halo(C$_1$-C$_6$)alkyl, (C$_1$-C$_6$)alkoxy, halo (C$_1$-C$_6$)alkoxy, (C$_1$-C$_6$)alkylsulphinyl, (C$_1$-C$_6$)alkylsulphanyl, (C$_1$-C$_6$)alkylsulphonyl, halo(C$_1$-C$_6$)alkylsulphinyl, halo(C$_1$-C$_6$)alkylsulphanyl, halo(C$_1$-C$_6$) alkylsulphonyl or optionally methyl-, fluorine-, chlorine-, cyano-substituted cyclopropyl;
R$^2$ is hydrogen; or
is (C$_1$-C$_6$)alkyl, (C$_3$-C$_6$)cycloalkyl(C$_1$-C$_3$)alkyl, (C$_2$-C$_6$)alkenyl, (C$_2$-C$_6$)alkynyl, halo(C$_1$-C$_6$)alkyl, cyano(C$_1$-C$_6$)alkyl, (C$_1$-C$_6$)alkoxy(C$_1$-C$_6$)alkyl or phenyl(C$_1$-C$_3$)alkyl, where the aforementioned radicals may each optionally be mono- to trisubstituted by halogen, cyano, nitro, hydroxyl, amino, (C$_1$-C$_6$)alkyl, halo(C$_1$-C$_6$)alkyl, (C$_1$-C$_6$)alkoxy, halo(C$_1$-C$_6$)alkoxy, (C$_1$-C$_6$)alkylsulphinyl, (C$_1$-C$_6$)alkylsulphanyl, (C$_1$-C$_6$)alkylsulphonyl, halo(C$_1$-C$_6$)alkylsulphinyl, halo(C$_1$-C$_6$)alkylsulphanyl, halo(C$_1$-C$_6$)alkylsulphonyl or optionally methyl-, fluorine-, chlorine-, cyano-substituted cyclopropyl; or
is (C$_3$-C$_6$)cycloalkyl, (C$_3$-C$_6$)cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, (C$_1$-C$_6$)alkyl, halo(C$_1$-C$_6$)alkyl, (C$_1$-C$_6$)alkoxy, halo (C$_1$-C$_6$)alkoxy, (C$_1$-C$_6$)alkylsulphinyl, (C$_1$-C$_6$)alkylsulphanyl, (C$_1$-C$_6$)alkylsulphonyl, halo(C$_1$-C$_6$)alkylsulphinyl, halo(C$_1$-C$_6$)alkylsulphanyl, halo(C$_1$-C$_6$) alkylsulphonyl or optionally methyl-, fluorine-, chlorine-, cyano-substituted cyclopropyl; or
is carboxyl;
R$^6$ is hydrogen; or
is (C$_1$-C$_6$)alkyl, (C$_3$-C$_6$)cycloalkyl(C$_1$-C$_3$)alkyl, (C$_2$-C$_6$)alkenyl, (C$_2$-C$_6$)alkynyl, halo(C$_1$-C$_6$)alkyl, cyano(C$_1$-

$C_6$)alkyl, $(C_1-C_6)$alkoxy$(C_1-C_6)$alkyl or phenyl$(C_1-C_3)$ alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo $(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$ alkylsulphonyl or optionally methyl-, fluorine-, chlorine-, cyano-substituted cyclopropyl;

$R^7$ and $R^8$ are each independently hydrogen, $(C_1-C_6)$alkyl, halo$(C_2-C_6)$alkyl, cyano$(C_1-C_6)$alkyl or $(C_3-C_6)$cycloalkyl, where the aforementioned radicals may optionally each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo $(C_1-C_6)$alkylsulphinyl, halo$(C_1-C_6)$alkylsulphanyl, halo $(C_1-C_6)$alkylsulphonyl or optionally methyl-, fluorine-, chlorine-, cyano- or cyclopropyl-substituted cyclopropyl;

or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^9$ and $R^{10}$ are each independently hydrogen, $(C_1-C_6)$alkyl, halo$(C_2-C_6)$alkyl, cyano$(C_1-C_6)$alkyl, $(C_3-C_6)$cycloalkyl, or together are $(C_2-C_6)$alkylidene, where the aforementioned radicals may each optionally be mono- to trisubstituted by halogen, cyano, nitro, hydroxyl, amino, $(C_1-C_6)$alkyl, halo$(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano- or cyclopropyl-substituted cyclopropyl;

or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^{11}$ is hydrogen; or is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$ alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo $(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$ alkylsulphonyl or optionally methyl-, fluorine-, chlorine-, cyano-substituted cyclopropyl;

$R^{12}$ is $(C_1-C_6)$alkyl, $(C_3-C_6)$cycloalkyl, $(C_2-C_6)$alkenyl, halo $(C_1-C_6)$alkyl, cyano$(C_1-C_6)$alkyl, phenyl$(C_1-C_3)$alkyl or $(C_3-C_6)$cycloalkyl$(C_1-C_6)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$ alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo $(C_1-C_6)$alkylsulphanyl, halo$(C_1-C_6)$alkylsulphonyl or optionally methyl-, fluorine-, chlorine-, cyano-substituted cyclopropyl;

$R^{13}$ is halogen;

W is hydrogen or halogen, especially fluorine or chlorine;

X, Y and Z are each independently hydrogen, fluorine, chlorine, bromine, cyano, nitro, amino, hydroxyl, $(C_1-C_4)$ alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;

or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and n is the number 0 or 1.

Likewise preferably, the substructure of the formula (I-A) is a substructure which is selected from the group consisting of

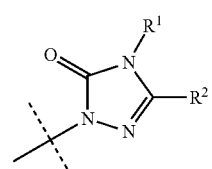

(I-A-1)

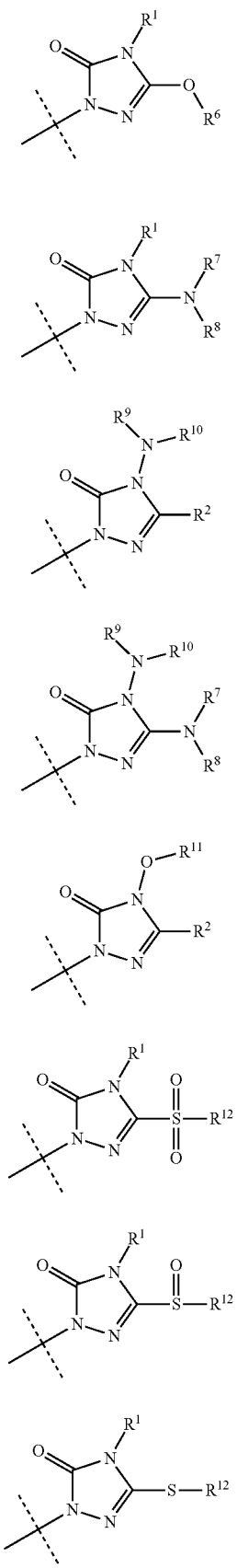

where
R¹ is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyridyl, pyrimidyl, pyridazinyl, pyrazinyl, triazinyl, thiazolyl, thiazadiazolyl, oxazolyl, oxadiazolyl, pyrazolyl or triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;
R² is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where all the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo($C_1$-$C_6$)alkylsulphanyl, halo($C_1$-$C_6$) alkylsulphonyl or optionally methyl-, fluorine-, chloro-, cyano-substituted cyclopropyl; or
is carboxyl;

$R^6$ is hydrogen; or
is ($C_1$-$C_6$)alkyl, ($C_3$-$C_6$)cycloalkyl($C_1$-$C_3$)alkyl, ($C_2$-$C_6$)alkenyl, ($C_2$-$C_6$)alkynyl, halo($C_1$-$C_6$)alkyl, cyano($C_1$-$C_6$)alkyl, ($C_1$-$C_6$)alkoxy($C_1$-$C_6$)alkyl or phenyl($C_1$-$C_3$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl; or
is ($C_3$-$C_6$)cycloalkyl, ($C_3$-$C_6$)cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiadiazolyl, oxazolyl, oxadiazolyl, pyrazolyl, triazolyl, where the aforementioned radicals may each be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo ($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;

$R^7$ and $R^8$ are each independently hydrogen, ($C_1$-$C_6$)alkyl, halo($C_2$-$C_6$)alkyl, cyano($C_1$-$C_6$)alkyl or ($C_3$-$C_6$)cycloalkyl, where the aforementioned radicals may optionally each be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano- or cyclopropyl-substituted cyclopropyl;
or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^9$ and $R^{10}$ are each independently hydrogen, ($C_1$-$C_6$)alkyl, halo($C_2$-$C_6$)alkyl, cyano($C_1$-$C_6$)alkyl, ($C_3$-$C_6$)cycloalkyl, or together are ($C_2$-$C_6$)alkylidene, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano- or cyclopropyl-substituted cyclopropyl;
or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^{11}$ is hydrogen; or
is ($C_1$-$C_6$)alkyl, ($C_3$-$C_6$)cycloalkyl($C_1$-$C_3$)alkyl, ($C_2$-$C_6$)alkenyl, ($C_2$-$C_6$)alkynyl, halo($C_1$-$C_6$)alkyl, cyano($C_1$-$C_6$)alkyl, ($C_1$-$C_6$)alkoxy($C_1$-$C_6$)alkyl or phenyl($C_1$-$C_3$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl; or
is ($C_3$-$C_6$)cycloalkyl, ($C_3$-$C_6$)cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiadiazolyl, oxazolyl, oxadiazolyl, pyrazolyl, triazolyl, where the aforementioned radicals may each be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo ($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;

$R^{12}$ is ($C_1$-$C_6$)alkyl, ($C_3$-$C_6$)cycloalkyl, ($C_2$-$C_6$)alkenyl, halo($C_1$-$C_6$)alkyl, cyano($C_1$-$C_6$)alkyl, phenyl($C_1$-$C_3$)alkyl or ($C_3$-$C_6$)cycloalkyl($C_1$-$C_6$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;

$R^{13}$ is halogen;

W is hydrogen or halogen, especially fluorine or chlorine;

X, Y and Z are each independently hydrogen, fluorine, chlorine, bromine, cyano, nitro, amino, hydroxyl, ($C_1$-$C_4$)alkyl, ($C_1$-$C_4$)haloalkyl, ($C_2$-$C_4$)alkenyl, ($C_2$-$C_4$)alkynyl, ($C_1$-$C_4$)alkoxy, ($C_1$-$C_4$)haloalkoxy or aminothiocarbonyl;
or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and n is the number 0 or 1.

If the substructure of the formula (I-A) is the substructure formula (I-A-1), it is preferable that $R^1$ is hydrogen; or
  is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or
  is $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;

$R^2$ is hydrogen; or
  is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or
  is $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl; or
  is carboxyl;

W is hydrogen or halogen, especially F or Cl;
X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;
Z is hydrogen; and
n is the number 0 or 1.

In this context, it is particularly preferable that
$R^1$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, cyclopropylmethyl, $CH_2CF_3$, $CH_2CHF_2$, $CH_2CN$, $CH_2CH_2OCH_3$, benzyl, cyclopropyl, cyclobutyl, phenyl or 4-methyl-3-(2,2,2-trifluoroethylsulphanyl)phenyl;
$R^2$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl, phenyl, 3-fluorophenyl, 2-fluoro-4-chlorophenyl or COOH;
W is hydrogen or fluorine;
X is hydrogen, chlorine, fluorine or methyl;
Y is fluorine, chlorine, bromine, cyano, methyl, methoxy or trifluoromethyl; where
X and Y are especially the following (Y,X) combinations: (Me,F), (Me,H), (Me,Cl), (Me,Me), (Cl,Cl), (Cl,F), (CN, F), (CN,H), (MeO,F), (MeO,H), (Cl,H), (Br,H), (Br,F), (F,F), (CF$_3$,H);
Z is hydrogen; and
n is the number 0 or 1.

In this context, it is very particularly preferable that
$R^1$ is hydrogen, methyl, ethyl, $CH(CH_3)_2$, $C(CH_3)_3$, $CH_2CF_3$, $CH_2CH_2OCH_3$, cyclopropyl, phenyl or 4-methyl-3-(2,2,2-trifluoroethylsulphanyl)phenyl;

$R^2$ is hydrogen, methyl, ethyl, $CH_2CH_2CH_3$, $CH_2CH_2CH_2CH_3$, $CH_2CH(CH_3)_2$, $CH(CH_3)CH_2CH_3$, $CH(CH_3)_2$, $C(CH_3)_3$, $CH=CHCH_3$, $CF_3$, $CH_2OCH_3$, $CH_2OCH_2CH_3$, $CH_2CH_2OCH_3$, cyclopropyl, cyclobutyl, phenyl, 3-fluorophenyl, 2-fluoro-4-chlorophenyl or COOH;
W is hydrogen or fluorine;
X is hydrogen, chlorine, fluorine or methyl;
Y is chlorine, cyano, methyl or methoxy; where
X and Y are especially the following (Y,X) combinations: (CN,F), (Me,F), (Me,H), (Me,Cl), (Me,Me), (Cl,H), (OCH$_3$,H)
Z is hydrogen; and
n is the number 0 or 1.

If the substructure of the formula (I-A) is the substructure formula (I-A-1), it is likewise preferable that
$R^1$ is hydrogen; or
  is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or
  is $(C_3-C_6)$cycloalkyl, $(C_3-C_6)$cycloalkenyl, phenyl or pyridyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;

$R^2$ is hydrogen; or
  is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or
  is $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl; or
  is carboxyl;

W is hydrogen or halogen, especially F or Cl;
X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;
Z is hydrogen; and
n is the number 0 or 1.

In this context, it is likewise very particularly preferable that
$R^1$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, cyclopropylmethyl, $CH_2CF_3$, $CH_2CHF_2$, $CH_2CN$, $CH_2CH_2OCH_3$, benzyl, cyclopropyl, cyclobutyl, phenyl, 3-pyridyl, 4-fluorophenyl or 4-methyl-3-(2,2,2-trifluoroethylsulphanyl)phenyl;

$R^2$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, $CH_2CH_2OCH(CH_3)_2$, benzyl, cyclopropyl, cyclobutyl, cyclopentyl, cyclohexyl, phenyl, 3-fluorophenyl, 2-fluoro-4-chlorophenyl, or COOH;

W is hydrogen or fluorine;
X is hydrogen, chlorine, fluorine or methyl;
Y is fluorine, chlorine, bromine, cyano, methyl, methoxy or trifluoromethyl; where
X and Y are especially the following (Y,X) combinations: (Me,F), (Me,H), (Me,Cl), (Me,Me), (Cl,Cl), (Cl,F), (CN, F), (CN,H), (MeO,F), (MeO,H), (Cl,H), (Br,H), (Br,F), (F,F), (CF$_3$,H);
Z is hydrogen; and
n is the number 0 or 1.

In this context, it is likewise very particularly preferable that
$R^1$ is hydrogen, methyl, ethyl, CH(CH$_3$)$_2$, C(CH$_3$)$_3$, CH$_2$CF$_3$, CH$_2$CH$_2$OCH$_3$, cyclopropyl, phenyl, 3-pyridyl, 4-fluorophenyl or 4-methyl-3-(2,2,2-trifluoroethylsulphanyl)phenyl;
$R^2$ is hydrogen, methyl, ethyl, CH$_2$CH$_2$CH$_3$, CH$_2$CH$_2$CH$_2$CH$_3$, CH$_2$CH(CH$_3$)$_2$, CH(CH$_3$)CH$_2$CH$_3$, CH(CH$_3$)$_2$, C(CH$_3$)$_3$, CH=CHCH$_3$, CF$_3$, CH$_2$OCH$_3$, CH$_2$OCH$_2$CH$_3$, CH$_2$CH$_2$OCH$_3$, CH$_2$CH$_2$OCH(CH$_3$)$_2$, cyclopropyl, cyclobutyl, cyclopentyl, cyclohexyl, phenyl, 3-fluorophenyl, 2-fluoro-4-chlorophenyl or COOH;
W is hydrogen or fluorine;
X is hydrogen, chlorine, fluorine or methyl;
Y is chlorine, cyano, methyl or methoxy; where
X and Y are especially the following (Y,X) combinations: (CN,F), (Me,F), (Me,H), (Me,Cl), (Me,Me), (Cl,H), (OCH$_3$,H)
Z is hydrogen; and
n is the number 0 or 1.

If the substructure of the formula (I-A) is the substructure formula (I-A-2), it is preferable that
$R^1$ is hydrogen; or
  is (C$_1$-C$_6$)alkyl, (C$_3$-C$_6$)cycloalkyl(C$_1$-C$_6$)alkyl, (C$_2$-C$_6$)alkenyl, (C$_2$-C$_6$)alkynyl, halo(C$_2$-C$_6$)alkyl, cyano(C$_1$-C$_6$)alkyl, (C$_1$-C$_6$)alkoxy(C$_1$-C$_6$)alkyl or phenyl(C$_1$-C$_3$)alkyl, where the aforementioned radicals may each optionally be substituted; or
  is (C$_3$-C$_6$)cycloalkyl, (C$_3$-C$_6$)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo(C$_1$-C$_3$)alkylsulphanyl or optionally methyl-, fluorine-, chlorine-, cyano-substituted cyclopropyl;
$R^6$ is hydrogen; or
  is (C$_1$-C$_6$)alkyl, (C$_3$-C$_6$)cycloalkyl(C$_1$-C$_6$)alkyl, (C$_2$-C$_6$)alkenyl, (C$_2$-C$_6$)alkynyl, halo(C$_1$-C$_6$)alkyl, cyano(C$_1$-C$_6$)alkyl, (C$_1$-C$_6$)alkoxy(C$_1$-C$_6$)alkyl or phenyl(C$_1$-C$_3$)alkyl, where the aforementioned radicals may each optionally be substituted; or
  is (C$_3$-C$_6$)cycloalkyl, (C$_3$-C$_6$)cycloalkenyl, oxetanyl, oxolanyl, oxanyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo(C$_1$-C$_3$)alkylsulphanyl or optionally methyl-, fluorine-, chlorine-, cyano-substituted cyclopropyl;
W is hydrogen or halogen, especially F or Cl;
X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;
Z is hydrogen; and
n is the number 0 or 1.

In this context, it is particularly preferable that
$R^1$ is hydrogen, methyl, ethyl, n-propyl, CH(CH$_3$)$_2$, n-butyl, sec-butyl, C(CH$_3$)$_3$, CH$_2$C(CH$_3$)$_3$, CH$_2$CH(CH$_3$)$_2$, CH$_2$CH=CH$_2$, cyclopropylmethyl, CH$_2$CF$_3$, CH$_2$CHF$_2$, CH$_2$CN, CH$_2$CH$_2$OCH$_3$, benzyl, cyclopropyl, cyclobutyl or phenyl;
$R^6$ is hydrogen, methyl, ethyl, n-propyl, CH(CH$_3$)$_2$, n-butyl, sec-butyl, C(CH$_3$)$_3$, CH$_2$C(CH$_3$)$_3$, CH$_2$CH(CH$_3$)$_2$, CH=CH$_2$, CH=CHCH$_3$, CH$_2$CH=CH$_2$, CH$_2$CH$_2$C(=CH$_2$)CH$_3$, CH$_2$CCH, cyclopropylmethyl, CF$_3$, CH$_2$CF$_3$, CH$_2$CHF$_2$, CH$_2$CN, CH$_2$OCH$_3$, CH$_2$OCH$_2$CH$_3$, CH$_2$CH$_2$OCH$_3$, benzyl, cyclopropyl, cyclobutyl, cyclohexyl, phenyl or 3-tetrahydrofuryl;
W is hydrogen or fluorine;
X is hydrogen, chlorine, fluorine or methyl;
Y is fluorine, chlorine, bromine, cyano, methyl, methoxy or trifluoromethyl; where
X and Y are especially the following (Y,X) combinations: (Me,F), (Me,H), (Me,Cl), (Me,Me), (Cl,Cl), (Cl,F), (CN, F), (CN,H), (MeO,F), (MeO,H), (Cl,H), (Br,H), (Br,F), (F,F), (CF$_3$,H);
Z is hydrogen; and
n is the number 0 or 1.

In this context, it is very particularly preferable that
$R^1$ is cyclopropyl, methyl, ethyl or CH$_2$CH=CH$_2$;
$R^6$ is phenyl, cyclohexyl, CH$_2$-cyclopropyl, benzyl, 3-tetrahydrofuryl, methyl, ethyl, CH$_2$CH$_2$CH$_3$, CH$_2$CH$_2$CH$_2$CH$_3$, CH$_2$CH$_2$OCH$_3$, CH$_2$CH$_2$C(=CH$_2$)CH$_3$, CH$_2$CH(CH$_3$)$_2$, CH$_2$CF$_3$, CH$_2$C(CH$_3$)$_3$, CH(CH$_3$)CH$_2$CH$_3$, CH(CH$_3$)$_2$ or C(CH$_3$)$_3$;
W is fluorine;
X is hydrogen, fluorine, chlorine or methyl;
Y is fluorine, chlorine, bromine, cyano, methyl, methoxy or trifluoromethyl; where
X and Y are especially the following (Y,X) combinations: (Me,F), (Me,Me), (Me,H), (Me,Cl), (Cl,Cl), (Cl,F), (CN, H), (MeO,F), (MeO,H), (Cl,H), (Br,H), (Br,F), (F,F), (CF$_3$,H);
Z is hydrogen; and
n is the number 0 or 1.

If the substructure of the formula (I-A) is the substructure formula (I-A-2), it is likewise preferable that
$R^1$ is hydrogen; or
  is (C$_1$-C$_6$)alkyl, (C$_3$-C$_6$)cycloalkyl(C$_1$-C$_6$)alkyl, (C$_2$-C$_6$)alkenyl, (C$_2$-C$_6$)alkynyl, halo(C$_2$-C$_6$)alkyl, cyano(C$_1$-C$_6$)alkyl, (C$_1$-C$_6$)alkoxy(C$_1$-C$_6$)alkyl or phenyl(C$_1$-C$_3$)alkyl, where the aforementioned radicals may each optionally be substituted; or
  is (C$_3$-C$_6$)cycloalkyl, (C$_3$-C$_6$)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo(C$_1$-C$_3$)alkylsulphanyl or optionally methyl-, fluorine-, chlorine-, cyano-substituted cyclopropyl;
$R^6$ is hydrogen; or
  is (C$_1$-C$_6$)alkyl, (C$_3$-C$_6$)cycloalkyl(C$_1$-C$_6$)alkyl, (C$_2$-C$_6$)alkenyl, (C$_2$-C$_6$)alkynyl, halo(C$_1$-C$_6$)alkyl, cyano(C$_1$-C$_6$)alkyl, (C$_1$-C$_6$)alkoxy(C$_1$-C$_6$)alkyl or phenyl(C$_1$-C$_3$)alkyl, where the aforementioned radicals may each optionally be substituted; or
  is (C$_3$-C$_6$)cycloalkyl, (C$_3$-C$_6$)cycloalkenyl, oxetanyl, oxolanyl, oxanyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo($C_1$-$C_3$)alkylsulphanyl or optionally methyl-, fluorine-, chlorine-, cyano-substituted cyclopropyl;

W is hydrogen or halogen, especially F or Cl;

X and Y are each independently hydrogen, fluorine, chlorine, bromine, methyl, ethyl, trifluoromethyl, 2,2-difluoromethyl, methoxy, difluoromethoxy, trifluoromethoxy, cyclopropyl, cyano, amino, hydroxyl or nitro;

Z is hydrogen; and n is the number 0 or 1.

In this context, it is likewise very particularly preferable that $R^1$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, cyclopropylmethyl, $CH_2CF_3$, $CH_2CHF_2$, $CH_2CN$, $CH_2CH_2OCH_3$, $CH_2CH_2CH_2OCH_3$, benzyl, cyclopropyl, cyclobutyl or phenyl;

$R^6$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CH_2C(=CH_2)CH_3$, $CH_2CCH$, cyclopropylmethyl, $CF_3$, $CH_2CF_3$, $CH_2CHF_2$, $CH_2CCl_3$, $CH_2CN$, $CH_2OCH_3$, $CH_2OCH_2CH_3$, $CH_2CH_2OCH_3$, benzyl, cyclopropyl, cyclobutyl, cyclohexyl, phenyl or 3-tetrahydrofuryl;

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN, F), (CN,H), (MeO,F), (MeO,H), (Cl,H), (Br,H), (Br,F), (F,F), (CF$_3$,H);

Z is hydrogen; and n is the number 0 or 1.

In this context, it is likewise very particularly preferable that $R^1$ is cyclopropyl, methyl, ethyl, n-propyl, $CH(CH_3)_2$, $CH_2CH=CH_2$, cyclopropylmethyl, $CH_2CF_3$ or $CH_2CH_2CH_2OCH_3$;

$R^6$ is phenyl, cyclohexyl, $CH_2$-cyclopropyl, benzyl, 3-tetrahydrofuryl, methyl, ethyl, $CH_2CH_2CH_3$, $CH_2CH_2CH_2CH_3$, $CH_2CH_2OCH_3$, $CH_2CH_2C(=CH_2)CH_3$, $CH_2CH(CH_3)_2$, $CH_2CF_3$, $CH_2C(CH_3)_3$, $CH(CH_3)CH_2CH_3$, $CH(CH_3)_2$, $CH_2CCl_3$, $CH_2CH=CH_2$ or $C(CH_3)_3$;

W is fluorine;

X is hydrogen, fluorine, chlorine or methyl;

Y is fluorine, chlorine, bromine, cyano, methyl, methoxy or trifluoromethyl; where X and Y are especially the following (Y,X) combinations: (Me,F), (Me,Me), (Me,H), (Me,Cl), (Cl,Cl), (Cl,F), (CN,H), (MeO,F), (MeO,H), (Cl,H), (Br,H), (Br,F), (F,F), (CF$_3$,H);

Z is hydrogen; and n is the number 0 or 1.

If the substructure of the formula (I-A) is the substructure formula (I-A-3), it is preferable that $R^1$ is hydrogen; or is ($C_1$-$C_6$)alkyl, ($C_3$-$C_6$)cycloalkyl($C_1$-$C_6$)alkyl, ($C_2$-$C_6$)alkenyl, ($C_2$-$C_6$)alkynyl, halo($C_2$-$C_6$)alkyl, cyano($C_1$-$C_6$)alkyl, ($C_1$-$C_6$)alkoxy($C_1$-$C_6$)alkyl or phenyl($C_1$-$C_3$)alkyl, where the aforementioned radicals may each optionally be substituted; or is ($C_3$-$C_6$)cycloalkyl, ($C_3$-$C_6$)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo($C_1$-$C_3$)alkylsulphanyl or optionally methyl-, fluorine-, chlorine-, cyano-substituted cyclopropyl;

$R^7$ and $R^8$ are each independently hydrogen, ($C_1$-$C_6$)alkyl, halo($C_2$-$C_6$)alkyl, cyano($C_1$-$C_6$)alkyl or ($C_3$-$C_6$)cycloalkyl, where the aforementioned radicals may optionally each be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo ($C_1$-$C_6$)alkylsulphinyl, halo($C_1$-$C_6$)alkylsulphanyl, halo ($C_1$-$C_6$)alkylsulphonyl or optionally methyl-, fluorine-, chlorine-, cyano- or cyclopropyl-substituted cyclopropyl;

or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

W is hydrogen or halogen, especially F or Cl;

X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z is hydrogen; and n is the number 0 or 1.

In this context, it is particularly preferable that $R^1$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, cyclopropylmethyl, $CH_2CF_3$, $CH_2CHF_2$, $CH_2CN$, $CH_2CH_2OCH_3$, benzyl, cyclopropyl, cyclobutyl or phenyl;

$R^7$ and $R^8$ are both simultaneously methyl or ethyl or, together with the nitrogen atom to which they are bonded, are morpholine, N-methylpiperazine, 4-methyl-5-oxo-3-phenoxy-1,2,4-triazol-1-yl), 4-ethyl-5-oxo-3-phenoxy-1,2,4-triazol-1-yl) or 4-cyclopropyl-5-oxo-3-phenoxy-1,2,4-triazol-1-yl);

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN, F), (CN,H), (MeO,F), (MeO,H), (Cl,H), (Br,H), (Br,F), (F,F), (CF$_3$,H);

Z is hydrogen; and n is the number 0 or 1.

In this context, it is very particularly preferable that $R^1$ is cyclopropyl or methyl;

$R^7$ and $R^8$ are both simultaneously methyl or, together with the nitrogen atom to which they are bonded, are 4-methyl-5-oxo-3-phenoxy-1,2,4-triazol-1-yl;

W is fluorine;

X is hydrogen or fluorine;

Y is methyl; where

X and Y are especially the following (Y,X) combinations: (Me,F), (Me,H);

Z is hydrogen; and n is the number 0 or 1.

If the substructure of the formula (I-A) is the substructure formula (I-A-4), it is preferable that
$R^2$ is hydrogen; or
  is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or
  is $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;
$R^9$ and $R^{10}$ are each independently hydrogen, $(C_1-C_6)$alkyl, halo$(C_2-C_6)$alkyl, cyano$(C_1-C_6)$alkyl or $(C_3-C_6)$cycloalkyl, where the aforementioned radicals may optionally each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano- or cyclopropyl-substituted cyclopropyl;
  or together are $(C_1-C_6)$alkylidene which may optionally be substituted by halogen, cyano, nitro, hydroxyl, amino, $(C_1-C_3)$alkyl, halo$(C_1-C_3)$alkyl, $(C_1-C_3)$alkoxy, halo$(C_1-C_3)$alkoxy or optionally methyl-, fluorine-, chlorine-, cyano-substituted cyclopropyl;
W is hydrogen or halogen, especially F or Cl;
X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;
Z is hydrogen; and
n is the number 0 or 1.
  In this context, it is particularly preferable that
$R^2$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl or phenyl;
$R^9$ and $R^{10}$ are each independently hydrogen, methyl or ethyl or, together with the nitrogen atom to which they are bonded, are $=C(CH_3)_2$, $=C(CH_3)CH_2CH_3$, $=C(CH_3)CH_2CH(CH_3)_2$;
W is hydrogen or fluorine;
X is hydrogen, chlorine, fluorine or methyl;
Y is fluorine, chlorine, bromine, cyano, methyl, methoxy or trifluoromethyl; where
X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), $(CF_3,H)$;
Z is hydrogen; and
n is the number 0 or 1.
  In this context, it is very particularly preferable that
$R^2$ is hydrogen, methyl, $CH(CH_3)_2$, $CH_2OCH_3$, cyclopropyl or $CF_3$;
$R^9$ and $R^{10}$ are each independently hydrogen or methyl or together are $=C(CH_3)CH_2CH(CH_3)_2$;
W is fluorine;
X is hydrogen or fluorine;
Y is methyl;

X and Y are especially the following (Y,X) combinations: (Me,F), (Me,H); and
Z is hydrogen;
n is the number 0 or 1.
  If the substructure of the formula (I-A) is the substructure formula (I-A-5), it is preferable that
$R^7$ and $R^8$ are each independently hydrogen, $(C_1-C_6)$alkyl, halo$(C_2-C_6)$alkyl, cyano$(C_1-C_6)$alkyl or $(C_3-C_6)$cycloalkyl, where the aforementioned radicals may optionally each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano- or cyclopropyl-substituted cyclopropyl;
$R^9$ and $R^{10}$ are each independently hydrogen, $(C_1-C_6)$alkyl, halo$(C_2-C_6)$alkyl, cyano$(C_1-C_6)$alkyl or $(C_3-C_6)$cycloalkyl, where the aforementioned radicals may optionally each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano- or cyclopropyl-substituted cyclopropyl;
  or together are $(C_1-C_6)$alkylidene which may optionally be substituted by halogen, cyano, nitro, hydroxyl, amino, $(C_1-C_3)$alkyl, halo$(C_1-C_3)$alkyl, $(C_1-C_3)$alkoxy, halo$(C_1-C_3)$alkoxy or optionally methyl-, fluorine-, chlorine-, cyano-substituted cyclopropyl;
W is hydrogen or halogen, especially F or Cl;
X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;
Z is hydrogen; and
n is the number 0 or 1.
  In this context, it is particularly preferable that
$R^7$ and $R^8$ are each independently hydrogen, methyl, ethyl, n-propyl, $CH(CH_3)_2$, n-butyl, sec-butyl, $C(CH_3)_3$, $CH_2C(CH_3)_3$ or $CH_2CH(CH_3)_2$;
$R^9$ and $R^{10}$ are each independently hydrogen, methyl or ethyl or, together with the nitrogen atom to which they are bonded, are $=C(CH_3)_2$, $=C(CH_3)CH_2CH_3$, $=C(CH_3)CH_2CH(CH_3)_2$;
W is hydrogen or fluorine;
X is hydrogen, chlorine, fluorine or methyl;
Y is fluorine, chlorine, bromine, cyano, methyl, methoxy or trifluoromethyl; where
X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), $(CF_3,H)$;
Z is hydrogen; and
n is the number 0 or 1.
  In this context, it is very particularly preferable that
$R^7$ and $R^8$ are each independently hydrogen, methyl, ethyl or $CH(CH_3)_2$; where
$R^7$ and $R^8$ are especially the following $(R^7,R^8)$ combinations: (Me,Me), (Me,H), (Et,Et), (iPr,H)
$R^9$ and $R^{10}$ are each independently hydrogen or methyl; where
$R^9$ and $R^{10}$ are especially the following $(R^9,R^{10})$ combinations: (Me,H), (H,H)
W is fluorine;
X is fluorine;
Y is methyl;
Z is hydrogen;
n is the number 0 or 1.

If the substructure of the formula (I-A) is the substructure formula (I-A-6), it is preferable that
$R^2$ is hydrogen; or
- is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or
- is $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;

$R^{11}$ is hydrogen; or
- is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or
- is $(C_3-C_6)$cycloalkyl, $(C_3-C_6)$cycloalkenyl, oxetanyl, oxolanyl, oxanyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;

W is hydrogen or halogen, especially F or Cl;
X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;
Z is hydrogen; and
n is the number 0 or 1.

In this context, it is particularly preferable that
$R^2$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl or phenyl;
$R^{11}$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl, phenyl;
W is hydrogen or fluorine;
X is hydrogen, chlorine, fluorine or methyl;
Y is fluorine, chlorine, bromine, cyano, methyl, methoxy or trifluoromethyl; where
X and Y are especially the following (Y,X) combinations: (Me,F), (Me,H), (Me,Cl), (Me,Me), (Cl,Cl), (Cl,F), (CN, F), (CN,H), (MeO,F), (MeO,H), (Cl,H), (Br,H), (Br,F), (F,F), (CF$_3$,H);
Z is hydrogen; and
n is the number 0 or 1.

In this context, it is very particularly preferable that
$R^2$ is methyl;
$R^{11}$ is methyl;
is fluorine;
X is fluorine;
Y is methyl; where
Z is hydrogen;
n is the number 0 or 1.

In this context, it is likewise very particularly preferable that
$R^2$ is methyl or $CH(CH_3)_2$;
$R^{11}$ is methyl;
W is fluorine;
X is fluorine;
Y is methyl; where
Z is hydrogen;
n is the number 0 or 1.

If the substructure of the formula (I-A) is the substructure formula (I-A-7), it is preferable that
$R^6$ is hydrogen; or
- is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or
- is $(C_3-C_6)$cycloalkyl, $(C_3-C_6)$cycloalkenyl, oxetanyl, oxolanyl, oxanyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, or optionally methyl-, fluorine-, chlorine-, cyano-substituted cyclopropyl;

$R^{11}$ is hydrogen; or
- is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or
- is $(C_3-C_6)$cycloalkyl, $(C_3-C_6)$cycloalkenyl, oxetanyl, oxolanyl, oxanyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, or optionally methyl-, fluorine-, chlorine-, cyano-substituted cyclopropyl;

W is hydrogen or halogen, especially F or Cl;
X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;
Z is hydrogen; and
n is the number 0 or 1.

In this context, it is particularly preferable that
$R^6$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl or phenyl;
$R^{11}$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl or phenyl;
W is hydrogen or fluorine;
X is hydrogen, chlorine, fluorine or methyl;
Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), ($CF_3$,H);
Z is hydrogen; and
n is the number 0 or 1.
In this context, it is very particularly preferable that
$R^6$ is ethyl;
$R^{11}$ is methyl;
W is fluorine;
X is hydrogen or fluorine;
Y is methyl; where
X and Y are especially the following (Y,X) combinations: (Me,F) or (Me,H); and
Z is hydrogen;
n is the number 0 or 1.

If the substructure of the formula (I-A) is the substructure formula (I-A-8), it is preferable that
$R^1$ is hydrogen; or
is ($C_1$-$C_6$)alkyl, ($C_3$-$C_6$)cycloalkyl($C_1$-$C_6$)alkyl, ($C_2$-$C_6$)alkenyl, ($C_2$-$C_6$)alkynyl, halo($C_2$-$C_6$)alkyl, cyano($C_1$-$C_6$)alkyl, ($C_1$-$C_6$)alkoxy($C_1$-$C_6$)alkyl or phenyl($C_1$-$C_3$)alkyl, where the aforementioned radicals may each optionally be substituted; or
is ($C_3$-$C_6$)cycloalkyl, ($C_3$-$C_6$)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo($C_1$-$C_3$)alkylsulphanyl or optionally methyl-, fluorine-, chlorine-, cyano-substituted cyclopropyl;
$R^{12}$ is ($C_1$-$C_6$)alkyl, ($C_3$-$C_6$)cycloalkyl, ($C_2$-$C_6$)alkenyl, halo($C_1$-$C_6$)alkyl or cyano($C_1$-$C_6$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;
W is hydrogen or halogen, especially F or Cl;
X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;
Z is hydrogen; and
n is the number 0 or 1.
In this context, it is particularly preferable that
$R^1$ is hydrogen, methyl, ethyl, n-propyl, CH($CH_3$)$_2$, n-butyl, sec-butyl, C($CH_3$)$_3$, $CH_2$C($CH_3$)$_3$, $CH_2$CH($CH_3$)$_2$, $CH_2$CH=$CH_2$, cyclopropylmethyl, $CH_2CF_3$, $CH_2CHF_2$, $CH_2CN$, $CH_2CH_2OCH_3$, benzyl, cyclopropyl, cyclobutyl or phenyl;
$R^{12}$ is hydrogen, methyl, ethyl, n-propyl, CH($CH_3$)$_2$, n-butyl, sec-butyl, C($CH_3$)$_3$, $CH_2$C($CH_3$)$_3$, $CH_2$CH($CH_3$)$_2$, CH=$CH_2$, CH=CH$CH_3$, $CH_2$CH=$CH_2$, $CF_3$, $CH_2CF_3$, $CH_2CHF_2$, $CH_2CN$, cyclopropyl or cyclobutyl;
W is hydrogen or fluorine;
X is hydrogen, chlorine, fluorine or methyl;
Y is fluorine, chlorine, bromine, cyano, methyl, methoxy or trifluoromethyl; where
X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), ($CF_3$,H);
Z is hydrogen; and
n is the number 0 or 1.
In this context, it is very particularly preferable that
$R^1$ is cyclopropyl;
$R^{12}$ is methyl;
W is fluorine;
X is fluorine;
Y is methyl; where
Z is hydrogen; and
n is the number 0 or 1.
In this context, it is likewise very particularly preferable that
$R^1$ is methyl, ethyl or cyclopropyl;
$R^{12}$ is methyl;
W is fluorine;
X is fluorine;
Y is methyl; where
Z is hydrogen; and
n is the number 0 or 1.

If the substructure of the formula (I-A) is the substructure formula (I-A-9), it is preferable that
$R^1$ is hydrogen; or
is ($C_1$-$C_6$)alkyl, ($C_3$-$C_6$)cycloalkyl($C_1$-$C_6$)alkyl, ($C_2$-$C_6$)alkenyl, ($C_2$-$C_6$)alkynyl, halo($C_2$-$C_6$)alkyl, cyano($C_1$-$C_6$)alkyl, ($C_1$-$C_6$)alkoxy($C_1$-$C_6$)alkyl or phenyl($C_1$-$C_3$)alkyl, where the aforementioned radicals may each optionally be substituted; or
is ($C_3$-$C_6$)cycloalkyl, ($C_3$-$C_6$)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo($C_1$-$C_3$)alkylsulphanyl or optionally methyl-, fluorine-, chlorine-, cyano-substituted cyclopropyl;
$R^{12}$ is ($C_1$-$C_6$)alkyl, ($C_3$-$C_6$)cycloalkyl, ($C_2$-$C_6$)alkenyl, halo($C_1$-$C_6$)alkyl or cyano($C_1$-$C_6$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;
W is hydrogen or halogen, especially F or Cl;
X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;
Z is hydrogen; and
n is the number 0 or 1.
In this context, it is particularly preferable that
$R^1$ is hydrogen, methyl, ethyl, n-propyl, CH($CH_3$)$_2$, n-butyl, sec-butyl, C($CH_3$)$_3$, $CH_2$C($CH_3$)$_3$, $CH_2$CH($CH_3$)$_2$, $CH_2$CH=$CH_2$, cyclopropylmethyl, $CH_2CF_3$, $CH_2CHF_2$, $CH_2CN$, $CH_2CH_2OCH_3$, benzyl, cyclopropyl, cyclobutyl or phenyl;
$R^{12}$ is hydrogen, methyl, ethyl, n-propyl, CH($CH_3$)$_2$, n-butyl, sec-butyl, C($CH_3$)$_3$, $CH_2$C($CH_3$)$_3$, $CH_2$CH($CH_3$)$_2$, CH=$CH_2$, CH=CH$CH_3$, $CH_2$CH=$CH_2$, $CF_3$, $CH_2CF_3$, $CH_2CHF_2$, $CH_2CN$, cyclopropyl or cyclobutyl;
W is hydrogen or fluorine;
X is hydrogen, chlorine, fluorine or methyl;
Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), (CF$_3$,H);

Z is hydrogen; and n is the number 0 or 1.

In this context, it is very particularly preferable that $R^1$ is cyclopropyl, methyl, ethyl, $CH_2CH=CH_2$;

$R^{12}$ is methyl, ethyl, $CH_2CH_2CH_3$, $CH_2$-cyclopropyl, $CH(CH_3)_2$, benzyl or $CH_2CHF_2$;

W is fluorine;

X is fluorine;

Y is methyl; where

Z is hydrogen; and n is the number 0 or 1.

If the substructure of the formula (I-A) is the substructure formula (I-A-10), it is preferable that $R^1$ is hydrogen; or is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or is $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;

$R^{12}$ is $(C_1-C_6)$alkyl, $(C_3-C_6)$cycloalkyl, $(C_2-C_6)$alkenyl, halo$(C_1-C_6)$alkyl or cyano$(C_1-C_6)$alkyl, where all the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

W is hydrogen or halogen, especially F or Cl;

X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z is hydrogen; and n is the number 0 or 1.

In this context, it is particularly preferable that $R^1$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, cyclopropylmethyl, $CH_2CF_3$, $CH_2CHF_2$, $CH_2CN$, $CH_2CH_2OCH_3$, benzyl, cyclopropyl, cyclobutyl or phenyl;

$R^{12}$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CF_3$, $CH_2CF_3$, $CH_2CHF_2$, $CH_2CN$, cyclopropyl or cyclobutyl;

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), (CF$_3$,H);

Z is hydrogen; and n is the number 0 or 1.

In this context, it is very particularly preferable that $(C_1-C_6)$ is cyclopropyl, methyl, ethyl or $CH_2CH=CH_2$;

$R^{12}$ is methyl, ethyl, $CH_2CHF_2$, $CH_2$-cyclopropyl, $CH_2CH_2CH_3$, $CH_2CH=CH_2$, $CH_2CF_3$, $CH(CH_3)_2$, $CF_3$ or benzyl;

W is fluorine;

X is fluorine;

Y is methyl; where z is hydrogen; and n is the number 0 or 1.

If the substructure of the formula (I-A) is the substructure formula (I-A-11), it is preferable that $R^1$ is hydrogen; or is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or is $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;

$R^2$ is hydrogen; or is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or is $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;

W is hydrogen or halogen, especially F or Cl;

X and Y are each independently hydrogen, fluorine, chlorine, bromine, methyl, ethyl, trifluoromethyl, 2,2-difluoromethyl, methoxy, difluoromethoxy, trifluoromethoxy, cyclopropyl, cyano, amino, hydroxyl or nitro;

Z is hydrogen; and is the number 0 or 1.

In this context, it is particularly preferable that $R^1$ is hydrogen, methyl, ethyl, n-propyl, $CH(CH_3)_2$, $C(CH_3)_3$, $CH_2CH(CH_3)_2$, $CH_2CH=CH_2$, $CH_2CF_3$, $CH_2CN$, benzyl, cyclopropyl, cyclobutyl or phenyl;

$R^2$ is hydrogen, methyl, ethyl, n-propyl, $CH(CH_3)_2$, n-butyl, sec-butyl, $C(CH_3)_3$, $CH_2CH(CH_3)_2$, $CH=CH_2$, $CH=CHCH_3$, $CH_2CH=CH_2$, $CH_2OCH_3$, $CH_2OCH_2CH_3$, $CH_2CH_2OCH_3$, $CH_2CH_2OCH_2CH_3$, $CF_3$, $CH_2CF_3$, $CH_2CHF_2$, $CH_2CN$, cyclopropyl, cyclobutyl, cyclopentyl, cyclohexyl or phenyl;

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), (CF$_3$,H);

Z is hydrogen; and
n is the number 0 or 1.

In this context, it is very particularly preferable that
R$^1$ is cyclopropyl, ethyl or CH(CH$_3$)$_2$;
R$^2$ is methyl, ethyl, n-propyl, n-butyl, CH(CH$_3$)$_2$, CH$_2$CH(CH$_3$)$_2$, CH$_2$OCH$_3$, CH$_2$OCH$_2$CH$_3$, CH(CH$_3$)CH$_2$CH$_3$, CH=CHCH$_3$, cyclopropyl, cyclobutyl, cyclopentyl, cyclohexyl, 2-methoxyphenyl or CF$_3$;
W is fluorine;
X is fluorine or hydrogen;
Y is methyl or methoxy; where
X and Y are especially the following (Y,X) combinations: (Me,F), (MeO,H),
Z is hydrogen; and
n is the number 0.

If the substructure of the formula (I-A) is the substructure formula (I-A-13), it is preferable that
R$^1$ is hydrogen; or
is (C$_1$-C$_6$)alkyl, (C$_3$-C$_6$)cycloalkyl(C$_1$-C$_6$)alkyl, (C$_2$-C$_6$)alkenyl, (C$_2$-C$_6$)alkynyl, halo(C$_2$-C$_6$)alkyl, cyano(C$_1$-C$_6$)alkyl, (C$_1$-C$_6$)alkoxy(C$_1$-C$_6$)alkyl or phenyl(C$_1$-C$_3$)alkyl, where the aforementioned radicals may each optionally be substituted; or
is (C$_3$-C$_6$)cycloalkyl, (C$_3$-C$_6$)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo(C$_1$-C$_3$)alkylsulphanyl or optionally methyl-, fluorine-, chlorine-, cyano-substituted cyclopropyl;
R$^{13}$ is halogen;
W is hydrogen or halogen, especially F or Cl;
X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;
Z is hydrogen; and
n is the number 0 or 1.

In this context, it is particularly preferable that
R$^1$ is hydrogen, methyl, ethyl, n-propyl, CH(CH$_3$)$_2$, n-butyl, sec-butyl, C(CH$_3$)$_3$, CH$_2$C(CH$_3$)$_3$, CH$_2$CH(CH$_3$)$_2$, CH$_2$CH=CH$_2$, cyclopropylmethyl, CH$_2$CF$_3$, CH$_2$CHF$_2$, CH$_2$CN, CH$_2$CH$_2$OCH$_3$, benzyl, cyclopropyl, cyclobutyl or phenyl;
R$^{13}$ is fluorine, chlorine or bromine;
W is hydrogen or fluorine;
X is hydrogen, chlorine, fluorine or methyl;
Y is fluorine, chlorine, bromine, cyano, methyl, methoxy or trifluoromethyl; where
X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), (CF$_3$,H);
Z is hydrogen; and In this context, it is very particularly preferable that
R$^1$ is cyclopropyl;
R$^{13}$ is bromine;
W is fluorine;
X is fluorine;
Y is methyl; where
Z is hydrogen; and
n is the number 0 or 1.

In this context, it is likewise very particularly preferable that
R$^1$ is methyl, ethyl, CH(CH$_3$)$_2$, C(CH$_3$)$_3$ or cyclopropyl;
R$^{13}$ is bromine;
W is fluorine;
X is fluorine;
Y is methyl; where
Z is hydrogen; and
n is the number 0 or 1.

Second Embodiment (I-B):
In a second embodiment of the present invention, the inventive compounds have a structure of the general formula (I) in which
A and B together with the atoms to which they are bonded are a substructure of the formula (I-B)

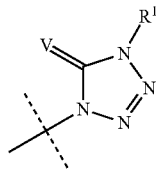

(I-B)

where
R$^1$ is hydrogen, cyano or nitro; or
is (C$_1$-C$_6$)alkyl, (C$_3$-C$_6$)cycloalkyl(C$_1$-C$_6$)alkyl, halo(C$_2$-C$_6$)alkyl, cyano(C$_1$-C$_6$)alkyl, hydroxy(C$_1$-C$_6$)alkyl, (C$_1$-C$_6$)alkoxy(C$_1$-C$_6$)alkyl, amino(C$_1$-C$_6$)alkyl, (C$_1$-C$_6$)alkoxycarbonyl(C$_1$-C$_6$)alkyl, (C$_1$-C$_6$)alkylsulphanyl(C$_1$-C$_6$)alkyl, (C$_1$-C$_6$)alkylsulphinyl(C$_1$-C$_6$)alkyl, (C$_1$-C$_6$)alkylsulphonyl(C$_1$-C$_6$)alkyl, halo(C$_1$-C$_6$)alkylsulphanyl(C$_1$-C$_6$)alkyl, halo(C$_1$-C$_6$)alkylsulphinyl(C$_1$-C$_6$)alkyl, halo(C$_1$-C$_6$)alkylsulphonyl(C$_1$-C$_6$)alkyl, (C$_1$-C$_6$)alkoxy(C$_1$-C$_6$)alkylsulphanyl(C$_1$-C$_6$)alkyl, (C$_1$-C$_6$)alkoxy(C$_1$-C$_6$)alkylsulphinyl(C$_1$-C$_6$)alkyl, (C$_1$-C$_6$)alkoxy(C$_1$-C$_6$)alkylsulphonyl(C$_1$-C$_6$)alkyl, phenyl(C$_1$-C$_6$)alkyl, phenoxy(C$_1$-C$_6$)alkyl, phenylsulphanyl(C$_1$-C$_6$)alkyl, phenylsulphinyl(C$_1$-C$_6$)alkyl, phenylsulphonyl(C$_1$-C$_6$)alkyl, hetaryl(C$_1$-C$_6$)alkyl, hetaryloxy(C$_1$-C$_6$)alkyl, hetarylsulphanyl(C$_1$-C$_6$)alkyl, hetarylsulphinyl(C$_1$-C$_6$)alkyl, hetarylsulphonyl(C$_1$-C$_6$)alkyl, where the aforementioned radicals may each optionally be substituted and/or, under the condition that, in the case of an unsaturated radical, the defined minimum number of carbon atoms is 2, the radicals may be saturated or unsaturated; or
is optionally substituted saturated or unsaturated (C$_3$-C$_6$)cycloalkyl which may optionally be interrupted by one or more heteroatoms; or
is (C$_1$-C$_6$)alkylcarbonyl, halo(C$_1$-C$_6$)alkylcarbonyl, hydroxy(C$_1$-C$_6$)alkylcarbonyl, (C$_1$-C$_6$)alkoxy(C$_1$-C$_6$)alkylcarbonyl, phenylcarbonyl, hetarylcarbonyl, (C$_1$-C$_6$)alkoxycarbonyl, halo(C$_1$-C$_6$)alkoxycarbonyl, aryloxycarbonyl, aminocarbonyl, (C$_1$-C$_6$)alkylaminocarbonyl, di(C$_1$-C$_6$)alkylaminocarbonyl, (C$_3$-C$_6$)cycloalkylaminocarbonyl, di(C$_3$-C$_6$)cycloalkylaminocarbonyl, (C$_3$-C$_6$)cycloalkyl((C$_1$-C$_6$)alkyl)aminocarbonyl, arylaminocarbonyl, diarylaminocarbonyl, (C$_1$-C$_6$)alkyl(aryl)aminocarbonyl, (C$_3$-C$_6$)cycloalkyl(aryl)aminocarbonyl, (C$_1$-C$_6$)alkylaminothiocarbonyl, di(C$_1$-C$_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or
is optionally substituted phenyl or optionally substituted hetaryl; or is $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or is hydroxyl; or is $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or is $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphanyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; and V is oxygen, sulphur or an optionally substituted nitrogen;

X, Y and Z each independently are hydrogen, halogen, hydroxyl, amino, cyano, nitro, OCN, SCN, $SF_5$; or are tri$(C_1-C_6)$alkylsilyl, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxycarbonyl$(C_1-C_6)$alkyl, $(C_1-C_6)$alkoxy$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, $(C_1-C_6)$alkoxy, halo$(C_1-C_6)$alkoxy, cyano$(C_1-C_6)$alkoxy, hydroxycarbonyl$(C_1-C_6)$alkoxy, $(C_1-C_6)$alkoxycarbonyl$(C_1-C_6)$alkoxy, $(C_1-C_6)$alkoxy$(C_1-C_6)$alkoxy, $(C_1-C_6)$alkylhydroxyimino, $(C_1-C_6)$alkoxyimino, $(C_1-C_6)$alkyl$(C_1-C_6)$alkoxyimino, halo$(C_1-C_6)$alkyl$(C_1-C_6)$alkoxyimino, $(C_1-C_6)$alkylthio, halo$(C_1-C_6)$alkylthio, $(C_1-C_6)$alkoxy$(C_1-C_6)$alkylthio, $(C_1-C_6)$alkylthio$(C_1-C_6)$alkyl, $(C_1-C_6)$alkylsulphinyl, halo$(C_1-C_6)$alkylsulphinyl, $(C_1-C_6)$alkoxy$(C_1-C_6)$alkylsulphinyl, $(C_1-C_6)$alkylsulphinyl$(C_1-C_6)$alkyl, $(C_1-C_6)$alkylsulphonyl, halo$(C_1-C_6)$alkylsulphonyl, $(C_1-C_6)$alkoxy$(C_1-C_6)$alkylsulphonyl, $(C_1-C_6)$alkylsulphonyl$(C_1-C_6)$alkyl, $(C_1-C_6)$alkylsulphonyloxy, $(C_1-C_6)$alkylcarbonyl, halo$(C_1-C_6)$alkylcarbonyl, carboxyl, $(C_1-C_6)$alkylcarbonyloxy, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_2-C_6)$alkenylaminocarbonyl, di$(C_2-C_6)$alkenylaminocarbonyl, $(C_3-C_6)$cyclo$(C_1-C_6)$alkylaminocarbonyl, $(C_1-C_6)$alkylsulphonylamino, aminosulphonyl, $(C_1-C_6)$alkylaminosulphonyl, di$(C_1-C_6)$alkylaminosulphonyl, $(C_1-C_6)$alkylsulphoximino, aminothiocarbonyl, $(C_1-C_6)$alkylaminothiocarbonyl or di$(C_1-C_6)$alkylaminothiocarbonyl, where all the aforementioned radicals may optionally be substituted by halogen; or are phenyl$(C_1-C_3)$alkyl, phenoxy, phenyl$(C_1-C_3)$alkyloxy, phenoxy$(C_1-C_3)$alkyl, phenylthio, phenylthio$(C_1-C_3)$alkyl, phenylsulphinyl, phenylsulphonyl, hetaryl$(C_1-C_3)$alkyl, hetaryloxy, hetaryl$(C_1-C_3)$alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are $(C_3-C_6)$cycloalkyl$(C_1-C_3)$alkyl, $(C_3-C_6)$cycloalkyloxy, $(C_3-C_6)$cycloalkyl$(C_1-C_3)$alkoxy, $(C_3-C_6)$cycloalkylthio, $(C_3-C_6)$cycloalkyl$(C_1-C_3)$alkylthio, $(C_3-C_6)$cycloalkylsulphinyl, $(C_3-C_6)$cycloalkyl$(C_1-C_3)$alkylsulphinyl, $(C_3-C_6)$cycloalkylsulphonyl, $(C_3-C_6)$cycloalkyl$(C_1-C_3)$alkylsulphonyl or $(C_3-C_8)$cycloalkenyl, where all the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"
where R' and R" each independently
are hydrogen, cyano, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, $(C_1-C_6)$alkylthio$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, acyl or $(C_1-C_6)$alkoxycarbonyl; or R' and R" together with the nitrogen atom to which they are bonded may form an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a $(C_3-C_6)$cycloalkyl, oxetanyl, oxolanyl, oxanyl, $(C_3-C_8)$cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

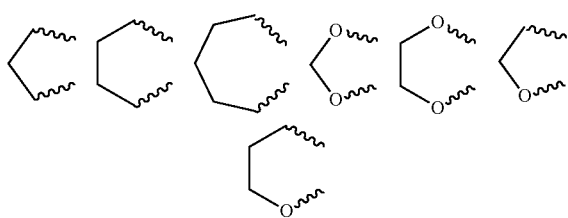

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

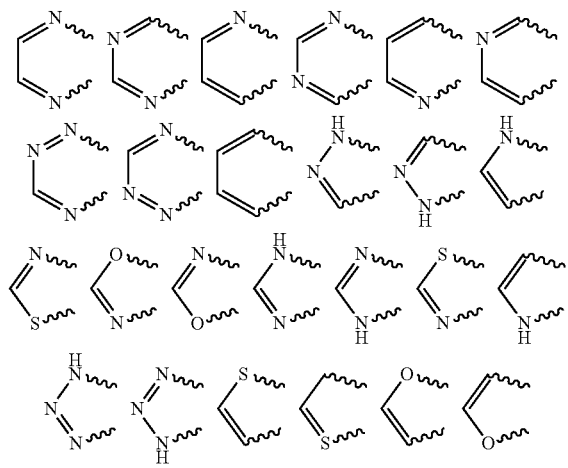

and
n is the number 0 or 1.

At the same time, it is preferable that
$R^1$ is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl or triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo $(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;
W is hydrogen or halogen;
V is oxygen, sulphur or an optionally substituted nitrogen;
X, Y and Z are each independently as defined above; and
n is the number 0 or 1.

Preferably, the substructure of the formula (I-B) is a substructure which is selected from the group consisting of

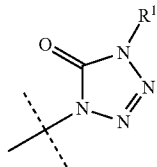

(I-B-1)

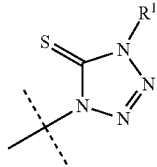

(I-B-2)

where
$R^1$ is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl or triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo $(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;
W is hydrogen or halogen, especially fluorine or chlorine;
X, Y and Z are each independently hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;
or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and n is the number 0 or 1.

More preferably, the substructure is of the substructure formula (I-B-1).

If the substructure of the formula (I-B) is the substructure formula (I-B-1), it is preferable that $R^1$ is hydrogen; or
  is ($C_1$-$C_6$)alkyl, ($C_3$-$C_6$)cycloalkyl($C_1$-$C_6$)alkyl, ($C_2$-$C_6$) alkenyl, ($C_2$-$C_6$)alkynyl, halo($C_2$-$C_6$)alkyl, cyano($C_1$-$C_6$)alkyl, ($C_1$-$C_6$)alkoxy($C_1$-$C_6$)alkyl or phenyl($C_1$-$C_3$) alkyl, where the aforementioned radicals may each optionally be substituted; or
  is ($C_3$-$C_6$)cycloalkyl, ($C_3$-$C_6$)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo($C_1$-$C_3$)alkylsulphanyl or optionally methyl-, fluorine-, chlorine-, cyano-substituted cyclopropyl;

W is hydrogen or halogen, especially F or Cl;

X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z is hydrogen; and n is the number 0 or 1.

In this context, it is particularly preferable that $R^1$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, cyclopropylmethyl, $CH_2CF_3$, $CH_2CHF_2$, $CH_2CN$, $CH_2CH_2OCH_3$, benzyl, cyclopropyl, cyclobutyl, phenyl or 4-chlorophenyl;

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), ($CF_3$,H);

Z is hydrogen; and n is the number 0 or 1.

In this context, it is very particularly preferable that $R^1$ is hydrogen, methyl, $CH_2CF_3$, $CH(CH_3)_2$ or 4-chlorophenyl;

W is fluorine;

X is hydrogen, methyl or fluorine;

Y is methyl; where

X and Y are especially the following (Y,X) combinations: (Me,F), (Me, Me), (Me,H);

Z is hydrogen; and n is the number 0 or 1.

If the substructure of the formula (I-B) is the substructure formula (I-B-1), it is likewise preferable that $R^1$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, cyclopropylmethyl, $CH_2CF_3$, $CH_2CHF_2$, $CH_2CF_2CF_3$, $CH_2CN$, $CH_2CH_2OCH_3$, benzyl, cyclopropyl, cyclobutyl, phenyl, 4-trifluoromethylphenyl or 4-chlorophenyl;

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), ($CF_3$,H);

Z is hydrogen; and n is the number 0 or 1.

In this context, it is very particularly preferable that $R^1$ is hydrogen, methyl, $CH(CH_3)_2$, $CH_2CF_3$, $CH_2CH_2OCH_3$, 4-trifluoromethylphenyl or 4-chlorophenyl;

W is fluorine;

X is hydrogen, methyl or fluorine;

Y is methyl; where

X and Y are especially the following (Y,X) combinations: (Me,F), (Me, Me), (Me,H);

Z is hydrogen; and n is the number 0 or 1.

Likewise more preferably, the substructure is of the substructure formula (I-B-2).

If the substructure of the formula (I-B) is the substructure formula (I-B-2), it is preferable that $R^1$ is hydrogen; or
  is ($C_1$-$C_6$)alkyl, ($C_3$-$C_6$)cycloalkyl($C_1$-$C_6$)alkyl, ($C_2$-$C_6$) alkenyl, ($C_2$-$C_6$)alkynyl, halo($C_2$-$C_6$)alkyl, cyano($C_1$-$C_6$)alkyl, ($C_1$-$C_6$)alkoxy($C_1$-$C_6$)alkyl or phenyl($C_1$-$C_3$) alkyl, where the aforementioned radicals may each optionally be substituted; or
  are ($C_3$-$C_6$)cycloalkyl, ($C_3$-$C_6$)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo($C_1$-$C_3$)alkylsulphanyl or optionally methyl-, fluorine-, chlorine-, cyano-substituted cyclopropyl;

W is hydrogen or halogen, especially F or Cl;

X and Y are each independently hydrogen, fluorine, chlorine, bromine, methyl, ethyl, trifluoromethyl, 2,2-difluoromethyl, methoxy, difluoromethoxy, trifluoromethoxy, cyclopropyl, cyano, amino, hydroxyl or nitro;

Z is hydrogen; and n is the number 0 or 1.

In this context, it is particularly preferable that $R^1$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, cyclopropylmethyl, $CH_2CF_3$, $CH_2CHF_2$, $CH_2CN$, $CH_2CH_2OCH_3$, benzyl, cyclopropyl, cyclobutyl, phenyl or 4-chlorophenyl;

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), ($CF_3$,H);

Z is hydrogen; and n is the number 0 or 1.

In this context, it is very particularly preferable that
R$^1$ is methyl;
W is fluorine;
X is fluorine;
Y is methyl; where
Z is hydrogen; and
n is the number 0 or 1.

Third Embodiment (I-C):

In a third embodiment of the present invention, the inventive compounds have a structure of the general formula (I) in which
A and B together with the atoms to which they are bonded are a substructure of the formula (I-C)

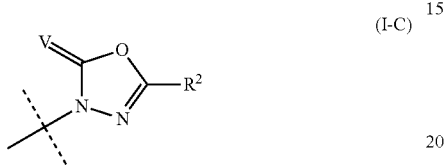

where
R$^2$ is hydrogen, cyano, halogen or nitro; or
is (C$_1$-C$_6$)alkyl, (C$_3$-C$_6$)cycloalkyl(C$_1$-C$_6$)alkyl, halo(C$_1$-C$_6$)alkyl, cyano(C$_1$-C$_6$)alkyl, hydroxy(C$_1$-C$_6$)alkyl, (C$_1$-C$_6$)alkoxy(C$_1$-C$_6$)alkyl, amino(C$_1$-C$_6$)alkyl, (C$_1$-C$_6$)alkoxycarbonyl(C$_1$-C$_6$)alkyl, (C$_1$-C$_6$)alkylsulphanyl(C$_1$-C$_6$)alkyl, (C$_1$-C$_6$)alkylsulphinyl(C$_1$-C$_6$)alkyl, (C$_1$-C$_6$)alkylsulphonyl(C$_1$-C$_6$)alkyl, halo(C$_1$-C$_6$)alkylsulphanyl(C$_1$-C$_6$)alkyl, halo(C$_1$-C$_6$)alkylsulphinyl(C$_1$-C$_6$)alkyl, halo(C$_1$-C$_6$)alkylsulphonyl(C$_1$-C$_6$)alkyl, (C$_1$-C$_6$)alkoxy(C$_1$-C$_6$)alkylsulphanyl(C$_1$-C$_6$)alkyl, (C$_1$-C$_6$)alkoxy(C$_1$-C$_6$)alkylsulphinyl(C$_1$-C$_6$)alkyl, (C$_1$-C$_6$)alkoxy(C$_1$-C$_6$)alkylsulphonyl(C$_1$-C$_6$)alkyl, phenyl(C$_1$-C$_6$)alkyl, phenoxy(C$_1$-C$_6$)alkyl, phenylsulphanyl(C$_1$-C$_6$)alkyl, phenylsulphinyl(C$_1$-C$_6$)alkyl, phenylsulphonyl(C$_1$-C$_6$)alkyl, hetaryl(C$_1$-C$_6$)alkyl, hetaryloxy(C$_1$-C$_6$)alkyl, hetarylthio(C$_1$-C$_6$)alkyl, where the aforementioned radicals may each optionally be substituted and/or, under the condition that, in the case of an unsaturated radical, the defined minimum number of carbon atoms is 2, the radicals may be saturated or unsaturated; or
is optionally substituted saturated or unsaturated (C$_3$-C$_6$)cycloalkyl which may optionally be interrupted by one or more heteroatoms; or
is (C$_1$-C$_6$)alkylcarbonyl, halo(C$_1$-C$_6$)alkylcarbonyl, hydroxy(C$_1$-C$_6$)alkylcarbonyl, (C$_1$-C$_6$)alkoxy(C$_1$-C$_6$)alkylcarbonyl, phenylcarbonyl, hetarylcarbonyl, (C$_1$-C$_6$)alkoxycarbonyl, halo(C$_1$-C$_6$)alkoxycarbonyl, aryloxycarbonyl, aminocarbonyl, (C$_1$-C$_6$)alkylaminocarbonyl, di(C$_1$-C$_6$)alkylaminocarbonyl, (C$_3$-C$_6$)cycloalkylaminocarbonyl, di(C$_3$-C$_6$)cycloalkylaminocarbonyl, (C$_3$-C$_6$)cycloalkyl((C$_1$-C$_6$)alkyl)aminocarbonyl, arylaminocarbonyl, diarylaminocarbonyl, (C$_1$-C$_6$)alkyl(aryl)aminocarbonyl, (C$_3$-C$_6$)cycloalkyl(aryl)aminocarbonyl, (C$_1$-C$_6$)alkylaminothiocarbonyl, di(C$_1$-C$_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or
is optionally substituted phenyl or optionally substituted hetaryl; or
is (C$_1$-C$_6$)alkoxy, halo(C$_1$-C$_6$)alkoxy, (C$_1$-C$_6$)alkoxy(C$_1$-C$_6$)alkoxy, aryloxy, aryl(C$_1$-C$_6$)alkyloxy, (C$_3$-C$_6$)cycloalkyloxy, (C$_3$-C$_6$)cycloalkyl(C$_1$-C$_6$)alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or is hydroxyl; or
is (C$_1$-C$_6$)alkylamino, di(C$_1$-C$_6$)alkylamino, halo(C$_1$-C$_6$)alkylamino, dihalo(C$_1$-C$_6$)alkylamino, (C$_3$-C$_6$)cycloalkylamino, di(C$_3$-C$_6$)cycloalkylamino, (C$_3$-C$_6$)cycloalkyl((C$_1$-C$_6$)alkyl)amino, arylamino, diarylamino, hetarylamino, dihetarylamino, (C$_1$-C$_6$)alkyl(aryl)amino, (C$_3$-C$_6$)cycloalkyl(aryl)amino, (C$_1$-C$_6$)alkylcarbonylamino, arylcarbonylamino, (C$_1$-C$_6$)alkoxycarbonylamino, aryloxycarbonylamino, (C$_1$-C$_6$)alkylcarbamoylamino, arylcarbamoylamino, (C$_1$-C$_6$)alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or
is (C$_1$-C$_6$)alkylsulphanyl, (C$_1$-C$_6$)alkylsulphinyl, (C$_1$-C$_6$)alkylsulphonyl, halo(C$_1$-C$_6$)alkylsulphanyl, halo(C$_1$-C$_6$)alkylsulphinyl, halo(C$_1$-C$_6$)alkylsulphonyl, (C$_3$-C$_6$)cycloalkylsulphanyl, (C$_3$-C$_6$)cycloalkylsulphinyl, (C$_3$-C$_6$)cycloalkylsulphonyl, (C$_3$-C$_6$)cycloalkyl(C$_1$-C$_6$)alkylsulphanyl, (C$_3$-C$_6$)cycloalkyl(C$_1$-C$_6$)alkylsulphinyl, (C$_3$-C$_6$)cycloalkyl(C$_1$-C$_6$)alkylsulphonyl, arylsulphanyl, arylsulphinyl, arylsulphonyl, aryl(C$_1$-C$_6$)alkylsulphanyl, aryl(C$_1$-C$_6$)alkylsulphinyl, aryl(C$_1$-C$_6$)alkylsulphonyl, aminosulphonyl, (C$_1$-C$_6$)alkylaminosulphonyl, di(C$_1$-C$_6$)alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; or
is an optionally singly or multiply, identically or differently halogen-, cyano-, nitro-, hydroxyl-, amino-, (C$_1$-C$_6$)alkyl-, halo(C$_1$-C$_6$)alkyl-, (C$_1$-C$_6$)alkoxy-, halo(C$_1$-C$_6$)alkoxy-, (C$_1$-C$_6$)alkylsulphinyl-, (C$_1$-C$_6$)alkylsulphanyl-, (C$_1$-C$_6$)alkylsulphonyl-, halo(C$_1$-C$_6$)alkylsulphinyl-, halo(C$_1$-C$_6$)alkylsulphanyl-, halo(C$_1$-C$_6$)alkylsulphonyl- or optionally substituted (C$_3$-C$_6$)cycloalkyl-substituted, saturated or unsaturated three- to six-membered ring optionally interrupted by heteroatoms from the group of O, S and N;
W is hydrogen or halogen;
V is oxygen, sulphur or an optionally substituted nitrogen;
X, Y and Z, each independently
are hydrogen, halogen, hydroxyl, amino, cyano, nitro, OCN, SCN, SF$_5$; or
are tri(C$_1$-C$_6$)alkylsilyl, (C$_1$-C$_6$)alkyl, halo(C$_1$-C$_6$)alkyl, cyano(C$_1$-C$_6$)alkyl, hydroxy(C$_1$-C$_6$)alkyl, (C$_1$-C$_6$)alkoxycarbonyl(C$_1$-C$_6$)alkyl, (C$_1$-C$_6$)alkoxy(C$_1$-C$_6$)alkyl, (C$_2$-C$_6$)alkenyl, halo(C$_2$-C$_6$)alkenyl, cyano(C$_2$-C$_6$)alkenyl, (C$_2$-C$_6$)alkynyl, halo(C$_2$-C$_6$)alkynyl, cyano(C$_2$-C$_6$)alkynyl, (C$_1$-C$_6$)alkoxy, halo(C$_1$-C$_6$)alkoxy, cyano(C$_1$-C$_6$)alkoxy, hydroxycarbonyl(C$_1$-C$_6$)alkoxy, (C$_1$-C$_6$)alkoxycarbonyl(C$_1$-C$_6$)alkoxy, (C$_1$-C$_6$)alkoxy(C$_1$-C$_6$)alkoxy, (C$_1$-C$_6$)alkylhydroxyimino, (C$_1$-C$_6$)alkoxyimino, (C$_1$-C$_6$)alkyl(C$_1$-C$_6$)alkoxyimino, halo(C$_1$-C$_6$)alkyl(C$_1$-C$_6$)alkoxyimino, (C$_1$-C$_6$)alkylthio, halo(C$_1$-C$_6$)alkylthio, (C$_1$-C$_6$)alkoxy(C$_1$-C$_6$)alkylthio, (C₁-C₆)alkylthio(C₁-C₆)alkyl, (C₁-C₆)alkylsulphinyl, halo(C₁-C₆)alkylsulphinyl, (C₁-C₆)alkoxy(C₁-C₆)alkylsulphinyl, (C₁-C₆)alkylsulphinyl(C₁-C₆)alkyl, (C₁-C₆)alkylsulphonyl, halo(C₁-C₆)alkylsulphonyl, (C₁-C₆)alkoxy(C₁-C₆)alkylsulphonyl, (C₁-C₆)alkylsulphonyl(C₁-C₆)alkyl, (C₁-C₆)alkylsulphonyloxy, (C₁-C₆)alkylcarbonyl, halo(C₁-C₆)alkylcarbonyl, carboxyl, (C₁-C₆)alkylcarbonyloxy, (C₁-C₆)alkoxycarbonyl, halo(C₁-C₆)alkoxycarbonyl, aminocarbonyl, (C₁-C₆)alkylaminocarbonyl, di(C₁-C₆)alkylaminocarbonyl, (C₂-C₆)alkenylaminocarbonyl, di(C₂-C₆)alkenylaminocarbonyl, (C₃-C₆)cycloalkylaminocarbonyl, (C₁-C₆)alkylsulphonylamino, aminosulphonyl, (C₁-C₆)alkylaminosulphonyl, di(C₁-C₆)alkylaminosulphonyl, (C₁-C₆)alkylsulphoximino, aminothiocarbonyl, (C₁-C₆)alkylaminothiocarbonyl or di(C₁-C₆)alkylaminothiocarbonyl, where all the aforementioned radicals may optionally be substituted by halogen; or are phenyl(C₁-C₃)alkyl, phenoxy, phenyl(C₁-C₃)alkyloxy, phenoxy(C₁-C₃)alkyl, phenylthio, phenylthio(C₁-C₃)alkyl, phenylsulphinyl, phenylsulphonyl, hetaryl(C₁-C₃)alkyl, hetaryloxy, hetaryl(C₁-C₃)alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are (C₃-C₆)cycloalkyl(C₁-C₃)alkyl, (C₃-C₆)cycloalkyloxy, (C₃-C₆)cycloalkyl(C₁-C₃)alkoxy, (C₃-C₆)cycloalkylthio, (C₃-C₆)cycloalkyl(C₁-C₃)alkylthio, (C₃-C₆)cycloalkylsulphinyl, (C₃-C₆)cycloalkyl(C₁-C₃)alkylsulphinyl, (C₃-C₆)cycloalkylsulphonyl, (C₃-C₆)cycloalkyl(C₁-C₃)alkylsulphonyl or (C₃-C₈)cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"
where R' and R" each independently
are hydrogen, cyano, (C₁-C₆)alkyl, halo(C₁-C₆)alkyl, cyano(C₁-C₆)alkyl, hydroxy(C₁-C₆)alkyl, (C₁-C₆)alkoxy(C₁-C₆)alkyl, (C₁-C₆)alkylthio(C₁-C₆)alkyl, (C₂-C₆)alkenyl, halo(C₂-C₆)alkenyl, cyano(C₂-C₆)alkenyl, (C₂-C₆)alkynyl, halo(C₂-C₆)alkynyl, cyano(C₂-C₆)alkynyl, acyl or (C₁-C₆)alkoxycarbonyl; or
R' and R" together with the nitrogen atom to which they are bonded may form an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or
are a (C₃-C₆)cycloalkyl, oxetanyl, oxolanyl, oxanyl, (C₃-C₈)cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

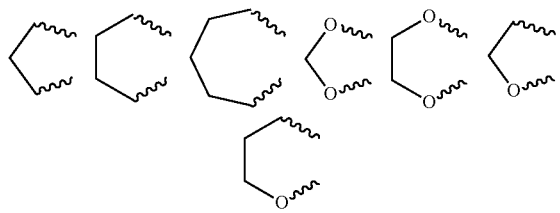

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

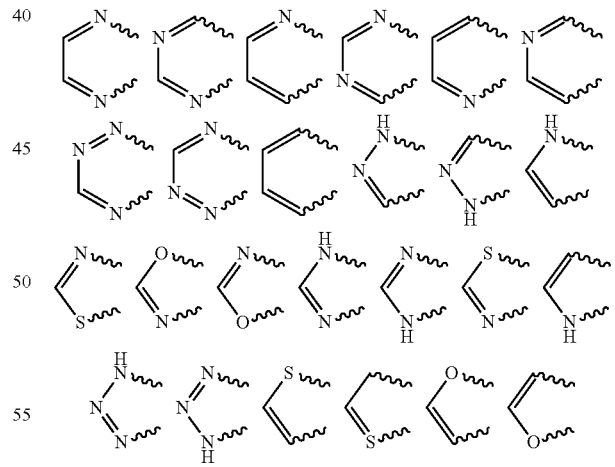

n is the number 0 or 1.
At the same time, it is preferable that
R² is hydrogen, cyano, halogen or nitro; or
is (C₁-C₆)alkyl, (C₃-C₆)cycloalkyl(C₁-C₆)alkyl, halo(C₁-C₆)alkyl, cyano(C₁-C₆)alkyl, (C₁-C₆)alkoxy(C₁-C₆)alkyl, (C₁-C₆)alkoxycarbonyl(C₁-C₆)alkyl, (C₁-C₆)alkylsulphanyl(C₁-C₆)alkyl, (C₁-C₆)alkylsulphinyl(C₁-C₆)alkyl, phenyl(C₁-C₆)alkyl, hetaryl(C₁-C₆)alkyl, (C₂-C₆)alkenyl, halo(C₂-C₆)alkenyl, (C₃-C₆)cycloalkenyl($C_1$-$C_6$)alkyl, ($C_2$-$C_6$)alkynyl, where the aforementioned radicals may each optionally be substituted; or is optionally substituted ($C_3$-$C_6$)cycloalkyl, ($C_3$-$C_6$)cycloalkenyl, which may optionally be interrupted by one or more heteroatoms from the group of O, S and N; or is ($C_1$-$C_6$)alkylcarbonyl, halo($C_1$-$C_6$)alkylcarbonyl, ($C_1$-$C_6$)alkoxy($C_1$-$C_6$)alkylcarbonyl, ($C_1$-$C_6$)alkoxycarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, ($C_1$-$C_6$)alkylaminothiocarbonyl, di($C_1$-$C_6$)alkylaminothiocarbonyl, ($C_2$-$C_6$)alkenylcarbonyl, ($C_3$-$C_6$)cycloalkenyl($C_1$-$C_6$)alkylcarbonyl, ($C_2$-$C_6$)alkynylcarbonyl or aminothiocarbonyl, where the aforementioned radicals may each optionally be substituted, or is carbonyl or carboxyl; or is optionally substituted phenyl or optionally substituted hetaryl; or is a phenyl or hetaryl ring which is optionally mono- or polysubstituted identically or differently by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally substituted ($C_3$-$C_6$)cycloalkyl; or is ($C_1$-$C_6$)alkoxy, halo($C_1$-$C_6$)alkoxy, ($C_1$-$C_6$)alkoxy($C_1$-$C_6$)alkoxy, ($C_3$-$C_6$)cycloalkyloxy, ($C_3$-$C_6$)cycloalkyl($C_1$-$C_6$)alkyloxy, ($C_2$-$C_6$)alkenyloxy, ($C_3$-$C_6$)cycloalkenyl($C_1$-$C_6$)alkoxy, ($C_2$-$C_6$)alkynyloxy or carbonyloxy, where the aforementioned radicals may each optionally be substituted, or is hydroxyl; or is ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_1$-$C_6$)alkylcarbonylamino, ($C_1$-$C_6$)alkoxycarbonylamino, ($C_1$-$C_6$)alkylcarbamoylamino, ($C_1$-$C_6$)alkylsulphonylamino, ($C_2$-$C_6$)alkenylamino, ($C_3$-$C_6$)cycloalkenyl($C_1$-$C_6$)alkylamino, ($C_2$-$C_6$)alkynylamino, where the aforementioned radicals may each optionally be substituted, or is amino; or is ($C_1$-$C_6$)alkylsulphinyl, ($C_1$-$C_6$)alkylsulphanyl, ($C_1$-$C_6$)alkylsulphonyl, halo($C_1$-$C_6$)alkylsulphanyl, halo($C_1$-$C_6$)alkylsulphinyl, halo($C_1$-$C_6$)alkylsulphanyl, ($C_3$-$C_6$)cycloalkyl($C_1$-$C_6$)alkylsulphanyl, ($C_3$-$C_6$)cycloalkyl($C_1$-$C_6$)alkylsulphinyl, ($C_3$-$C_6$)cycloalkyl($C_1$-$C_6$)alkylsulphonyl, aminosulphonyl, ($C_1$-$C_6$)alkylaminosulphonyl, di($C_1$-$C_6$)alkylaminosulphonyl or arylaminosulphonyl, where the aforementioned radicals may each optionally be substituted, or is sulphanyl; or is an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated three- to six-membered ring optionally interrupted by heteroatoms from the group of O, S and N;

W is hydrogen, fluorine or chlorine;

X, Y and Z are each independently hydrogen, fluorine, chlorine, bromine, cyano, nitro, amino, hydroxyl, ($C_1$-$C_4$)alkyl, ($C_1$-$C_4$)haloalkyl, ($C_2$-$C_4$)alkenyl, ($C_2$-$C_4$)alkynyl, ($C_1$-$C_4$)alkoxy, ($C_1$-$C_4$)haloalkoxy or aminothiocarbonyl;

or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

n is the number 0 or 1.

Preferably, the substructure of the formula (I-C) is the substructure

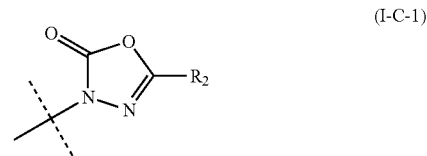

(I-C-1)

where $R^2$ is hydrogen; or is ($C_1$-$C_6$)alkyl, ($C_3$-$C_6$)cycloalkyl($C_1$-$C_6$)alkyl, ($C_2$-$C_6$)alkenyl, ($C_2$-$C_6$)alkynyl, halo($C_1$-$C_6$)alkyl, ($C_1$-$C_6$)alkoxy($C_1$-$C_6$)alkyl or phenyl($C_1$-$C_3$)alkyl, where the aforementioned radicals may each optionally be substituted; or is ($C_3$-$C_6$)cycloalkyl, ($C_3$-$C_6$)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo($C_1$-$C_3$)alkylsulphanyl or optionally methyl-, fluorine-, chlorine-, cyano-substituted cyclopropyl;

W is hydrogen or halogen, especially F or Cl;

X and Y are each independently hydrogen, fluorine, chlorine, bromine, methyl, ethyl, trifluoromethyl, 2,2-difluoromethoxy, difluoromethoxy, trifluoromethoxy, cyclopropyl, cyano, amino, hydroxyl or nitro;

Z is hydrogen; and n is the number 0 or 1.

In this case, it is particularly preferable when $R^2$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl or phenyl;

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN, F), (CN,H), (MeO,F), (MeO,H), (Cl,H), (Br,H), (Br,F), (F,F), ($CF_3$,H);

Z is hydrogen; and n is the number 0 or 1.

In this context, it is very particularly preferable when
R² is CF₃;
W is fluorine;
X is fluorine;
Y is cyano and methyl;
X and Y are especially the following (Y,X) combinations: (CN,F), (Me,F);
Z is hydrogen; and
n is the number 0 or 1.

If the substructure of the formula (I-C) is the substructure formula (I-C-1), it is likewise preferable that
R² is hydrogen; or
is (C₁-C₆)alkyl, (C₃-C₆)cycloalkyl(C₁-C₆)alkyl, (C₂-C₆)alkenyl, (C₂-C₆)alkynyl, halo(C₁-C₆)alkyl, cyano(C₁-C₆)alkyl, (C₁-C₆)alkoxy(C₁-C₆)alkyl or phenyl(C₁-C₃)alkyl, where the aforementioned radicals may each optionally be substituted; or
is (C₃-C₆)cycloalkyl, (C₃-C₆)cycloalkenyl, phenyl, pyridyl, pyrimidyl, pyridazinyl, pyrazinyl, furyl, thienyl, triazinyl, thiazolyl, thiadiazolyl, oxazolyl, oxadiazolyl, pyrazolyl or triazolyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo(C₁-C₃)alkylsulphanyl or optionally methyl-, fluorine-, chlorine-, cyano-substituted cyclopropyl;
W is hydrogen or halogen, especially F or Cl;
X and Y are each independently hydrogen, fluorine, chlorine, bromine, methyl, ethyl, trifluoromethyl, 2,2-difluoromethyl, methoxy, difluoromethoxy, trifluoromethoxy, cyclopropyl, cyano, amino, hydroxyl or nitro;
Z is hydrogen; and
n is the number 0 or 1.

In this case, it is particularly preferable when
R² is hydrogen, methyl, ethyl, n-propyl, CH(CH₃)₂, n-butyl, sec-butyl, C(CH₃)₃, CH₂C(CH₃)₃, CH₂CH(CH₃)₂, CH=CH₂, CH=CHCH₃, CH₂CH=CH₂, CH₂CCH, cyclopropylmethyl, CF₃, CH₂CF₃, CH₂CHF₂, CH₂CH₂CH₂Cl, CH₂CN, CH₂OCH₃, CH₂OCH₂CH₃, CH₂CH₂OCH₃, benzyl, cyclopropyl, cyclobutyl, phenyl, 3-fluorophenyl, 4-chlorophenyl, 4-methoxyphenyl, 4-nitrophenyl, 2-thienyl, 2-furyl or 4-pyridyl;
W is hydrogen or fluorine;
X is hydrogen, chlorine, fluorine or methyl;
Y is fluorine, chlorine, bromine, cyano, methyl, methoxy or trifluoromethyl; where
X and Y are especially the following (Y,X) combinations: (Me,F), (Me,H), (Me,Cl), (Me,Me), (Cl,Cl), (Cl,F), (CN, F), (CN,H), (MeO,F), (MeO,H), (Cl,H), (Br,H), (Br,F), (F,F), (CF₃,H);
Z is hydrogen; and
n is the number 0 or 1.

In this context, it is very particularly preferable when
R² is hydrogen, methyl, ethyl, n-propyl, CH(CH₃)₂, n-butyl, C(CH₃)₃, CH₂OCH₃, CH₂OCH₂CH₃, CH₂CH₂CH₂Cl, benzyl, cyclopropyl, phenyl, 3-fluorophenyl, 4-chlorophenyl, 4-methoxyphenyl, 4-nitrophenyl, 2-thienyl, 2-furyl, 4-pyridyl or CF₃;
W is fluorine;
X is fluorine or methyl;
Y is cyano or methyl;
especially where X and Y are the following (Y,X) combinations: (CN,F), (Me,F), (Me,Me);
Z is hydrogen; and
n is the number 0 or 1.

Fourth Embodiment (I-D):
In a fourth embodiment of the present invention, the inventive compounds have a structure of the general formula (I) in which
A and B together with the atoms to which they are bonded are a substructure of the formula (I-D)

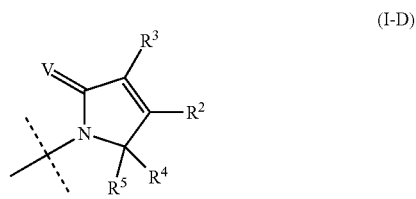

(I-D)

where
R², R³, R⁴, and R⁵ each independently
are hydrogen, cyano, halogen or nitro; or
are (C₁-C₆)alkyl, (C₃-C₆)cycloalkyl(C₁-C₆)alkyl, halo(C₁-C₆)alkyl, cyano(C₁-C₆)alkyl, hydroxy(C₁-C₆)alkyl, (C₁-C₆)alkoxy(C₁-C₆)alkyl, amino(C₁-C₆)alkyl, (C₁-C₆)alkoxycarbonyl(C₁-C₆)alkyl, (C₁-C₆)alkylsulphanyl(C₁-C₆)alkyl, (C₁-C₆)alkylsulphinyl(C₁-C₆)alkyl, (C₁-C₆)alkylsulphonyl(C₁-C₆)alkyl, halo(C₁-C₆)alkylsulphanyl(C₁-C₆)alkyl, halo(C₁-C₆)alkylsulphinyl(C₁-C₆)alkyl, halo(C₁-C₆)alkylsulphonyl(C₁-C₆)alkyl, (C₁-C₆)alkoxy(C₁-C₆)alkylsulphanyl(C₁-C₆)alkyl, (C₁-C₆)alkoxy(C₁-C₆)alkylsulphinyl(C₁-C₆)alkyl, (C₁-C₆)alkoxy(C₁-C₆)alkylsulphonyl(C₁-C₆)alkyl, phenyl(C₁-C₆)alkyl, phenoxy(C₁-C₆)alkyl, phenylsulphanyl(C₁-C₆)alkyl, phenylsulphinyl(C₁-C₆)alkyl, phenylsulphonyl(C₁-C₆)alkyl, hetaryl(C₁-C₆)alkyl, hetaryloxy(C₁-C₆)alkyl, hetarylthio(C₁-C₆)alkyl, where the aforementioned radicals may each optionally be substituted and/or, under the condition that, in the case of an unsaturated radical, the defined minimum number of carbon atoms is 2, the radicals may be saturated or unsaturated; or
are optionally substituted saturated or unsaturated (C₃-C₆)cycloalkyl which may optionally be interrupted by one or more heteroatoms; or
are (C₁-C₆)alkylcarbonyl, halo(C₁-C₆)alkylcarbonyl, hydroxy(C₁-C₆)alkylcarbonyl, (C₁-C₆)alkoxy(C₁-C₆)alkylcarbonyl, phenylcarbonyl, hetarylcarbonyl, (C₁-C₆)alkoxycarbonyl, halo(C₁-C₆)alkoxycarbonyl, aryloxycarbonyl, aminocarbonyl, (C₁-C₆)alkylaminocarbonyl, di(C₁-C₆)alkylaminocarbonyl, (C₃-C₆)cycloalkylaminocarbonyl, di(C₃-C₆)cycloalkylaminocarbonyl, (C₃-C₆)cycloalkyl((C₁-C₆)alkyl)aminocarbonyl, arylaminocarbonyl, diarylaminocarbonyl, (C₁-C₆)alkyl(aryl)aminocarbonyl, (C₃-C₆)cycloalkyl(aryl)aminocarbonyl, (C₁-C₆)alkylaminothiocarbonyl, di(C₁-C₆)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or are carbonyl or carboxyl; or
are optionally substituted phenyl or optionally substituted hetaryl; or
are (C₁-C₆)alkoxy, halo(C₁-C₆)alkoxy, (C₁-C₆)alkoxy(C₁-C₆)alkoxy, aryloxy, aryl(C₁-C₆)alkyloxy, (C₃-C₆)cycloalkyloxy, (C₃-C₆)cycloalkyl(C₁-C₆)alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or are hydroxyl; or are $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or are amino; or are $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or are sulphanyl; or $R^4$ and $R^5$ together with the atom to which they are bonded may form an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N; or $R^2$ is an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

W is hydrogen or halogen;

V is oxygen, sulphur or an optionally substituted nitrogen;

W is hydrogen or halogen;

X, Y and Z, each independently
  are hydrogen, halogen, hydroxyl, amino, cyano, nitro, OCN, SCN, $SF_5$; or
  are tri$(C_1-C_6)$alkylsilyl, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxycarbonyl$(C_1-C_6)$alkyl, $(C_1-C_6)$alkoxy$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, $(C_1-C_6)$alkoxy, halo$(C_1-C_6)$alkoxy, cyano$(C_1-C_6)$alkoxy, hydroxycarbonyl$(C_1-C_6)$alkoxy, $(C_1-C_6)$alkoxycarbonyl$(C_1-C_6)$alkoxy, $(C_1-C_6)$alkoxy$(C_1-C_6)$alkoxy, $(C_1-C_6)$alkylhydroxyimino, $(C_1-C_6)$alkoxyimino, $(C_1-C_6)$alkyl$(C_1-C_6)$alkoxyimino, halo$(C_1-C_6)$alkyl$(C_1-C_6)$alkoxyimino, $(C_1-C_6)$alkylthio, halo$(C_1-C_6)$alkylthio, $(C_1-C_6)$alkoxy$(C_1-C_6)$alkylthio, $(C_1-C_6)$alkylthio$(C_1-C_6)$alkyl, $(C_1-C_6)$alkylsulphinyl, halo$(C_1-C_6)$alkylsulphinyl, $(C_1-C_6)$alkoxy$(C_1-C_6)$alkylsulphinyl, $(C_1-C_6)$alkylsulphinyl$(C_1-C_6)$alkyl, $(C_1-C_6)$alkylsulphonyl, halo$(C_1-C_6)$alkylsulphonyl, $(C_1-C_6)$alkoxy$(C_1-C_6)$alkylsulphonyl, $(C_1-C_6)$alkylsulphonyl$(C_1-C_6)$alkyl, $(C_1-C_6)$alkylsulphonyloxy, $(C_1-C_6)$alkylcarbonyl, halo$(C_1-C_6)$alkylcarbonyl, carboxyl, $(C_1-C_6)$alkylcarbonyloxy, $(C_1-C_6)$alkoxycarbonyl, halo$(C_1-C_6)$alkoxycarbonyl, aminocarbonyl, $(C_1-C_6)$alkylaminocarbonyl, $C_6)$alkylaminocarbonyl, $(C_2-C_6)$alkenylaminocarbonyl, di$(C_2-C_6)$alkenylaminocarbonyl, $(C_3-C_6)$cycloalkylaminocarbonyl, $(C_1-C_6)$alkylsulphonylamino, aminosulphonyl, $(C_1-C_6)$alkylaminosulphonyl, di$(C_1-C_6)$alkylaminosulphonyl, $(C_1-C_6)$alkylsulphoximino, aminothiocarbonyl, $(C_1-C_6)$alkylaminothiocarbonyl or di$(C_1-C_6)$alkylaminothiocarbonyl, where all the aforementioned radicals may optionally be substituted by halogen; or are phenyl$(C_1-C_3)$alkyl, phenoxy, phenyl$(C_1-C_3)$alkyloxy, phenoxy$(C_1-C_3)$alkyl, phenylthio, phenylthio$(C_1-C_3)$alkyl, phenylsulphinyl, phenylsulphonyl, hetaryl$(C_1-C_3)$alkyl, hetaryloxy, hetaryl$(C_1-C_3)$alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are $(C_3-C_6)$cycloalkyl$(C_1-C_3)$alkyl, $(C_3-C_6)$cycloalkyloxy, $(C_3-C_6)$cycloalkyl$(C_1-C_3)$alkoxy, $(C_3-C_6)$cycloalkylthio, $(C_3-C_6)$cycloalkyl$(C_1-C_3)$alkylthio, $(C_3-C_6)$cycloalkylsulphinyl, $(C_3-C_6)$cycloalkyl$(C_1-C_3)$alkylsulphinyl, $(C_3-C_6)$cycloalkylsulphonyl, $(C_3-C_6)$cycloalkyl$(C_1-C_3)$alkylsulphonyl or $(C_3-C_8)$cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"
  where R' and R" each independently
    are hydrogen, cyano, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, $(C_1-C_6)$alkylthio$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, acyl or $(C_1-C_6)$alkoxycarbonyl; or
  R' and R" together with the nitrogen atom to which they are bonded may form an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a $(C_3\text{-}C_6)$cycloalkyl, oxetanyl, oxolanyl, oxanyl, $(C_3\text{-}C_8)$cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

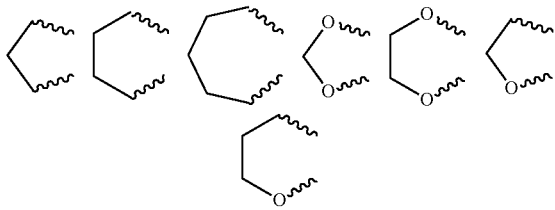

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

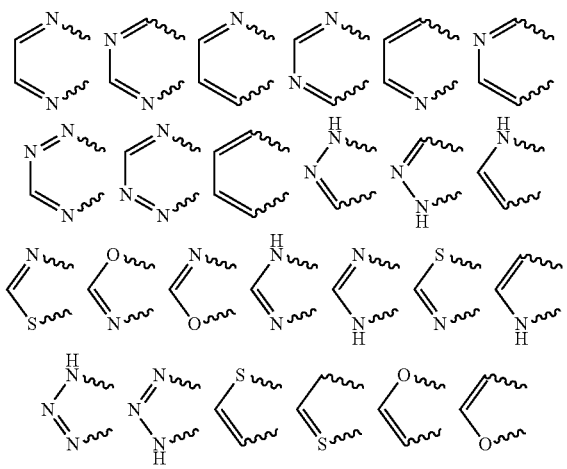

n is the number 0 or 1.

At the same time, it is preferable that $R^2$, $R^3$, $R^4$ and $R^5$, each independently, are hydrogen, cyano, halogen or nitro; or are $(C_1\text{-}C_6)$alkyl, $(C_3\text{-}C_6)$cycloalkyl$(C_1\text{-}C_6)$alkyl, halo$(C_1\text{-}C_6)$alkyl, cyano$(C_1\text{-}C_6)$alkyl, $(C_1\text{-}C_6)$alkoxy$(C_1\text{-}C_6)$alkyl, $(C_1\text{-}C_6)$alkoxycarbonyl$(C_1\text{-}C_6)$alkyl, $(C_1\text{-}C_6)$alkylsulphanyl$(C_1\text{-}C_6)$alkyl, $(C_1\text{-}C_6)$alkylsulphinyl$(C_1\text{-}C_6)$alkyl, phenyl$(C_1\text{-}C_6)$alkyl, hetaryl$(C_1\text{-}C_6)$alkyl, $(C_2\text{-}C_6)$alkenyl, halo$(C_2\text{-}C_6)$alkenyl, $(C_3\text{-}C_6)$cycloalkenyl$(C_1\text{-}C_6)$alkyl, $(C_2\text{-}C_6)$alkynyl, where the aforementioned radicals may each optionally be substituted; or are optionally substituted $(C_3\text{-}C_6)$cycloalkyl, $(C_3\text{-}C_6)$cycloalkenyl, which may optionally be interrupted by one or more heteroatoms from the group of O, S and N; or are $(C_1\text{-}C_6)$alkylcarbonyl, halo$(C_1\text{-}C_6)$alkylcarbonyl, $(C_1\text{-}C_6)$alkoxy$(C_1\text{-}C_6)$alkylcarbonyl, $(C_1\text{-}C_6)$alkoxycarbonyl, halo$(C_1\text{-}C_6)$alkoxycarbonyl, aminocarbonyl, $(C_1\text{-}C_6)$alkylaminocarbonyl, di$(C_1\text{-}C_6)$alkylaminocarbonyl, $(C_3\text{-}C_6)$cycloalkylaminocarbonyl, $(C_1\text{-}C_6)$alkylaminothiocarbonyl, di$(C_1\text{-}C_6)$alkylaminothiocarbonyl, $(C_2\text{-}C_6)$alkenylcarbonyl, $(C_3\text{-}C_6)$cycloalkenyl$(C_1\text{-}C_6)$alkylcarbonyl, $(C_2\text{-}C_6)$alkynylcarbonyl or aminothiocarbonyl, where the aforementioned radicals may each optionally be substituted, or are carbonyl or carboxyl; or are a phenyl or hetaryl ring which is optionally mono- or polysubstituted identically or differently by halogen, cyano, nitro, hydroxyl, amino, $(C_1\text{-}C_6)$alkyl, halo$(C_1\text{-}C_6)$alkyl, $(C_1\text{-}C_6)$alkoxy, halo$(C_1\text{-}C_6)$alkoxy, $(C_1\text{-}C_6)$alkylsulphinyl, $(C_1\text{-}C_6)$alkylsulphanyl, $(C_1\text{-}C_6)$alkylsulphonyl, halo$(C_1\text{-}C_6)$alkylsulphinyl, halo$(C_1\text{-}C_6)$alkylsulphanyl, halo$(C_1\text{-}C_6)$alkylsulphonyl or optionally substituted $(C_3\text{-}C_6)$cycloalkyl; or are $(C_1\text{-}C_6)$alkoxy, halo$(C_1\text{-}C_6)$alkoxy, $(C_1\text{-}C_6)$alkoxy$(C_1\text{-}C_6)$alkoxy, $(C_3\text{-}C_6)$cycloalkyloxy, $(C_3\text{-}C_6)$cycloalkyl$(C_1\text{-}C_6)$alkyloxy, $(C_2\text{-}C_6)$alkenyloxy, $(C_3\text{-}C_6)$cycloalkenyl$(C_1\text{-}C_6)$alkoxy, $(C_2\text{-}C_6)$alkynyloxy or carbonyloxy, where the aforementioned radicals may each optionally be substituted, or are hydroxyl; or are $(C_1\text{-}C_6)$alkylamino, halo$(C_1\text{-}C_6)$alkylamino, dihalo$(C_1\text{-}C_6)$alkylamino, di$(C_1\text{-}C_6)$alkylamino, $(C_3\text{-}C_6)$cycloalkylamino, di$(C_3\text{-}C_6)$cycloalkylamino, $(C_1\text{-}C_6)$alkylcarbonylamino, $(C_1\text{-}C_6)$alkoxycarbonylamino, $(C_1\text{-}C_6)$alkylcarbamoylamino, $(C_1\text{-}C_6)$alkylsulphonylamino, $(C_2\text{-}C_6)$alkenylamino, $(C_3\text{-}C_6)$cycloalkenyl$(C_1\text{-}C_6)$alkylamino, $(C_2\text{-}C_6)$alkynylamino, where the aforementioned radicals may each optionally be substituted, or are amino; or are $(C_1\text{-}C_6)$alkylsulphanyl, $(C_1\text{-}C_6)$alkylsulphinyl, $(C_1\text{-}C_6)$alkylsulphonyl, halo$(C_1\text{-}C_6)$alkylsulphanyl, halo$(C_1\text{-}C_6)$alkylsulphinyl, halo$(C_1\text{-}C_6)$alkylsulphanyl, $(C_3\text{-}C_6)$cycloalkyl$(C_1\text{-}C_6)$alkylsulphanyl, $(C_3\text{-}C_6)$cycloalkyl$(C_1\text{-}C_6)$alkylsulphinyl, $(C_3\text{-}C_6)$cycloalkyl$(C_1\text{-}C_6)$alkylsulphonyl, aminosulphonyl, $(C_1\text{-}C_6)$alkylaminosulphonyl, di$(C_1\text{-}C_6)$alkylaminosulphonyl or arylaminosulphonyl, where the aforementioned radicals may each optionally be substituted, or are sulphanyl; or $R^4$ and $R^5$ together with the atom to which they are bonded may form an optionally singly or multiply, identically or differently halogen-, cyano-, nitro-, hydroxyl-, amino-, $(C_1\text{-}C_6)$alkyl-, halo$(C_1\text{-}C_6)$alkyl-, $(C_1\text{-}C_6)$alkoxy-, halo$(C_1\text{-}C_6)$alkoxy-, $(C_1\text{-}C_6)$alkylsulphinyl-, $(C_1\text{-}C_6)$alkylsulphanyl-, $(C_1\text{-}C_6)$alkylsulphonyl-, halo$(C_1\text{-}C_6)$alkylsulphinyl-, halo$(C_1\text{-}C_6)$alkylsulphanyl-, halo$(C_1\text{-}C_6)$alkylsulphonyl- or optionally substituted $(C_3\text{-}C_6)$cycloalkyl-substituted, saturated or unsaturated three- to six-membered ring optionally interrupted by heteroatoms from the group of O, S and N; or
are an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated three- to six-membered ring optionally interrupted by heteroatoms from the group of O, S and N;

W is hydrogen or halogen, especially fluorine and chlorine;
V is oxygen, sulphur or an optionally substituted nitrogen;
X, Y and Z are each independently hydrogen, fluorine, chlorine, bromine, cyano, nitro, amino, hydroxyl, $(C_1-C_4)$ alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;
or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
n is the number 0 or 1.

Preferably, the substructure of the formula (I-D) is a substructure which is selected from the group consisting of

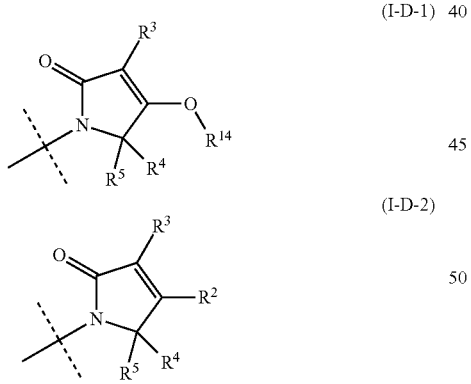

(I-D-1)

(I-D-2)

where
$R^2$, $R^3$, $R^4$ and $R^5$ each independently
are hydrogen; or
are $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
are $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo $(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
are carboxyl; or
$R^4$ and $R^5$ together with the atom to which they are bonded may form an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

$R^{14}$ is $(C_1-C_6)$alkyl, halo$(C_1-C_6)$alkyl, cyano$(C_1-C_6)$alkyl, $(C_1-C_6)$alkoxy$(C_1-C_3)$alkyl, phenyl$(C_1-C_3)$alkyl, $(C_3-C_6)$ cycloalkyl or $(C_3-C_6)$cycloalkyl$(C_1-C_3)$alkyl, where the aforementioned radicals may each be mono- to trisubstituted by halogen, cyano, nitro, hydroxyl, amino, $(C_1-C_6)$ alkyl, halo$(C_1-C_6)$alkyl, $(C_1-C_6)$alkoxy, halo$(C_1-C_6)$ alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo $(C_1-C_6)$alkylsulphanyl, halo$(C_1-C_6)$alkylsulphonyl or optionally methyl-, fluorine-, chlorine-, cyano-substituted cyclopropyl;

X, Y and Z are each independently hydrogen, fluorine, chlorine, bromine, cyano, nitro, amino, hydroxyl, $(C_1-C_4)$ alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;
or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
n is the number 0 or 1.

More preferably, the substructure is of the substructure formula (I-D-1).

If the substructure of the formula (I-D) is the substructure formula (I-D-1), it is preferable that $R^3$, $R^4$ and $R^5$ are each independently hydrogen; or are (C$_1$-C$_6$)alkyl, (C$_3$-C$_6$)cycloalkyl(C$_1$-C$_6$)alkyl, (C$_2$-C$_6$)alkenyl, (C$_2$-C$_6$)alkynyl, halo(C$_1$-C$_6$)alkyl, cyano(C$_1$-C$_6$)alkyl, (C$_1$-C$_6$)alkoxy(C$_1$-C$_6$)alkyl or phenyl(C$_1$-C$_3$)alkyl, where the aforementioned radicals may each optionally be substituted; or are (C$_3$-C$_6$)cycloalkyl, (C$_3$-C$_6$)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo(C$_1$-C$_3$)alkylsulphanyl or optionally methyl-, fluorine-, chlorine-, cyano-substituted cyclopropyl; or R$^4$ and R$^5$ together with the atom to which they are bonded may form an optionally singly or multiply, identically or differently halogen-, cyano-, nitro-, hydroxyl-, amino-, methyl-, ethyl-, trifluoromethyl-, difluoromethyl-, trifluoroethyl-, difluoroethyl-, trifluoromethoxy-, difluoromethoxy- or optionally halogen-, cyano-, methyl- or cyclopropyl-substituted cyclopropyl-substituted cyclopropyl, cyclobutyl, cyclopentyl or cyclohexyl ring;

R$^{14}$ is (C$_1$-C$_6$)alkyl, halo(C$_1$-C$_6$)alkyl, cyano(C$_1$-C$_6$)alkyl, (C$_1$-C$_6$)alkoxy(C$_1$-C$_3$)alkyl, phenyl(C$_1$-C$_3$)alkyl, (C$_3$-C$_6$)cycloalkyl or (C$_3$-C$_6$)cycloalkyl(C$_1$-C$_3$)alkyl, where the aforementioned radicals may each be mono- to trisubstituted by halogen, cyano, nitro, hydroxyl, amino, (C$_1$-C$_6$)alkyl, halo(C$_1$-C$_6$)alkyl, (C$_1$-C$_6$)alkoxy, halo(C$_1$-C$_6$)alkoxy, (C$_1$-C$_6$)alkylsulphinyl, (C$_1$-C$_6$)alkylsulphanyl, (C$_1$-C$_6$)alkylsulphonyl, halo(C$_1$-C$_6$)alkylsulphinyl, halo(C$_1$-C$_6$)alkylsulphanyl, halo(C$_1$-C$_6$)alkylsulphonyl or optionally methyl-, fluorine-, chlorine-, cyano-substituted cyclopropyl;

W is hydrogen or halogen, especially F and Cl;

X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z is hydrogen; and n is the number 0 or 1.

In this context, it is particularly preferable that

R$^3$, R$^4$ and R$^5$ are each independently hydrogen, methyl, ethyl, benzyl, cyclopropyl, phenyl; or R$^4$ and R$^5$ together with the atom to which they are bonded may form a cyclopropyl ring;

R$^{14}$ is methyl, ethyl, n-propyl, CH(CH$_3$)$_2$, n-butyl, sec-butyl, C(CH$_3$)$_3$, CH$_2$C(CH$_3$)$_3$, CH$_2$CH(CH$_3$)$_2$, cyclopropylmethyl, CH$_2$CH$_2$OCH$_3$, CH$_2$CH$_2$OCH$_2$CH$_3$, benzyl, cyclopropyl, cyclobutyl or cyclopentyl;

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN, F), (CN,H), (MeO,F), (MeO,H), (Cl,H), (Br,H), (Br,F), (F,F), (CF$_3$,H);

Z is hydrogen; and n is the number 0 or 1.

In this context, it is very particularly preferable when

R$^3$ is hydrogen;

R$^4$ is hydrogen;

R$^5$ is hydrogen;

R$^{14}$ is cyclopentyl, CH$_2$-cyclopropyl, methyl, ethyl, CH$_2$CH$_2$OCH$_3$, CH$_2$CH$_2$CH$_3$, CH$_2$CH$_2$CH$_2$CH$_3$, CH(CH$_3$)$_2$ or benzyl;

W is fluorine;

X is hydrogen, fluorine, chlorine or methyl;

Y is cyano, chlorine, CF$_3$ or CH$_3$; where

X and Y are especially the following (Y,X) combinations: (CN,F), (Me,F), (Me,H), (Me,Cl), (Me,Me), (Cl,H), (Cl,Cl), (Cl,F), (CF$_3$,H);

Z is hydrogen; and n is the number 0 or 1.

Fifth Embodiment (I-E):

In a fifth embodiment of the present invention, the inventive compounds have a structure of the general formula (I) in which A and B together with the atoms to which they are bonded are a substructure of the formula (I-E)

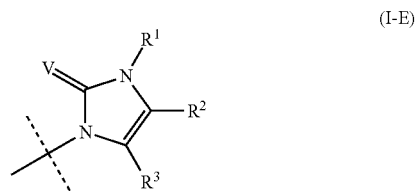

(I-E)

R$^1$ is hydrogen, cyano or nitro; or is (C$_1$-C$_6$)alkyl, (C$_3$-C$_6$)cycloalkyl(C$_1$-C$_6$)alkyl, halo(C$_2$-C$_6$)alkyl, cyano(C$_1$-C$_6$)alkyl, hydroxy(C$_1$-C$_6$)alkyl, (C$_1$-C$_6$)alkoxy(C$_1$-C$_6$)alkyl, amino(C$_1$-C$_6$)alkyl, (C$_1$-C$_6$)alkoxycarbonyl(C$_1$-C$_6$)alkyl, (C$_1$-C$_6$)alkylsulphanyl(C$_1$-C$_6$)alkyl, (C$_1$-C$_6$)alkylsulphinyl(C$_1$-C$_6$)alkyl, (C$_1$-C$_6$)alkylsulphonyl(C$_1$-C$_6$)alkyl, halo(C$_1$-C$_6$)alkylsulphanyl(C$_1$-C$_6$)alkyl, halo(C$_1$-C$_6$)alkylsulphinyl(C$_1$-C$_6$)alkyl, halo(C$_1$-C$_6$)alkylsulphonyl(C$_1$-C$_6$)alkyl, (C$_1$-C$_6$)alkoxy(C$_1$-C$_6$)alkylsulphanyl(C$_1$-C$_6$)alkyl, (C$_1$-C$_6$)alkoxy(C$_1$-C$_6$)alkylsulphinyl(C$_1$-C$_6$)alkyl, (C$_1$-C$_6$)alkoxy(C$_1$-C$_6$)alkylsulphonyl(C$_1$-C$_6$)alkyl, phenyl(C phenoxy(C$_1$-C$_6$)alkyl, phenylsulphanyl(C$_1$-C$_6$)alkyl, phenylsulphinyl(C$_1$-C$_6$)alkyl, phenylsulphonyl(C$_1$-C$_6$)alkyl, hetaryl(C$_1$-C$_6$)alkyl, hetaryloxy(C$_1$-C$_6$)alkyl, hetarylsulphanyl(C$_1$-C$_6$)alkyl, hetarylsulphinyl(C$_1$-C$_6$)alkyl, hetarylsulphonyl(C$_1$-C$_6$)alkyl, where the aforementioned radicals may each optionally be substituted and/or, under the condition that, in the case of an unsaturated radical, the defined minimum number of carbon atoms is 2, the radicals may be saturated or unsaturated; or is optionally substituted saturated or unsaturated (C$_3$-C$_6$)cycloalkyl which may optionally be interrupted by one or more heteroatoms; or is (C$_1$-C$_6$)alkylcarbonyl, halo(C$_1$-C$_6$)alkylcarbonyl, hydroxy(C$_1$-C$_6$)alkylcarbonyl, (C$_1$-C$_6$)alkoxy(C$_1$-C$_6$)alkylcarbonyl, phenylcarbonyl, hetarylcarbonyl, (C$_1$-C$_6$)alkoxycarbonyl, halo(C$_1$-C$_6$)alkoxycarbonyl, aryloxycarbonyl, aminocarbonyl, (C$_1$-C$_6$)alkylaminocarbonyl, di(C$_1$-C$_6$)alkylaminocarbonyl, (C$_3$-C$_6$)cycloalkylaminocarbonyl, di(C$_3$-C$_6$)cycloalkylaminocarbonyl, (C$_3$-C$_6$)cycloalkyl((C$_1$-C$_6$)alkyl)aminocarbonyl, arylaminocarbonyl, diarylaminocarbonyl, (C$_1$-C$_6$)alkyl(aryl)aminocarbonyl, (C$_3$-C$_6$)cycloalkyl(aryl)aminocarbonyl, (C$_1$-C$_6$)alkylaminothiocarbonyl, di(C$_1$-C$_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or is optionally substituted phenyl or optionally substituted hetaryl; or is $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or is hydroxyl; or is $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or is $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; and $R^2$ and $R^3$ independently are hydrogen, cyano, halogen or nitro; or are $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylthio$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or are optionally substituted saturated or unsaturated $(C_3-C_6)$cycloalkyl which may optionally be interrupted by one or more heteroatoms; or are $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or are carbonyl or carboxyl; or are optionally substituted phenyl or optionally substituted hetaryl; or are $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or are hydroxyl; or are $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or are amino; or are $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or are sulphanyl; or are an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

W is hydrogen or halogen;

V is oxygen, sulphur or an optionally substituted nitrogen;

X, Y and Z, each independently
- are hydrogen, halogen, hydroxyl, amino, cyano, nitro, OCN, SCN, $SF_5$; or
- are tri($C_1$-$C_6$)alkylsilyl, ($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxycarbonyl($C_1$-$C_6$)alkyl, ($C_1$-$C_6$)alkoxy($C_1$-$C_6$)alkyl, ($C_2$-$C_6$)alkenyl, halo($C_2$-$C_6$)alkenyl, cyano($C_2$-$C_6$)alkenyl, ($C_2$-$C_6$)alkynyl, halo($C_2$-$C_6$)alkynyl, cyano($C_2$-$C_6$)alkynyl, ($C_1$-$C_6$)alkoxy, halo($C_1$-$C_6$)alkoxy, cyano($C_1$-$C_6$)alkoxy, hydroxycarbonyl($C_1$-$C_6$)alkoxy, ($C_1$-$C_6$)alkoxycarbonyl($C_1$-$C_6$)alkoxy, ($C_1$-$C_6$)alkoxy($C_1$-$C_6$)alkoxy, ($C_1$-$C_6$)alkylhydroxyimino, ($C_1$-$C_6$)alkoxyimino, ($C_1$-$C_6$)alkyl($C_1$-$C_6$)alkoxyimino, halo($C_1$-$C_6$)alkyl($C_1$-$C_6$)alkoxyimino, ($C_1$-$C_6$)alkylthio, halo($C_1$-$C_6$)alkylthio, ($C_1$-$C_6$)alkoxy($C_1$-$C_6$)alkylthio, ($C_1$-$C_6$)alkylthio($C_1$-$C_6$)alkyl, ($C_1$-$C_6$)alkylsulphinyl, halo($C_1$-$C_6$)alkylsulphinyl, ($C_1$-$C_6$)alkoxy($C_1$-$C_6$)alkylsulphinyl, ($C_1$-$C_6$)alkylsulphinyl($C_1$-$C_6$)alkyl, ($C_1$-$C_6$)alkylsulphonyl, halo($C_1$-$C_6$)alkylsulphonyl, ($C_1$-$C_6$)alkoxy($C_1$-$C_6$)alkylsulphonyl, ($C_1$-$C_6$)alkylsulphonyl($C_1$-$C_6$)alkyl, ($C_1$-$C_6$)alkylsulphonyloxy, ($C_1$-$C_6$)alkylcarbonyl, halo($C_1$-$C_6$)alkylcarbonyl, carboxyl, ($C_1$-$C_6$)alkylcarbonyloxy, ($C_1$-$C_6$)alkoxycarbonyl, halo ($C_1$-$C_6$)alkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_6$)cycloalkylaminocarbonyl, ($C_1$-$C_6$)alkylsulphonylamino, aminosulphonyl, ($C_1$-$C_6$)alkylaminosulphonyl, di($C_1$-$C_6$)alkylaminosulphonyl, ($C_1$-$C_6$)alkylsulphoximino, aminothiocarbonyl, ($C_1$-$C_6$)alkylaminothiocarbonyl or di($C_1$-$C_6$)alkylaminothiocarbonyl, where all the aforementioned radicals may optionally be substituted by halogen; or
- are phenyl($C_1$-$C_3$)alkyl, phenoxy, phenyl($C_1$-$C_3$)alkyloxy, phenoxy($C_1$-$C_3$)alkyl, phenylthio, phenylthio($C_1$-$C_3$)alkyl, phenylsulphinyl, phenylsulphonyl, hetaryl ($C_1$-$C_3$)alkyl, hetaryloxy, hetaryl($C_1$-$C_3$)alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or
- are ($C_3$-$C_6$)cycloalkyl($C_1$-$C_3$)alkyl, ($C_3$-$C_6$)cycloalkyloxy, ($C_3$-$C_6$)cycloalkyl($C_1$-$C_3$)alkoxy, ($C_3$-$C_6$)cycloalkylthio, ($C_3$-$C_6$)cycloalkyl($C_1$-$C_3$)alkylthio, ($C_3$-$C_6$)cycloalkylsulphinyl, ($C_3$-$C_6$)cycloalkyl($C_1$-$C_3$)alkylsulphinyl, ($C_3$-$C_6$)cycloalkylsulphonyl, ($C_3$-$C_6$)cycloalkyl($C_1$-$C_3$)alkylsulphonyl or ($C_3$-$C_8$)cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or
- are NR'R"
    - where R' and R" each independently
        - are hydrogen, cyano, ($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, ($C_1$-$C_6$)alkylthio($C_1$-$C_6$)alkyl, ($C_2$-$C_6$)alkenyl, halo($C_2$-$C_6$)alkenyl, cyano($C_2$-$C_6$)alkenyl, ($C_2$-$C_6$)alkynyl, halo($C_2$-$C_6$)alkynyl, cyano ($C_2$-$C_6$)alkynyl, acyl or ($C_1$-$C_6$)alkoxycarbonyl; or
    - R' and R" together with the nitrogen atom to which they are bonded may form an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or
- are a ($C_3$-$C_6$)cycloalkyl, oxetanyl, oxolanyl, oxanyl, ($C_3$-$C_8$)cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;
- or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

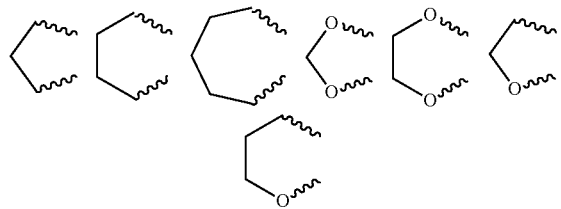

- or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

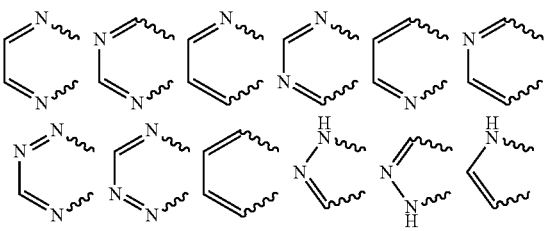

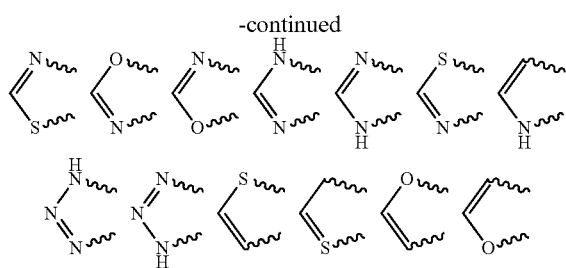

and n is the number 0 or 1.

At the same time, it is preferable that $R^1$ is hydrogen; or is $(C_1-C_6)$alkyl, $(C_3-C_6)$cycloalkyl$(C_1-C_6)$alkyl, halo$(C_2-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may optionally be substituted; or is optionally substituted $(C_3-C_6)$cycloalkyl, $(C_3-C_6)$cycloalkenyl, which may optionally be interrupted by one or more heteroatoms from the group of O, S and N; or is $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or is carbonyl or carboxyl; or is a phenyl or hetaryl ring which is optionally mono- or polysubstituted identically or differently by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally substituted $(C_3-C_6)$cycloalkyl; or is $(C_1-C_6)$alkoxy, halo$(C_1-C_6)$alkoxy, $(C_3-C_6)$cycloalkyloxy, or carbonyloxy, where the aforementioned radicals may each optionally be substituted, or is hydroxyl; or is $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulphonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or is amino; or is $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphanyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted, or is sulphanyl; and $R^2$ and $R^3$ are hydrogen, cyano, halogen or nitro; or are $(C_1-C_6)$alkyl, $(C_3-C_6)$cycloalkyl$(C_1-C_6)$alkyl, halo$(C_1-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may each optionally be substituted; or are optionally substituted $(C_3-C_6)$cycloalkyl, $(C_3-C_6)$cycloalkenyl, which may optionally be interrupted by one or more heteroatoms from the group of O, S and N; or are $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or are carbonyl or carboxyl; or are optionally substituted phenyl or optionally substituted hetaryl; or are a phenyl or hetaryl ring which is optionally mono- or polysubstituted identically or differently by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally substituted $(C_3-C_6)$cycloalkyl; or are $(C_1-C_6)$alkoxy, halo$(C_1-C_6)$alkoxy, $(C_1-C_6)$alkoxy$(C_1-C_6)$alkoxy, $(C_3-C_6)$cycloalkyloxy, $(C_3-C_6)$cycloalkyl$(C_1-C_6)$alkyloxy, $(C_2-C_6)$alkenyloxy, $(C_3-C_6)$cycloalkenyl$(C_1-C_6)$alkoxy, $(C_2-C_6)$alkynyloxy or carbonyloxy, where the aforementioned radicals may each optionally be substituted, or are hydroxyl; or are $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulphonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or are amino; or are $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted, or are sulphanyl; or are an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated three- to six-membered ring optionally interrupted by heteroatoms from the group of O, S and N;

W is hydrogen or halogen, especially fluorine and chlorine;

V is oxygen, sulphur or an optionally substituted nitrogen;

X, Y and Z are each independently hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;

or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

n is the number 0 or 1.

Preferably, the substructure of the formula (I-E) is the substructure

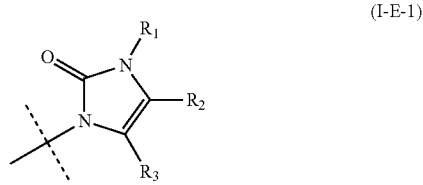

(I-E-1)

where $R^1$ is hydrogen; or is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is $(C_3-C_6)$cycloalkyl, $(C_3-C_6)$cycloalkenyl, oxetanyl, oxolanyl, oxanyl, phenyl, pyrimidyl, pyridazinyl, pyrazinyl, triazinyl, thiazolyl, thiadiazolyl, oxazolyl, oxadiazolyl, pyrazolyl or triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

$R^2$ and $R^3$ each independently are hydrogen; or are $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or are $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

W is hydrogen or halogen, especially fluorine or chlorine;

X, Y and Z are each independently hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;

or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and n is the number 0 or 1.

In this context, it is further preferable that $R^1$ is hydrogen; or is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or is $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;

$R^2$ and $R^3$ each independently are hydrogen; or are $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_1-C_6)$alkyl, $(C_1-C_6)$ alkoxy($C_1$-$C_6$)alkyl or phenyl($C_1$-$C_3$)alkyl, where the aforementioned radicals may each optionally be substituted; or are ($C_3$-$C_6$)cycloalkyl, ($C_3$-$C_6$)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo($C_1$-$C_3$)alkylsulphanyl or optionally methyl-, fluorine-, chlorine-, cyano-substituted cyclopropyl;

W is hydrogen or halogen, especially F or Cl;

X and Y are each independently hydrogen, fluorine, chlorine, bromine, methyl, ethyl, trifluoromethyl, 2,2-difluoromethyl, methoxy, difluoromethoxy, trifluoromethoxy, cyclopropyl, cyano, amino, hydroxyl or nitro;

Z is hydrogen; and n is the number 0 or 1.

In this context, it is particularly preferable when $R^1$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, cyclopropylmethyl, $CH_2CF_3$, $CH_2CHF_2$, $CH_2CN$, $CH_2CH_2OCH_3$, benzyl, cyclopropyl, cyclobutyl or phenyl;

$R^2$ and $R^3$ are each independently hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl or phenyl;

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), ($CF_3$,H);

Z is hydrogen; and n is the number 0 or 1.

In this context, it is very particularly preferable when $R^1$ is ethyl and $C(CH_3)_3$;

$R^2$ and $R^3$ are hydrogen;

W is fluorine;

X is fluorine;

Y is methyl;

Z is hydrogen; and n is the number 0 or 1.

Sixth Embodiment (I-F):

In a sixth embodiment of the present invention, the inventive compounds have a structure of the general formula (I) in which A and B together with the atoms to which they are bonded are a substructure of the formula (I-F)

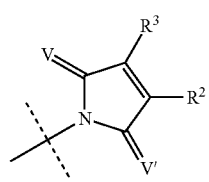

(I-F)

$R^2$ and $R^3$ each independently are hydrogen, cyano, halogen or nitro; or are ($C_1$-$C_6$)alkyl, ($C_3$-$C_6$)cycloalkyl($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylsulphanyl($C_1$-$C_6$)alkyl, ($C_1$-$C_6$)alkylsulphinyl($C_1$-$C_6$)alkyl, ($C_1$-$C_6$)alkylsulphonyl($C_1$-$C_6$)alkyl, halo($C_1$-$C_6$)alkylsulphanyl($C_1$-$C_6$)alkyl, halo($C_1$-$C_6$)alkylsulphinyl($C_1$-$C_6$)alkyl, halo($C_1$-$C_6$)alkylsulphonyl($C_1$-$C_6$)alkyl, ($C_1$-$C_6$)alkoxy($C_1$-$C_6$)alkylsulphanyl($C_1$-$C_6$)alkyl, ($C_1$-$C_6$)alkoxy($C_1$-$C_6$)alkylsulphinyl($C_1$-$C_6$)alkyl, ($C_1$-$C_6$)alkoxy($C_1$-$C_6$)alkylsulphonyl($C_1$-$C_6$)alkyl, phenyl($C_1$-$C_6$)alkyl, phenoxy($C_1$-$C_6$)alkyl, phenylsulphanyl($C_1$-$C_6$)alkyl, phenylsulphinyl($C_1$-$C_6$)alkyl, phenylsulphonyl($C_1$-$C_6$)alkyl, hetaryl($C_1$-$C_6$)alkyl, hetaryloxy($C_1$-$C_6$)alkyl, hetarylthio($C_1$-$C_6$)alkyl, where the aforementioned radicals may each optionally be substituted and/or, under the condition that, in the case of an unsaturated radical, the defined minimum number of carbon atoms is 2, the radicals may be saturated or unsaturated; or are optionally substituted saturated or unsaturated ($C_3$-$C_6$)cycloalkyl which may optionally be interrupted by one or more heteroatoms; or are ($C_1$-$C_6$)alkylcarbonyl, halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, ($C_1$-$C_6$)alkoxycarbonyl, halo($C_1$-$C_6$)alkoxycarbonyl, aryloxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or are carbonyl or carboxyl; or are optionally substituted phenyl or optionally substituted hetaryl; or are ($C_1$-$C_6$)alkoxy, halo($C_1$-$C_6$)alkoxy, ($C_1$-$C_6$)alkoxy($C_1$-$C_6$)alkoxy, aryloxy, aryl($C_1$-$C_6$)alkyloxy, ($C_3$-$C_6$)cycloalkyloxy, ($C_3$-$C_6$)cycloalkyl($C_1$-$C_6$)alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or are hydroxyl; or are ($C_1$-$C_6$)alkylamino, di($C_1$-$C_6$)alkylamino, halo($C_1$-$C_6$)alkylamino, dihalo($C_1$-$C_6$)alkylamino, ($C_3$-$C_6$)cycloalkylamino, di($C_3$-$C_6$)cycloalkylamino, ($C_3$-$C_6$)cycloalkyl(($C_1$-$C_6$)alkyl)amino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or are amino; or are $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or are sulphanyl; or are an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

W is hydrogen or halogen;

V and V' are oxygen, sulphur or an optionally substituted nitrogen;

X, Y and Z each independently are hydrogen, halogen, hydroxyl, amino, cyano, nitro, OCN, SCN, $SF_5$; or are tri$(C_1-C_6)$alkylsilyl, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxycarbonyl$(C_1-C_6)$alkyl, $(C_1-C_6)$alkoxy$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, $(C_1-C_6)$alkoxy, halo$(C_1-C_6)$alkoxy, cyano$(C_1-C_6)$alkoxy, hydroxycarbonyl$(C_1-C_6)$alkoxy, $(C_1-C_6)$alkoxycarbonyl$(C_1-C_6)$alkoxy, $(C_1-C_6)$alkoxy$(C_1-C_6)$alkoxy, $(C_1-C_6)$alkylhydroxyimino, $(C_1-C_6)$alkoxyimino, $(C_1-C_6)$alkyl$(C_1-C_6)$alkoxyimino, halo$(C_1-C_6)$alkyl$(C_1-C_6)$alkoxyimino, $(C_1-C_6)$alkylthio, halo$(C_1-C_6)$alkylthio, $(C_1-C_6)$alkoxy$(C_1-C_6)$alkylthio, $(C_1-C_6)$alkylthio$(C_1-C_6)$alkyl, $(C_1-C_6)$alkylsulphinyl, halo$(C_1-C_6)$alkylsulphinyl, $(C_1-C_6)$alkoxy$(C_1-C_6)$alkylsulphinyl, $(C_1-C_6)$alkylsulphinyl$(C_1-C_6)$alkyl, $(C_1-C_6)$alkylsulphonyl, halo$(C_1-C_6)$alkylsulphonyl, $(C_1-C_6)$alkoxy$(C_1-C_6)$alkylsulphonyl, $(C_1-C_6)$alkylsulphonyl$(C_1-C_6)$alkyl, $(C_1-C_6)$alkylsulphonyloxy, $(C_1-C_6)$alkylcarbonyl, halo$(C_1-C_6)$alkylcarbonyl, carboxyl, $(C_1-C_6)$alkylcarbonyloxy, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_2-C_6)$alkenylaminocarbonyl, di$(C_2-C_6)$alkenylaminocarbonyl, $(C_3-C_6)$cyclo$(C_1-C_6)$alkylaminocarbonyl, $(C_1-C_6)$alkylsulphonylamino, aminosulphonyl, $(C_1-C_6)$alkylaminosulphonyl, di$(C_1-C_6)$alkylaminosulphonyl, $(C_1-C_6)$alkylsulphoximino, aminothiocarbonyl, $(C_1-C_6)$alkylaminothiocarbonyl or di$(C_1-C_6)$alkylaminothiocarbonyl, where all the aforementioned radicals may optionally be substituted by halogen; or are phenyl$(C_1-C_3)$alkyl, phenoxy, phenyl$(C_1-C_3)$alkyloxy, phenoxy$(C_1-C_3)$alkyl, phenylthio, phenylthio$(C_1-C_3)$alkyl, phenylsulphinyl, phenylsulphonyl, hetaryl$(C_1-C_3)$alkyl, hetaryloxy, hetaryl$(C_1-C_3)$alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are $(C_3-C_6)$cycloalkyl$(C_1-C_3)$alkyl, $(C_3-C_6)$cycloalkyloxy, $(C_3-C_6)$cycloalkyl$(C_1-C_3)$alkoxy, $(C_3-C_6)$cycloalkylthio, $(C_3-C_6)$cycloalkyl$(C_1-C_3)$alkylthio, $(C_3-C_6)$cycloalkylsulphinyl, $(C_3-C_6)$cycloalkyl$(C_1-C_3)$alkylsulphinyl, $(C_3-C_6)$cycloalkylsulphonyl, $(C_3-C_6)$cycloalkyl$(C_1-C_3)$alkylsulphonyl or $(C_3-C_8)$cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"
  where R' and R" each independently
  are hydrogen, cyano, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, $(C_1-C_6)$alkylthio$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, acyl or $(C_1-C_6)$alkoxycarbonyl; or
  R' and R" together with the nitrogen atom to which they are bonded may form an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a $(C_3-C_6)$cycloalkyl, oxetanyl, oxolanyl, oxanyl, $(C_3-C_8)$cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

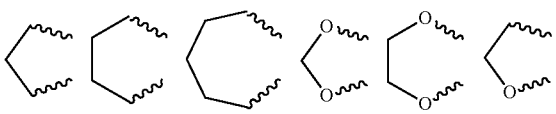

-continued

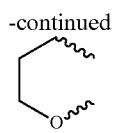

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

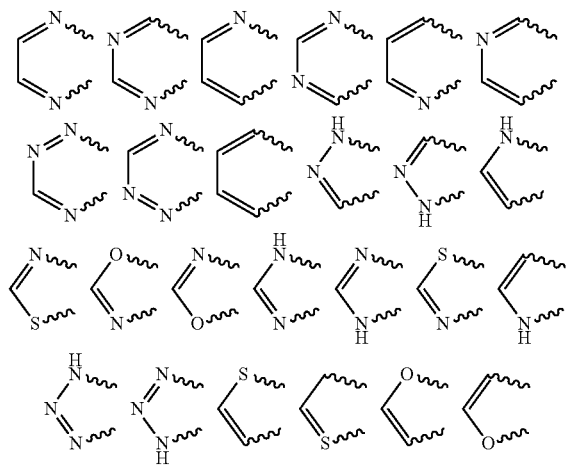

and
n is the number 0 or 1.

At the same time, it is preferable that
$R^2$ and $R^3$, each independently,
  are hydrogen, cyano, halogen or nitro; or
  are $(C_1-C_6)$alkyl, $(C_3-C_6)$cycloalkyl$(C_1-C_6)$alkyl, halo$(C_1-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may each optionally be substituted; or
  are optionally substituted $(C_3-C_6)$cycloalkyl, $(C_3-C_6)$cycloalkenyl, which may optionally be interrupted by one or more heteroatoms from the group of O, S and N; or
  are $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or are carbonyl or carboxyl; or
  are optionally substituted phenyl or optionally substituted hetaryl; or
  are a phenyl or hetaryl ring which is optionally mono- or polysubstituted identically or differently by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally substituted $(C_3-C_6)$cycloalkyl; or
  are $(C_1-C_6)$alkoxy, halo$(C_1-C_6)$alkoxy, $(C_1-C_6)$alkoxy$(C_1-C_6)$alkoxy, $(C_3-C_6)$cycloalkyloxy, $(C_3-C_6)$cycloalkyl$(C_1-C_6)$alkyloxy, $(C_2-C_6)$alkenyloxy, $(C_3-C_6)$cycloalkenyl$(C_1-C_6)$alkoxy, $(C_2-C_6)$alkynyloxy or carbonyloxy, where the aforementioned radicals may each optionally be substituted, or are hydroxyl; or
  are $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulphonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or are amino; or
  are $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphanyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted, or are sulphanyl; or
  are an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated three- to six-membered ring optionally interrupted by heteroatoms from the group of O, S and N;

W is hydrogen, fluorine or chlorine;
V and V' are each independently oxygen, sulphur or an optionally substituted nitrogen;
X, Y and Z are each independently hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;
  or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
  or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
n is the number 0 or 1.

Preferably, the substructure of the formula (I-F) is the substructure

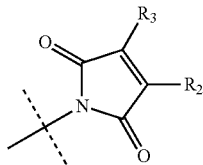

(I-F-1)

where

R² and R³ each independently are hydrogen or halogen; or
are $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or
are $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;

W is hydrogen or halogen, especially F or Cl;

X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z is hydrogen; and n is the number 0 or 1.

In this context, it is particularly preferable that

R² is hydrogen, fluorine, chlorine, bromine, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl or phenyl;

R³ is hydrogen, fluorine, chlorine, bromine, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl or phenyl;

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN,F), (CN,H), (MeO,F), (MeO,H), (Cl,H), (Br,H), (Br,F), (F,F), ($CF_3$,H);

Z is hydrogen; and n is the number 0 or 1.

In this context, it is very particularly preferable that

R² is chlorine, bromine or methyl;

R³ is hydrogen, chlorine or methyl;

W is fluorine;

X is fluorine or methyl;

Y is methyl; where

X and Y are especially the following (Y,X) combinations: (Me,F), (Me,Me);

Z is hydrogen; and n is the number 0 or 1.

Seventh Embodiment (I-G):

In a seventh embodiment of the present invention, the inventive compounds have a structure of the general formula (I) in which A and B together with the atoms to which they are bonded are a substructure of the formula (I-G)

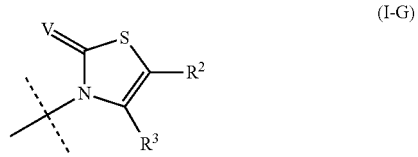

(I-G)

R² and R³ each independently
are hydrogen, cyano, halogen or nitro; or
are $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylthio$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or
are optionally substituted saturated or unsaturated $(C_3-C_6)$cycloalkyl which may optionally be interrupted by one or more heteroatoms; or
are $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or are carbonyl or carboxyl; or
are optionally substituted phenyl or optionally substituted hetaryl; or
are $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$ cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or are hydroxyl; or are $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or are amino; or are $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or are sulphanyl; or are an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

W is hydrogen or halogen;

V is oxygen, sulphur or an optionally substituted nitrogen;

X, Y and Z each independently are hydrogen, halogen, hydroxyl, amino, cyano, nitro, OCN, SCN, $SF_5$; or are tri$(C_1-C_6)$alkylsilyl, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxycarbonyl$(C_1-C_6)$alkyl, $(C_1-C_6)$alkoxy$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, $(C_1-C_6)$alkoxy, halo$(C_1-C_6)$alkoxy, cyano$(C_1-C_6)$alkoxy, hydroxycarbonyl$(C_1-C_6)$alkoxy, $(C_1-C_6)$alkoxycarbonyl$(C_1-C_6)$alkoxy, $(C_1-C_6)$alkoxy$(C_1-C_6)$alkoxy, $(C_1-C_6)$alkylhydroxyimino, $(C_1-C_6)$alkoxyimino, $(C_1-C_6)$alkyl$(C_1-C_6)$alkoxyimino, halo$(C_1-C_6)$alkyl$(C_1-C_6)$alkoxyimino, $(C_1-C_6)$alkylthio, halo$(C_1-C_6)$alkylthio, $(C_1-C_6)$alkoxy$(C_1-C_6)$alkylthio, $(C_1-C_6)$alkylthio$(C_1-C_6)$alkyl, $(C_1-C_6)$alkylsulphinyl, halo$(C_1-C_6)$alkylsulphinyl, $(C_1-C_6)$alkoxy$(C_1-C_6)$alkylsulphinyl, $(C_1-C_6)$alkylsulphinyl$(C_1-C_6)$alkyl, $(C_1-C_6)$alkylsulphonyl, halo$(C_1-C_6)$alkylsulphonyl, $(C_1-C_6)$alkoxy$(C_1-C_6)$alkylsulphonyl, $(C_1-C_6)$alkylsulphonyl$(C_1-C_6)$alkyl, $(C_1-C_6)$alkylsulphonyloxy, $(C_1-C_6)$alkylcarbonyl, halo$(C_1-C_6)$alkylcarbonyl, carboxyl, $(C_1-C_6)$alkylcarbonyloxy, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_2-C_6)$alkenylaminocarbonyl, di$(C_2-C_6)$alkenylaminocarbonyl, $(C_3-C_6)$cyclo$(C_1-C_6)$alkylaminocarbonyl, $(C_1-C_6)$alkylsulphonylamino, aminosulphonyl, $(C_1-C_6)$alkylaminosulphonyl, di$(C_1-C_6)$alkylaminosulphonyl, $(C_1-C_6)$alkylsulphoximino, aminothiocarbonyl, $(C_1-C_6)$alkylaminothiocarbonyl or di$(C_1-C_6)$alkylaminothiocarbonyl, where all the aforementioned radicals may optionally be substituted by halogen; or are phenyl$(C_1-C_3)$alkyl, phenoxy, phenyl$(C_1-C_3)$alkyloxy, phenoxy$(C_1-C_3)$alkyl, phenylthio, phenylthio$(C_1-C_3)$alkyl, phenylsulphinyl, phenylsulphonyl, hetaryl$(C_1-C_3)$alkyl, hetaryloxy, hetaryl$(C_1-C_3)$alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are $(C_3-C_6)$cycloalkyl$(C_1-C_3)$alkyl, $(C_3-C_6)$cycloalkyloxy, $(C_3-C_6)$cycloalkyl$(C_1-C_3)$alkoxy, $(C_3-C_6)$cycloalkylthio, $(C_3-C_6)$cycloalkyl$(C_1-C_3)$alkylthio, $(C_3-C_6)$cycloalkylsulphinyl, $(C_3-C_6)$cycloalkyl$(C_1-C_3)$alkylsulphinyl, $(C_3-C_6)$cycloalkylsulphonyl, $(C_3-C_6)$cycloalkyl$(C_1-C_3)$alkylsulphonyl or $(C_3-C_8)$cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"
where R' and R" each independently
are hydrogen, cyano, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, $(C_1-C_6)$alkylthio$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, acyl or $(C_1-C_6)$alkoxycarbonyl; or R' and R" together with the nitrogen atom to which they are bonded may form an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a $(C_3-C_6)$cycloalkyl, oxetanyl, oxolanyl, oxanyl, $(C_3-C_8)$cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

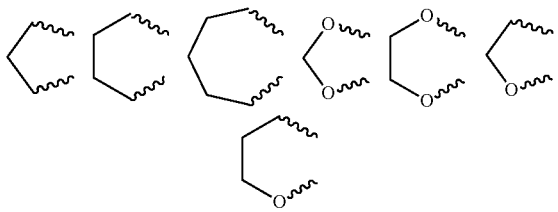

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

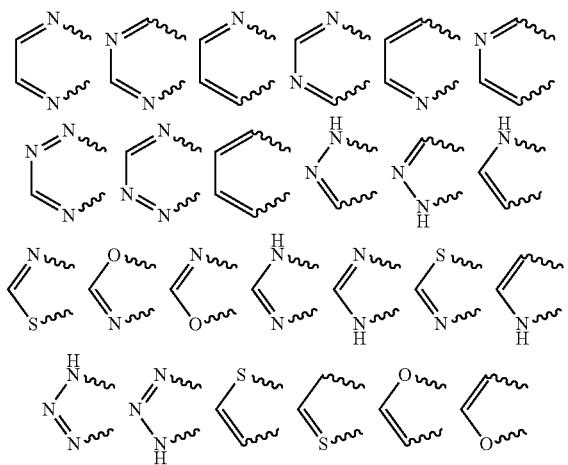

and
n is the number 0 or 1.

At the same time, it is preferable that
$R^2$ and $R^3$, each independently,
are hydrogen, cyano, halogen or nitro; or
are $(C_1-C_6)$alkyl, $(C_3-C_6)$cycloalkyl$(C_1-C_6)$alkyl, halo$(C_1-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may each optionally be substituted; or are optionally substituted $(C_3-C_6)$cycloalkyl, $(C_3-C_6)$cycloalkenyl, which may optionally be interrupted by one or more heteroatoms from the group of O, S and N; or
are $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or are carbonyl or carboxyl; or
are a phenyl or hetaryl ring which is optionally mono- or polysubstituted identically or differently by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally substituted $(C_3-C_6)$cycloalkyl; or
are $(C_1-C_6)$alkoxy, halo$(C_1-C_6)$alkoxy, $(C_1-C_6)$alkoxy$(C_1-C_6)$alkoxy, $(C_3-C_6)$cycloalkyloxy, $(C_3-C_6)$cycloalkyl$(C_1-C_6)$alkyloxy, $(C_2-C_6)$alkenyloxy, $(C_3-C_6)$cycloalkenyl$(C_1-C_6)$alkoxy, $(C_2-C_6)$alkynyloxy or carbonyloxy, where the aforementioned radicals may each optionally be substituted, or are hydroxyl; or
are $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulphonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or are amino; or
are $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted, or are sulphanyl; or
are an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated three- to six-membered ring optionally interrupted by heteroatoms from the group of O, S and N;
W is hydrogen, fluorine or chlorine;
V is oxygen, sulphur or an optionally substituted nitrogen;
X, Y and Z are each independently hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;
or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

n is the number 0 or 1.

Preferably, the substructure of the formula (I-G) is the substructure

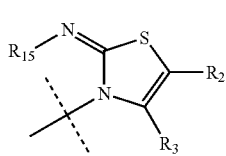

(I-G-1)

where $R^2$ and $R^3$ each independently are hydrogen; or are $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or are $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

$R^{15}$ is hydrogen; or is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is $(C_3-C_6)$cycloalkyl, $(C_3-C_6)$cycloalkenyl, oxetanyl, oxolanyl, oxanyl, phenyl, pyrimidyl, pyridazinyl, pyrazinyl, triazinyl, thiazolyl, thiazadiazolyl, oxazolyl, oxadiazolyl, pyrazolyl or triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

W is hydrogen or halogen, especially fluorine or chlorine;

X, Y and Z are each independently hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;

or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and n is the number 0 or 1.

In this context, the E and Z isomers of the substructure of the formula (I-G) are especially also included.

If the substructure of the formula (I-G) is the substructure formula (I-G-1), it is preferable that $R^2$ and $R^3$ each independently are hydrogen; or are $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or are $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;

$R^{15}$ is hydrogen; or is $(C_1-C_6)$alkyl, $(C_3-C_6)$cycloalkyl$(C_1-C_6)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be substituted; or is $(C_3-C_6)$cycloalkyl, $(C_3-C_6)$cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo$(C_1-C_3)$alkylsulphanyl or optionally methyl-, fluorine-, chlorine-, cyano-substituted cyclopropyl;

W is hydrogen or halogen, especially F or Cl;

X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z is hydrogen; and n is the number 0 or 1.

In this context, it is particularly preferable that $R^2$ is hydrogen, fluorine, chlorine, bromine, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl or phenyl;

$R^3$ is hydrogen, fluorine, chlorine, bromine, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH=CH_2$, $CH=CHCH_3$, $CH_2CH=CH_2$, $CH_2CCH$, cyclopropylmethyl, $CF_3$, $CH_2CF_3$, $CH_2CHF_2$, $CH_2CN$, $CH_2OCH_3$, $CH_2OCH_2CH_3$, $CH_2CH_2OCH_3$, benzyl, cyclopropyl, cyclobutyl or phenyl;

$R^{15}$ is hydrogen, methyl, ethyl, n-propyl, $CH(CH_3)_2$, n-butyl, sec-butyl, $C(CH_3)_3$, $CH_2C(CH_3)_3$, $CH_2CH(CH_3)_2$, $CH_2CH=CH_2$, cyclopropylmethyl, $CH_2CF_3$, $CH_2CHF_2$, $CH_2CN$, $CH_2CH_2OCH_3$, benzyl, cyclopropyl, cyclobutyl or phenyl;

W is hydrogen or fluorine;

X is hydrogen, chlorine, fluorine or methyl;

Y is fluorine, chlorine, bromine, cyano, methyl, methoxy or trifluoromethyl; where X and Y are especially the following (Y,X) combinations: (Me,F), (Me,H), (Me,Cl), (Me,Me), (Cl,Cl), (Cl,F), (CN, F), (CN,H), (MeO,F), (MeO,H), (Cl,H), (Br,H), (Br,F), (F,F), ($CF_3$,H);

Z is hydrogen; and n is the number 0 or 1.

In this context, it is very particularly preferable when $R^2$ is methyl;

$R^3$ is methyl;

$R^{15}$ is $CH_2CF_3$;

W is fluorine;

X is fluorine;

Y is methyl; where

Z is hydrogen; and n is the number 0 or 1.

In this context, it is likewise very particularly preferable when $R^2$ is hydrogen or methyl;

$R^3$ is hydrogen or methyl;

$R^{15}$ is $CH_2CF_3$;

W is fluorine;

X is fluorine;

Y is methyl; where

Z is hydrogen; and n is the number 0 or 1.

The above-recited general radical definitions and elucidations or those recited in preference ranges may be combined arbitrarily with one another, in other words including combinations between the respective ranges and preference ranges. They apply both to the end products and, correspondingly, to precursors and intermediates.

Preference is given in accordance with the invention to the compounds of the formula (I) in which there is a combination of the definitions recited above as preferred.

Particular preference is given in accordance with the invention to the compounds of the formula (I) in which there is a combination of the definitions recited above as particularly preferred.

Saturated or unsaturated hydrocarbon radicals, such as alkyl, alkynyl or alkenyl, may each be straight-chain or branched as far as possible, including in conjunction with heteroatoms, as, for example, in alkoxy.

Unless indicated otherwise, optionally substituted radicals may be mono- or polysubstituted, where the substituents in the case of polysubstitutions may be the same or different.

In the context of the present invention, halogen is fluorine, chlorine, bromine and iodine, more preferably fluorine, chlorine and bromine and most preferably fluorine and chlorine.

In addition, alkyl is straight-chain or branched $C_1$- to $C_8$-alkyl, preferably straight-chain or branched $C_1$- to $C_6$-alkyl, further preferably straight-chain or branched $C_1$- to $C_4$-alkyl, especially methyl and ethyl.

Alkoxy is straight-chain or branched $C_1$- to $C_8$-alkoxy, preferably straight-chain or branched $C_1$- to $C_6$-alkoxy, further preferably straight-chain or branched $C_1$- to $C_4$-alkoxy, in particular methoxy.

Haloalkyl and haloalkoxy arise from substituted alkyl and alkoxy radicals in accordance with the above definition.

Alkyl radicals in cycloalkyl, alkoxycarbonyl, alkylthioalkyl, alkylsulphinylalkyl, phenylalkyl, hetarylalkyl and alkylsulphonylalkyl likewise arise from the above definition of alkyl.

Preparation Processes

The compounds of the general formula (I) can be divided into compounds with n=0 (Ia) and n=1 (Ib) and can in principle be prepared by the general processes P1, P2, P3 and P3'.

Process P1 includes all the methods which—usually in a multistage process—enable formation of the 5-membered ring, especially proceeding from the anilines of the general formula (IVa), according to the following scheme:

PROCESS P1

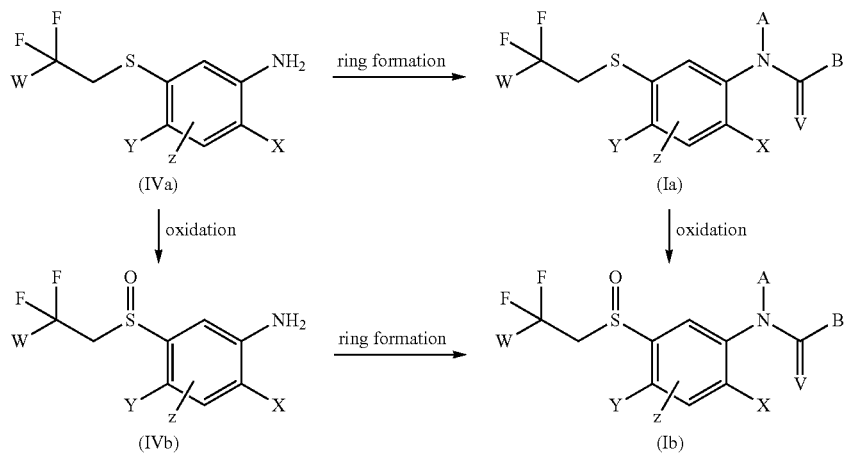

where X, Y, Z, A, B and V are each as defined above.

By oxidation of the thioethers of the general formula (Ia) by methods known from the literature, it is possible to obtain the sulphoxides of the general formula (Ib).

Alternatively, some of the methods described in process P1 can also be employed proceeding from sulphoxides of the general formula (IVb) to give the sulphoxides of the general formula (Ib). The sulphoxides of the formula (IVb) can be prepared from the sulphides (IVa) by methods known from the literature.

Process P1 is especially suitable for preparation of embodiments I-A to I-G.

Alternatively, the compounds of the general formula (Ia) can also be prepared by Process P2, according to the following scheme:

PROCESS P2

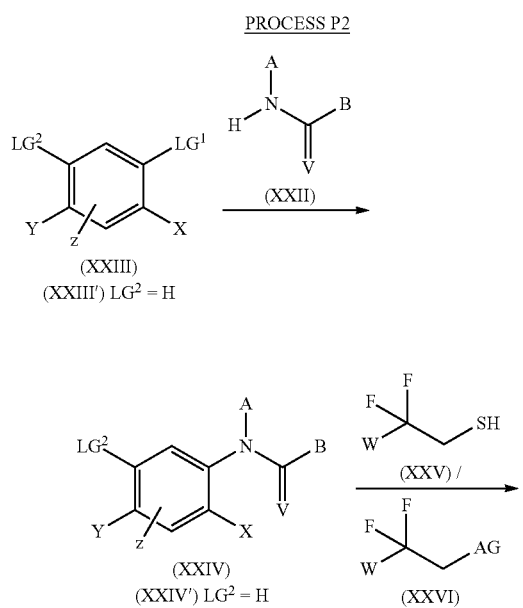

-continued

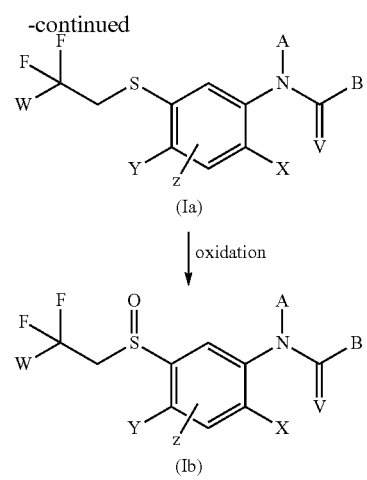

where Z, A, B, V and W are each as defined above, X is hydrogen or an electron-withdrawing group (especially nitro, chlorine, fluorine, cyano), Y represents electron-withdrawing substituents (especially nitro, chlorine, fluorine, cyano), $LG^1$ represents typical leaving groups in nucleophilic substitution reactions (especially fluoride, chloride) and $LG^2$ may represent hydrogen or typical leaving groups in nucleophilic substitution reactions (especially fluoride, chloride).

The reaction of compounds of the general formula (XXIII) with heterocyclic compounds of the general formula (XXII), usually under basic reaction conditions as, for example, in U.S. Pat. No. 6,906,006 and DE 19500439 for triazolinones, WO 2010/0119194 for hydantoins, DE 4431218 for pyrimidin(ethi)ones, WO 2009/012275 and WO 2008/155034 for pyridones or DE 19528305 for uracils, gives the compounds of the general formula (XXIV). Through another nucleophilic aromatic substitution with thiols of the general formula (XXV), the thioethers of the formula (Ia) can be prepared. Suitable reaction conditions for such reactions are described in WO 2007/131680 and WO 2008/086226.

By oxidation of the thioethers of the general formula (Ia) by methods known from the literature, it is possible to obtain the sulphoxides of the general formula (Ib).

Compounds of the formula (XXIII) in which LG² is hydrogen are referred to as (XXIII') and can be reacted in a manner similar to that described above with compounds of the formula (XXII), in this case to give compounds of the formula (XXIV').

Some compounds of the formula (XXIV') are commercially available.

The compounds of the formula (XXIV') can be converted in a multistage process to the inventive compounds (Ia). The steps required include chlorosulphonation, reduction and alkylation with haloalkyl electrophiles of the formula (XXVI), all possible by methods known from the literature. The chlorosulphonation of the compounds (XXIV') with chlorosulphonic acid gives the corresponding sulphonyl chlorides and these can be converted to their disulphides by methods known from the literature, for example iron in hydrochloric acid or iodide. The reaction of the disulphides with haloalkyl electrophiles of the formula (XXVI) gives the sulphides (Ia).

By oxidation of the thioethers of the general formula (Ia) by methods known from the literature, it is possible to obtain the sulphoxides of the general formula (Ib).

Process P2 is especially suitable for preparation of embodiments I-A to I-G in which X is hydrogen or represents electron-withdrawing substituents (especially nitro, chloride, fluoride, cyano) and Y represents electron-withdrawing substituents (especially nitro, chloride, fluoride, cyano).

Alternatively, the compounds of the general formula (Ia) can be prepared by Processes P3 and P3', as shown in the following scheme:

illustrative reaction conditions are disclosed in the literature, for example in WO 2006/117657 A1, in US 2010/99725 A1, in WO 2010/47956 A1, in Chem. Pharm. Bull. 1997, vol. 45, no. 4, 719-721, in J. Amer. Chem. Soc. 2003, vol. 125, no. 37, 11253-11258 or else in Bull. Korean Chem. Soc. 2010, vol. 31, no. 8, 2143-2146. Preference is given to using copper or copper salts, for example copper(I) iodide, copper (I) oxide, copper(I) triflate or copper(II) triflate, as catalyst, frequently in the presence of a ligand, for example diamine ligands such as N,N'-dimethylethylenediamine, N,N-dimethylethylenediamine or trans-N,N'-dimethyl-1,2-cyclohexanediamine A review can be found, for example, in Chem. Sci. 2010, vol. 1, 13-31. Alternatively, it is possible to use 1,3-diketones, for example 2,4-pentanedione, 2,2,6,6-tetramethyl-3,5-heptanedione or dibenzoylmethane, amino acids, for example L-proline or glycine, or other compounds such as 8-hydroxyquinoline (Tetrahedron Lett. 2009, vol. 50, 7293-7296), dibenzylideneacetone, bipyridine or phenanthroline. In general, the reaction is performed in the presence of a base, frequently carbonate or phosphate bases, for example potassium carbonate, sodium carbonate, caesium carbonate or potassium phosphate, in suitable solvents, for example dioxane, toluene, dimethyl sulphoxide or N,N-dimethylformamide. It is additionally possible to use other additives, for example potassium iodide, caesium fluoride or other salts.

Alternatively, it is possible to perform reactions of this kind under palladium catalysis, for instance using catalysts, for example palladium acetate, tetrakis(triphenylphosphine) palladium, bis(triphenylphosphine)palladium(II) chloride,

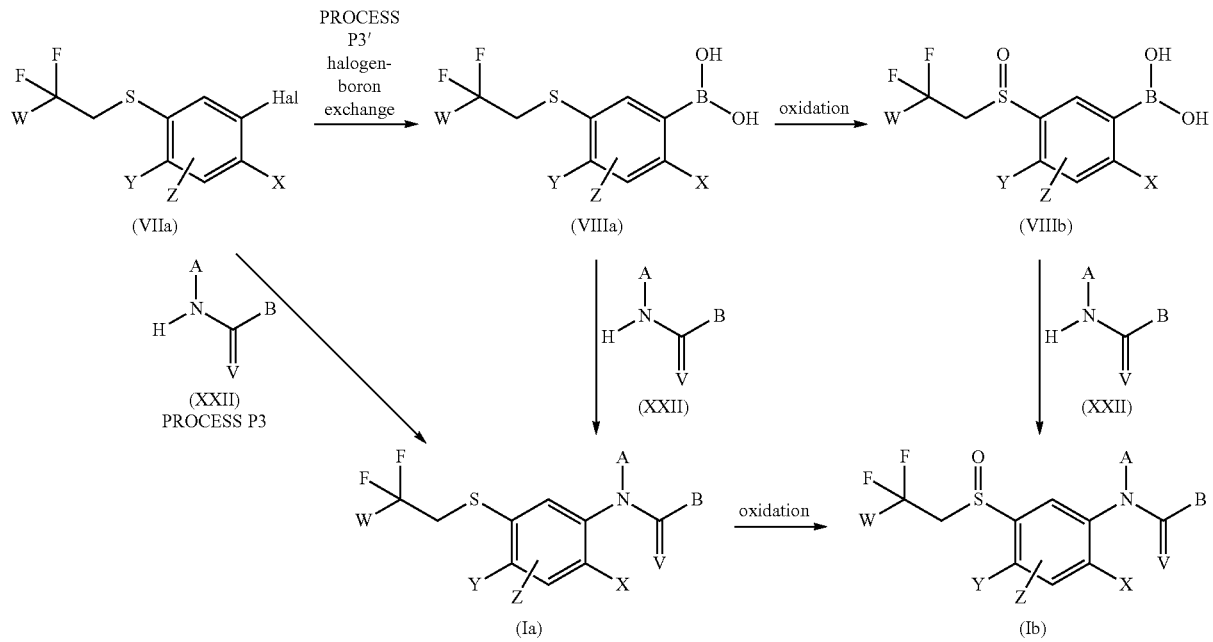

where X, Y, Z, W, A, B and V are each as defined above and Hal is halogen (preferably chlorine, bromine, iodine).

According to Process P3, compounds of the general formula (Ia) can be prepared by methods known from the literature by reaction of aryl halides of the general formula (VIIa) with heterocyclic compounds of the general formula (XXII). The reaction preferably takes place through transition metal catalysis or mediation. Numerous examples of tris(dibenzylideneacetone)dipalladium(0) in the presence of ligands, for example 2,2'-bis(diphenylphosphino)-1,1'-binaphthyl, 9,9-dimethyl-4,5-bis(diphenylphosphino)xanthene, 1,1'-bis(diphenylphosphino)ferrocene, and bases, for example potassium carbonate, sodium carbonate, caesium carbonate or potassium phosphate, in suitable solvents, for example dioxane, toluene, dimethyl sulphoxide or N,N-dimethylformamide Compounds of the general formula (Ia) can alternatively be prepared by Process P3' by reaction of boronic acids of the general formula (VIIIa) with heterocyclic compounds of the general formula (XXII).

In general, the reactions take place under catalysis or mediation by copper(II) salts, for example copper(II) acetate, copper(II) triflate, or else by copper(I) salts, for example copper(I) chloride, copper(I) acetate, under an air or oxygen atmosphere, frequently under dehydrating conditions (for example with molecular sieve). Bases used are, for example, triethylamine, N-ethyldiisopropylamine, pyridine, 2,6-lutidine, N-methylmorpholine or 1,8-diazabicycloundec-7-ene in suitable solvents, for example dichloromethane, dichloroethane, methanol, N,N-dimethylformamide, tetrahydrofuran, dioxane, acetonitrile, ethyl acetate or toluene. The literature describes numerous examples, some of them in Bioorg. Med. Chem. Lett. 2010, vol. 20, no. 13, 3920-3924, in Proc. Natl. Acad. Sci. USA 2011, vol. 108, no. 17, 6781-6786, in Chem. Eur. J. 2009, vol. 15, no. 29, 7044-7047, in Synlett 2004, vol. 6, 1095-97, in J. Org. Chem. 2005, 70, 4, 1486-1489, in Tetrahedron Lett. 1998, vol. 39, 2933-2936, in WO 2005/85226 A1 or in WO 2008/62905 A2.

Comprehensive reviews can be found, for example, in Synthesis 2011, no. 6, 829-856 or in Tetrahedron 2012, vol. 68, 7735-7754. Instead of the boronic acid, it is also possible to use other boron compounds, for instance potassium trifluoroborate, boronic esters, etc., or else other organometallic compounds, for instance stannanes, silanes or bismuthanes.

By oxidation of the thioethers of the general formula (Ia) by methods known from the literature, it is possible to obtain the sulphoxides of the general formula (Ib). Alternatively, the oxidative transition metal-mediated carbon-nitrogen coupling to give aryl sulphoxides of the general formula (Ib) can be enabled proceeding from boronic sulphoxides of the general formula (VIIIb), which are obtainable by oxidation of the boronic acids (VIIIa), for example with sodium periodate, or analogous derivatives.

Processes P3 and P3' are especially suitable for preparation of embodiments I-A, I-B, I-C, I-D and I-F.

Processes Pa1 to Pa5 are suitable for preparation of embodiment I-A of the compounds of the formula (I).

Processes Pa1 and Pa2 (I-A-1, I-A-2, I-A-3, I-A-4, I-A-6, I-A-8, I-A-10)

The 2-aryltriazolin-3-ones of the general formula (I-A-1, I-A-2, I-A-3, I-A-4, I-A-6, I-A-8, I-A-10) can be divided into (I-A-1a, I-A-2a, I-A-3a, I-A-4a, I-A-6a, I-A-8a, I-A-10a) (n=0) and (I-A-1b, I-A-2b, I-A-3b, I-A-4b, I-A-6b, I-A-8b, I-A-10b) (n=1) and can be prepared, for example, by Process Pa1, as in the following scheme:

PROCESS Pa1

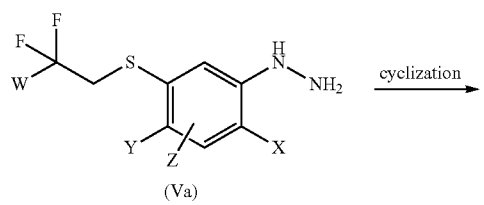

(Va)

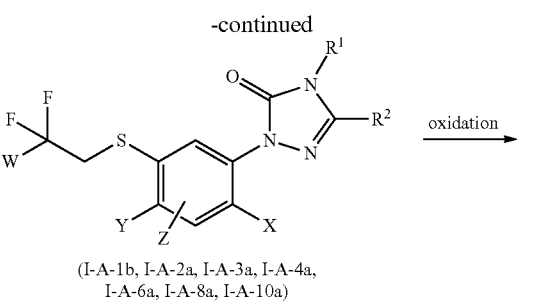

(I-A-1b, I-A-2a, I-A-3a, I-A-4a, I-A-6a, I-A-8a, I-A-10a)

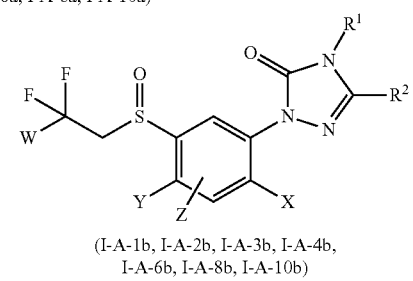

(I-A-1b, I-A-2b, I-A-3b, I-A-4b, I-A-6b, I-A-8b, I-A-10b)

where X, Y, Z, W, $R^1$ and $R^2$ are each as defined above.

Compounds of the general formula (I-A-1a, I-A-2a, I-A-3a, I-A-4a, I-A-6a, I-A-8a, I-A-10a) can be prepared proceeding from hydrazines of the general formula (Va) in multistage processes.

The preparation of the 2-aryltriazolin-3-ones of the general formula (I-A-1a) is possible, for example, through condensation of hydrazines of the general formula (Va) with suitable α-dicarbonyl compounds or surrogates thereof and subsequent cyclization. Numerous methods are to be found in the literature, for example with α-keto acids/diphenylphosphoryl azide($R^1$=H, $R^2$=H, alkyl, aryl: Synth. Comm 1986, 16, 2, 163-167; $R^1$=H, $R^2$=H: Eur. J. Med. Chem. 2011, 46, 10, 5039-5045; $R^1$=H, $R^2$=aryl: J. Med. Chem. 2007, 50, 3, 528-542), with imidoyl chlorides/chloroformic esters ($R^1$=aryl, $R^2$=haloalkyl: Tetrahedron Lett. 1990, 31, 19, 2717-2718), with alkyl N-(alkoxycarbonyl)alkylimidoates/triethylamine ($R^1$=H, alkyl, aryl, benzyl, $R^2$=alkyl, cycloalkyl: J. Med. Chem. 1993, 36, 2558-2568), with cyanogen bromide/hydrogen sulphide/methyl iodide/trichlorotrifluoroacetone ($R^1$=H, $R^2$=haloalkyl: J. Heterocycl. Chem. 1983, 20, 1533-1537), with N-alkoxycarbonylthioamides ($R^1$=H, $R^2$=alkyl, aryl, heteroaryl: J. Org. Chem. 1976, 41, 20, 3233-3237).

In addition, 2-aryltriazolin-3-ones of the general formula (I-A-2a) can be prepared by condensation of hydrazines of the general formula (Va) with carbamoylurea to give urazoles and subsequent alkylation, for example with diazomethane, as described, for example, in J. Phys. Org. Chem. 1993, 6, 601-608 or in Chem. Ber. 1903, 36, 3139-3154 ($R^1$=methyl, $R^2$=methoxy).

The synthesis of 2-aryltriazolin-3-ones of the general formula (I-A-3a) is described, for example, in Liebigs Ann. 1959, 627, 162-165 proceeding from aryl semicarbazides with cyanogen bromide ($R^1$=aryl, $R^2$=amino) Synthesis of 3-alkoxycarbonylamino-1,2,4-triazolinones ($R^1$=methyl, $R^2$=N(CH$_3$)CO$_2$CH$_3$) is possible according to Ind. J. Chem. Sect. B 1980, 19, 9, 805-809.

There are likewise known literature methods for preparation of 4-amino-1,2,4-triazolin-3-ones of the general formula (I-A-4a). The condensation of two hydrazone derivatives with subsequent cyclization, for example with phosgene, leads, according to Liebigs Ann. 1982, 5, 994-1000, to 4-amino-1,2,4-triazolin-3-ones ($R^1$=amino, $R^2$=H, COOalkyl). A further synthesis of 4-amino-1,2,4-triazolin-3-ones ($R^1$=N($CO_2$alkyl')alkyl, $R^2$=aryl, heteroaryl) proceeding from aldehyde hydrazones, which are in turn obtainable from hydrazines of the general formula (Va), in a cascade reaction is described in Tetrahedron 2010, 66, 13, 2427-2432 or in J. Computational Chem. 2012, 33, 7, 715-722. In addition, 4-amino-1,2,4-triazolin-3-ones ($R^1$=amino, NHC(O)$CH_3$, $R^2$=alkyl) can be prepared from the corresponding 1,3,4-oxadiazol-2(3H)-ones, which are likewise obtainable in a multistage process from hydrazines of the general formula (Va), as described, for example, in J. Chem. Res. Synopses 2003, 5, 275-278.

Arch. Pharm. 1987, 320, 11, 1167-1173 describes the synthesis of 4-hydroxy-1,2,4-triazolin-5-ones of the general formula (I-A-6a) ($R^1$=OH, $R^2$=alkyl).

The preparation of 2-aryltriazolin-3-ones of the general formula (I-A-8a) is reported, for example, in J. Amer. Chem. Soc. 1915, 37, 183-189 and J. Amer. Chem. Soc. 1917, 39, 950-961 ($R^1$=alkyl, $R^2$=$SO_2CH_3$).

Condensation of hydrazines of the general formula (Va) with dialkyl N-carbomethoxyimidodithiocarbonates ($R^1$=H, $R^2$=S-alkyl: Z. Chem. 1980, 20, 10, 371-372) leads to the corresponding 5-(alkylsulphanyl)-2-aryl-2,4-dihydro-3H-1,2,4-triazol-3-ones of the general formula (I-A-10a). The latter can be converted by methods known from the literature, by oxidation to the corresponding 5-(alkylsulphinyl)-2-aryl-2,4-dihydro-3H-1,2,4-triazol-3-ones of the general formula (I-A-9a).

The 2-aryltriazolin-3-one of the general formula (I-A-1) can alternatively be prepared by Process Pa2, as shown in the following scheme:

PROCESS Pa2

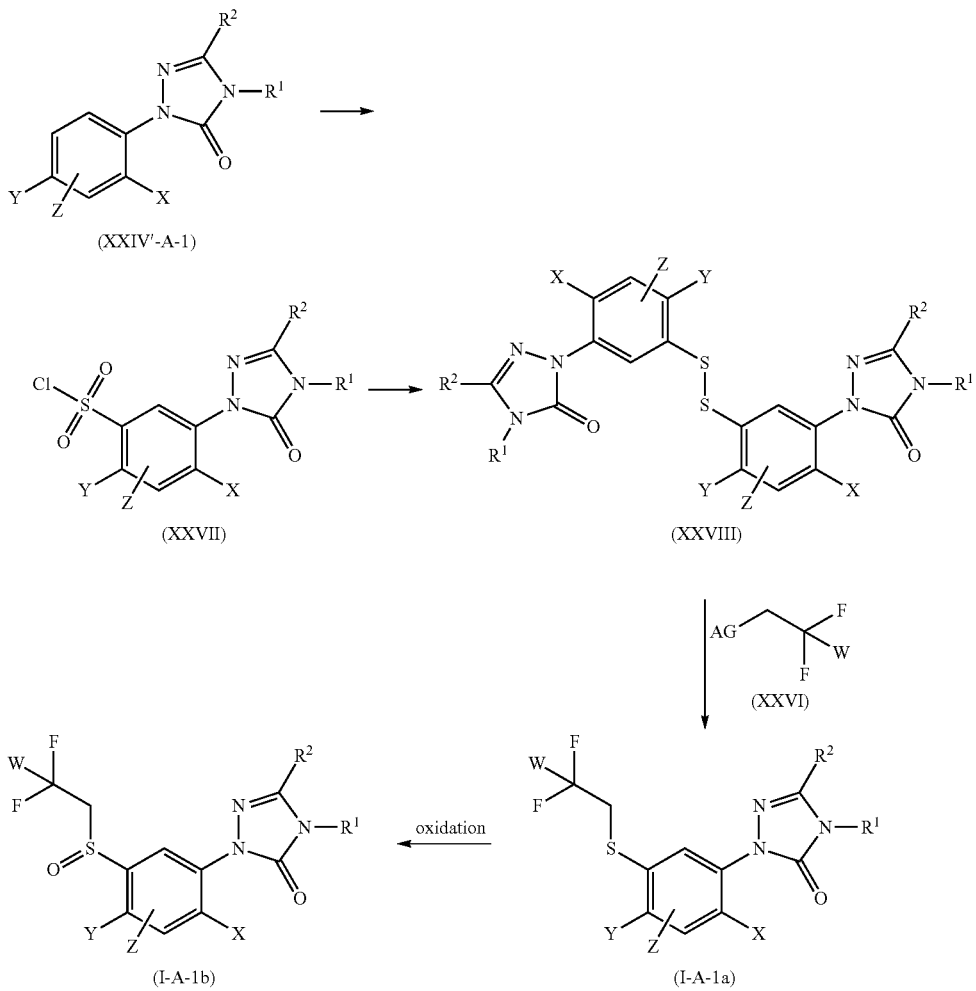

where X, Y, Z, W, $R^1$ and $R^2$ are each as defined above and AG is a leaving group, for example chlorine, bromine, iodine, tosylate, mesylate or triflate.

In embodiment (I-A-1) of the present invention, the compounds of the general formula (XXVII) are prepared by chlorosulphonation of the aryltriazolinones (XXIV'-A-1) with chlorosulphonic acid, especially under the conditions specified in the preparation examples.

The 2-aryl-2,4-dihydro-3H-1,2,4-triazol-3-ones (XXIV'-A-1) required as starting compounds can be prepared by literature methods, for example analogously to EP 301946, EP 597360, WO 2002012203, WO 2009088025 or J. Chem. Soc. (1954), 3319-3324 or Chem. Ber. (1958), 91 2578-2580.

The reduction of the sulphonyl chlorides (XXVII) to the disulphides (XXVIII) is possible by methods known from the literature, for example iron in hydrochloric acid or iodide, especially under the conditions specified in the preparation examples. The reaction of the disulphides (XXVIII) with haloalkyl electrophiles of the formula (XXVI) gives the compounds of the formula (I-A-1a).

The thioethers (I-A-1a) can be converted to the corresponding sulphoxides (I-A-1b) by processes that are sufficiently well known through reaction with oxidizing agents.

Processes Pa3 and Pa4 (I-A-12)

The 2-aryl-1,2,4-triazoline-3-thiones of the general formula (I-A-12) where $R^2$ is a dimethylamino group can be divided into (I-A-12a) (n=0) and (I-A-12b) (n=1) and can be prepared, for example, by Process Pa3, as shown in the following scheme:

PROCESS Pa3

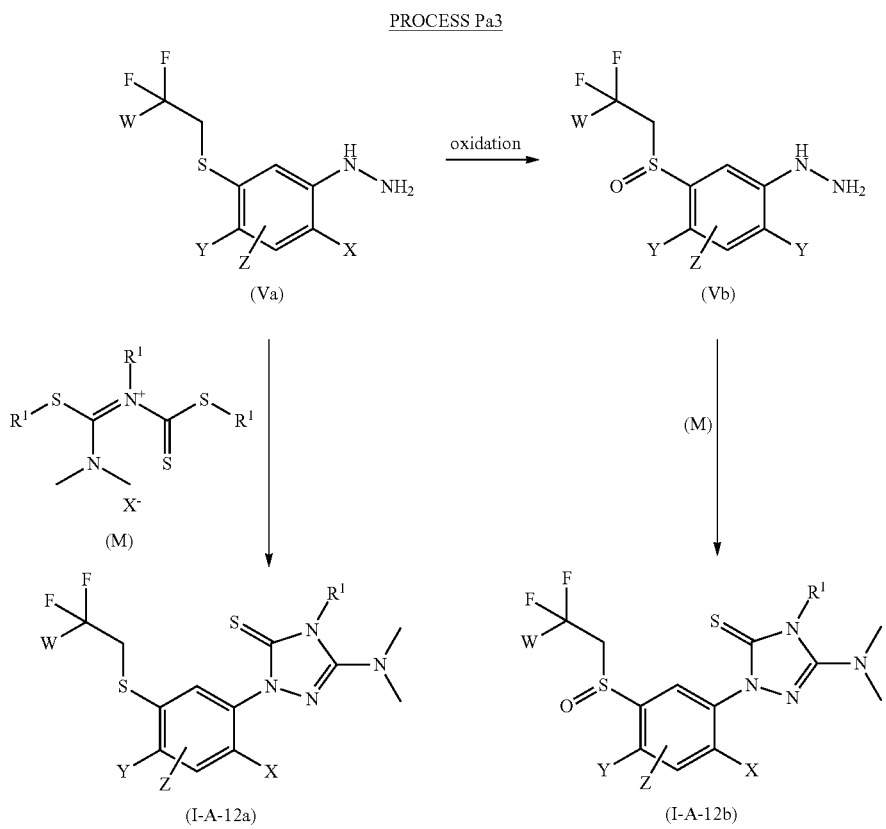

where W, X, Y, Z, A and $R^1$ are each as defined above.

Hydrazines of the formula (Va) or (Vb) can be converted to the triazolinethiones of the formula (I-A-12a) or (I-A-12b), for example according to M. Yokoyama in J. Chem. Soc. (Perkin Trans. 1), 1982, 1059-1062, by admixing them with methylimmonium salts of the formula (M) in ethanol while heating. These methylimmonium salts can, as described by M. Yokoyama, be prepared from dialkylthioureas with carbon disulphide and an excess of an alkylating agent.

The 2-aryl-1,2,4-triazoline-3-thiones of the general formula (I-A-12) in which $R^2$ is a monosubstituted amino group can alternatively be prepared by Process Pa4, as shown in the following scheme:

PROCESS Pa4

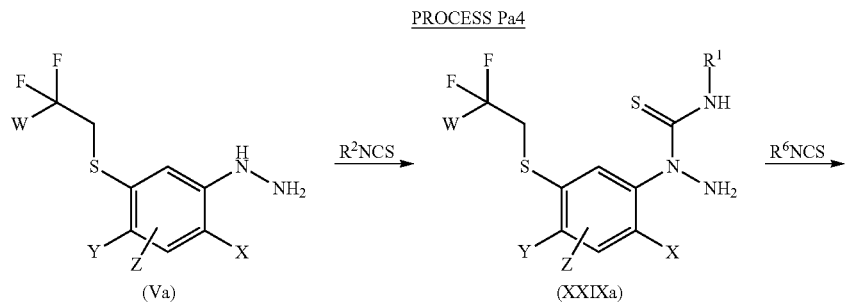

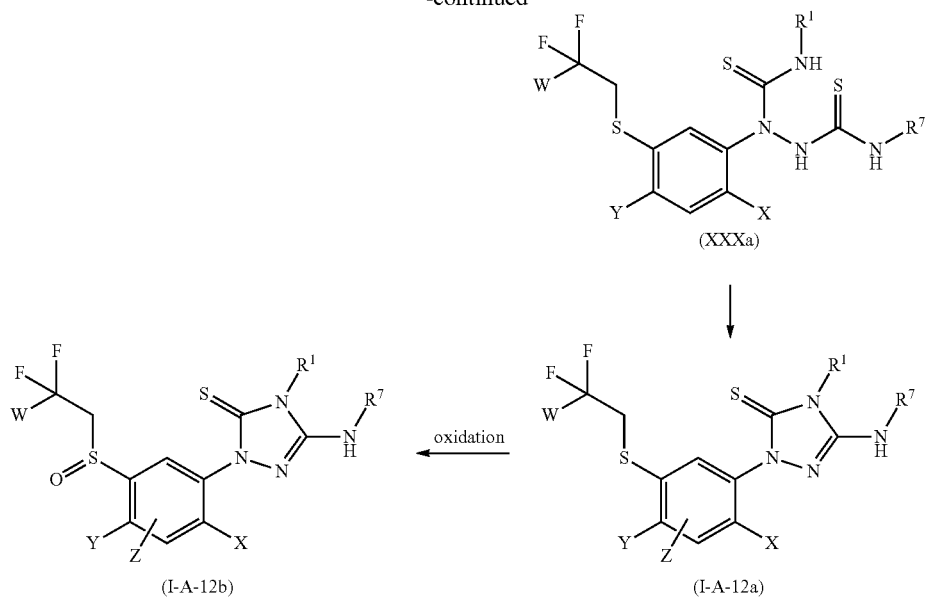

(XXXa)

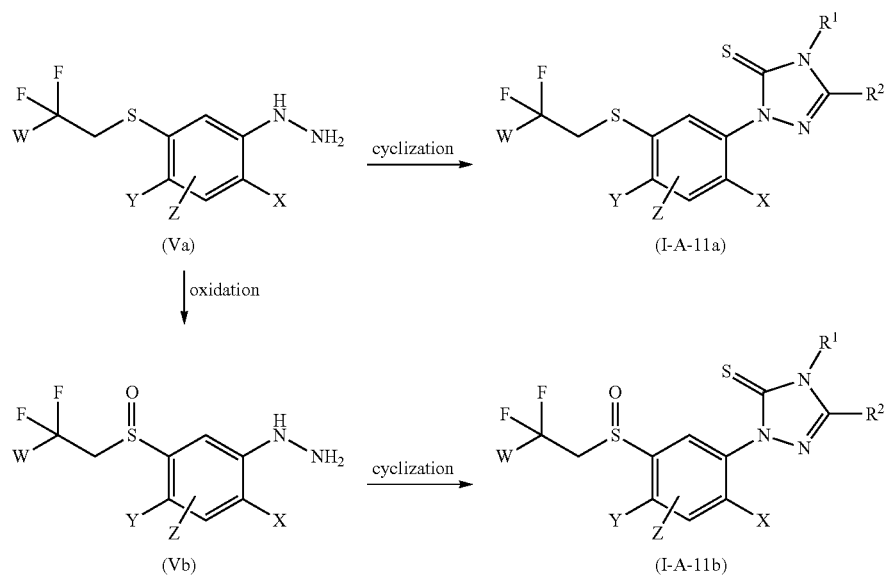

where W, X, Y, Z, A, $R^1$ and $R^7$ are each as defined above.

The hydrazines of the formula (Va) can be reacted with isothiocyanates to give thiosemicarbazides of the formula (XXIXa), for example according to M. Yokomoto in J. Med. Chem. 2012, 55, 7772-7785, in an alcohol as solvent. The thiosemicarbazides (XXIXa) can be reacted with suitable isothiocyanates to give bisthioureas of the formula (XXXa), for example when the reaction is performed in toluene or acetonitrile according to K. Schulze in J. Het. Chem. 1995, 32, 275-281. This may be followed by cyclization to give the desired triazoline-3-thiones of the formula (Ia), for example by reaction with 0.5 equivalent of sodium ethoxide in ethanol, as described by K. Schulze.

The thioethers (I-A-12a) can then be converted to the corresponding sulphoxides (I-A-12b) by processes known from the literature, through reaction with oxidizing agents.
Process Pa5 (I-A-11)

The 2,4-dihydro-3H-1,2,4-triazole-3-thione of the general formula (I-A-11) can be divided into (I-A-11a) (n=0) and (I-A-11b) (n=1) and can be prepared, for example, by Process Pa5, as shown in the following scheme:

PROCESS Pa5 where X, Y, Z, W, $R^1$ and $R^2$ are each as defined above.

2,4-Dihydro-3H-1,2,4-triazole-3-thiones of the general formula (I-A-11) can be prepared proceeding from hydrazines of the general formula (Va) in frequently multistage processes. Numerous methods are to be found in the literature, for example condensation with isothiocyanates and subsequent cyclization, for example with formic acid or orthoesters, as described, for instance, in J. Heterocycl. Chem. 1998, 35, 29-32 ($R^1$=hetaryl, $R^2$=H, alkyl), with acid chlorides or acid anhydrides, as described, for example, in J. Chem. Soc. 1959, 3789-3794 ($R^1$=alkyl, $R^2$=alkyl) or in Helv. Chim. Acta 1996, 79, 61-83 ($R^1$=aryl, $R^2$=haloalkyl).

The formation of thiosemicarbazones from hydrazines of the general formula (Va) and subsequent oxidative cyclization with iron(III) chloride or copper perchlorate is described in J. Heterocycl. Chem. 1999, 36, 667-674 ($R^1$=aryl, $R^2$=aryl) or in J. Heterocycl. Chem. 1991, 28, 1421-1427 ($R^1$=aryl, $R^2$=alkyl).

Through reaction of thiosemicarbazides obtainable from the corresponding hydrazines (Va) with ketones and subsequent hydrocarbon elimination according to Tetrahedron Lett. 1989, 30, 2369-2370 ($R^1$=alkyl, alkenyl, $R^2$=alkyl), the synthesis of 2,4-dihydro-3H-1,2,4-triazole-3-thiones is likewise possible.

Processes Pb1 to Pb4 are suitable for preparation of embodiment I-B of the compounds of the formula (I).

Processes Pb1 and Pb2 (I-B-1)

The tetrazolinones of the general formula (I-B-1) can be divided into (I-B-1a) (n=0) and (I-B-1b) (n=1) and can be prepared, for example, by Process Pb1, as shown in the following scheme:

general formula (IIIa) or (IIIb), which are preparable from the corresponding anilines of the general formula (IVa), for example according to JP 2011/042611, with azides (for example trimethylsilyl azide or sodium azide), optionally in the presence of Lewis acids (for example aluminium chloride). Literature examples include those to be found in J. Org. Chem. 2011, 76, 216-222, in US2011/130415 A1, in J. Org. Chem. 1980, 45, 25, 5130-5136, in J. Am. Chem. Soc. 1959, 81, 12, 3076-3079, in J. Heterocycl. Chem. 2007, 44, 4, 937-943 and in Tetrahedron 1975, 31, 7, 765-775.

The N-alkylation or N-arylation of the tetrazolinones (I-B-1a') with appropriate alkylating agents or arylating agents leads to N-alkylated or N-arylated tetrazolinones of the general formula (I-B-1a). Examples of N-alkylation are described in Bioorg. Med. Chem. Lett. 1999, 9, 1251-1254. The N-arylation can be effected, for example, with arylboronic acids, for example according to Bioorg. Med. Chem. Lett. 2010, 20, 3920-3924, or alternatively by oxidation of the corresponding N-cyclohexenylated tetrazolinones (I-B-1a) or (I-B-1 b) with oxidizing agents, for example dichlorodicyano-1,4-benzoquinone (DDQ), as described in Chem. Ber. 1985, 118, 526-540. This oxidation of tetrazolinones of the formula (I-B-1a) can lead in some cases to the inventive compounds of the formula (I-B-1b).

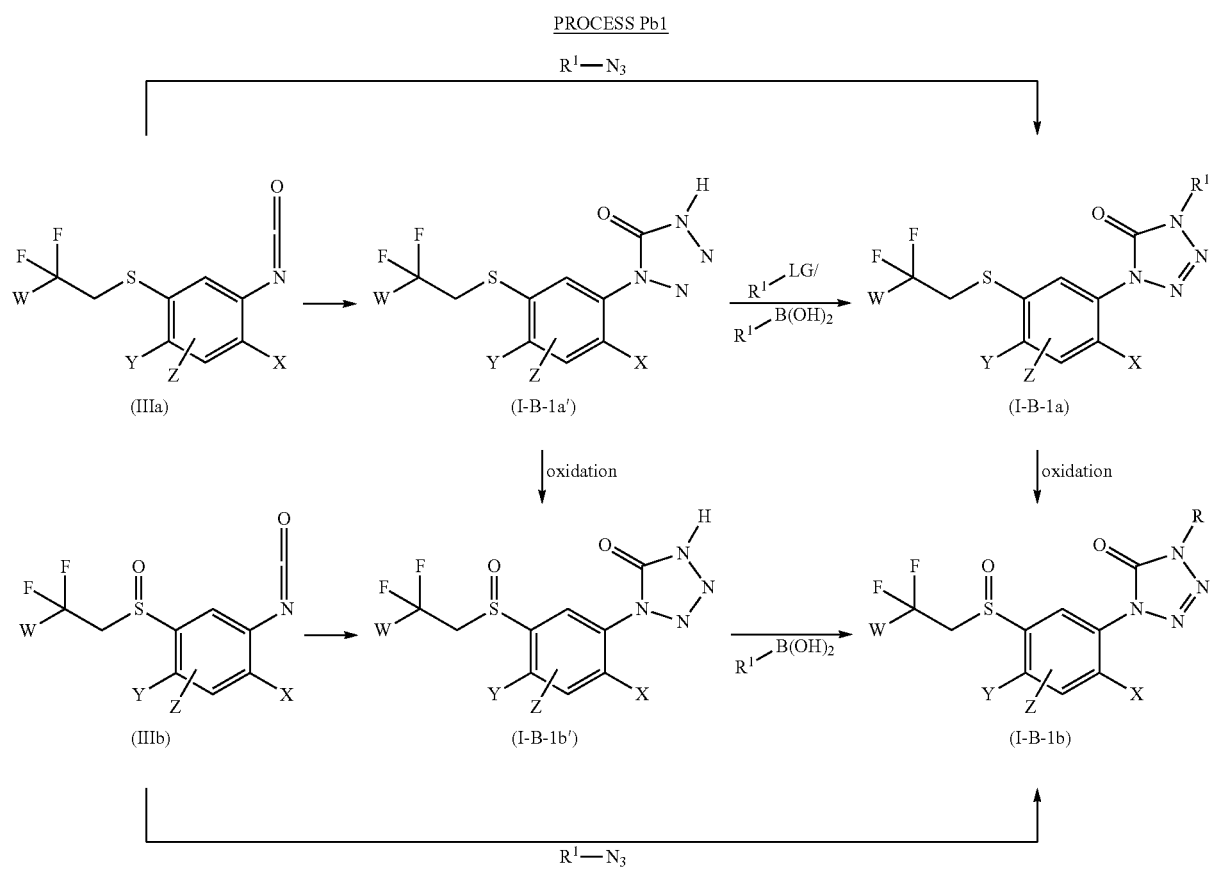

where X, Y, Z, W and $R^1$ are each as defined above and LG is a conventional leaving group such as iodide, bromide, chloride, tosylate, mesylate, methylsulphate or triflate.

Tetrazolinones of the general formula (I-B-1a') or (I-B-1b') can be prepared by cycloaddition of isocyanates of the The tetrazolinones of the general formula (I-B-1b') can analogously be N-arylated, for example with arylboronic acids according to Bioorg. Med. Chem. Lett. 2010, 20, 3920-3924.

The thioethers (I-B-1a) and (I-B-1a') can then be converted to the corresponding sulphoxides (I-B-1b) and (I-B-1b') by known processes, through reaction with oxidizing agents.

Alternatively, the cycloaddition may take place proceeding from isocyanates of the general formula (IIIa) or (IIIb) directly with appropriate alkyl or aryl azides, the majority of which are commercially available, to give the corresponding N-functionalized tetrazolinones (I-B-1a) or (I-B-1b) (for example according to J. Fluor. Chem. 2008, 129, 11, 1073-1075 or according to Tetrahedron Lett. 1999, 40, 37, 6739-6744).

Alternatively, the tetrazolinones of the general formula (I-B-1) can be prepared by Process Pb2, as shown in the following scheme:

2009, 933, 38-45. Isocyanide dihalides can be prepared, among other routes, by chlorination from isocyanates of the general formula (IIIa, A=O), isothiocyanates of the general formula (IIIa, A=S) or formamides of the general formula (Xa, PG=CHO), as described, for example, in Angew. Chem. 1967, 79, 663-680, in Synth. Commun 1997, 27, 2645-2650 or in J. Amer. Chem. Soc. 1922, 44, 2896-2903.

The requisite synthesis intermediates (IIIa) (isocyanates when V=O, isothiocyanates when V=S) and formamides (Xa, PG=CHO) are known from the literature or can be prepared from the anilines of the general formula (IVa) by methods known from the literature. Isocyanates and isothiocyanates of the general formula (IIIa) are known from JP2011/042611 or can be prepared by methods known from

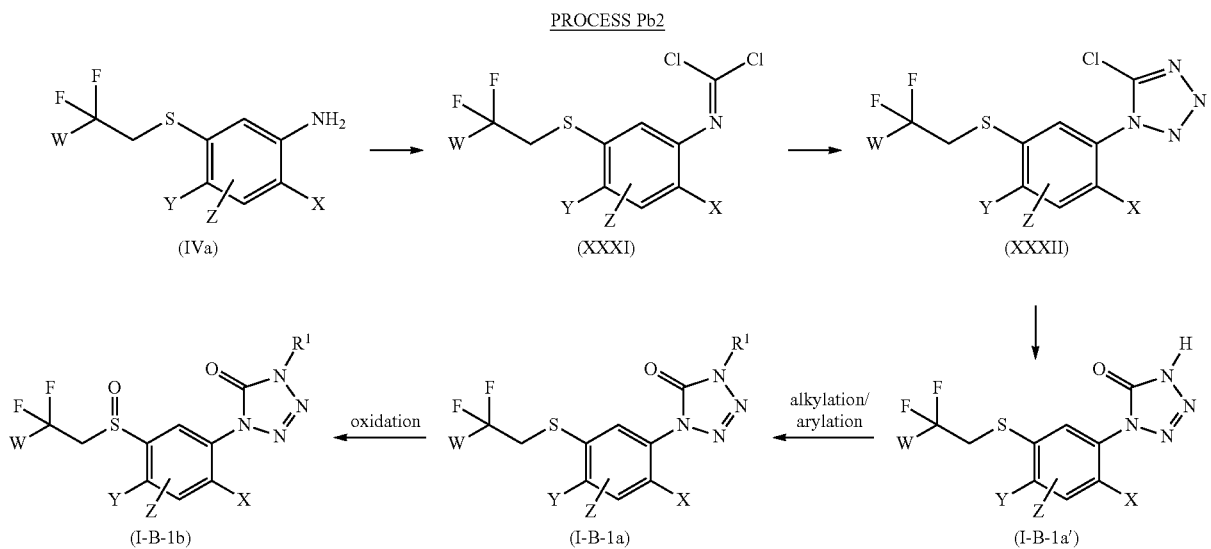

PROCESS Pb2 where X, Y, Z, W and R¹ are each as defined above.

Tetrazolinones of the general formula (I-B-1a') can alternatively be prepared by 1,3-dipolar cycloaddition of isocyanide dichlorides of the formula (XXXI) with sodium azide to give 5-chlorotetrazole (XXXII) and subsequent basic hydrolysis, as described, for example, in J. Mol. Struct.

preparation examples. Formamides of the general formula (Xa) can be prepared by methods known from the literature from anilines, for example according to J. Het. Chem. 1968, 5, 165-177; J. Med. Chem. 2001, 44(12), 1972-1985; Tetrahedron 2002, 58, 2101-2116.

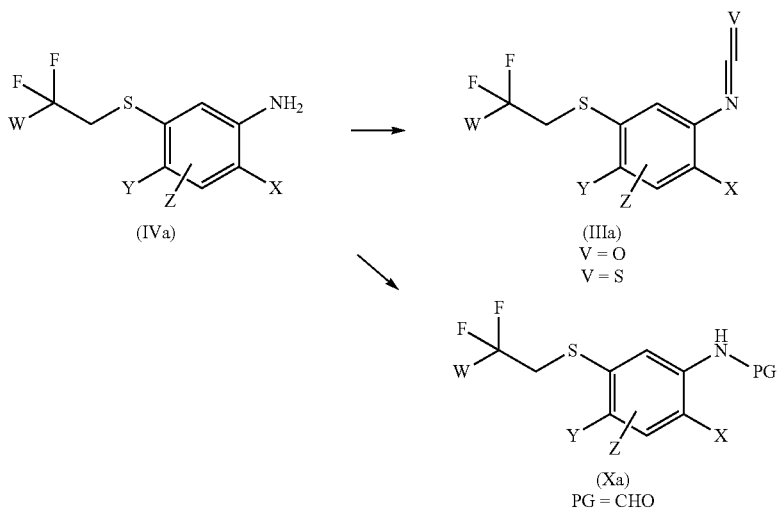

Tetrazolinones of the general formula (I-B-1a') can then lead, through N-functionalization as in Process Pb1, to the tetrazolinones of the general formula (I-B-1a).

Through oxidation of the thioethers of the general formula (I-B-1a) by methods known from the literature, it is possible to obtain the sulphoxides of the general formula (I-B-1b). Processes Pb3 and Pb4 (I-B-2)

The tetrazolinethiones of the general formula (I-B-2) can be divided into (I-B-2a) (n=0) and (I-B-2b) (n=1) and can be prepared, for example, by Process Pb3, as shown in the following scheme:

conditions, as described, for example in Can. J. Chem. 1957, 37, 101-105 or in Bull. Kor. Chem. Soc. 2012, 33, 55-59. Alternatively, azide derivatives of nickel compounds, antimony compounds, germanium compounds or arsenic compounds are usable (for example Inorg. Chem. 1987, 26, 2969-2974; J. Fluor. Chem. 2003, 122, 2, 165-170; Synthesis and Reactivity in Inorganic and Metal-Organic Chemistry 1999, 29, 1579-1592; Synthesis and Reactivity in Inorganic and Metal-Organic Chemistry 1984, 14, 477-484). Subsequent N-alkylation to give tetrazolinethiones of the general formula (I-B-2a) is possible by methods known from

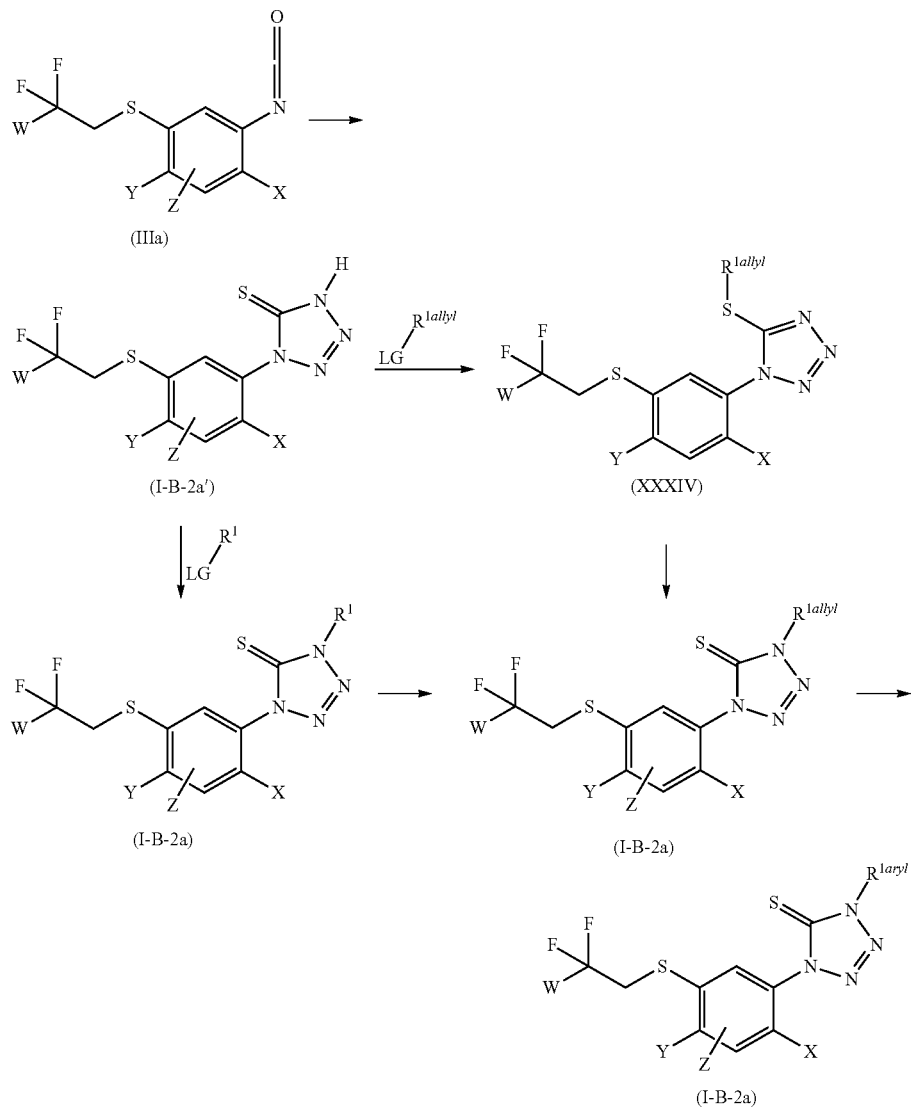

PROCESS Pb3 where X, Y, Z, W and $R^1$ are each as defined above, $R^{1allyl}$ is specifically the $R^1$ radicals that are allylic in nature and $R^{1aryl}$ is specifically $R^1$ radicals that are arylic in nature, as per the radical definitions given above.

Nitrogen-unsubstituted tetrazolinethiones of the general formula (I-B-2a') can be prepared by Process Pb3 through cycloaddition of isothiocyanates of the general formula (IIIa) with azides, for example sodium azide. The cycloaddition can be performed under neutral or basic reaction the literature, for example with α,β-unsaturated aldehydes in aza-Michael reactions to give N-(carbonylalkyl)tetrazolinethiones (Org. Lett. 2011, 13, 336-339), with acrylonitriles in Michael additions to give N-(cyanoalkyl)tetrazolinethiones (Russ. J. Appl. Chem. 1996, 69, 1841-1848), with aldehydes/amines in Mannich reactions to give N-(aminoalkyl)tetrazolinethiones (Heteroatom Chem. 2007, 18, 637-643), with formaldehyde to give N-(hydroxyalkyl) tetrazolinethiones (Monatsh. Chem. 1995, 126, 1035-1044)

or by alkylation under thermodynamic conditions with halomethyluracils (J. Org. Chem. 1985, 50, 980-987). There has also been a description of S-alkylation with allylic $R^{1\,allyl}$ to give compounds of the formula (XXXIV) with subsequent Claisen rearrangement in Chem. Ber. 1985, 118, 526-540 for synthesis of tetrazolinethiones of the general formula (I-B-2a) where LG is a conventional leaving group such as iodide, bromide, chloride, tosylate, mesylate, methylsulphate or triflate. If the alkylation is performed with $R^{1\,allyl}$=cyclohex-2-en-1-yl, a subsequent oxidation with oxidizing agents, for example dichlorodicyano-1,4-benzoquinone (DDQ) to give N-aryl-substituted tetrazolinethiones of the general formula (I-B-2a) is possible.

Tetrazolinethiones of the general formula (I-B-2a) or (I-B-2b) can alternatively be prepared by Process Pb4 through sulphonation of the tetrazolinones of the general formula (I-B-1a) or (I-B-1b), for example with phosphorus (V) sulphide or Lawesson's reagent, as described, for example, in J. Mol. Struct. 2009, 933, 38-45 or in Bioorg. Med. Chem. Lett. 2010, 20, 3920-3924, and as shown in the following scheme:

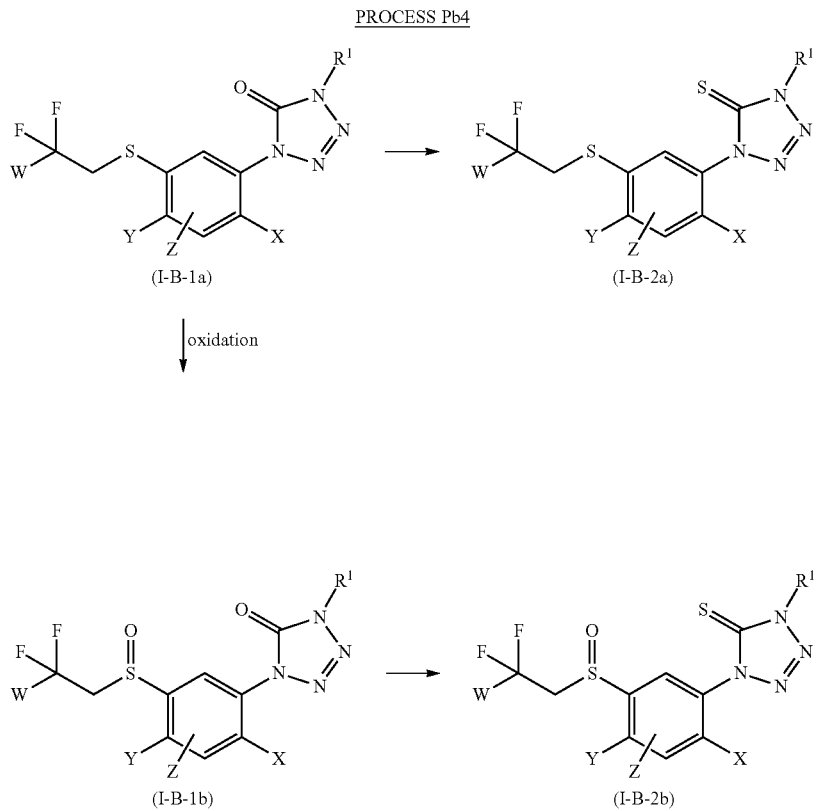

where X, Y, Z, $R^1$ and W are each as defined above.

Process Pc1 is suitable for preparation of embodiment I-C of the compounds of the formula (I).

Process Pc1 (I-C-1)

The 1,3,4-oxadiazol-2(3H)-ones of the general formula (I-C-1) can be divided into (I-C-1a) (n=0) and (I-C-1b) (n=1) and can be prepared, for example, by Process Pc1, as in the following scheme:

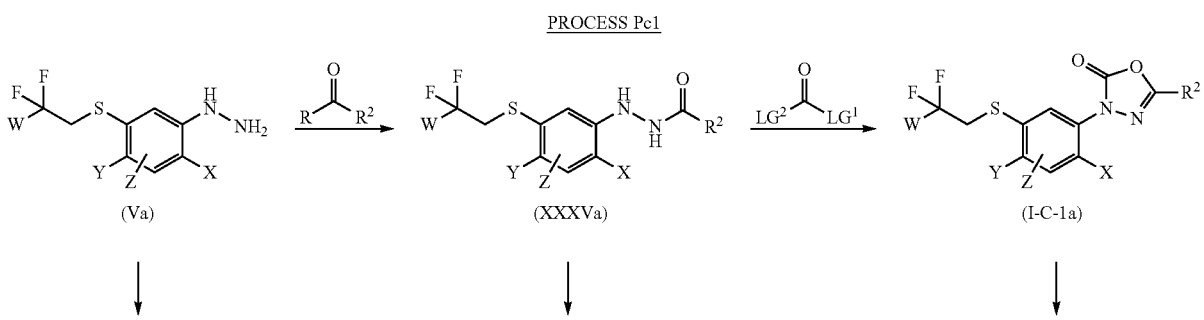

-continued

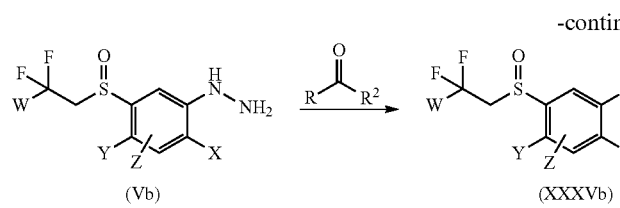

(Vb) → (XXXVb) → (I-C-1b)

where X, Y, Z, W and $R^2$ are each as defined above, R is halogen (especially chlorine) or alkylcarboxyl (especially isopropylcarboxyl) and $LG^1$ and $LG^2$ are each independently leaving groups such as chloride, alkoxide, phenoxide, imidazole, trichloromethyl or 1-hydroxypyrrolidine-2,5-dione.

1,3,4-Oxadiazol-2(3H)-ones of the general formula (I-C-1a) can be prepared by acylation of hydrazines of the general formula (Va) with acid halides or mixed anhydrides (preparable from chloroformic esters—for example isopropyl chloroformate—and acids) to give the corresponding hydrazides (XXXVa) and subsequent cyclization with C1 units, for example 1,1'-carbonyldiimidazole, phosgene, diphosgene, triphosgene, diphenyl carbonate or N-hydroxydicarboximidyl chloroformates. Literature examples can be found, for example, in J. Med. Chem. 2007, 50, 528-542, in J. Heterocycl. Chem. 1982, 19, 823-828, Bioorg. Med. Chem. 2001, 9, 1307-1323, in J. Agric. Food Chem. 2010, 58, 2643-2651 or in Pharmazie 1990, 45, 138-139.

Through oxidation of the thioethers of the general formula (I-C-1a) by methods known from the literature, it is possible to obtain the sulphoxides of the general formula (I-C-1b). Alternatively, the reactions described in process Pc1 can also be effected proceeding from sulphoxides of the general formula (Vb) directly to give sulphoxides of the general formula (I-C-1b).

Processes Pd1 to Pd4 are suitable for preparation of embodiment I-D of the compounds of the formula (I).

Processes Pd1, Pd2 and Pd3 (I-D-1)

4-Alkoxy-1,5-dihydro-2H-pyrrol-2-ones of the general formula (I-D-1) can be divided into (I-D-1a) (n=0) and (I-D-1b) (n=1) and can be prepared, for example, by Process Pd1, as in the following scheme:

PROCESS Pd1

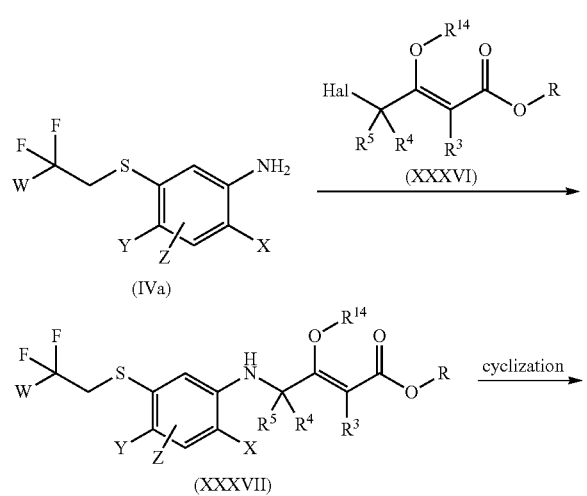

-continued

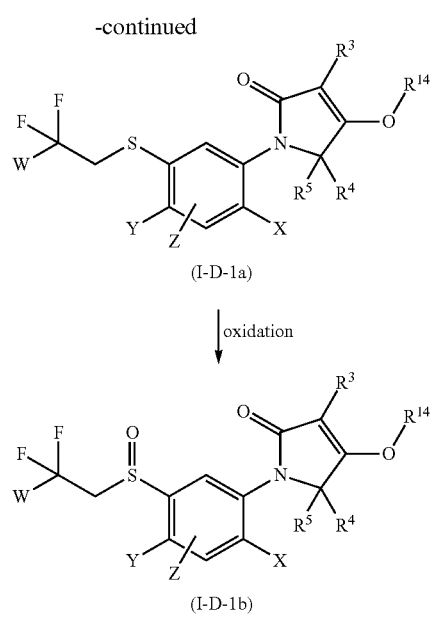

where X, Y, Z, W, $R^3$, $R^4$, $R^5$ and $R^{14}$ are each as defined above, Hal is halogen (especially chlorine, bromine, iodine) and R is optionally substituted alkyl (especially methyl, ethyl).

Through the alkylation of anilines of the general formula (IVa) with 4-halo-3-alkoxyalkenyl esters of the formula (XXXVI) (some are commercially available, or preparable by methods known from the literature; see Synthesis 1992, 391-394), it is possible to prepare compounds of the formula (XXXVII). The acid-catalysed cyclization from the alkylated anilines (XXXVII) leads to the inventive pyrrolinones of the general formula (I-D-1a), as described, for example, in J. Med. Chem. 2006, 49, 1855-1866, in Tetrahedron Lett. 1984, 25, 1871-1874 or in Jordan J. Chem. 2010, 5, 13-21 for $R^3=R^4=R^5=$hydrogen.

Through oxidation of the thioethers of the general formula (I-C-1a) by methods known from the literature, it is possible to obtain the sulphoxides of the general formula (I-C-1b).

Alternatively, 4-alkoxy-1,5-dihydro-2H-pyrrol-2-ones of the general formula (I-D-1a) in which $R^4$ and $R^5$ are each hydrogen can be prepared by Process Pd2, according to the following scheme:

PROCESS Pd2

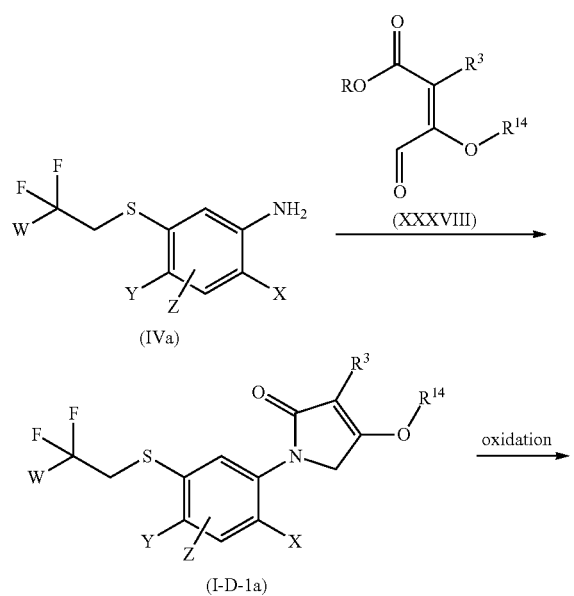
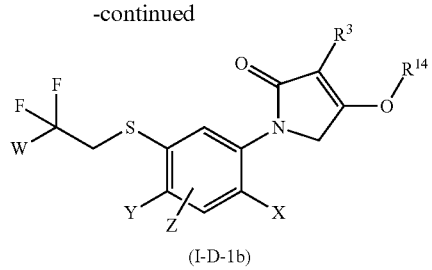

where X, Y, Z, W, R³ and R¹⁴ are each as defined above and R is optionally substituted alkyl (especially methyl, ethyl).

Through reaction of anilines of the general formula (IVa) with alkyl 3-(alkyloxy)-4-oxobut-2-enoates of the formula (XXXVIII) in a reaction sequence composed of reductive amination and cyclization, the inventive compounds of the formula (I-D-1b) can be prepared, as described, for example, in Synthesis 2002, 869-874.

Functionalizations of the 4-alkoxy position in compounds of the general formula (I-D-1a') where R¹⁴ is methyl can be performed by Process Pd3, as shown in the following scheme:

PROCESS Pd3

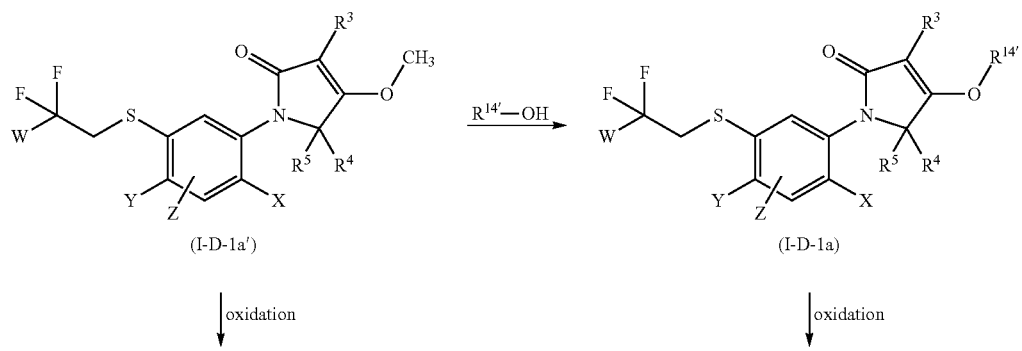

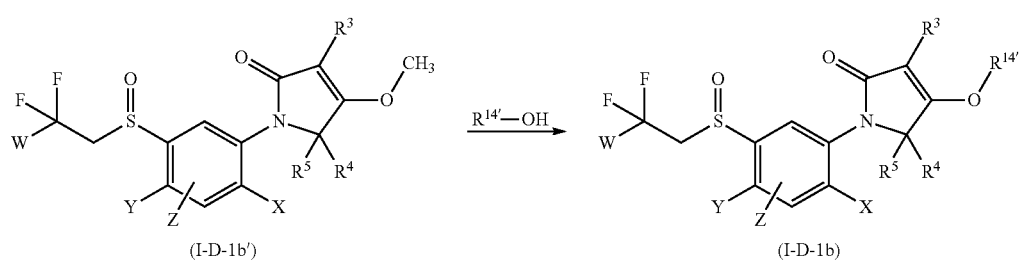

where X, Y, Z, W, R³, R⁴ and R⁵ are each as defined above and R¹⁴' represents the above-specified radical definitions for R¹⁴ except for methyl.

The introduction of different R¹⁴' radicals can be effected, for example, by alcoholysis with alcohols R¹⁴' OH under acid catalysis and in the presence of molecular sieve proceeding from methyl esters of the general formula (I-D-1a'), as described, for example, in J. Org. Chem. 2008, 73, 2345-2356 with R³=hydrogen.

Through oxidation of the thioethers of the general formula (I-D-1a) by methods known from the literature, it is possible to obtain the sulphoxides of the general formula (I-D-1b). Alternatively, the reactions described in Process Pd3 can also be effected proceeding from sulphoxides of the general formula (I-D-1b') directly to give sulphoxides of the general formula (I-D-1b).

Process Pd4 (I-D-2)

The 1-aryl-1,5-dihydro-2H-pyrrol-2-one of the formula (I-D-2b) where R⁴ and R⁵ are each hydrogen can be prepared, for example, by Process Pd4, as shown in the following scheme:

1-Aryl-1,5-dihydro-2H-pyrrol-2-ones of the formula (I-D-2a) or (I-D-2b) having a more complex substitution pattern in the 5-membered ring are obtainable by numerous further processes.

One method of preparing of 4-aryl-substituted 1-aryl-1, 5-dihydro-2H-pyrrol-2-ones of the formula (I-D-2a) or (I-D-2b) (with R²=aryl) involves reacting anilines of the formula (IVa) or (IVb) with esters of the general structure (XL-Ar) (described, for example, in JP 6145142).

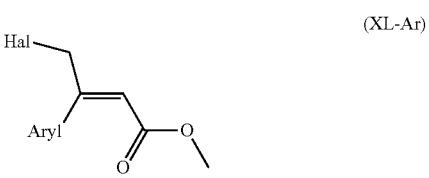
(XL-Ar)

PROCESS Pd4

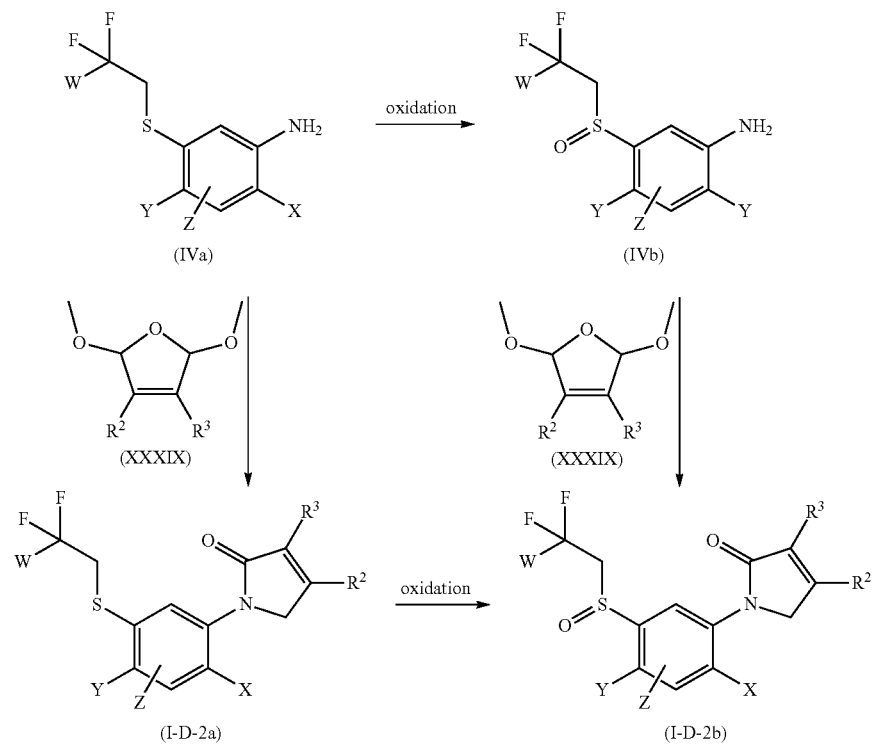

where X, Y, Z, W, R² and R³ are each as defined above.

Anilines of the formula (IVa) or (IVa) can be converted in accordance with the literature method from J. Med. Chem. 2006, 49, 6015-6026, by the reaction with 2,5-dimethoxy-2,5-dihydrofurans of the formula (XXXIX) to give the sulphides or sulphoxides of the formula (I-D-2a) or (I-D-2b).

The thioethers (I-D-2a) can be converted by known processes to the corresponding sulphoxides (I-D-2b).

Other suitable cyclization reagents are 2,4-dibromobutyryl bromide or 2,4-dichlorobutyryl chloride (analogously to JP 46037339).

-continued

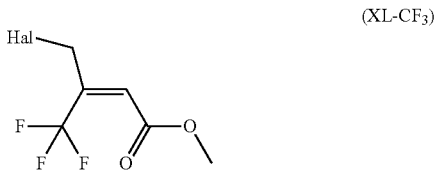
(XL-CF₃)

A process for preparing 4-aryl-substituted 1,5-dihydro-2H-pyrrol-2-ones of the formula (I-D-2a) or (I-D-2b) (with R²=aryl) by the reaction of anilines of the formula (IVa) or (IVb) with esters of the general structure (XL-Ar) is described in J. Med. Chem. 2006, 49, 1855-1866 or in Bioscience, Biotechnology, and Biochemistry 1992, 56(7), 1164-1154.

The analogous reactions of the anilines with the trifluoromethyl derivatives (XL-CF$_3$) give mixtures of the 1-aryl-1,5-dihydro-2H-pyrrol-2-ones of the formula (I-D-2a) or (I-D-2b) (with R$^2$=CF$_3$) and the corresponding double bond isomers, 1-aryl-1,3-dihydro-2H-pyrrol-2-ones (e.g. Chem. Pharm. Bull. 1985, 33(9), 4026-4029).

Process Pe1 is suitable for preparation of embodiment I-E of the compounds of the formula (I).

Process Pe1 (I-E-1)

The 1-aryl-1,3-dihydro-2H-imidazol-2-ones of the formula (I-E-1) can be divided into (I-E-1a) (n=0) and (I-E-1b) (n=1) can be prepared, for example, by Process Pe1, as in the following scheme:

means of suitable alkylating reagents of the general formula R$^2$-AG (where AG is a leaving group, for example chlorine, bromine, tosylate, mesylate or triflate) by processes that are sufficiently well-known. These syntheses are described, for example, in Can. J. Chem. 2004, 82, 1649-1661. Further synthesis variants are described in U.S. Pat. No. 3,133,079 or WO 2004/011438.

Through the conversion of corresponding carbamates, it is likewise possible to synthesize 1-aryl-1,3-dihydro-2H-imidazol-2-ones, in analogy to U.S. Pat. No. 4,279,637. The process described in J. Med. Chem. 1966, 9 (6), 858-860 uses, as starting compounds, the corresponding anilines of the formula (IVa).

The thioethers (I-E-1a) can be converted to the corresponding sulphoxides (I-E-1b) by process that are sufficiently well known through reaction with oxidizing agents.

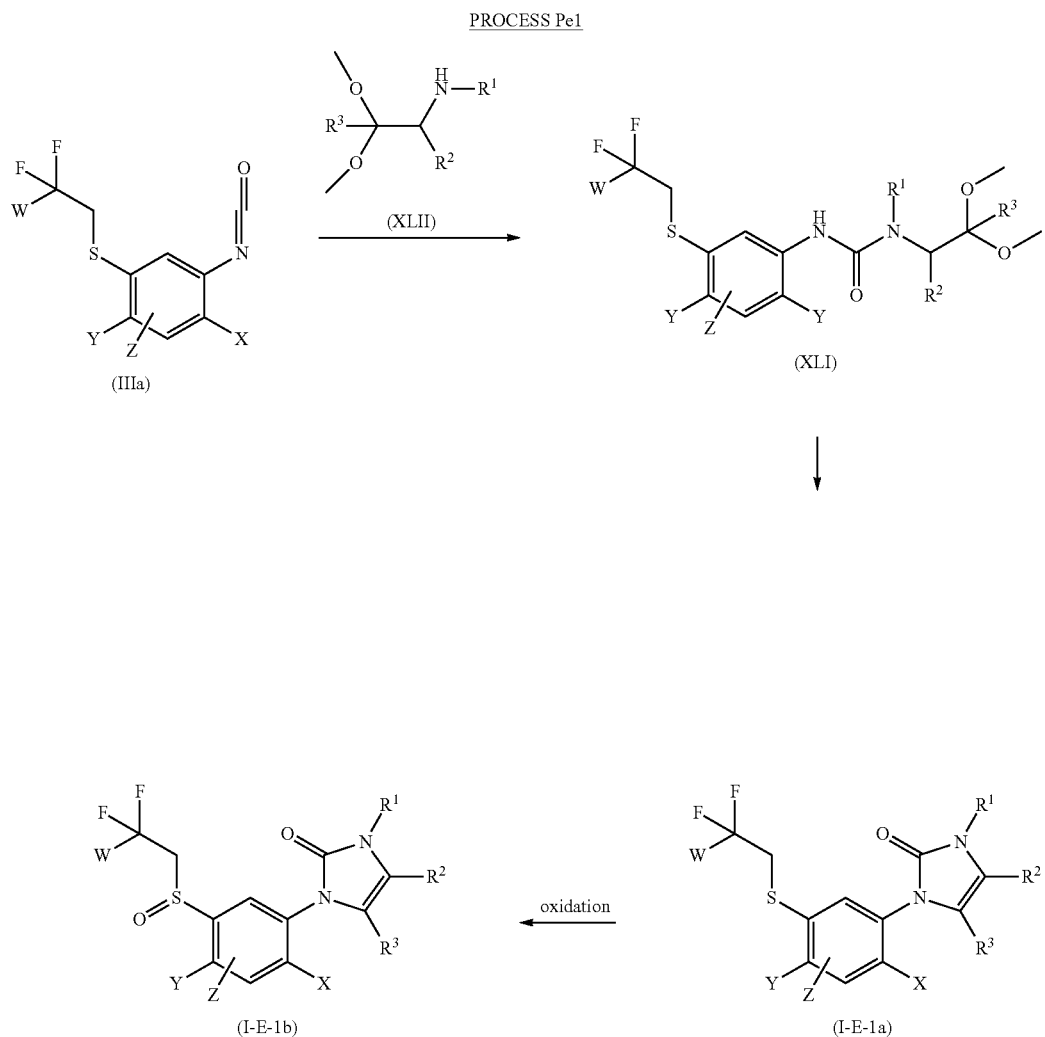

where X, Y, Z, W, R$^1$, R$^2$ and R$^3$ are each as defined above.

Isocyanates of the formula (IIIa) can be converted by the reaction with 2,2-dialkoxyethylamines of the formula (XLII) to the ureas of the formula (XLI). The subsequent acidic hydrolysis gives the 1-aryl-1,3-dihydro-2H-imidazol-2-ones of the formula (I-E-1a). It is possible to alkylate the sulphides of the formula (I-E-1a) with R$^1$=H subsequently by Process Pf1 is suitable for preparation of embodiment I-F of the compounds of the formula (I).

Process Pf1 (I-F-1)

1-Aryl-1H-pyrrole-2,5-diones of the general formula (I-F-1) can be divided into (I-F-1a) (n=0) and (I-F-1b) (n=1) and can be prepared, for example, by Process Pf1, as in the following scheme:

PROCESS Pf1

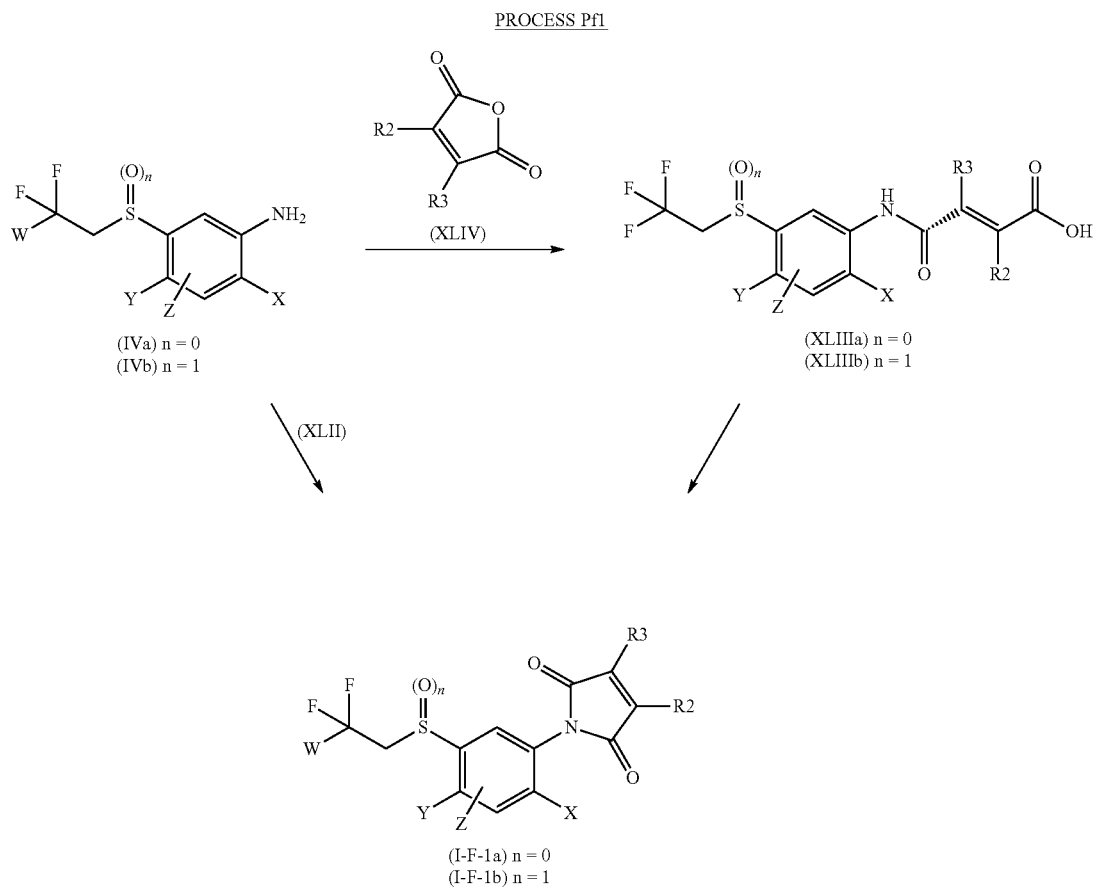

where X, Y, Z, W, $R^2$ and $R^3$ are each as defined above.

The compounds of the general formula (I-F-1a) or (I-F-1b) can be prepared by converting anilines of the formula (IV) with furan-2,5-diones of the formula (XLIV) to the corresponding 4-aryl-4-oxobut-2-enoic acids (XLIIIa) or (XLIIIb) and then cyclizing the latter in the presence of a condensing agent to give the inventive compounds of the formula (I-F-1a) or (I-F-1b), for example according to Angewandte Makromolekulare Chemie 1988, 157, 59-78 or U.S. Pat. No. 3,853,912.

Suitable condensing agents are especially dehydrating chemicals. These preferably include acid anhydrides and acid halides, for example acetic anhydride, propionic anhydride, phosphorus(V) oxide, phosphoryl chloride, phosphoryl bromide, phosphorus trichloride, phosphorus tribromide, thionyl chloride, oxalyl chloride, phosgene, diphosgene, methyl formate, ethyl formate, and also carbodiimides, for example N,N'-dicyclohexylcarbodiimide (DCC) or 1-ethyl-3-(3-dimethylaminopropyl)carbodiimide hydrochloride (EDC-HCl). Other known condensing agents are triphenylphosphine/carbon tetrachloride, 4-(4,6-dimethoxy[1.3.5]triazin-2-yl)-4-methylmorpholinium chloride hydrate or hydroxybenzotriazole (HOBt). Particular mention should be made here of the combination of 1-ethyl-3-(3-dimethylaminopropyl)carbodiimide hydrochloride (EDC-HCl) and hydroxybenzotriazole (HOBt).

Alternatively—as described in EP 260228—the 1-aryl-1H-pyrrole-2,5-diones of the formula (I-F-1a) or (I-F-1b) can also be prepared directly by the reaction of anilines of the formula (IVa) or (IVb) with furan-2,5-diones of the formula (XLII) in the presence of alkylcarboxylic acids, for example acetic acid.

The compounds of the general formula (XLIV) are commercially available or known from the literature, or can be prepared by methods known from the literature.

The thioethers (XLIIIa) or (I-F-II1a) can be converted to the corresponding sulphoxides (XLIb) or (I-F-1b) by processes that are sufficiently well-known through reaction with oxidizing agents.

The inventive compounds of the general formula (XLI) and (I-F-1) are optionally prepared using one or more diluents. Useful diluents include particularly organic solvents, for example alkyl alcohols, dialkyl ethers, toluene, xylene, chlorobenzene, dichlorobenzene, petroleum ether, hexane, cyclohexane, dichloromethane, chloroform, tetrachloromethane, tetrahydrofuran, dioxane, acetonitrile, dimethylformamide, formic acid, acetic acid and propionic acid.

The reaction temperatures in the course of performance of process I-F can be varied within a relatively wide range. In general, temperatures between 0° C. and 150° C., preferably between 10° C. and 120° C., are used.

Process Pg1 is suitable for preparation of embodiment I-G of the compounds of the formula (I).
Process Pg1 (I-G-1)

The 2-alkylimino-3-aryl-1,3-oxazoles (V=O) and 2-alkylimino-3-aryl-1,3-thiazoles (V=S) of the general formula (I) can be divided into compounds of the formula (I-G-1a) (n=0) and (I-G-1b) (n=1) and can be prepared, for example, by Process Pg1, as in the following scheme:

PROCESS Pg1

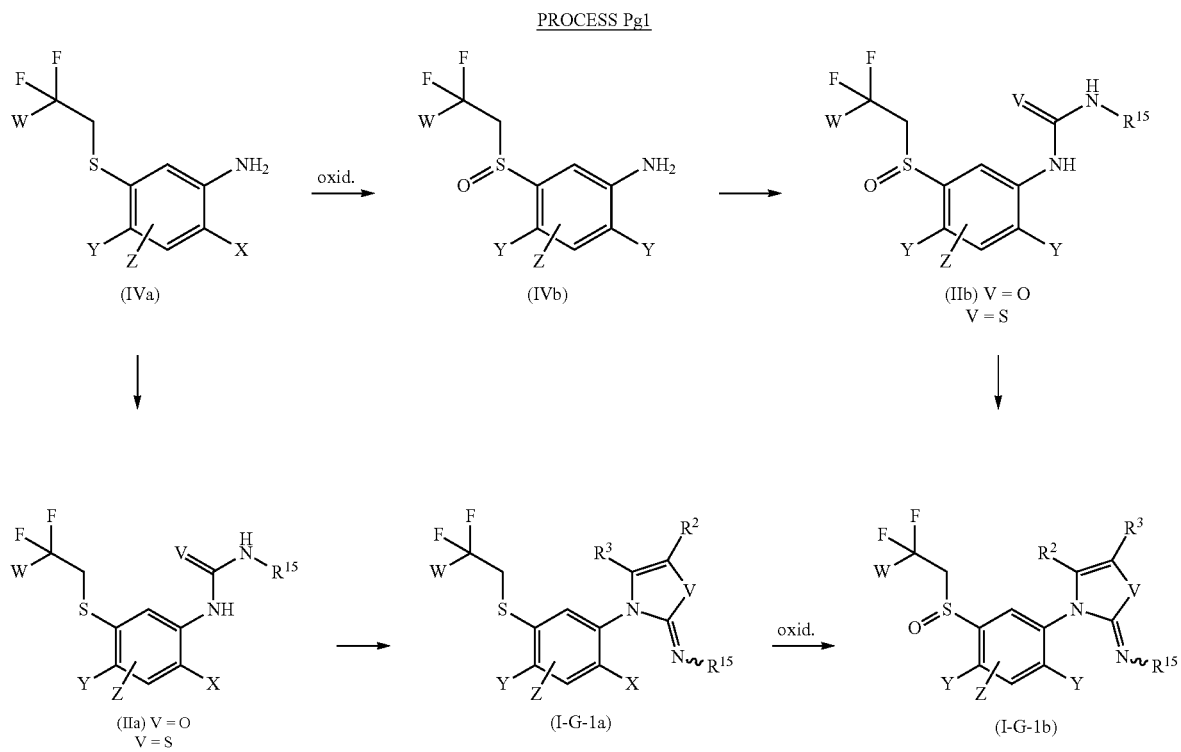

where W, X, Y, Z, $R^2$, $R^3$ and $R^{15}$ are each as defined above and V is oxygen or sulphur.

Anilines of the formula (IVa) or (IVb) can be converted to the ureas (V=O) and thioureas (S) of the formula (IIa) or (IIb) by methods known from the literature, for example according to JP 2011/042611, by admixing them with isocyanates (when V=O) and isothiocyanates (when V=S), optionally in the presence of a base and optionally in the presence of an organic solvent, or by converting them by commonly known methods to the isocyanates (V=O) and isothiocyanates (V=S) thereof and reacting the latter with amines to give the ureas or thioureas.

The ureas (V=O) and thioureas (V=S) of the general formula (IIa) or (IIb) can be used to synthesize the 2-alkylimino-3-aryl-1,3-oxazoles (V=O) and -thiazoles (V=S) of the general formula (I-G-1a) or (I-G-1b), for example by cycloacylation with an appropriate halocarbonyl derivative in an inert solvent, usually at temperatures higher than 100° C. Suitable halocarbonyl derivatives are, for example, 2-chloro-1,1-diethoxyethane when $R^2=R^3=H$ according to the U.S. Pat. No. 4,079,144,3-bromo-2-butanone when $R^2=R^3$=methyl.

In the performance of the processes according to the invention, it is optionally possible to use any commercial microwave apparatus suitable for these reactions (e.g. Anton Paar Monowave 300, CEM Discover S, Biotage Initiator 60).

Thionation:

A further general process for preparing the inventive compounds of the general formula (Ia) or (Ib) in which V is sulphur involves the conversion of the carbonyl in corresponding precursors to the thiocarbonyl group with the aid of suitable thionating reagents, for example phosphorus pentasulphide or Lawesson's reagent in a suitable solvent, for example pyridine, xylene or cumene. This variant is described in numerous publications, for example in J. Amer. Chem. Soc. 1956, 1938-1941, Chem. Pharm. Bull. 1962, 10, 647-652, U.S. Pat. No. 3,007,927, DE 2554866 or WO 2000026194.

Oxidation:

Compounds of the general formula (Ib) can be prepared through oxidation by processes known from the literature from compounds of the general formula (Ia), for example by means of an oxidizing agent in a suitable solvent and diluent. Suitable oxidizing agents are, for example, dilute nitric acid, hydrogen peroxide and peroxycarboxylic acids, for example meta-chloroperbenzoic acid. Suitable solvents are inert organic solvents, typically acetonitrile and halogenated solvents such as dichloromethane, chloroform or dichloroethane.

A large number of different methods are suitable for generating enantiomerically enriched sulphoxides, as described by A. R. Maguire in ARKIVOC, 2011(i), 1-110: metal-catalysed asymmetric oxidations of thioethers, for example with titanium and vanadium as the most frequently employed catalyst sources, in the form of $Ti(O^iPr_4)$ and $VO(acac)_2$, together with a chiral ligand and an oxidizing agent such as tert-butyl hydroperoxide (TBHP), 2-phenylpropan-2-yl hydroperoxide (CHP) or hydrogen peroxide; non-metal-catalysed asymmetric oxidations employing chiral oxidizing agents or chiral catalysts; electrochemical or biological asymmetric oxidations and also kinetic resolution of sulphoxides and nucleophilic shift (according to Andersen's method).

The enantiomers can also be obtained from the racemate by separating them preparatively, for example, on a chiral HPLC column.

Alternatively, compounds of the general formula (Ib) can be prepared by methods similar to those specified here in another sequence.

Illustration of the Starting Materials and Intermediates
Anilines of the General Formula (IVa) and (IVb)

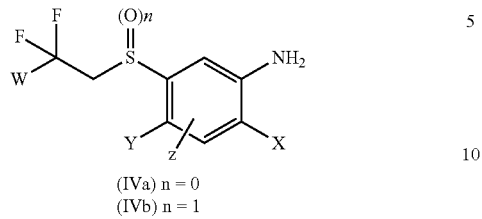

(IVa) n = 0
(IVb) n = 1

Some of the anilines of the formula (IVa) are known from the literature, for example from JP 2007/284356, or they can be synthesized by processes known from the literature, especially under the conditions specified in the preparation examples.

The compounds of the formula (IVb) are novel and can be prepared by oxidation, especially under the conditions specified in the preparation examples.

The anilines of the general formula (IVa) can preferably be prepared as in the following scheme:

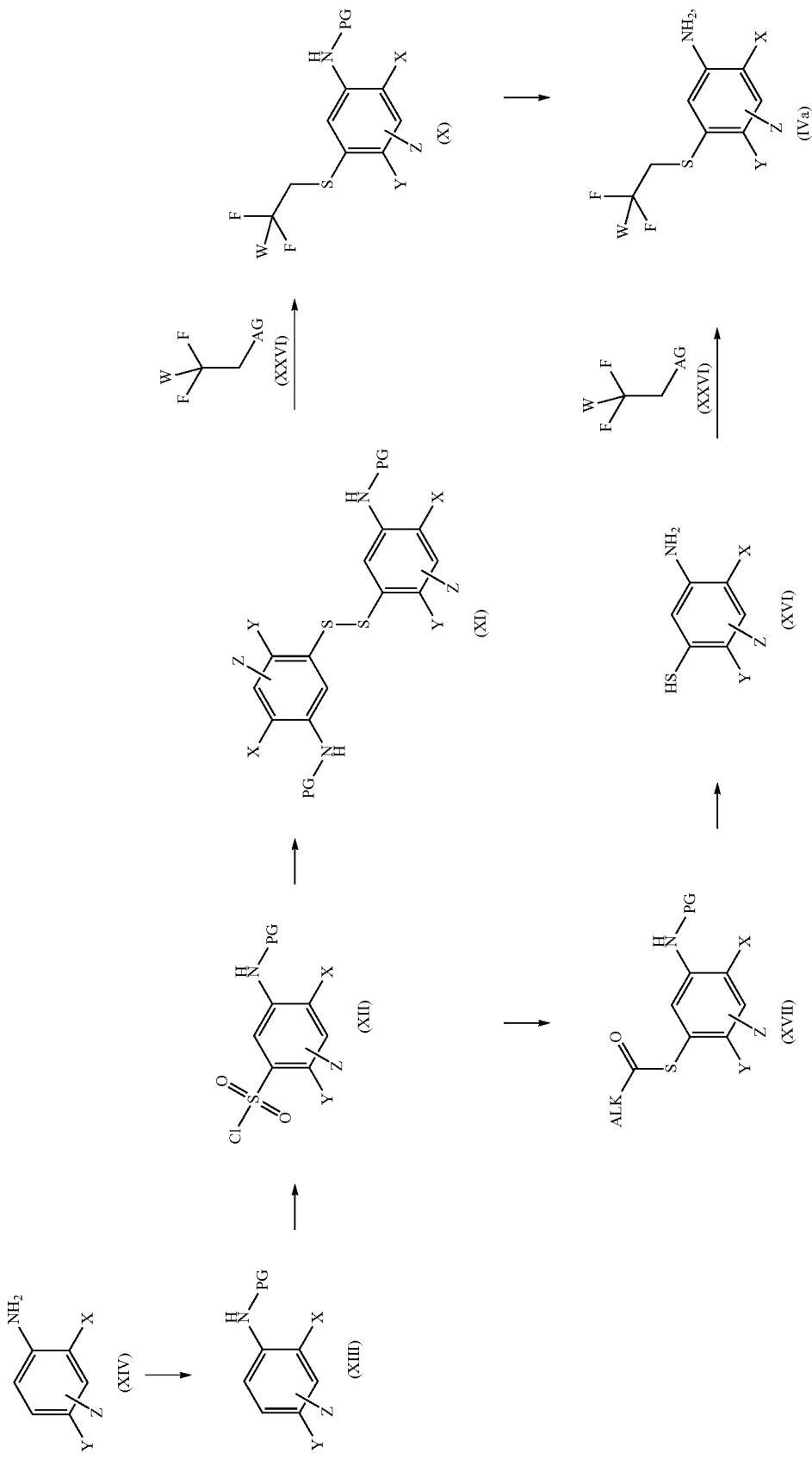

where X, Y, Z and W are each as defined above, AG is a leaving group and PG is a protecting group.

Anilines of the formula (XIV) are either commercially available or can be prepared by known methods. They can be protected with a suitable protective group, for example an acetyl group, to give compounds of the formula (XIII). In the presence of acids, acid anhydrides or acid chlorides, for example, the anilines (XIV) can be converted to the corresponding anilides (XIII). The chlorosulphonation of the protected anilines (XIII) with chlorosulphonic acid gives the corresponding sulphonyl chlorides (XII). The reduction of the sulphonyl chlorides (XII) to the disulphides (XI) is possible by methods known from the literature, for example iron in hydrochloric acid or iodide. The reaction of the disulphides (XI) with haloalkyl electrophiles of the formula (XXVI) where AG is a leaving group, for example chlorine, bromine, tosylate, mesylate or triflate, gives the sulphides (X). The protecting group can be removed by suitable methods known from the literature, so as to obtain anilines of the formula (IVa).

Instead of the reduction to the disulphide (XI), the sulphonyl chloride (XII) can be reduced with a suitable reducing agent, for example, iodine/phosphorus, to give the alkyl thioate (XVII), and then deprotected by a suitable method, for example the reaction with potassium hydroxide solution, to give thiols of the formula (XVI). The reaction of the thiols (XVI) with haloalkyl electrophiles of the formula (XXVI) gives the sulphides (IVa).

The compounds of the formulae (X), (XI), (XII), (XIII), (XVI) and (XVII) are novel and can be prepared particularly under the conditions specified in the preparation examples.

Likewise preferably, the thioethers of the formula (IVa) can alternatively be prepared according to the following scheme:

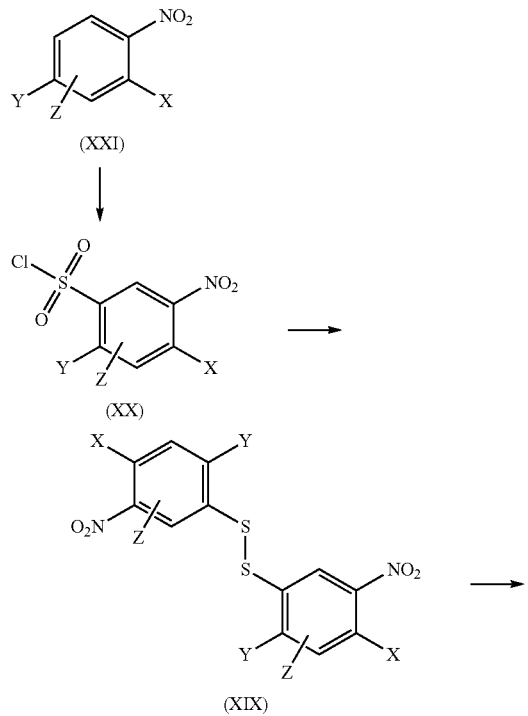

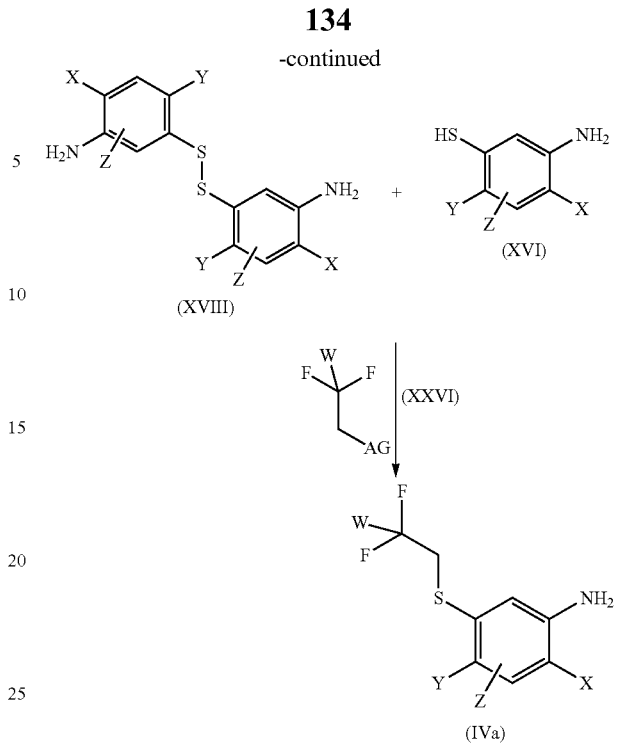

where X, Y, Z and W are each as defined above, AG is a leaving group and PG is a protecting group.

The chlorosulphonation of the nitroaromatics of the formula (XXI) with chlorosulphonic acid gives the corresponding sulphonyl chlorides (XX). The reduction of the sulphonyl chlorides (XX) to the bis(nitroaryl) disulphides (XIX) is possible by methods known from the literature, for example iodide. The reduction of the disulphides (XXI) to the disulphanediyldianilines (XIX), some of which are formed as a mixture with the corresponding aminoarylthiols (XVI), is possible with commonly known reducing agents, for example hydrogen, optionally with the aid of heterogeneous catalysts, for example, Raney nickel, platinum on activated carbon or palladium on activated carbon. The reaction of the disulphides (XVIII) or thiophenols (XVI) with haloalkyl electrophiles of the formula (XXVI) where AG is a leaving group, for example chlorine, bromine, iodine, tosylate, mesylate or triflate, gives the 3[(2,2,2-trifluoroethyl)sulphanyl]anilines of the formula (IVa).

The compounds of the formulae (XVI), (XVIII), (XIX) and (XX) are novel and can be prepared in particular under the conditions mentioned in the Preparation Examples.

Halides of the General Formula (VIIa)

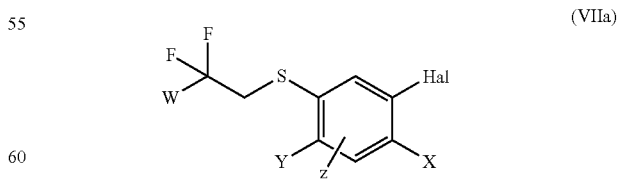

in which X, Y, Z and W are each as defined above and Hal is chlorine, bromine or iodine are known from the literature, from WO 2007/034755, JP 2007/081019, JP 2007/284385, JP 2008/260706, JP 2008/308448, JP 2009/023910 or WO 2012/176856, or can be synthesized by processes known from the literature, which may optionally be slightly modified, especially as described in the specific synthesis examples.

Suitable starting materials for the synthesis of the iodides of the general formula (VIIa) are bromides of the same formula, for example in halogen exchange reactions by methods known from the literature, optionally with metal catalysis (see H. Suzuki, Chem. Let. 1985, 3, 411-412; S. L. Buchwald, J. Amer. Chem. Soc. 2002, 124 (50), 14844-14845), especially under the conditions specified in the synthesis examples. Synthesis is likewise possible proceeding from anilines of the formula (IVa) under Sandmeyer reaction conditions, as described by E. B. Merkushev in Synthesis 1988, 12, 923-937.

Boronic Acids of the General Formula (VIIIa) and (VIIIb)

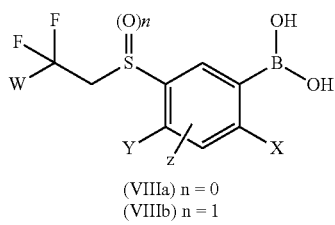

(VIIIa) n = 0
(VIIIb) n = 1 in which X, Y, Z and W are each as defined above are known from the literature, for example from WO2007/034755, JP2007/284385, JP2009/023910 and WO2012/176856, or can be synthesized by processes known from the literature, especially as in the specific synthesis examples.

Hydrazines of the General Formula (Va)

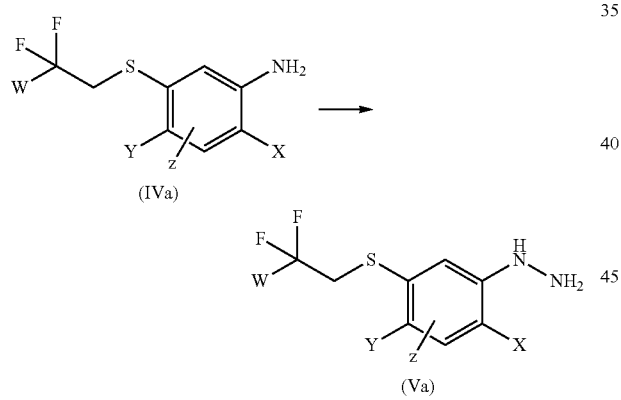

Some hydrazines of the general formula (Va) are known from the literature, for example from EP 1803712 A1 and WO 2006043635, or they can be synthesized by processes known from the literature, as described, for example, in J. Med. Chem. 2003, 46, 4405-4418.

Isocyanates of the Formula (IIIa)

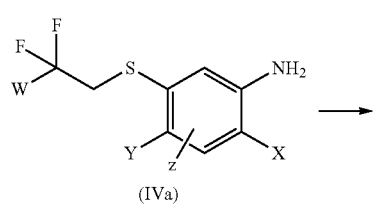

(IVa)

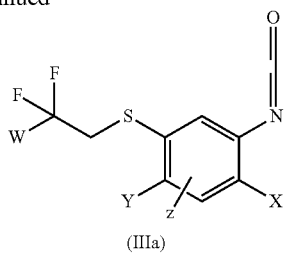

(IIIa)

Some isocyanates of the general formula (IIIa) are known from the literature, for example from JP 2011/042611 A, or they can be synthesized by processes known from the literature, as described, for example, in EP 1183229 B1, in J. Amer. Chem. Soc. 1940, 62, 2965-2966, in Angew. Chem. 1995, 107, 2746-2749 or in US2010/160388 A1, especially as described in the specific synthesis examples.

Heterocyclic Compounds of the Formula (XXII)

in which A and B are each as defined above are commercially available or known from the literature, or they can be synthesized by processes known from the literature. As examples, the different heterocyclic compounds are divided into and specified in their subclasses.

2,4-Dihydro-3H-1,2,4-triazol-3-ones of the formula (XXII-A)

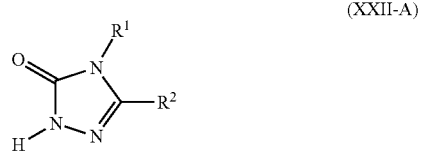

(XXII-A)

2,4-Dihydro-3H-1,2,4-triazol-3-ones of the general formula (XXII-A) are commercially available or known from the literature, or they can be synthesized by processes known from the literature (analogously to the references cited below). Examples include the following compounds: 2,4-dihydro-3H-1,2,4-triazol-3-one (commercially available), 4-cyclopropyl-5-methyl-2,4-dihydro-3H-1,2,4-triazol-3-one (commercially available), 5-methyl-2,4-dihydro-3H-1,2,4-triazol-3-one (see, for example, Chem. Ber. 1965, 98, 3025-3034), 4-cyclopropyl-5-isopropyl-2,4-dihydro-3H-1,2,4-triazol-3-one (see, for example, EP 422469 A2), 4-methyl-5-phenyl-2,4-dihydro-3H-1,2,4-triazol-3-one (see, for example, J. Med. Chem. 1990, 33, 2772-2777; Synthesis 1987, 10, 912-914), 4-ethyl-5-(trifluoromethyl)-2,4-dihydro-3H-1,2,4-triazol-3-one (see, for example, EP 657437 A1), 4-allyl-5-methoxy-2,4-dihydro-3H-1,2,4-triazol-3-one (see, for example, EP 507171 A1), 4-methyl-5-(2,2,2-trifluoroethoxy)-2,4-dihydro-3H-1,2,4-triazol-3-one (see, for example, DE 19508118 A1), 4-methyl-5-(tetrahydrofuran-3-yloxy)-2,4-dihydro-3H-1,2,4-triazol-3-one (see, for example, DE 19525973 A1), 4-cyclopropyl-5-(dimethylamino)-2,4-dihydro-3H-1,2,4-triazol-3-one (see, for example, EP 422469 A2), 4-amino-5-(methoxymethyl)-2,4-dihydro-3H-1,2,4-triazol-3-one (see, for example, EP 422469 A2), 4-(dimethylamino)-5-(trifluoromethyl)-2,4-dihydro-3H-1,2,4-triazol-3-one (see, for example, DE 4339412 A1; EP 726258 A1), 4-amino-5-(dimethylamino)-2,4-dihydro-3H-1,2,4-triazol-3-one (see, for example, EP 415196 A2), 4-methoxy-5-methyl-2,4-dihydro-3H-1,2,4-triazol-3-one (see, for example, EP 422469 A2; DE 4239296 A1), 5-ethoxy-4-methoxy-2,4-dihydro-3H-1,2,4-triazol-3-one (see, for example, EP 534266 A1), 4-methyl-5-(methylsulphanyl)-2,4-dihydro-3H-1,2,4-triazol-3-one (commercially available), 4-cyclopropyl-5-(methylsulphanyl)-2,4-dihydro-3H-1,2,4-triazol-3-one (see, for example, DE 3936623 A1; U.S. Pat. No. 5,599,944 A), 4-methyl-5-[(trifluoromethyl)sulphanyl]-2,4-dihydro-3H-1,2,4-triazol-3-one (see, for example, DE 19508119 A1), 4-ethyl-5-(methylsulphanyl)-2,4-dihydro-3H-1,2,4-triazol-3-one (see, for example, Tetrahedron 2001, 57, 2003-2010), 5-bromo-4-cyclopropyl-2,4-dihydro-3H-1,2,4-triazol-3-one (see, for example, EP 425948 A2).

1,4-Dihydro-5H-tetrazol-5-ones of the general formula (XXII-B)

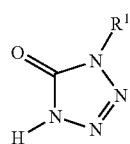

(XXII-B)

1,4-Dihydro-5H-tetrazol-5-ones of the general formula (XXII-B) are commercially available or known from the literature, or can be synthesized by processes known from the literature. Examples include: 1,4-dihydro-5H-tetrazol-5-one (commercially available), 1-(2,2,2-trifluoroethyl)-1,4-dihydro-5H-tetrazol-5-one (see, for example, EP 711761 A1; EP 643049 A1); 1-(4-chlorophenyl)-1,4-dihydro-5H-tetrazol-5-one (see, for example, J. Org. Chem. 1980, 45, 5130-5136; Chem. Lett. 2011, 40, 1149-1151; J. Heterocycl. Chem. 2007, 44, 937-943), 1-methyl-1,4-dihydro-5H-tetrazol-5-one (see, for example, U.S. Pat. No. 5,502,204 A1; J. Amer. Chem. Soc. 1959, 81, 3076-3079; US 20110130415), 1-isopropyl-1,4-dihydro-5H-tetrazol-5-one (see, for example, EP 643049 A1; EP 638561 A1; J. Med. Chem. 1986, 29, 2290-2297).

1,3,4-Oxadiazol-2(3H)-ones of the formula (XXII-C)

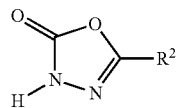

(XXII-C)

1,3,4-Oxadiazol-2(3H)-ones of the formula (XXII-C) are commercially available or known from the literature, or can be synthesized by processes known from the literature. One example is: 5-(trifluoromethyl)-1,3,4-oxadiazol-2(3H)-one (commercially available).

1,5-Dihydro-2H-pyrrol-2-ones of the formula (XXII-D)

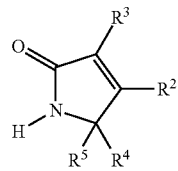

(XXII-D)

1,5-Dihydro-2H-pyrrol-2-ones of the formula (XXII-D) are commercially available or known from the literature, or can be synthesized by processes known from the literature. One example is: 4-methoxy-1,5-dihydro-2H-pyrrol-2-one (commercially available).

Compounds of the General Formula (XXIII) and (XXIII')

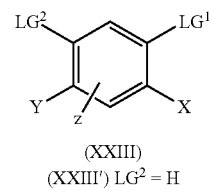

(XXIII)
(XXIII') $LG^2 = H$ in which Z is as defined above, X is hydrogen or an electron-withdrawing group (especially nitro, chlorine, fluorine, cyano), Y represents electron-withdrawing substituents (especially nitro, chlorine, fluorine, cyano), $LG^1$ represents typical leaving groups in nucleophilic substitution reactions (especially fluoride, chloride) and $LG^2$ may be hydrogen or represent typical leaving groups in nucleophilic substitution reactions (especially fluoride, chloride) are commercially available or known from the literature, or can be synthesized by processes known from the literature.

Examples include the following commercially available compounds: 2,4,5-trifluorobenzonitrile (Y=CN, X=$LG^1$=$LG^2$=F, Z=H), 2,4-difluorobenzonitrile (Y=CN, X=Z=H, $LG^1$=$LG^2$=F), 3,4-difluorobenzonitrile (Y=CN, X=$LG^1$=F, $LG^2$=Z=H).

Compounds of the General Formula (XXIV) and (XXIV')

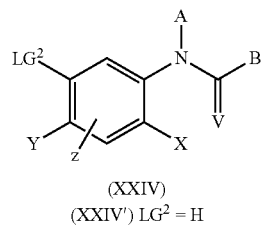

(XXIV)
(XXIV') $LG^2 = H$ in which A, B, V and Z are each as defined above, X is hydrogen or an electron-withdrawing group (especially nitro, chloride, fluoride, cyano), Y represents electron-withdrawing substituents (especially nitro, chloride, fluoride, cyano) and $LG^2$ may be hydrogen or represent typical leaving groups in nucleophilic substitution reactions (especially fluoride, chloride) are commercially available or known from the literature, or can be prepared by methods known from the literature, especially as described in the specific synthesis examples.

Examples include the following compounds: 4-[4-cyclopropyl-5-oxo-3-(trifluoromethyl)-4,5-dihydro-1H-1,2,4-triazol-1-yl]-2,5-difluorobenzonitrile (Y=CN, X=$LG^2$=F, Z=H) (see synthesis examples), ethyl 4-methyl-5-oxo-1-phenyl-4,5-dihydro-1H-1,2,4-triazole-3-carboxylate (Y=CN, X=F, LG²=Z=H) (commercially available), methyl 1-(2-fluoro-4-methylphenyl)-4-isopropyl-5-oxo-4,5-dihydro-1H-1,2,4-triazole-3-carboxylate (synthesis according to DE 2725148).

Thiols of the General Formula (XXV)

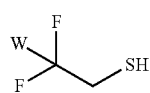

(XXV)

in which W is as defined above are commercially available or known from the literature, or are synthesized by processes known from the literature.

Examples include the following thiols: 2,2,2-trifluoroethanethiol (W=F) (commercially available), 2,2-difluoroethanethiol (W=H) (synthesis according to J. Amer. Chem. Soc. 1963, 85, 749-754), 2-chloro-2,2-difluoroethanethiol (W=Cl) (synthesis according to Phosp., Sulf., Sil. and rd. Elem. 1996, 119, 161-168).

Electrophiles of the General Formula (XXVI)

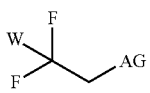

(XXVI)

in which W is as defined above and AG is halogen (especially chlorine, iodine) are commercially available or known from the literature, or are synthesized by processes known from the literature.

Examples include the following commercially available electrophiles: 2-chloro-1,1,1-trifluoroethane (W=F, AG=Cl), 2-chloro-1,1-difluoroethane (W=H, AG=Cl), 2-bromo-1,1,1-trifluoroethane (W=F, AG=Br), 2-bromo-1,1-difluoroethane (W=H, AG=Br), 2-iodo-1,1,1-trifluoroethane (W=F, AG=I), 2-iodo-1,1-difluoroethane (W=H, AG=I), 2,2,2-trifluoroethyl methanesulphonate (W=F, AG=—SO₂Me), 2,2,2-trifluoroethyl triflate (W=F, AG=—SO₂CF₃), 2,2,2-trifluoroethyl tosylate (W=F, AG=—SO₂(4-CH₃C₆H₄))

Furan-2,5-diones of the general formula (XLIV)

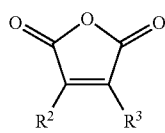

(XLIV)

are known from the literature or can be synthesized by processes known from the literature.

Examples include the following commercially available furandiones: 3-bromofuran-2,5-dione, 3,4-dichlorofuran-2,5-dione, 3-methylfuran-2,5-dione, 3,4-dimethylfuran-2,5-dione.

Use

The inventive active ingredients, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection agents. They are effective against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Psylliodes* spp., *Ptinus* spp., *Rhizobius ventralis*, *Rhizopertha dominica*, *Sitophilus* spp., *Sphenophorus* spp., *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Cochliomyia* spp., *Contarinia* spp., *Cordylobia anthropophaga*, *Culex* spp., *Cuterebra* spp., *Dacus oleae*, *Dasyneura* spp., *Delia* spp., *Dermatobia hominis*, *Droso-*

*phila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia* spp., *Phorbia* spp., *Prodiplosis* spp., *Psila rosae*, *Rhagoletis* spp., *Stomoxys* spp., *Tabanus* spp., *Tannia* spp., *Tetanops* spp., *Tipula* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale*, *Ancylostoma ceylanicum*, *Acylostoma braziliensis*, *Ancylostoma* spp., *Ascaris lumbricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Strongyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichiura*, *Wuchereria bancrofti*.

It is furthermore possible to control protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma pini*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes* spp., *Trioza* spp., *Typhlocyba* spp., *Unaspis* spp., *Viteus vitifolii*, *Zygina* spp.

From the order of the Hymenoptera, for example, *Athalia* spp., *Diprion* spp., *Hoplocampa* spp., *Lasius* spp., *Monomorium pharaonis*, *Vespa* spp.

From the order of the Isopoda, for example, *Armadillidium vulgare*, *Oniscus asellus* and *Porcellio scaber*.

From the order of the Isoptera, for example, *Acromyrmex* spp., *Atta* spp., *Cornitermes cumulans*, *Microtermes obesi*, *Odontotermes* spp., *Reticulitermes* spp.

From the order of the Lepidoptera, for example, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia kuehniella*, *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthedon* spp., *Tecia solanivora*, *Thermesia gemmatalis*, *Tinea pellionella*, *Tineola bisselliella*, *Tortrix* spp., *Trichoplusia* spp., *Tuta absoluta*, *Virachola* spp.

From the order of the Orthoptera, for example, *Acheta domesticus*, *Blatta orientalis*, *Blattella germanica*, *Dichroplus* spp., *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella* spp.

From the order of the Thysanoptera, for example, *Anaphothrips obscurus*, *Baliothrips biformis*, *Drepanothris reu-*

*teri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

If appropriate, the inventive compounds can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*mycoplasma*-like organisms) and RLO (*rickettsia*-like organisms). If appropriate, they can also be used as intermediates or precursors for the synthesis of other active ingredients.

The present invention further relates to formulations and use forms prepared therefrom as crop protection compositions and/or pesticides, for example drench, drip and spray liquors, comprising at least one of the inventive active ingredients. In some cases, the use forms comprise further crop protection compositions and/or pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations optionally comprise, as well as one or more inventive active ingredients, further active agrochemical ingredients.

These are preferably formulations or use forms which comprise auxiliaries, for example extenders, solvents, spontaneity promoters, carriers, emulsifiers, dispersants, antifreezes, biocides, thickeners and/or further auxiliaries, for example adjuvants. An adjuvant in this context is a component which enhances the biological effect of the formulation, without the component itself having any biological effect. Examples of adjuvants are agents which promote retention, spreading, adhesion to the leaf surface or penetration.

These formulations are produced in a known manner, for example by mixing the active ingredients with auxiliaries, for example extenders, solvents and/or solid carriers and/or further auxiliaries, for example surfactants. The formulations are produced either in suitable facilities or else before or during application.

The auxiliaries used may be substances suitable for imparting special properties, such as certain physical, technical and/or biological properties, to the formulation of the active ingredient, or to the use forms prepared from these formulations (for example ready-to-use crop protection compositions such as spray liquors or seed dressing products).

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons such as xylene, toluene or alkylnaphthalenes, chlorinated aromatic or chlorinated aliphatic hydrocarbons such as chlorobenzene, chloroethylene or methylene chloride, aliphatic hydrocarbons such as cyclohexane, paraffins, petroleum fractions, mineral and vegetable oils, alcohols such as methanol, ethanol, isopropanol, butanol or glycol and their ethers and esters, ketones such as acetone, methyl ethyl ketone, methyl isobutyl ketone or cyclohexanone, strongly polar solvents such as dimethyl sulphoxide, and water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous when one of the active ingredients and/or one of the inert carriers is insoluble in water and when application is effected in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam formers or antifoams may also be present.

In addition, the formulations and the use forms derived therefrom may also comprise, as additional auxiliaries, stickers such as carboxymethyl cellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the active ingredients can be combined with any solid or liquid additive which is commonly used for formulation purposes.

Useful retention promoters include all those substances which reduce the dynamic surface tension, for example dioctyl sulphosuccinate, or increase the viscoelasticity, for example hydroxypropylguar polymers.

Penetrants contemplated in the present context include all those substances which are commonly used to promote the penetration of active agrochemical ingredients into plants. Penetrants are defined in this context by their ability to penetrate from the (generally aqueous) application liquor and/or from the spray coating into the cuticle of the plant and thereby increase the mobility of active ingredients in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations contain preferably between 0.00000001% and 98% by weight of active ingredient or more preferably between 0.01% and 95% by weight of active ingredient, more preferably between 0.5% and 90% by weight of active ingredient, based on the weight of the formulation.

The active ingredient content of the use forms (crop protection compositions) prepared from the formulations can vary within wide limits. The active ingredient concentration of the use forms may typically be between 0.00000001% and 95% by weight of active ingredient, preferably between 0.00001% and 1% by weight, based on the weight of the use form. The compounds are applied in a customary manner appropriate for the use forms.

The inventive active ingredients can be used as such or in formulations thereof, including in a mixture with one or more suitable fungicides, bactericides, acaricides, nematicides, insecticides, microbicides, fertilizers, attractants, phytotonics, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. In addition, plant growth can be improved by those combinations which enhance tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processibility of the harvested products. In general, combination of the inventive active ingredients and mixing partners gives synergistic effects, meaning that the efficacy of the mixture in question is greater than the efficacy of the individual components. It is generally possible to use the combinations in premixes, tank mixes or ready mixes, and also in seed applications.

Particularly favourable mixing partners are, for example, the following:

Insecticides/Acaricides/Nematicides

The active ingredients mentioned here under their "common names" are known and are described for example in The Pesticide Manual, 14th Ed., British Crop Protection Council 2006, or can be searched for on the Internet (e.g. http://www.alanwood.net/pesticides).

(1) Acetylcholinesterase (AChE) inhibitors, for example
carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or
organophosphates, for example acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists, for example cyclodiene organochlorines, e.g. chlordane and endosulfan; or
phenylpyrazoles (fiproles), e.g. ethiprole and fipronil.

(3) Sodium channel modulators/voltage-dependent sodium channel blockers, for example
pyrethroids, for example acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrine (pyrethrum), resmethrin, silafluofen, tefluthrin, tetramethrin, tetramethrin [(1R) isomers], tralomethrin and transfluthrin; or
DDT; or methoxychlor.
(4) Nicotinergic acetylcholine receptor (nAChR) agonists, for example
neonicotinoids, for example acetamiprid, clothianidin, dinotefuran, imidacloprid, nitenpyram, thiacloprid and thiamethoxam; or
nicotine.
(5) Nicotinergic acetylcholine receptor (nAChR) allosteric activators, for example
spinosyns, for example spinetoram and spinosad.
(6) Chloride channel activators, for example
avermectins/milbemycins, for example abamectin, emamectin benzoate, lepimectin and milbemectin.
(7) Juvenile hormone imitators, for example
juvenile hormone analogs, for example hydroprene, kinoprene and methoprene; or
fenoxycarb; or pyriproxyfen.
(8) Active ingredients with unknown or nonspecific mechanisms of action, for example
alkyl halides, for example methyl bromide and other alkyl halides; or
chloropicrin; or sulphuryl fluoride; or borax; or tartar emetic.
(9) Selective antifeedants, for example pymetrozine; or flonicamid
(10) Mite growth inhibitors, for example clofentezine, hexythiazox and diflovidazin; or
etoxazole.
(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.
(12) Oxidative phosphorylation inhibitors, ATP disruptors, for example diafenthiuron; or
organotin compounds, e.g. azocyclotin, cyhexatin and fenbutatin oxide; or
propargite; or tetradifon.
(13) Oxidative phosphorylation decouplers that interrupt the H proton gradient, for example chlorfenapyr, DNOC and sulfluramid.
(14) Nicotinergic acetylcholine receptor antagonists, for example bensultap, cartap hydrochloride, thiocyclam, and thiosultap-sodium.
(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.
(16) Chitin biosynthesis inhibitors, type 1, for example buprofezin.
(17) Molting disruptors, dipteran, for example cyromazine.
(18) Ecdysone receptor agonists, for example chromafenozide, halofenozide, methoxyfenozide and tebufenozide.
(19) Octopaminergic agonists, for example amitraz.
(20) Complex-III electron transport inhibitors, for example hydramethylnone; or acequinocyl; or fluacrypyrim.
(21) Complex-I electron transport inhibitors, for example METI acaricides, for example fenazaquin, fenpyroximate, pyrimidifen, pyridaben, tebufenpyrad and tolfenpyrad; or rotenone (Derris).
(22) Voltage-dependent sodium channel blockers, for example indoxacarb; or metaflumizone.
(23) Inhibitors of acetyl-CoA carboxylase, for example tetronic and tetramic acid derivatives, for example spirodiclofen, spiromesifen and spirotetramat.
(24) Complex-IV electron transport inhibitors, for example phosphines, for example aluminium phosphide, calcium phosphide, phosphine and zinc phosphide; or cyanide.
(25) Complex-II electron transport inhibitors, for example cyenopyrafen.
(28) Ryanodine receptor effectors, for example
diamides, for example chlorantraniliprole and flubendiamide.
Further active ingredients having an unknown mechanism of action, for example amidoflumet, azadirachtin, benclothiaz, benzoximate, bifenazate, bromopropylate, chinomethionat, cryolite, cyantraniliprole (Cyazypyr), cyflumetofen, dicofol, diflovidazin, fluensulphone, flufenerim, flufiprole, fluopyram, fufenozide, imidaclothiz, iprodione, meperfluthrin, pyridalyl, pyrifluquinazon, tetramethylfluthrin and iodomethane; and additionally preparations based on *Bacillus firmus* (particularly strain CNCM 1-1582, for example VOTiVO™, BioNem), and the following known active compounds:
3-bromo-N-{2-bromo-4-chloro-6-[(1-cyclopropylethyl) carbamoyl]phenyl}-1-(3-chloropyridin-2-yl)-1H-pyrazole-5-carboxamide (known from WO 2005/077934), 4-{[(6-bromopyrid-3-yl)methyl](2-fluoroethyl)amino}furan-2 (5H)-one (known from WO 2007/115644), 4-{[(6-fluoropyrid-3-yl)methyl](2,2-difluoroethyl)amino}furan-2 (5H)-one (known from WO 2007/115644), 4-{[(2-chloro-1, 3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), flupyradifurone, 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl) methyl](cyclopropyl)amino}furan-2(5H)-one (known from WO 2007/115643), 4-{[(6-chloropyrid-3-yl)methyl](cyclopropyl)amino}furan-2(5H)-one (known from EP A 0 539 588), 4-{[(6-chloropyrid-3-yl)methyl](methyl) amino}furan-2(5H)-one (known from EP A 0 539 588), {[1-(6-chloropyridin-3-yl)ethyl](methyl)oxido-$\lambda^4$-sulphanylidene}cyanamide (known from WO2007/149134) and its diastereomers {[(1R)-1-(6-chloropyridin-3-yl)ethyl] (methyl)oxido-$\lambda^4$-sulphanylidene}cyanamide (A) and {[(1S)-1-(6-chloropyridin-3-yl)ethyl](methyl)oxido-$\lambda^4$-sulphanylidene}cyanamide (B) (likewise known from WO 2007/149134) and sulfoxaflor and its diastereomers [(R)-methyl(oxido){(1R)-1-[6-(trifluoromethyl)pyridin-3-yl] ethyl}-$\lambda^4$-sulphanylidene]cyanamide (A1) and [(S)-methyl (oxido){(1S)-1-[6-(trifluoromethyl)pyridin-3-yl]ethyl}-$\lambda^4$-sulphanylidene]cyanamide (A2), identified as diastereomer group A (known from WO 2010/074747, WO 2010/074751), [(R)-methyl(oxido){(1S)-1-[6-(trifluoromethyl)pyridin-3-yl]ethyl}-λ⁴-sulphanylidene]cyanamide (B1) and [(S)-methyl(oxido){(1R)-1-[6-(trifluoromethyl)pyridin-3-yl]ethyl}-λ⁴-sulphanylidene]cyanamide (B2), identified as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-{2-fluoro-4-methyl-5-[(2,2,2-trifluoroethyl)sulphinyl]phenyl}-3-(trifluoromethyl)-1H-1,2,4-triazol-5-amine (known from WO 2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO 2008/066153), 2-cyano-3-(difluoromethoxy)-N,N-dimethylbenzenesulphonamide (known from WO 2006/056433), 2-cyano-3-(difluoromethoxy)-N-methylbenzenesulphonamide (known from WO 2006/100288), 2-cyano-3-(difluoromethoxy)-N-ethylbenzenesulphonamide (known from WO 2005/035486), 4-(difluoromethoxy)-N-ethyl-N-methyl-1,2-benzothiazol-3-amine-1,1-dioxide (known from WO 2007/057407), N-[1-(2,3-dimethylphenyl)-2-(3,5-dimethylphenyl)ethyl]-4,5-dihydro-1,3-thiazol-2-amine (known from WO 2008/104503), {[(2E)-3-(4-chlorophenyl)prop-2-en-1-yl]-5-fluorospiro[indol-3,4'-piperidine]-1(2H)-yl}(2-chloropyridin-4-yl)methanone (known from WO 2003/106457), 3-(2,5-dimethylphenyl)-4-hydroxy-8-methoxy-1,8-diazaspiro[4.5]dec-3-en-2-one (known from WO 2009/049851), 3-(2,5-dimethylphenyl)-8-methoxy-2-oxo-1,8-diazaspiro[4.5]dec-3-en-4-yl ethyl carbonate (known from WO 2009/049851), 4-(but-2-yn-1-yloxy)-6-(3,5-dimethylpiperidin-1-yl)-5-fluoropyrimidine (known from WO 2004/099160), (2,2,3,3,4,4,5,5-octafluoropentyl)(3,3,3-trifluoropropyl)malononitrile (known from WO 2005/063094), (2,2,3,3,4,4,5,5-octafluoropentyl)(3,3,4,4,4-pentafluorobutyl)malononitrile (known from WO 2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO 2007/040280), flometoquin, PF1364 (CAS Reg. No. 1204776-60-2) (known from JP 2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO 2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO 2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO 2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO 2010/005692), NNI-0711 (known from WO 2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO 2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO 2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO 2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO 2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO 2007/101369), 2-{6-[2-(5-fluoropyridin-3-yl)-1,3-thiazol-5-yl]pyridin-2-yl}pyrimidine (known from WO 2010/006713), 2-{6-[2-(pyridin-3-yl)-1,3-thiazol-5-yl]pyridin-2-yl}pyrimidine (known from WO 2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO 2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO 2010/069502), (1E)-N-[(6-chloropyridin-3-yl)methyl]-N'-cyano-N-(2,2-difluoroethyl)ethanimidamide (known from WO 2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN 102057925) and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO 2011/049233).

Fungicides (1) Inhibitors of ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorphacetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifin (65472-88-0), (1.33) nuarimol (63284-71-9), (1.34) oxpoconazole (174212-12-5), (1.35) paclobutrazole (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafin (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl) cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy] phenyl}imidoformamide and (1.64) O-[1-(4-methoxyphenoxy)-3,3-dimethylbutan-2-yl]1H-imidazole-1-carbothioate (111226-71-2).

(2) Respiration inhibitors (respiratory chain inhibitors), for example (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam mixture of the syn-epimeric racemate 1RS,4SR, 9RS and the anti-empimeric racemate 1RS,4SR,9SR (881685-58-1), (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamid (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7), (2.28) 5,8-difluoro-N-[2-(2-fluoro-4-[4-(trifluoromethyl)pyridin-2-yl] oxy phenyl)ethyl]quinazoline-4-amine (1210070-84-0) (known from WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) that act on complex III of the respiratory chain, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.5) dimoxystrobin (141600-52-4), (3.6) enestroburin (238410-11-2) (known from WO 2004/058723), (3.9) famoxadone (131807-57-3) (known from WO 2004/058723), (3.10) fenamidone (161326-34-7) (known from WO 2004/058723), (3.11) fenoxystrobin (918162-02-4), (3.12) fluoxastrobin (361377-29-9) (known from WO 2004/058723), (3.13) kresoxim-methyl (143390-89-0) (known from WO 2004/058723), (3.14) metominostrobin (133408-50-1) (known from WO 2004/058723), (3.15) orysastrobin (189892-69-1) (known from WO 2004/058723), (3.16) picoxystrobin (117428-22-5) (known from WO 2004/058723), (3.17) pyraclostrobin (175013-18-0) (known from WO 2004/058723), (3.18) pyrametostrobin (915410-70-7) (known from WO 2004/058723), (3.19) pyraoxystrobin (862588-11-2) (known from WO 2004/058723), (3.20) pyribencarb (799247-52-2) (known from WO 2004/058723), (3.21) triclopyricarb (902760-40-1), (3.22) trifloxystrobin (141517-21-7) (known from WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (known from WO 2004/058723), (3.24) (2E)-2-(methoxyimino)-N-methyl-2-(2-{[({(1E)-1-[3-(trifluoromethyl)phenyl]ethylidene}amino)oxy] methyl}phenyl)ethanamide (known from WO 2004/058723), (3.25) (2E)-2-(methoxyimino)-N-methyl-2-2-[(E)-({1-[3-(trifluoromethyl)phenyl]ethoxylimino)methyl] phenyl}ethanamide (158169-73-4), (3.26) (2E)-2-{2-[({[(1E)-1-(3-{[(E)-1-fluoro-2-phenylethenyl]oxy}phenyl) ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene] amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy] methyl}phenyl)-2,4-dihydro-3H-1,2,4-triazol-3-one, (3.30) methyl (2E)-2-{2-[({cyclopropyl[(4-methoxyphenyl)imino] methyl}sulphanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolid (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds having multisite activity, for example (5.1) Bordeaux mixture (8011-63-0), (5.2) captafol (2425-06-1), (5.3) captan (133-06-2) (known from WO 02/12172), (5.4) chlorothalonil (1897-45-6), (5.5) copper preparations such as copper hydroxide (20427-59-2), (5.6) copper naphthenate (1338-02-9), (5.7) copper oxide (1317-39-1), (5.8) copper oxychloride (1332-40-7), (5.9) copper sulphate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) zinc metiram (9006-42-2), (5.27) copper-oxine (10380-28-6), (5.28) propamidine (104-32-5), (5.29) propineb (12071-83-9), (5.30) sulphur and sulphur preparations, for example calcium polysulphide (7704-34-9), (5.31) thiram (137-26-8), (5.32) tolylfluanid (731-27-1), (5.33) zineb (12122-67-7) and (5.34) ziram (137-30-4).

(6) Resistance inducers, for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of amino acid and protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (known from WO2005070917).

(8) ATP production inhibitors, for example (8.1) fentin acetate (900-95-8), (8.2) fentin chloride (639-58-7), (8.3) fentin hydroxide (76-87-9) and (8.4) silthiofam (175217-20-6).

(9) Inhibitors of cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Melanin biosynthesis inhibitors, for example (11.1) carpropamid (104030-54-8), (11.2) diclocymet (139920-32-4), (11.3) fenoxanil (115852-48-7), (11.4) fthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (known from WO2005042474).

(12) Inhibitors of nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazole (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Signal transduction inhibitors, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Decouplers, for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, for example (15.1) benthiazole (21564-17-0), (15.2) bethoxazine (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulphate (43222-48-6), (15.17) diphenylamine (122-39-4), (15.18) EcoMate, (15.19) fenpyrazamine (473798-59-3), (15.20) flumetover (154025-04-4), (15.21) fluoromid (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and its salts (87-86-5), (15.40) phenothrin, (15.41) phosphoric acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrin (1018-71-9) (known from EP-A 1 559 320), (15.47) tebufloquin (376645-78-2), (15.48) teclofatlam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (known from WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulphonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7), (15.62) 2-[5-methyl-3-(trifluoromethyl)-1H-pyrazol-1-yl]-1-(4-14-[(5S)-5-phenyl-4,5-dihydro-1,2-oxazol-3-yl]-1,3-thiazol-2-yl}piperidin-1-yl)ethanone (1003316-54-8), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and its salts (90-43-7), (15.67) 3-(4,4,5-trifluoro-3,3-dimethyl-3,4-dihydroisoquinolin-1-yl)quinoline (861647-85-0) (known from WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiole, (15.73) 5-chloro-N'-phenyl-N'-(prop-2-yn-1-yl)thiophene-2-sulphonohydrazide (134-31-6), (15.74) 5-fluoro-2-[(4-fluorobenzyl)oxy]pyrimidine-4-amine (1174376-11-4) (known from WO2009094442), (15.75) 5-fluoro-2-[(4-methylbenzyl)oxy]pyrimidine-4-amine (1174376-25-0) (known from WO2009094442), (15.76) 5-methyl-6-octyl[1,2,4]triazolo[1,5-a]pyrimidine-7-amine, (15.77) ethyl-(2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5), (15.90) pentyl-{6-[({[(1-methyl-1H-tetrazol-5-yl) (phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulphate (2:1) (134-31-6) and (15.94) tert-butyl {6-[({[(1-methyl-1H-tetrazol-5-yl)(phenyl)methylene]amino}oxy) methyl]pyridin-2-yl}carbamate.

(16) Further compounds, for example (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazol-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide, (16.7) 5-fluoro-1,3-dimethyl-N-[4'-(prop-1-yn-1-yl)biphenyl-2-yl]-1H-pyrazole-4-carboxamide, (16.8) 2-chloro-N-[4'-(prop-1-yn-1-yl)biphenyl-2-yl]pyridine-3-carboxamide, (16.9) 3-(difluoromethyl)-N-[4'-(3,3-dimethylbut-1-yn-1-yl)biphenyl-2-yl]-1-methyl-1H-pyrazole-4-carboxamide, (16.10) N-[4'-(3,3-dimethylbut-1-yn-1-yl) biphenyl-2-yl]-5-fluoro-1,3-dimethyl-1H-pyrazole-4-carboxamide, (16.11) 3-(difluoromethyl)-N-(4'-ethynylbiphenyl-2-yl)-1-methyl-1H-pyrazole-4-carboxamide, (16.12) N-(4'-ethynylbiphenyl-2-yl)-5-fluoro-1,3-dimethyl-1H-pyrazole-4-carboxamide, (16.13) 2-chloro-N-(4'-ethynylbiphenyl-2-yl)pyridine-3-carboxamide, (16.14) 2-chloro-N-[4'-(3,3-dimethylbut-1-yn-1-yl)biphenyl-2-yl]pyridine-3-carboxamide (known from EP-A 1 559 320), (16.15) 4-(difluoromethyl)-2-methyl-N-[4'-(trifluoromethyl)biphenyl-2-yl]-1,3-thiazole-5-carboxamide, (16.16) 5-fluoro-N-[4'-(3-hydroxy-3-methylbut-1-yn-1-yl) biphenyl-2-yl]-1,3-dimethyl-1H-pyrazole-4-carboxamide, (16.17) 2-chloro-N-[4'-(3-hydroxy-3-methylbut-1-yn-1-yl) biphenyl-2-yl]pyridine-3-carboxamide, (16.18) 3-(difluoromethyl)-N-[4'-(3-methoxy-3-methylbut-1-yn-1-yl)biphenyl-2-yl]-1-methyl-1H-pyrazole-4-carboxamide, (16.19) 5-fluoro-N-[4'-(3-methoxy-3-methylbut-1-yn-1-yl)biphenyl-2-yl]-1,3-dimethyl-1H-pyrazole-4-carboxamide, (16.20) 2-chloro-N-[4'-(3-methoxy-3-methylbut-1-yn-1-yl) biphenyl-2-yl]pyridine-3-carboxamide, (16.21) (5-bromo-2-methoxy-4-methylpyridin-3-yl)(2,3,4-trimethoxy-6-methylphenyl)methanone, (16.22) N-[2-(4-{[3-(4-chlorophenyl)prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid and (16.24) but-3-yn-1-yl {6-[({[(Z)-(1-methyl-1H-tetrazol-5-yl)(phenyl) methylene]amino}oxy)methyl]pyridin-2-yl}carbamate.

All the mixing partners mentioned in classes (1) to (16), as the case may be, may form salts with suitable bases or acids if they are capable of doing do on the basis of their functional groups.

Another possibility is a mixture with other known active ingredients, such as herbicides, fertilizers, growth regulators, safeners, semiochemicals, or else with agents for improving the plant properties.

When used as insecticides, the inventive active ingredients may also be present in their commercially available formulations and in the use forms, prepared from these formulations, as a mixture with synergists. Synergists are compounds which enhance the action of the active ingredients, without any need for the synergist added to be active itself.

When used as insecticides, the inventive active ingredients may also be present in their commercially available formulations and in the use forms, prepared from these formulations, as a mixture with inhibitors which reduce degradation of the active ingredient after use in the environment of the plant, on the surface of parts of plants or in plant tissues.

All plants and parts of plants can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Parts of plants shall be understood to mean all above-ground and below-ground parts and organs of plants, such as shoot, leaf, flower and root, examples including leaves, needles, stems, trunks, flowers, fruit bodies, fruits and seeds, and also roots, tubers and rhizomes. Parts of plants also include harvested material and vegetative and generative propagation material, for example cuttings, tubers, rhizomes, slips and seed.

The inventive treatment of the plants and plant parts with the active ingredients is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and parts thereof in accordance with the invention. In a preferred embodiment, wild plant species and plant cultivars, or those obtained by conventional biological breeding techniques, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts" or "parts of plants" or "plant parts" have been explained above.

More preferably, plants of the plant cultivars which are commercially available or are in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the inventive treatment may also result in superadditive ("synergistic") effects. For example, the following effects extending beyond the effects that are actually to be expected are possible: reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active ingredients. Examples of transgenic plants include the important crop plants, such as cereals (wheat, rice), maize, soya, potatoes, sugarbeet, tomatoes, peas and other vegetable types, cotton, tobacco, oilseed rape, and also fruit plants (with the following fruits: apples, pears, citrus fruits and grapes), particular emphasis being given to maize, soya, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defence of plants against fungi, bacteria and viruses by systemic acquired resistance (SAR), systemin, phytoalexins, elicitors, and also resistance genes and correspondingly expressed proteins and toxins. Traits that are additionally particularly emphasized are the increased tolerance of the plants to certain active herbicidal ingredients, for example imidazolinones, sulphonylureas, glyphosate or phosphinothricin (for example the "PAT" gene). The genes which impart the desired traits in question may also be present in combinations with one another in the transgenic plants. Examples of "Bt plants" include corn varieties, cotton varieties, soya varieties and potato varieties which are sold under the trade names YIELD GARD® (for example corn, cotton, soya), KnockOut® (for example corn), StarLink® (for example corn), Bollgard® (cotton), Nucotn® (cotton) and NewLeaf® (potato). Examples of herbicide-tolerant plants include corn varieties, cotton varieties and soya varieties which are sold under the trade names Roundup Ready® (tolerance to glyphosate, for example maize, cotton, soya), Liberty Link® (tolerance to phosphinothricin, for example oilseed rape), IMI® (tolerance to imidazolinones) and STS® (tolerance to sulphonylureas, for example maize) Herbicide-resistant plants (plants bred in a conventional manner for herbicide tolerance) also include the varieties sold under the Clearfield® name (for example maize). Of course, these statements also apply to plant cultivars which have these genetic traits or genetic traits which are yet to be developed and will be developed and/or marketed in the future.

The plants listed can be treated in accordance with the invention in a particularly advantageous manner with the compounds of the general formula (I) and/or the inventive active ingredient mixtures. The areas of preference stated above for the active ingredients or mixtures also apply to the treatment of these plants. Particular emphasis is given to the treatment of plants with the compounds or mixtures specifically mentioned in the present text.

The inventive active ingredients are not just active against plant pests, hygiene pests and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sar-*

*cophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The inventive active ingredients of the formula (I) are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals, for example dogs, cats, caged birds, aquarium fish, and experimental animals, for example hamsters, guinea pigs, rats and mice. The control of these arthropods is intended to reduce or prevent cases of deaths and reductions in performance (in the case of meat, milk, wool, hides, eggs, honey and the like), such that more economical and simpler animal husbandry is possible through the use of the inventive active ingredients.

The application of the inventive active ingredients in the veterinary sector and in animal husbandry is accomplished in a known manner by enteral administration in the form of, for example, tablets, capsules, potions, drenches, granules, pastes, boluses, the feed-through method and suppositories, by parenteral administration, for example by injections (intramuscular, subcutaneous, intravenous, intraperitoneal and the like), implants, by nasal administration, by dermal use in the form, for example, of dipping or bathing, spraying, pouring-on and spotting-on, washing and powdering, and also with the aid of active ingredient-containing molded articles, such as collars, ear marks, tail marks, limb bands, halters, marking devices and the like.

When used for livestock, poultry, domestic animals and the like, the active ingredients of the formula (I) can be used as formulations (for example powders, emulsions, flowables) comprising the active ingredients in an amount of 1 to 80% by weight, either directly or after 100 to 10 000-fold dilution, or they may be used as a chemical bath.

It has also been found that the inventive compounds have strong insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;* dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccharina.*

Industrial materials in the present context are understood to mean inanimate materials, such as preferably plastics, adhesives, sizes, papers and cards, leather, wood, processed wood products and coating compositions.

The ready-to-use compositions may optionally also comprise other insecticides, and optionally also one or more fungicides.

At the same time, the inventive compounds can be used for protection of objects which come into contact with saltwater or brackish water, especially hulls, screens, nets, buildings, moorings and signalling systems, against fouling.

In addition, the inventive compounds can be used as antifouling compositions, alone or in combinations with other active ingredients.

The active ingredients are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active ingredients and auxiliaries in domestic insecticide products. They are effective against sensitive and resistant species, and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Aviculariidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina*, Lepismodes inquilinus.

From the order of the *Blattaria*, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of domestic insecticides, they are used alone or in combination with other suitable active ingredients, such as phosphoric esters, carbamates, pyrethroids, neonicotinoids, growth regulators or active ingredients from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Elucidation of the Processes and Intermediates

The preparation and use examples which follow illustrate the invention without limiting it. The products were characterized by means of 1H NMR spectroscopy and/or LC-MS (liquid chromatography-mass spectrometry) and/or GC-MS (gas chromatography-mass spectrometry).

The log P values were determined analogously to OECD Guideline 117 (EC Directive 92/69/EEC) by HPLC (high-performance liquid chromatography) using reversed-phase columns (C 18), by the following methods:

[a] The LC-MS determination in the acidic range is effected at pH 2.7 with 0.1% aqueous formic acid and acetonitrile (contains 0.1% formic acid) as eluents; linear gradient from 10% acetonitrile to 95% acetonitrile.

[b] The LC-MS determination in the neutral range is effected at pH 7.8 with 0.001 molar aqueous ammonium hydrogencarbonate solution and acetonitrile as eluents; linear gradient from 10% acetonitrile to 95% acetonitrile.

Calibration is effected with solutions of a homologous series of unbranched alkan-2-ones (having 3 to 16 carbon atoms) with known log P values (log P values determined on the basis of the retention times by linear interpolation between two successive alkanones).

The NMR spectra were measured with a Bruker II Avance 400 equipped with a 1.7 mm TCI probe head. In individual cases, the NMR spectra were determined using a Bruker Avance II 600.

The NMR data for selected examples are listed in conventional form (δ values, multiplet splitting, number of hydrogen atoms). The splitting of the signals was described as follows: s (singlet), d (doublet), t (triplet), q (quartet), m (multiplet), broad (for broad signals). Solvents used were $CD_3CN$, $CDCl_3$ or D6-DMSO, and tetramethylsilane (0.00 ppm) was used as reference.

The GC-MS spectra were determined using an Agilent 6890 GC, HP 5973 MSD on a dimethylsilicone phase, using a temperature gradient from 50° C. to 320° C. GC-MS indices are determined as Kovats indices using solutions of a homologous series of n-alkanes (having an even number of 8 to 38 carbon atoms).

The enantiomers were obtained from the racemate by separating them preparatively by means of HPLC using a chiral column (ChiralCel OJ-H, e.g. 5 nm 250×4.6 mm) with heptane/methanol/ethanol (95:2.5:2.5) eluent.

PREPARATION EXAMPLES

Preparation Example 1

2-{2-Fluoro-4-methyl-5-[(2,2,2-trifluoroethyl)sulphanyl]phenyl}-4-isopropyl-2,4-dihydro-3H-1,2,4-triazol-3-one (Ex. No. 4)

Stage 1: 1-{2-Fluoro-4-methyl-5-[(2,2,2-trifluoroethyl)sulphanyl]phenyl}-4-isopropyl-5-oxo-4,5-dihydro-1H-1,2,4-triazole-3-carboxylic acid

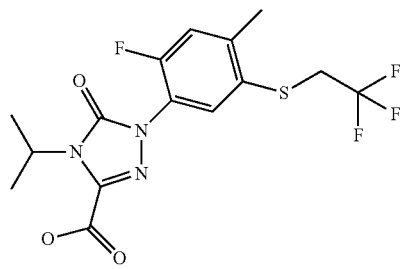 [SMILES: Cc1cc(F)c(-n2nc(C(=O)O)n(C(C)C)c2=O)cc1SCC(F)(F)F]

1.50 g (2.31 mmol) of dimethyl-1,1'-[disulphanediylbis(6-fluoro-4-methylbenzene-3,1-diyl)]bis(4-isopropyl-5-oxo-4,5-dihydro-1H-1,2,4-triazole-3-carboxylate) (XXVIII-1) are initially charged in 30 ml of N,N-dimethylformamide, 0.83 g of sodium dithionite, 1.9 g of potassium carbonate and 0.7 g of sodium biphosphate and 15 ml of water are added and then the mixture is stirred at 60° C. for 3 h. After cooling, 1.70 g (8.1 mmol) of 1,1,1-trifluoro-2-iodoethane are added and the mixture is stirred at 70° C. for a further 12 h. After removal of the solvent under reduced pressure, the residue that remains is acidified with concentrated hydrochloric acid and the precipitate formed is filtered off with suction. This gives 570 mg (86% pure, 63% of theory) of product as a grey solid.

log P{a}: 2.16

Stage 2: 2-{2-Fluoro-4-methyl-5-[(2,2,2-trifluoro-ethyl)sulphanyl]phenyl}-4-isopropyl-2,4-dihydro-3H-1,2,4-triazol-3-one (Ex. No. 4)

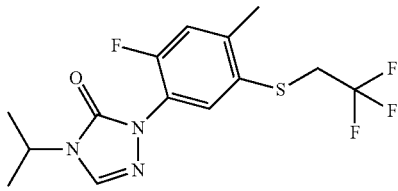 [SMILES: Cc1cc(F)c(-n2ncn(C(C)C)c2=O)cc1SCC(F)(F)F]

300 mg (0.76 mmol) of 1-{2-fluoro-4-methyl-5-[(2,2,2-trifluoroethyl)sulphanyl]phenyl}-4-isopropyl-5-oxo-4,5-dihydro-1H-1,2,4-triazole-3-carboxylic acid are heated under reflux in 5 ml of xylene for 18 h. Removal of the solvent under reduced pressure gives 260 mg (89% pure, 99% of theory) of product as a beige solid.

log P{a}: 2.82; log P[b]: 2.97; 1H NMR (D6-DMSO, 400 MHz) δ ppm: 8.36(s,1H), 7.73-7.71(m,1H), 7.41-7.38(m, 1H), 4.17(sept,1H), 3.99-3.91(q,2H), 2.43(s,3H), 1.38-1.36 (d,6H)

Preparation Example 2

2-{2-Fluoro-4-methyl-5-[(2,2,2-trifluoroethyl)sulphinyl]phenyl}-4-isopropyl-2,4-dihydro-3H-1,2,4-triazol-3-one (Ex. No. 6)

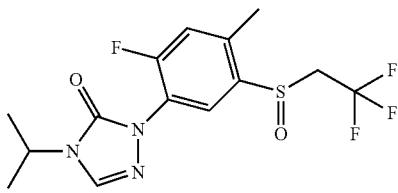 [SMILES: Cc1cc(F)c(-n2ncn(C(C)C)c2=O)cc1S(=O)CC(F)(F)F]

To a solution of 26 mg (0.07 mmol) of 2-{2-fluoro-4-methyl-5-[(2,2,2-trifluoroethyl)sulphanyl]phenyl}-4-isopropyl-2,4-dihydro-3H-1,2,4-triazol-3-one in 20 ml of trichloromethane and 20 mg of buffer solution pH 7 ($KH_2PO_4/Na_2HPO_4$) are added, in portions at 0-4° C., 22 mg (70%, 0.1 mmol) of meta-chloroperbenzoic acid (about 77%), and the reaction mixture is stirred at RT for 24 h. After adding a 33% aqueous bisulphite solution, the mixture is extracted twice with ethyl acetate. The combined organic phases are washed with water, dried over sodium sulphate and filtered. Removal of the solvent under reduced pressure gives 18 mg (86% pure, 66% of theory) of sulphoxide.

log P[a]: 1.88; log P[b]: 2.02; 1H NMR (D6-DMSO, 400 MHz) δ ppm: 8.42(s,1H), 7.99-7.97 (m,1H), 7.53-7.50(m, 1H), 4.26-4.02(m,3H), 2.42(s,3H), 1.39-1.37(d,6H)

Preparation Example 3

2-{2-Fluoro-4-methyl-5-[(2,2,2-trifluoroethyl)sulphanyl]phenyl}-4,5-dimethyl-2,4-dihydro-3H-1,2,4-triazol-3-one (Ex. No. 10)

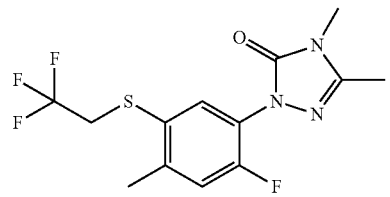 [SMILES: Cc1cc(F)c(-n2nc(C)n(C)c2=O)cc1SCC(F)(F)F]

454.6 mg (1.5 mmol) of 5-bromo-4-fluoro-2-methylphenyl-2,2,2-trifluoroethyl sulphide, 203.6 mg (1.8 mmol) of 4,5-dimethyl-2,4-dihydro-3H-1,2,4-triazol-3-one (synthesis, for example, Bull. Soc. Chim. Fr. 1975, 1191-1194), 28.6 mg (0.15 mmol) of copper(I) iodide, 42.7 mg (0.30 mmol) of trans-N,N'-dimethylcyclohexane-1,2-diamine (racemic), 74.7 mg (0.45 mmol) of potassium iodide and 621.9 mg (4.50 mmol) of potassium carbonate are stirred in 3 ml of dry degassed dioxane at 115° C. for 2 d. After cooling to room temperature, the reaction mixture is diluted with ethyl acetate and filtered through silica gel using ethyl acetate. Purification by column chromatography on silica gel by means of MPLC with cyclohexane/ethyl acetate as eluent gives 136 mg (100% pure, 27% of theory) of the title compound as a colourless oil.

log P[a]: 2.42; log P[b]: 2.38; 1H NMR (D6-DMSO, 400 MHz) δ ppm: 7.68(d,1H), 7.38(d,1H), 3.93(q,2H), 3.20(s, 3H), 2.43(s,3H), 2.25(s,3H)

Preparation Example 4

2-{2-Fluoro-4-methyl-5-[(2,2,2-trifluoroethyl)sulphinyl]phenyl}-4,5-dimethyl-2,4-dihydro-3H-1,2,4-triazol-3-one (Ex. No. 11)

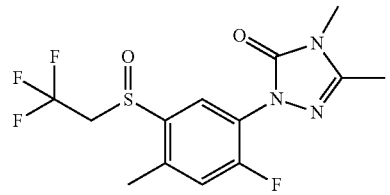 [SMILES: Cc1cc(F)c(-n2nc(C)n(C)c2=O)cc1S(=O)CC(F)(F)F]

To a solution of 95.0 mg (0.28 mmol) of 2-{2-fluoro-4-methyl-5-[(2,2,2-trifluoroethyl)sulphanyl]phenyl}-4,5-dimethyl-2,4-dihydro-3H-1,2,4-triazol-3-one in 10 ml of dichloromethane are added 63.5 mg (0.28 mmol) of meta-chloroperbenzoic acid (about 77%). The reaction mixture is stirred at room temperature overnight, washed with saturated aqueous sodium bicarbonate solution, dried over magnesium sulphate, filtered and freed of the solvent under reduced pressure. Purification by column chromatography on silica gel by means of MPLC with cyclohexane/ethyl acetate as eluent gives 70 mg (100% pure, 70% of theory) of the title compound as a colourless oil.

log P[a]: 1.57; log P[b]: 1.50; 1H NMR (D6-DMSO, 400 MHz) δ ppm: 7.94(d,1H), 7.49 (d,1H), 4.28-4.16(m,1H), 4.10-3.98(m,1H), 3.21(s,3H), 2.41(s,3H), 2.27(s,3H)

Preparation Example 5

2-{2-Fluoro-4-methyl-5-[(2,2,2-trifluoroethyl)sulphanyl]phenyl}-4-methyl-5-(trifluoromethyl)-2,4-dihydro-3H-1,2,4-triazol-3-one (Ex. No. 9)

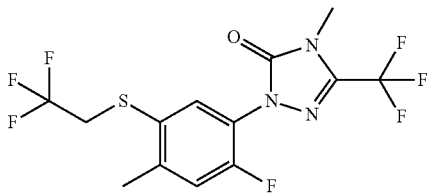 [SMILES: Cc1cc(F)c(-n2nc(C(F)(F)F)n(C)c2=O)cc1SCC(F)(F)F]

Preparation by Process P3: 454.6 mg (1.5 mmol) of 5-bromo-4-fluoro-2-methylphenyl-2,2,2-trifluoroethyl sulphide, 300.8 mg (1.8 mmol) of 4-methyl-5-(trifluoromethyl)-2,4-dihydro-3H-1,2,4-triazol-3-one (synthesis according to DE 4339412), 28.6 mg (0.15 mmol) of copper (I) iodide, 42.7 mg (0.30 mmol) of trans-N,N'-dimethylcyclohexane-1,2-diamine (racemic), 74.7 mg (0.45 mmol) of potassium iodide and 621.9 mg (4.50 mmol) of potassium carbonate are stirred in 3 ml of dry degassed dioxane under microwave irradiation (Anton-Paar, 2-5 ml vessel) at 160° C. for 3 h. After cooling to room temperature, the reaction mixture is diluted with ethyl acetate and filtered through silica gel using ethyl acetate. Purification by column chromatography on silica gel by means of MPLC with cyclohexane/ethyl acetate as eluent gives 70 mg (100% pure, 12% of theory) of the title compound as a yellow oil.

Preparation by Process P3': 268.0 mg (1.0 mmol) of {2-fluoro-4-methyl-5-[(2,2,2-trifluoroethyl)sulphanyl]phenyl}boronic acid, 334 mg (2.00 mmol) of 4-methyl-5-(trifluoromethyl)-2,4-dihydro-3H-1,2,4-triazol-3-one, 272 mg (1.5 mmol) of copper(II) acetate, 158 mg (2.0 mmol) of pyridine and 0.5 g of activated 3A molecular sieve are stirred in 5 ml of dry dichloromethane at room temperature for 3 d. The reaction mixture is adsorbed on kieselguhr and purified by column chromatography on silica gel by means of MPLC with cyclohexane/ethyl acetate as eluent. This gives 98 mg (87% pure, 22% of theory) of the title compound as a colourless oil.

log P[a]: 3.58; log P[b]: 3.53; 1H NMR (D6-DMSO, 400 MHz) δ ppm: 7.79(d,1H), 7.47(d,1H), 3.95(q,2H), 3.38(s, 3H), 2.45(s,3H)

Preparation Example 6

2-{2-Fluoro-4-methyl-5-[(2,2,2-trifluoroethyl)sulphinyl]phenyl}-4-methyl-5-(trifluoromethyl)-2,4-dihydro-3H-1,2,4-triazol-3-one (Ex. No. 12)

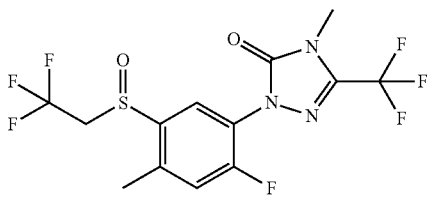 [SMILES: Cc1cc(F)c(-n2nc(C(F)(F)F)n(C)c2=O)cc1S(=O)CC(F)(F)F]

To a solution of 70.0 mg (0.18 mmol) of 2-{2-fluoro-4-methyl-5-[(2,2,2-trifluoroethyl)sulphanyl]phenyl}-4-methyl-5-(trifluoromethyl)-2,4-dihydro-3H-1,2,4-triazol-3-one in 10 ml of dichloromethane are added 40.3 mg (0.18 mmol) of meta-chloroperbenzoic acid (about 77%). The reaction mixture is stirred at room temperature overnight, washed with saturated aqueous sodium bicarbonate solution, dried over magnesium sulphate, filtered and freed of the solvent under reduced pressure. Purification by column chromatography on silica gel by means of MPLC with cyclohexane/ethyl acetate as eluent gives 51 mg (95% pure, 65% of theory) of the title compound as a colourless solid.

log P[a]: 2.52; log P[b]: 2.46; 1H NMR (D6-DMSO, 400 MHz) δ ppm: 8.04(d,1H), 7.58(d,1H), 4.32-4.20(m,1H), 4.09-3.98(m,1H), 3.38(s,3H), 2.44(s,3H)

Preparation Example 7

4-[4-Cyclopropyl-5-oxo-3-(trifluoromethyl)-4,5-dihydro-1H-1,2,4-triazol-1-yl]-5-fluoro-2-[(2,2,2-trifluoroethyl)sulphinyl]benzonitrile (Ex. No. 47)

Stage 1: 4-[4-Cyclopropyl-5-oxo-3-(trifluoromethyl)-4,5-dihydro-1H-1,2,4-triazol-1-yl]-5-fluoro-2-[(2,2,2-trifluoroethyl)sulphanyl]benzonitrile

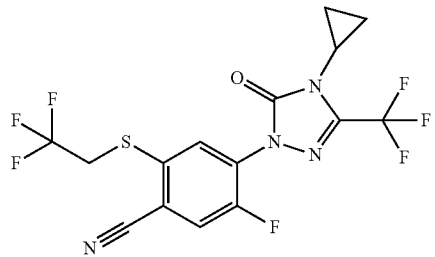 [SMILES: N#Cc1cc(F)c(-n2nc(C(F)(F)F)n(C3CC3)c2=O)cc1SCC(F)(F)F]

To a solution of 64 mg (1.6 mmol) of sodium hydride (60% in mineral oil) in 25 ml of N,N-dimethylformamide are added, at 5-10° C., 116 mg (1.6 mmol) of 2,2,2-trifluoroethylthiol. After stirring at room temperature for 30 minutes, this solution is added dropwise to a solution, cooled to −15° C., of 0.5 g (1.5 mmol) of 4-[4-cyclopropyl-5-oxo-3-(trifluoromethyl)-4,5-dihydro-1H-1,2,4-triazol-1-yl]-2,5-difluorobenzonitrile (XXIV-1) in 25 ml of N,N-dimethylformamide, and the mixture is stirred at −20° C. to −10° C. for 2 h. The reaction mixture is poured into water, neutralized with saturated aqueous ammonium chloride solution and extracted with ethyl acetate. The combined organic phases are washed successively with water and saturated aqueous sodium chloride solution, dried over magnesium sulphate, filtered and freed of the solvent under reduced pressure. Purification by column chromatography on RP(C-18) silica gel by means of MPLC with water/acetonitrile as eluent gives 47 mg (82% pure, 6% of theory) of the title compound as a pale yellow solid.

Stage 2: 4-[4-Cyclopropyl-5-oxo-3-(trifluoromethyl)-4,5-dihydro-1H-1,2,4-triazol-1-yl]-5-fluoro-2-[(2,2,2-trifluoroethyl)sulphinyl]benzonitrile (Ex. No. 47)

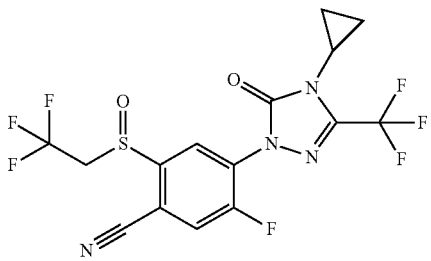 [SMILES: N#Cc1cc(F)c(-n2nc(C(F)(F)F)n(C3CC3)c2=O)cc1S(=O)CC(F)(F)F]

To a solution of 37.0 mg (0.09 mmol) of 4-[4-cyclopropyl-5-oxo-3-(trifluoromethyl)-4,5-dihydro-1H-1,2,4-triazol-1-yl]-5-fluoro-2-[(2,2,2-trifluoroethyl)sulphanyl]benzonitrile in 10 ml of dichloromethane are added, at 0° C., 19.5 mg (0.09 mmol) of meta-chloroperbenzoic acid (about 77%). The reaction mixture is stirred at 0° C. for 2 h and at room temperature overnight, then sodium hydroxide solution (about 0.25 M) is added and extraction is effected with dichloromethane. The combined organic phases are dried over magnesium sulphate, filtered and freed of the solvent under reduced pressure. Purification by column chromatography on silica gel by means of MPLC with cyclohexane/ethyl acetate as eluent gives 7 mg (92% pure, 17% of theory) of the title compound as a colourless solid.

log P[a]: 2.92; log P[b]: 2.84; 1H NMR (D6-DMSO, 400 MHz) δ ppm: 8.46(d,1H), 8.24(d,1H), 4.52-4.40(m,1H), 4.33-4.22(m,1H), 3.10-3.05(m,1H), 1.15-1.02(m,4H)

Preparation Example 8

5-Methoxy-4-methyl-2-{3-[(2,2,2-trifluoroethyl)sulphanyl]-4-(trifluoromethyl)phenyl}-2,4-dihydro-3H-1,2,4-triazol-3-one (Ex. No. 95)

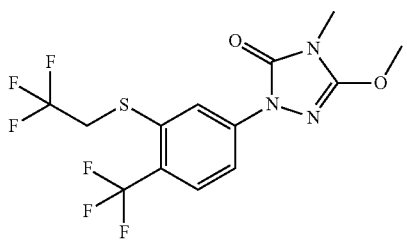 [SMILES: COc1nn(-c2ccc(C(F)(F)F)c(SCC(F)(F)F)c2)c(=O)n1C]

678 mg (2.0 mmol) of 5-bromo-2-(trifluoromethyl)phenyl-2,2,2-trifluoroethyl sulphide, 309.9 mg (2.4 mmol) of 5-methoxy-4-methyl-2,4-dihydro-3H-1,2,4-triazol-3-one (synthesis, for example, according to U.S. Pat. No. 5,599,945), 38.1 mg (0.2 mmol) of copper(I) iodide, 56.9 mg (0.4 mmol) of trans-N,N'-dimethylcyclohexane-1,2-diamine (racemic), 99.6 mg (0.6 mmol) of potassium iodide and 829.2 mg (6.0 mmol) of potassium carbonate are stirred in 8 ml of dry degassed dioxane at 120° C. overnight. After cooling to room temperature, the reaction mixture is diluted with ethyl acetate, filtered through silica gel with ethyl acetate and freed of the solvent under reduced pressure. Purification by column chromatography on RP(C-18) silica gel by means of MPLC with water/acetonitrile as eluent gives 86 mg (92% pure, 10% of theory) of the title compound as a yellow oil.

log P[a]: 3.74; log P[b]: 3.64; 1H NMR (D6-DMSO, 400 MHz) δ ppm: 8.34(d,1H), 7.94-7.92(m,1H), 7.87-7.84(m,1H), 4.11-4.04(m,5H), 3.11(s,3H)

Preparation Example 9

5-Methoxy-4-methyl-2-{3-[(2,2,2-trifluoroethyl)sulphinyl]-4-(trifluoromethyl)phenyl}-2,4-dihydro-3H-1,2,4-triazol-3-one (Ex. No. 96)

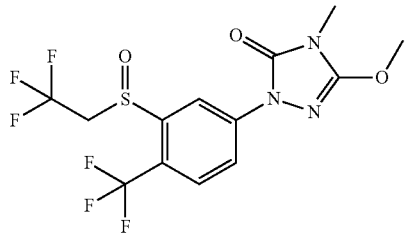 [SMILES: COc1nn(-c2ccc(C(F)(F)F)c(S(=O)CC(F)(F)F)c2)c(=O)n1C]

To a solution of 65.0 mg (0.17 mmol) of 5-methoxy-4-methyl-2-{3-[(2,2,2-trifluoroethyl)sulphanyl]-4-(trifluoromethyl)phenyl}-2,4-dihydro-3H-1,2,4-triazol-3-one in 10 ml of dichloromethane are added, at 0° C., 33.8 mg (0.15 mmol) of meta-chloroperbenzoic acid (about 77%). The reaction mixture is stirred at 0° C. for 2 h, washed with 1M sodium hydroxide solution and freed of the solvent under reduced pressure.

Purification by column chromatography on silica gel by means of MPLC with cyclohexane/ethyl acetate as eluent gives 43 mg (99% pure, 63% of theory) of the title compound as a colourless solid.

log P[a]: 2.89; log P[b]: 2.83; 1H NMR (D6-DMSO, 400 MHz) δ ppm: 8.70 (d,1H), 8.32-8.29(m,1H), 8.03(d,1H), 4.15(q,2H), 4.09(s,3H), 3.13(s,3H)

Preparation Example 10

5-Cyclopropyl-4-(dimethylamino)-2-{2-fluoro-4-methyl-5-[(2,2,2-trifluoroethyl)sulphanyl]phenyl}-2,4-dihydro-3H-1,2,4-triazol-3-one (Ex. No. 195)

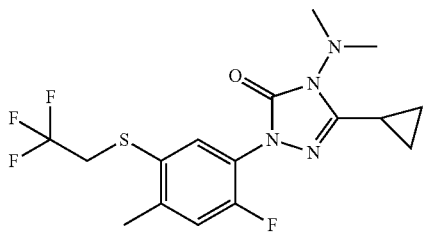 [SMILES: Cc1cc(F)c(-n2nc(C3CC3)n(N(C)C)c2=O)cc1SCC(F)(F)F]

303.1 mg (1.0 mmol) of 5-bromo-4-fluoro-2-methylphenyl-2,2,2-trifluoroethyl sulphide, 201.8 mg (1.2 mmol) of 5-cyclopropyl-4-(dimethylamino)-2,4-dihydro-3H-1,2,4-triazol-3-one (synthesis according to U.S. Pat. No. 5,516,749), 38.1 mg (0.20 mmol) of copper(I) iodide, 35.3 mg (0.40 mmol) of N,N-dimethylethylenediamine and 424.5 mg (2.0 mmol) of potassium phosphate in 3 ml of dry degassed dioxane are stirred at 110° C. overnight. After cooling to room temperature, the reaction mixture is diluted with dichloromethane, washed successively with water and saturated aqueous sodium chloride solution, dried over magnesium sulphate, filtered and freed of the solvent under reduced pressure. Purification by column chromatography on silica gel by means of MPLC with cyclohexane/ethyl acetate as eluent gives 105 mg (99% pure, 27% of theory) of the title compound as a colourless oil.

log P[a]: 3.75; log P[b]: 3.73; 1H NMR (D6-DMSO, 400 MHz) δ ppm: 7.67(d,1H), 7.37(d,1H), 3.94(q,2H), 2.95(s, 6H), 2.43(s,3H), 2.04-1.97(m,1H), 0.99-0.93(m,2H), 0.91-0.85(m,2H)

Preparation Example 11

5-Cyclopropyl-4-(dimethylamino)-2-{2-fluoro-4-methyl-5-[(2,2,2-trifluoroethyl)sulphinyl]phenyl}-2,4-dihydro-3H-1,2,4-triazol-3-one (Ex. No. 197)

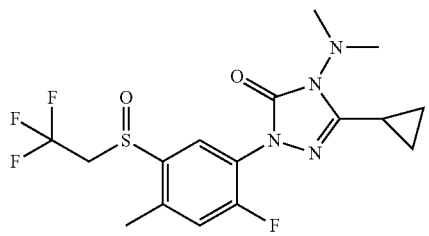 [SMILES: Cc1cc(F)c(-n2nc(C3CC3)n(N(C)C)c2=O)cc1S(=O)CC(F)(F)F]

To a solution of 75.0 mg (0.19 mmol) of 5-cyclopropyl-4-(dimethylamino)-2-{2-fluoro-4-methyl-5-[(2,2,2-trifluoroethyl)sulphanyl]phenyl}-2,4-dihydro-3H-1,2,4-triazol-3-one in 15 ml of dichloromethane are added 38.7 mg (0.17 mmol) of meta-chloroperbenzoic acid (about 77%). The reaction mixture is stirred at room temperature overnight, washed successively with 40% aqueous sodium bisulphite solution and saturated aqueous sodium bicarbonate solution, dried over magnesium sulphate, filtered and freed of the solvent under reduced pressure. Purification by column chromatography on silica gel by means of MPLC with cyclohexane/ethyl acetate as eluent gives 50 mg (100% pure, 64% of theory) of the title compound as a colourless oil.

log P[a]: 2.60; log P[b]: 2.59; 1H NMR (D6-DMSO, 400 MHz) δ ppm: 7.91(d,1H), 7.49(d,1H), 4.27-4.00(m,2H), 2.96(s,3H), 2.50(s,6H), 2.40(s,3H), 2.06-1.98(m,1H), 1.00-0.95(m,2H), 0.94-0.87(m,2H)

Preparation Example 12

5-(Ethylsulphanyl)-2-{2-fluoro-4-methyl-5-[(2,2,2-trifluoroethyl)sulphanyl]phenyl}-4-methyl-2,4-dihydro-3H-1,2,4-triazol-3-one (Ex. No. 273)

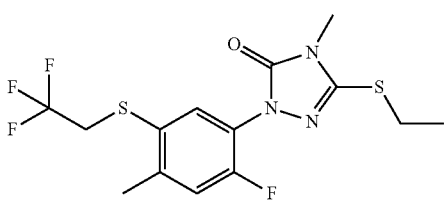 [SMILES: CCSc1nn(-c2cc(SCC(F)(F)F)c(C)cc2F)c(=O)n1C]

454.6 mg (1.5 mmol) of 5-bromo-4-fluoro-2-methylphenyl-2,2,2-trifluoroethyl sulphide, 286.6 mg of (1.8 mmol) 5-(ethylsulphanyl)-4-methyl-2,4-dihydro-3H-1,2,4-triazol-3-one (synthesis, for example, according to DE 2250572), 28.6 mg (0.15 mmol) of copper(I) iodide, 42.7 mg (0.30 mmol) of trans-N,N'-dimethylcyclohexane-1,2-diamine (racemic), 74.7 mg (0.45 mmol) of potassium iodide and 621.9 mg (4.50 mmol) of potassium carbonate are stirred in 3 ml of dry degassed dioxane at 110° C. overnight. After cooling to room temperature, the reaction mixture is diluted with ethyl acetate and filtered through silica gel using ethyl acetate. Purification by column chromatography on silica gel by means of MPLC with cyclohexane/ethyl acetate as eluent gives 470 mg (100% pure, 82% of theory) of the title compound as a colourless oil.

log P[a]: 3.51; log P[b]: 3.44; 1H NMR (D6-DMSO, 400 MHz) δ ppm: 7.72(d,1H), 7.40(d,1H), 3.95(q,2H), 3.18(s, 3H), 3.11(q,2H), 2.43(s,3H), 1.34(t,3H)

Preparation Example 13

5-(Ethylsulphanyl)-2-{2-fluoro-4-methyl-5-[(2,2,2-trifluoroethyl)sulphinyl]phenyl}-4-methyl-2,4-dihydro-3H-1,2,4-triazol-3-one (Ex. No. 274), 5-(ethylsulphinyl)-2-{2-fluoro-4-methyl-5-[(2,2,2-trifluoroethyl)sulphanyl]phenyl}-4-methyl-2,4-dihydro-3H-1,2,4-triazol-3-one (Ex. No. 243) and 5-(ethylsulphinyl)-2-{2-fluoro-4-methyl-5-](2,2,2-trifluoroethyl)sulphinyl]phenyl}-4-methyl-2,4-dihydro-3H-1,2,4-triazol-3-one (Ex. No. 244)

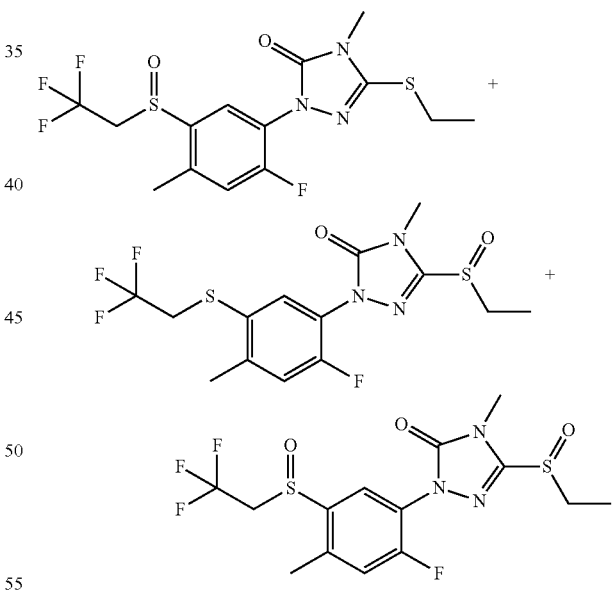

To a solution of 235 mg (0.62 mmol) of 5-(ethylsulphanyl)-2-{2-fluoro-4-methyl-5-[(2,2,2-trifluoroethyl)sulphanyl]phenyl}-4-methyl-2,4-dihydro-3H-1,2,4-triazol-3-one in 19 ml of dichloromethane are added, at 0° C., 165.7 mg (0.74 mmol) of meta-chloroperbenzoic acid (about 77%). The reaction mixture is stirred at 0° C. for 2 h, washed with 1M sodium hydroxide solution and freed of the solvent under reduced pressure. Purification by column chromatography on silica gel by means of MPLC with cyclohexane/ethyl acetate as eluent gives 93 mg (100% pure, 38% of theory) of 5-(ethylsulphanyl)-2-{2-fluoro-4-methyl-5-[(2,2, 2-trifluoroethyl)sulphinyl]phenyl}-4-methyl-2,4-dihydro-3H-1,2,4-triazol-3-on, 12 mg (95% pure, 5% of theory) of 5-(ethylsulphinyl)-2-{2-fluoro-4-methyl-5-[(2,2,2-trifluoroethyl)sulphanyl]phenyl}-4-methyl-2,4-dihydro-3H-1,2,4-triazol-3-one (100% pure, 40% of theory) of 5-(ethylsulphinyl)-2-{2-fluoro-4-methyl-5-[(2,2,2-trifluoroethyl)sulphinyl]phenyl}-4-methyl-2,4-dihydro-3H-1,2,4-triazol-3-one, each as colourless oils which crystallize gradually at room temperature to give colourless solids.

5-(Ethylsulphanyl)-2-{2-fluoro-4-methyl-5-[(2,2,2-trifluoroethyl)sulphinyl]phenyl}-4-methyl-2,4-dihydro-3H-1,2,4-triazol-3-one (Ex. No. 274): log P[a]: 2.42; log P[b]: 2.36; 1H NMR (D6-DMSO, 400 MHz) δ ppm: 7.98(d,1H), 7.52(d,1H), 4.26-4.20(m,1H), 4.09-4.03(m,1H), 3.19(s,3H), 3.12(q,2H), 2.42(s,3H), 1.34(t,3H)

5-(Ethylsulphinyl)-2-{2-fluoro-4-methyl-5-[(2,2,2-trifluoroethyl)sulphanyl]phenyl}-4-methyl-2,4-dihydro-3H-1,2,4-triazol-3-one (Ex. No. 243): log P[a]: 2.55; log P[b]: 2.51; 1H NMR (D6-DMSO, 400 MHz) δ ppm: 7.77(d,1H), 7.45(d,1H), 3.96(q,2H), 3.45(s,3H), 3.43-3.35(m,2H), 2.45 (s,3H), 1.27(t,3H)

5-(Ethylsulphinyl)-2-{2-fluoro-4-methyl-5-[(2,2,2-trifluoroethyl)sulphinyl]phenyl}-4-methyl-2,4-dihydro-3H-1,2,4-triazol-3-one (Ex. No. 244): log P[a]: 1.69; log P[b]: 1.65; 1H NMR (D6-DMSO, 400 MHz) δ ppm: 8.02(d,1H), 7.56(d,1H), 4.28-4.19(m,1H), 4.08-4.00 (m,1H), 3.45(s,3H), 3.43-3.34(m,2H), 2.43(s,3H), 1.29-1.25(m,3H)

Preparation Example 14

1-(4-Chlorophenyl)-4-{2-fluoro-4-methyl-5-[(2,2,2-trifluoroethyl)sulphanyl]phenyl}-1,4-dihydro-5H-tetrazol-5-one (Ex. No. 306)

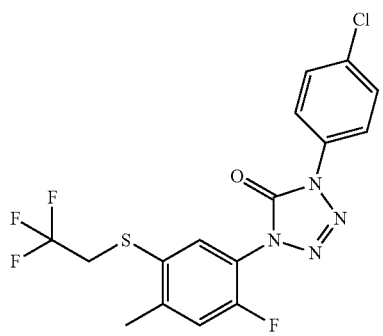 [SMILES: Cc1cc(F)c(-n2nnn(-c3ccc(Cl)cc3)c2=O)cc1SCC(F)(F)F]

268.0 mg (1.0 mmol) of {2-fluoro-4-methyl-5-[(2,2,2-trifluoroethyl)sulphanyl]phenyl}boronic acid, 272 mg (2.00 mmol) of 1-(4-chlorophenyl)-1,4-dihydro-5H-tetrazol-5-one (for example according to J. Org. Chem. 1980, 45, 5130-5136), 272 mg (1.5 mmol) of copper(II) acetate, 158 mg (2.0 mmol) of pyridine and 0.5 g of activated 3A molecular sieve are stirred in 5 ml of dry dichloromethane at room temperature for 4 d. The reaction mixture is adsorbed on kieselguhr and purified by column chromatography on silica gel by means of MPLC with cyclohexane/ethyl acetate as eluent. This gives 109 mg (98% pure, 26% of theory) of the title compound as a colourless solid.

log P[a]: 4.75; log P[b]: 4.59; 1H NMR (D6-DMSO, 400 MHz) δ ppm: 7.98-7.93(m,3H), 7.72-7.69(m,2H), 7.59(d, 1H), 3.98(q,2H), s,3H beneath DMSO signal Preparation Example 15

1-(4-Chlorophenyl)-4-{2-fluoro-4-methyl-5-[(2,2,2-trifluoroethyl)sulphinyl]phenyl}-1,4-dihydro-5H-tetrazol-5-one (Ex. No. 307)

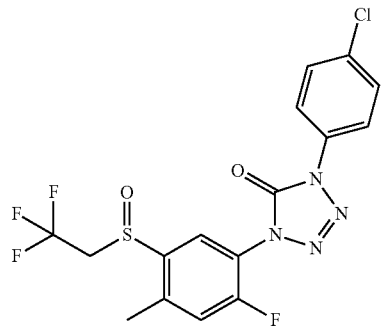 [SMILES: Cc1cc(F)c(-n2nnn(-c3ccc(Cl)cc3)c2=O)cc1S(=O)CC(F)(F)F]

To a solution of 70.0 mg (0.17 mmol) of 1-(4-chlorophenyl)-4-{2-fluoro-4-methyl-5-[(2,2,2-trifluoroethyl)sulphanyl]phenyl}-1,4-dihydro-5H-tetrazol-5-one in 10 ml of dichloromethane are added, at 0° C., 37.5 mg (0.17 mmol) of meta-chloroperbenzoic acid (about 77%). The reaction mixture is stirred at 0° C. for 2 h, washed with 1M sodium hydroxide solution and freed of the solvent under reduced pressure. Purification by column chromatography on silica gel by means of MPLC with cyclohexane/ethyl acetate as eluent gives 55 mg (100% pure, 76% of theory) of the title compound as a colourless solid.

log P[a]: 3.53; log P[b]: 3.49; 1H NMR (D6-DMSO, 400 MHz) δ ppm: 8.25(d,1H), 7.96-7.92(m,2H), 7.72-7.68(m, 3H), 4.35-4.26(m,1H), 4.08-3.96(m,1H), 2.48(s,3H)

Preparation Example 16

1-{2-Fluoro-4-methyl-5-[(2,2,2-trifluoroethyl)sulphanyl]phenyl}-1,4-dihydro-5H-tetrazol-5-one (Ex. No. 299)

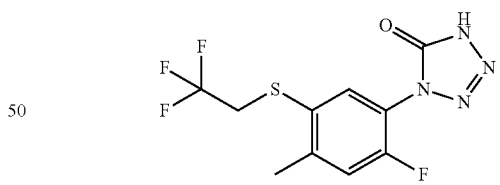

A solution of 2.00 g (7.5 mmol) of 4-fluoro-5-isocyanato-2-methylphenyl-2,2,2-trifluoroethyl sulphide in 10 ml of toluene is admixed at room temperature with 3.48 g (30.2 mmol) of trimethylsilyl azide and stirred at 100° C. overnight. After cooling to 0° C., trimethylsilyl azide is evaporated under reduced pressure into a receiver containing sodium hydroxide and ethanol, and then sodium nitrite solution is added cautiously. The residue is taken up in ethyl acetate and washed with saturated aqueous ammonium chloride solution and dilute hydrochloric acid, dried over magnesium sulphate, filtered and freed of the solvent under reduced pressure. Purification by column chromatography on silica gel by means of MPLC with cyclohexane/ethyl acetate as eluent gives 869 mg (96% pure, 36% of theory) of the title compound as a light brown solid.

log P[a]: 2.45; log P[b]: 0.90; 1H NMR (D6-DMSO, 400 MHz) δ ppm: 14.78(s,1H), 7.89(d,1H), 7.52(d,1H), 4.00(q,2H), 2.46(s,3H)

Preparation Example 17

1-{2-Fluoro-4-methyl-5-[(2,2,2-trifluoroethyl)sulphinyl]phenyl}-1,4-dihydro-5H-tetrazol-5-one (Ex. No. 303)

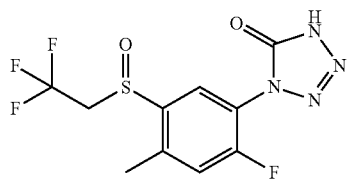 [SMILES: Cc1cc(F)c(-n2nn[nH]c2=O)cc1S(=O)CC(F)(F)F]

To a solution of 100 mg (0.32 mmol) of 1-{2-fluoro-4-methyl-5-[(2,2,2-trifluoroethyl)sulphanyl]phenyl}-1,4-dihydro-5H-tetrazol-5-one in 3 ml of acetonitrile are added, at 0° C., 2.7 mg (0.008 mmol) of sodium tungstate(VI) dihydrate and 34 mg (0.36 mmol) of 3% aqueous hydrogen peroxide solution. The reaction mixture is stirred at 0° C.-room temperature overnight, 40% aqueous sodium bisulphite solution is added (15 ml) and extraction is effected with dichloromethane. The combined organic phases are washed with saturated aqueous ammonium chloride solution, dried over magnesium sulphate, filtered and freed of the solvent under reduced pressure. Purification by column chromatography on silica gel by means of MPLC with cyclohexane/ethyl acetate as eluent gives 91 mg (95% pure, 82% of theory) of the title compound as a beige solid.

log P[a]: 1.59; log P[b]: 0.37; 1H NMR (D6-DMSO, 400 MHz) δ ppm: 8.13(d,1H), 7.64(d,1H), 4.30-4.21(m,1H), 4.12-4.01(m,1H), 2.46(s,3H)

Preparation Example 18

1-{2-Fluoro-4-methyl-5-[(2,2,2-trifluoroethyl)sulphanyl]phenyl}-4-methyl-1,4-dihydro-5H-tetrazol-5-one (Ex. No. 302)

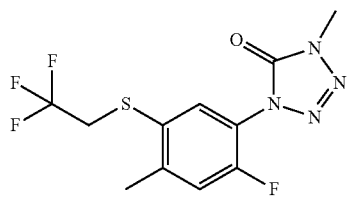

To a solution of 183.5 mg (0.6 mmol) of 1-{2-fluoro-4-methyl-5-[(2,2,2-trifluoroethyl)sulphanyl]phenyl}-1,4-dihydro-5H-tetrazol-5-one in 3 ml of N,N-dimethylformamide are added, at 5° C., 138.2 mg (1.8 mmol) of potassium carbonate and 141.9 mg of methyl iodide. The reaction mixture is stirred at 5° C.-room temperature for 1 h, then applied to a silica gel cartridge and purified by column chromatography on silica gel by means of MPLC with cyclohexane/ethyl acetate as eluent. This gives 176 mg (95% pure, 86% of theory) of the title compound as a yellowish oil.

log P[a]: 2.89; log P[b]: 2.86; 1H NMR (D6-DMSO, 400 MHz) δ ppm: 7.88(d,1H), 7.54(d,1H), 3.99(q,2H), 3.63(s,3H), 2.46(s,3H)

Preparation Example 19

1-{2-Fluoro-4-methyl-5-[(2,2,2-trifluoroethyl)sulphinyl]phenyl}-4-methyl-1,4-dihydro-5H-tetrazol-5-one (Ex. No. 301)

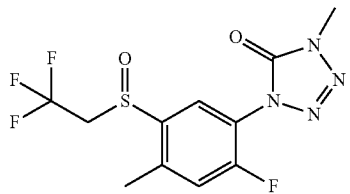 [SMILES: Cc1cc(F)c(-n2nnn(C)c2=O)cc1S(=O)CC(F)(F)F]

To a solution of 88.9 mg (0.28 mmol) of 1-{2-fluoro-4-methyl-5-[(2,2,2-trifluoroethyl)sulphanyl]phenyl}-4-methyl-1,4-dihydro-5H-tetrazol-5-one in 10 ml of dichloromethane are added, at 0° C., 61.8 mg (0.28 mmol) of meta-chloroperbenzoic acid (about 77%). The reaction mixture is stirred at 0° C. for 1 h, washed with 1M sodium hydroxide solution and freed of the solvent under reduced pressure. Purification by column chromatography on silica gel by means of MPLC with cyclohexane/ethyl acetate as eluent gives 76.5 mg (95% pure, 78% of theory) of the title compound as a colourless oil.

log P[a]: 1.87; log P[b]: 1.82; 1H NMR (D6-DMSO, 400 MHz) δ ppm: 8.13(d,1H), 7.65(d,1H), 4.32-4.22(m,1H), 4.08-4.01(m,1H), 3.61(s,3H), 2.46(s,3H)

Preparation Example 20

1-{2-Fluoro-4-methyl-5-[(2,2,2-trifluoroethyl)sulphanyl]phenyl}-4-methoxy-1,5-dihydro-2H-pyrrol-2-one (Ex. No. 310)

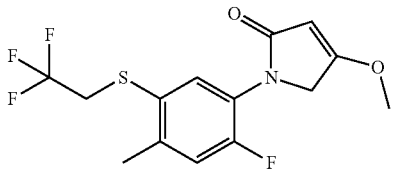 [SMILES: COC1=CC(=O)N(c2cc(SCC(F)(F)F)c(C)cc2F)C1]

400.0 mg (1.3 mmol) of 5-bromo-4-fluoro-2-methylphenyl-2,2,2-trifluoroethyl sulphide, 182.1 mg (1.6 mmol) of 4-methoxy-3-pyrrolin-2-one, 16.3 mg (0.09 mmol) of copper(I) iodide, 14.5 mg (0.17 mmol) of N,N'-dimethylethylenediamine and 364.8 mg (2.6 mmol) of potassium carbonate are stirred in 2 ml of dry degassed toluene at 115° C. overnight. After cooling to room temperature, another 91.0 mg (0.81 mmol) of 4-methoxy-3-pyrrolin-2-one, 8.2 mg (0.04 mmol) of copper(I) iodide and 7.9 mg (0.09 mmol) of N,N'-dimethylethylenediamine are added and the mixture is stirred again at 115° C. overnight. After cooling to room temperature, the reaction mixture is filtered through silica gel with ethyl acetate/cyclohexane (1:1) and freed of the solvent under reduced pressure. Purification by column chromatography on silica gel by means of MPLC with cyclohexane/ethyl acetate as eluent gives 155 mg (100% pure, 35% of theory) of the title compound as a colourless solid.

log P[a]: 2.87; log P[b]: 2.81; 1H NMR (D6-DMSO, 400 MHz) δ ppm: 7.73(d,1H), 7.26(d,1H), 5.34(s,1H), 4.42(s, 2H), 3.90(q,2H), 3.85(s,3H), 2.38(s,3H)

Preparation Example 21

1-{2-Fluoro-4-methyl-5-[(2,2,2-trifluoroethyl)sulphinyl]phenyl}-4-methoxy-1,5-dihydro-2H-pyrrol-2-one (Ex. No. 311)

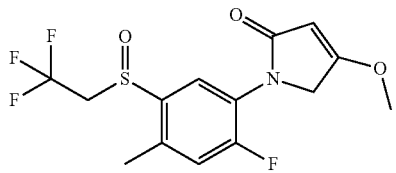 [SMILES: COC1=CC(=O)N(c2cc(S(=O)CC(F)(F)F)c(C)cc2F)C1]

To a solution of 50 mg (0.15 mmol) of 1-{2-fluoro-4-methyl-5-[(2,2,2-trifluoroethyl)sulphanyl]phenyl}-4-methoxy-1,5-dihydro-2H-pyrrol-2-one and 10 ml of dichloromethane are added, at 0° C., 33.4 mg (0.15 mmol) of meta-chloroperbenzoic acid (about 77%). The reaction mixture is stirred at 0° C. for 2 h, washed successively with 40% aqueous sodium hydrogensulphite solution and saturated aqueous sodium bicarbonate solution, dried over magnesium sulphate, filtered and freed of the solvent under reduced pressure. Purification by column chromatography on silica gel by means of MPLC with cyclohexane/ethyl acetate as eluent gives 44 mg (99% pure, 83% of theory) of the title compound as a colourless oil.

log P[a]: 1.83; log P[b]: 1.84; 1H NMR (D6-DMSO, 400 MHz) δ ppm: 8.06(d,1H), 7.37(d,1H), 5.38(s,1H), 4.48-4.44 (m,2H), 4.20-4.13(m,1H), 4.06-3.94(m,1H), 3.86(s,3H), 2.38(s,3H)

Preparation Example 22

4-(Cyclopentyloxy)-1-{2-fluoro-4-methyl-5-[(2,2,2-trifluoroethyl)sulphanyl]phenyl}-1,5-dihydro-2H-pyrrol-2-one (Ex. No. 329)

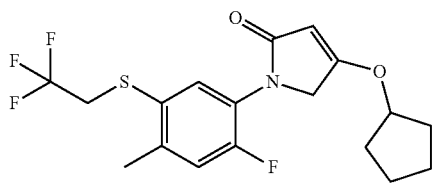 [SMILES: Cc1cc(F)c(N2CC(OC3CCCC3)=CC2=O)cc1SCC(F)(F)F]

150.0 mg (0.45 mmol) of 1-{2-fluoro-4-methyl-5-[(2,2,2-trifluoroethyl)sulphanyl]phenyl}-4-methoxy-1,5-dihydro-2H-pyrrol-2-one, 231.2 mg (2.68 mmol) of cyclopentanol and 4.3 mg (0.05 mmol) of methanesulphonic acid are dissolved in 3 ml of toluene, activated 4A molecular sieve is added and the mixture is stirred at 110° C. overnight. After cooling to room temperature, the reaction mixture is filtered through silica gel with toluene and freed of the solvent under reduced pressure. Purification by column chromatography on silica gel by means of MPLC with cyclohexane/ethyl acetate as eluent gives 81.2 mg (100% pure, 47% of theory) of the title compound as a brown oil.

log P[a]: 4.20; log P[b]: 4.06; 1H NMR (D6-DMSO, 400 MHz) δ ppm: 7.72(d,1H), 7.71(d,1H), 5.28(s,1H), 4.80-4.76 (m,1H), 4.37(s,2H), 3.91(q,2H), 2.37(s,3H), 1.96-1.89(m, 2H), 1.80-1.58(m,6H)

Preparation Example 23

4-(Cyclopentyloxy)-1-{2-fluoro-4-methyl-5-[(2,2,2-trifluoroethyl)sulphinyl]phenyl}-1,5-dihydro-2H-pyrrol-2-one (Ex. No. 336)

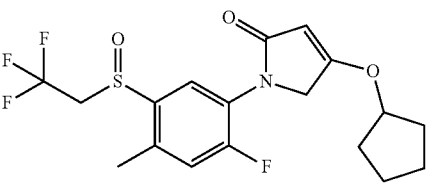 [SMILES: Cc1cc(F)c(N2CC(OC3CCCC3)=CC2=O)cc1S(=O)CC(F)(F)F]

To a solution of 65 mg (0.17 mmol) of 4-(cyclopentyloxy)-1-{2-fluoro-4-methyl-5-[(2,2,2-trifluoroethyl)sulphanyl]phenyl}-1,5-dihydro-2H-pyrrol-2-one in 4 ml of dichloromethane are added, at 0° C., 40.3 mg (0.17 mmol) of meta-chloroperbenzoic acid (about 77%). The reaction mixture is stirred at 0° C. for 2 h, washed with 1M sodium hydroxide solution and freed of the solvent under reduced pressure. This gives 64.7 mg (99% pure, 95% of theory) of the title compound as a yellow solid.

log P[a]: 2.97; log P[b]: 2.91; 1H NMR (D6-DMSO, 400 MHz) δ ppm: 8.07(d,1H), 7.36(d,1H), 5.33(s,1H), 4.81-4.77 (m,1H), 4.04(s,2H), 4.19-4.10(m,1H), 4.00-3.91(m,1H), 2.37(s,3H), 1.98-1.90(m,2H), 1.81-1.76(m,2H), 1.73-1.58 (m,4H)

Preparation Example 24

1-{2-Fluoro-4-methyl-5-[(2,2,2-trifluoroethyl)sulphanyl]phenyl}-3,4-dimethyl-1H-pyrrole-2,5-dione (Ex. No. 339)

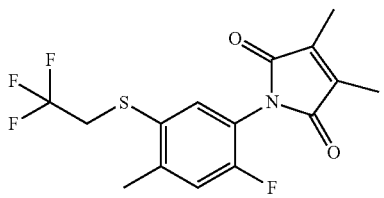 [SMILES: CC1=C(C)C(=O)N(c2cc(SCC(F)(F)F)c(C)cc2F)C1=O]

100 mg (0.42 mmol) of 2-fluoro-4-methyl-5-[(2,2,2-trifluoroethyl)sulphanyl]aniline are heated under reflux in 15 ml of acetic acid together with 60 mg (0.48 mmol) of 3,4-dimethylfuran-2,5-dione for 4 h. After the addition of 50 ml of water, the mixture is extracted twice with dichloromethane. The combined organic phases are washed with water, dried over sodium sulphate and filtered. After removal of the solvent under reduced pressure, 100 mg of crude product are obtained. Purification by column chromatography by means of MPLC on RP(C-18) using water/acetonitrile gives 30 mg (100% pure, 20.7% of theory) of product as a white, wax-like substance.

log P[a]: 3.60; log P[b]: 3.61; 1H NMR (D6-DMSO, 400 MHz) δ ppm: 7.63-7.62(m,1H), 7.41-7.38(m,1H), 3.95-3.88 (q,2H), 2.43(s,3H), 2.00(s,6H)

Preparation Example 25

2,2,2-Trifluoro-N-[3-{2-fluoro-4-methyl-5-[(2,2,2-trifluoroethyl)sulphanyl]phenyl}-4,5-dimethyl-1,3-thiazol-2(3H)-ylidene]ethanamine (Ex. No. 343)

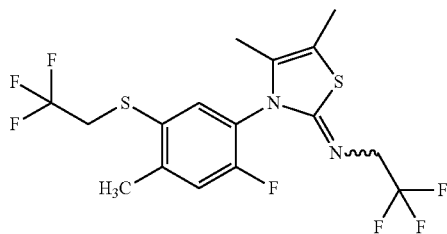 [SMILES: Cc1cc(F)c(-n2c(C)c(C)sc2=NCC(F)(F)F)cc1SCC(F)(F)F]

100 mg (0.26 mmol) of 1-{2-fluoro-4-methyl-5-[(2,2,2-trifluoroethyl)sulphanyl]phenyl}-3-(2,2,2-trifluoroethyl)thiourea are initially charged in 1 ml of toluene, 77 mg (0.51 mmol) of 3-bromo-2-butanone are added and the mixture is stirred at reflux for 4 h. After cooling, the reaction mixture is freed of the solvent under reduced pressure. The residue is purified by means of MPLC on RP(C-18) using water/acetonitrile. The isolated fraction is purified by means of MPLC using RP(C-18) with water/acetonitrile/0.1% formic acid. In this way, 14 mg (100% pure, 14% of theory) of the title compound are isolated.

log P[a]: 3.02; log P[b]: 4.91; 1H NMR (D6-DMSO, 400 MHz) δ ppm: 7.63(d,1H), 7.37 (d,1H), 4.08-4.02(m,1H), 3.95-3.90 (m,1H), 3.64-3.59(m,2H), 2.41(s,3H), 2.11(s,3H), 1.71(s,3H)

Preparation Example 26

2,2,2-Trifluoro-N-[3-{2-fluoro-4-methyl-5-[((2,2,2-trifluoroethyl)sulphinyl]phenyl}-4,5-dimethyl-1,3-thiazol-2(3H)-ylidene]ethanamine (Ex. No. 342)

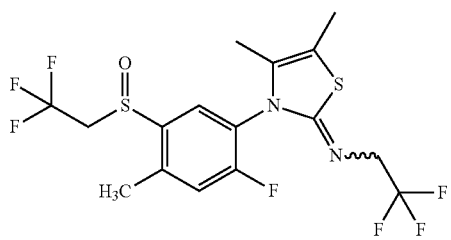 [SMILES: Cc1cc(F)c(-n2c(C)c(C)sc2=NCC(F)(F)F)cc1S(=O)CC(F)(F)F]

180 mg (0.45 mmol) of 1-{2-fluoro-4-methyl-5-[(2,2,2-trifluoroethyl)sulphinyl]phenyl}-3-(2,2,2-trifluoroethyl)thiourea are initially charged in 2 ml of toluene, 137 mg (0.91 mmol) of 3-bromo-2-butanone are added and the mixture is stirred at reflux for 8 h. After cooling, the reaction mixture is freed of the solvent under reduced pressure. Purification by column chromatography by means of MPLC using RP(C-18) with water/acetonitrile/0.1% formic acid gives 45 mg (100% pure, 22% of theory) of the title compound.

log P[a]: 2.07; log P[b] 3.67; 1H NMR (D6-DMSO, 400 MHz) δ ppm: 7.81(m,1H), 7.52(d,1H), 4.36-4.17(m,2H), 3.89-3.56(m, 2H), 2.45-2.44(m,3H), 2.13-2.12(m,3H), 1.77-1.74(m,3H)

Preparation Example 27

5-Cyclopentyl-4-cyclopropyl-2-{2-fluoro-4-methyl-5-[(2,2,2-trifluoroethyl)sulphanyl]phenyl}-2,4-dihydro-3H-1,2,4-triazol-3-one (Ex. No. 358)

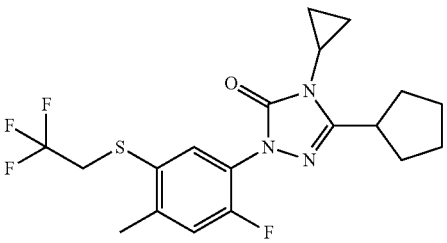 [SMILES: Cc1cc(F)c(-n2nc(C3CCCC3)n(C3CC3)c2=O)cc1SCC(F)(F)F]

454.6 mg (1.5 mmol) of 5-bromo-4-fluoro-2-methylphenyl-2,2,2-trifluoroethyl sulphide, 304.0 mg (1.58 mmol) of 5-cyclopentyl-4-cyclopropyl-2,4-dihydro-3H-1,2,4-triazol-3-one, 28.6 mg (0.15 mmol) of copper(I) iodide, 42.7 mg (0.30 mmol) of trans-N,N'-dimethylcyclohexane-1,2-diamine (racemic), 74.7 mg (0.45 mmol) of potassium iodide and 621.9 mg (4.50 mmol) of potassium carbonate are stirred in 3 ml of dry degassed dioxane at 110° C. overnight. After cooling to room temperature, the reaction mixture is diluted with ethyl acetate, filtered through silica gel with ethyl acetate and concentrated. Purification by column chromatography on silica gel by means of MPLC with cyclohexane/ethyl acetate as eluent gives 502 mg (99% pure, 80% of theory) of the title compound as a yellow oil.

log P[a]: 4.18; log P[b]: 4.20; $^1$H NMR (D$^6$-DMSO, 400 MHz) δ ppm: 7.66(d,1H), 7.36(d,1H), 3.92(q,2H), 3.31-3.23 (m,1H), 2.91-2.86(m,1H), 2.42(s,3H), 2.08-2.00(m,2H), 1.86-1.77(m,2H), 1.75-1.60(m,4H), 1.02-0.98(m,4H)

Preparation Example 28

2-{2-Fluoro-4-methyl-5-[(2,2,2-trifluoroethyl)sulphanyl]phenyl}-4-methyl-5-(methylsulphonyl)-2,4-dihydro-3H-1,2,4-triazol-3-one (Ex. No. 420)

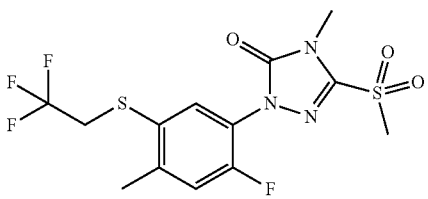 [SMILES: Cc1cc(F)c(-n2nc(S(C)(=O)=O)n(C)c2=O)cc1SCC(F)(F)F]

268.0 mg (1.0 mmol) of {2-fluoro-4-methyl-5-[(2,2,2-trifluoroethyl)sulphanyl]phenyl}boronic acid, 354 mg (2.00 mmol) of 4-methyl-5-(methylsulphonyl)-2,4-dihydro-3H-1,2,4-triazol-3-one, 272 mg (1.5 mmol) of copper(II) acetate, 158 mg (2.0 mmol) of pyridine and 0.5 g of activated 3 Å molecular sieve are stirred in 5 ml of dry dichloromethane and stirred at room temperature for 4 d. The reaction mixture is adsorbed on kieselguhr and purified by column chromatography on silica gel by means of MPLC with cyclohexane/ethyl acetate as eluent. This gives 41 mg (100% pure, 10% of theory) of the title compound as a colourless solid.

log P[a]: 2.70; log P[b]: 2.77; $^1$H NMR (D$^6$-DMSO, 400 MHz) δ ppm: 7.80(d,1H), 7.48(d,1H), 3.95(q,2H), 3.57(s, 3H), 3.47(s,3H), 2.46(s,3H)

Preparation Example 29

2-{2-Fluoro-4-methyl-5-[(2,2,2-trifluoroethyl)sulphinyl]phenyl}-4-methyl-5-(methylsulphonyl)-2,4-dihydro-3H-1,2,4-triazol-3-one (Ex. No. 421)

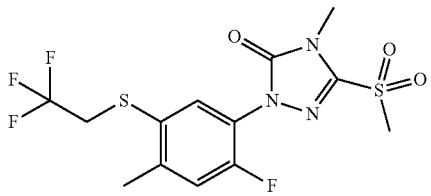 [SMILES: Cc1cc(F)c(-n2nc(S(C)(=O)=O)n(C)c2=O)cc1SCC(F)(F)F]

To a solution of 30.0 mg (0.075 mmol) of 2-{2-fluoro-4-methyl-5-[(2,2,2-trifluoroethyl)sulphanyl]phenyl}-4-methyl-5-(methylsulphonyl)-2,4-dihydro-3H-1,2,4-triazol-3-one in 10 ml of dichloromethane are added, at 0° C., 17.7 mg (0.079 mmol) of meta-chloroperbenzoic acid (about 77%). The reaction mixture is stirred at 0° C. for 2 h, washed with 1M sodium hydroxide solution and freed of the solvent under reduced pressure. This gives 29 mg (96% pure, 89% of theory) of the title compound as a colourless solid.

log P[a]: 1.88; log P[b]: 1.84; $^1$H NMR (D$^6$-DMSO, 400 MHz) δ ppm: 8.05(d,1H), 7.59(d,1H), 4.30-4.24(m,1H), 4.06-4.00(m,1H), 3.57(s,3H), 3.47(s,3H), 2.44(s,3H)

Preparation Example 30

5-Bromo-2-{2-fluoro-4-methyl-5-[(2,2,2-trifluoroethyl)sulphanyl]phenyl}-4-isopropyl-2,4-dihydro-3H-1,2,4-triazol-3-one (Ex. No. 439)

Stage 1: 5-Bromo-4-isopropyl-2,4-dihydro-3H-1,2,4-triazol-3-one

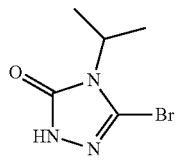

A solution of 412 mg (10.3 mmol) of sodium hydroxide and 936 mg (7.4 mmol) of 4-isopropyl-2,4-dihydro-3H-1,2,4-triazol-3-one in water is admixed with 1.18 g (7.4 mmol) of bromine and stirred at room temperature overnight. The precipitated yellow solid is filtered, washed with water and dried on a clay tile. The solids obtained are stirred in sodium hydrogensulphite solution, filtered, washed with water and dried again on a clay tile. This gives 722 mg (89% pure, 42% of theory) of the title compound as a yellowish solid.

log P[a]: 0.86; log P[b]: 0.83; $^1$H NMR (D$^6$-DMSO, 400 MHz) δ ppm: 12.03(s,1H), 4.27-4.21(m,1H), 1.40(d,6H)

Stage 2: 5-Bromo-2-{2-fluoro-4-methyl-5-[(2,2,2-trifluoroethyl)sulphanyl]phenyl}-4-isopropyl-2,4-dihydro-3H-1,2,4-triazol-3-one (Ex. No. 439)

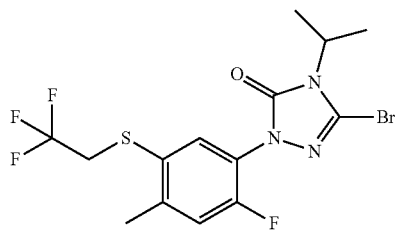 [SMILES: Cc1cc(F)c(-n2nc(Br)n(C(C)C)c2=O)cc1SCC(F)(F)F]

402.0 mg (1.5 mmol) of {2-fluoro-4-methyl-5-[(2,2,2-trifluoroethyl)sulphanyl]phenyl}boronic acid, 309 mg (1.5 mmol) of 5-bromo-4-isopropyl-2,4-dihydro-3H-1,2,4-triazol-3-one, 409 mg (2.25 mmol) of copper(II) acetate, 237 mg (3.0 mmol) of pyridine and 1.0 g of activated 3 Å molecular sieve are stirred in 5 ml of dry dichloromethane at room temperature for 4 d. The reaction mixture is adsorbed on kieselguhr and purified by column chromatography on silica gel by means of MPLC with cyclohexane/ethyl acetate as eluent. This gives 38 mg (97% pure, 6% of theory) of the title compound as a colourless oil.

log P[a]: 3.83; log P[b]: 3.80; $^1$H NMR (D$^6$-DMSO, 400 MHz) δ ppm: 7.75(d,1H), 7.41(d,1H), 4.43-4.31(m,1H), 3.96(q,2H), 2.43(s,3H), 1.47(d,6H)

Preparation Example 31

5-Bromo-2-{2-fluoro-4-methyl-5-[(2,2,2-trifluoroethyl)sulphinyl]phenyl}-4-isopropyl-2,4-dihydro-3H-1,2,4-triazol-3-one (Ex. No. 442)

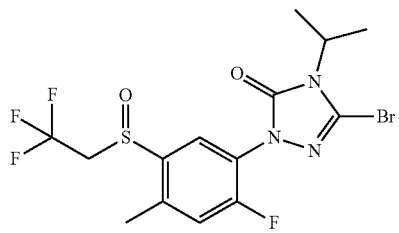 [SMILES: Cc1cc(F)c(-n2nc(Br)n(C(C)C)c2=O)cc1S(=O)CC(F)(F)F]

To a solution of 28.0 mg (0.065 mmol) of 5-bromo-2-{2-fluoro-4-methyl-5-[(2,2,2-trifluoroethyl)sulphanyl]phenyl}-4-isopropyl-2,4-dihydro-3H-1,2,4-triazol-3-one in 10 ml of dichloromethane are added, at 0° C., 14.7 mg (0.065 mmol) of meta-chloroperbenzoic acid (about 77%). The reaction mixture is stirred at 0° C. for 2 h, washed with 1M sodium hydroxide solution and freed of the solvent under reduced pressure. This gives 30 mg (98% pure, 100% of theory) of the title compound as a colourless oil.

log P[a]: 2.68; log P[b]: 2.62; $^1$H NMR (D$^6$-DMSO, 400 MHz) δ ppm: 8.00(d,1H), 7.53(d,1H), 4.40-4.31(m,1H), 4.30-4.19(m,1H), 4.12-4.00(m,1H), 2.42(s,3H), 1.49-1.47(m,6H)

Preparation Example 32

1-{2-Fluoro-4-methyl-5-[(2,2,2-trifluoroethyl)sulphanyl]phenyl}-4-methyl-1,4-dihydro-5H-tetrazole-5-thione (Ex. No. 447)

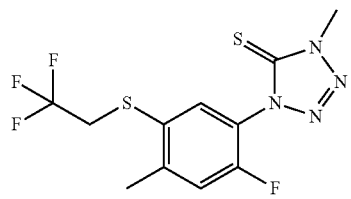 [SMILES: Cc1cc(F)c(-n2nnn(C)c2=S)cc1SCC(F)(F)F]

To a solution of 100.0 mg (0.31 mmol) of 1-{2-fluoro-4-methyl-5-[(2,2,2-trifluoroethyl)sulphanyl]phenyl}-4-methyl-1,4-dihydro-5H-tetrazol-5-one in 10 ml of toluene are added 377 mg (0.93 mmol) of 2,4-bis(4-methoxyphenyl)-1,3,2,4-dithiadiphosphetane 2,4-disulphide (Lawesson's reagent). The reaction mixture is heated to reflux under argon overnight, then concentrated. Purification by column chromatography on silica gel by means of MPLC with cyclohexane/ethyl acetate as eluent gives 73 mg (94% pure, 65% of theory) of the title compound as a colourless solid.

log P[a]: 3.51; log P[b]: 3.49; $^1$H NMR (D$^6$-DMSO, 400 MHz) δ ppm: 7.96(d,1H), 7.58(d,1H), 3.99(q,2H), 3.93(s, 3H), 2.49(s,3H)

Preparation Example 33

3-{2-Fluoro-4-methyl-5-[(2,2,2-trifluoroethyl)sulphanyl]phenyl}-5-methyl-1,3,4-oxadiazol-2(3H)-one (Ex. No. 448)

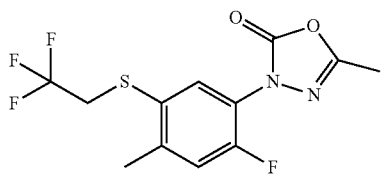 [SMILES: Cc1nn(-c2cc(SCC(F)(F)F)c(C)cc2F)c(=O)o1]

268.0 mg (1.0 mmol) of {2-fluoro-4-methyl-5-[(2,2,2-trifluoroethyl)sulphanyl]phenyl}boronic acid, 200 mg (2.00 mmol) of 5-methyl-1,3,4-oxadiazol-2(3H)-one, 272 mg (1.5 mmol) of copper(II) acetate, 158 mg (2.0 mmol) of pyridine and 0.5 g of activated 3 Å molecular sieve are stirred in 5 ml of dry dichloromethane at room temperature for 3 d. The reaction mixture is adsorbed on kieselguhr and purified by column chromatography on silica gel by means of MPLC with cyclohexane/ethyl acetate as eluent. This gives 56 mg (98% pure, 17% of theory) of the title compound as a colourless oil.

log P[a]: 3.11; log P[b]: 3.09; $^1$H NMR (D$^6$-DMSO, 400 MHz) δ ppm: 7.80(d,1H), 7.45(d,1H), 3.95(q,2H), 2.44(s, 3H), 2.34(s,3H)

Preparation Example 34

3-{2-Fluoro-4-methyl-5-[(2,2,2-trifluoroethyl)sulphinyl]phenyl}-5-methyl-1,3,4-oxadiazol-2(3H)-one (Ex. No. 451)

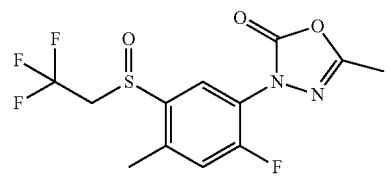 [SMILES: Cc1nn(-c2cc(S(=O)CC(F)(F)F)c(C)cc2F)c(=O)o1]

To a solution of 36.0 mg (0.112 mmol) of 3-{2-fluoro-4-methyl-5-[(2,2,2-trifluoroethyl)sulphanyl]phenyl}-5-methyl-1,3,4-oxadiazol-2(3H)-one in 10 ml of dichloromethane are added, at 0° C., 26.3 mg (0.117 mmol) of meta-chloroperbenzoic acid (about 77%). The reaction mixture is stirred at 0° C. for 2 h, washed with 1M sodium hydroxide solution and freed of the solvent under reduced pressure. This gives 40 mg (100% pure, 100% of theory) of the title compound as a colourless solid.

log P[a]: 1.99; log P[b]: 2.02; $^1$H NMR (D$^6$-DMSO, 400 MHz) δ ppm: 8.05(d,1H), 7.56(d,1H), 4.31-4.19(m,1H), 4.07-3.94(m,1H), 2.42(s,3H), 2.35(s,3H)

Preparation Example 35

1-Ethyl-3-{2-fluoro-4-methyl-5-[(2,2,2-trifluoroethyl)sulphanyl]phenyl}-1,3-dihydro-2H-imidazol-2-one (Ex. No. 486)

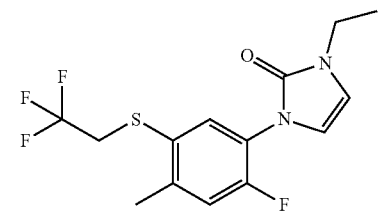 [SMILES: CCn1ccn(-c2cc(SCC(F)(F)F)c(C)cc2F)c1=O]

454.6 mg (1.5 mmol) of 5-bromo-4-fluoro-2-methylphenyl-2,2,2-trifluoroethyl sulphide, 185.0 mg (1.65 mmol) of 1-ethyl-1,3-dihydro-2H-imidazol-2-one, 28.6 mg (0.15 mmol) of copper(I) iodide, 42.7 mg (0.30 mmol) of trans-N,N'-dimethylcyclohexane-1,2-diamine (racemic), 74.7 mg (0.45 mmol) of potassium iodide and 621.9 mg (4.50 mmol) of potassium carbonate are stirred in 2.4 ml of dry degassed dioxane at 110° C. overnight. After cooling to room temperature, the reaction mixture is diluted with ethyl acetate and filtered through silica gel using ethyl acetate. Purification by column chromatography on silica gel by means of MPLC with cyclohexane/ethyl acetate as eluent gives 167 mg (100% pure, 33% of theory) of the title compound as a colourless oil.

log P[a]: 2.84; log P[b]: 2.79; $^1$H NMR (D$^6$-DMSO, 400 MHz) δ ppm: 7.72(d,1H), 7.36(d,1H), 6.77(d,1H), 6.73-6.72(m,1H), 3.94(q,2H), 3.60(q,2H), 2.41(s,3H), 1.22(t,3H)

Preparation Example 36

1-Ethyl-3-{2-fluoro-4-methyl-5-[(2,2,2-trifluoro-ethyl)sulphinyl]phenyl}-1,3-dihydro-2H-imidazol-2-one (Ex. No. 487)

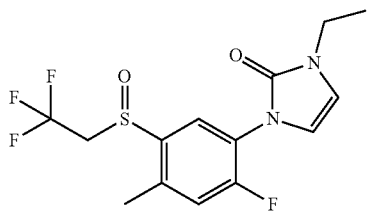 [SMILES: CCn1ccn(-c2cc(S(=O)CC(F)(F)F)c(C)cc2F)c1=O]

To a solution of 84.0 mg (0.25 mmol) of 1-ethyl-3-{2-fluoro-4-methyl-5-[(2,2,2-trifluoroethyl)sulphanyl]phenyl}-1,3-dihydro-2H-imidazol-2-one in 10 ml of dichloromethane are added, at 0° C., 59.1 mg (0.26 mmol) of meta-chloroperbenzoic acid (about 77%). The reaction mixture is stirred at 0° C. for 2 h, washed with 1M sodium hydroxide solution and freed of the solvent under reduced pressure. Purification by column chromatography on silica gel by means of MPLC with cyclohexane/ethyl acetate as eluent gives 45 mg (95% pure, 49% of theory) of the title compound as a colourless oil.

log P[a]: 1.83; log P[b]: 1.81; $^1$H NMR (D$^6$-DMSO, 400 MHz) δ ppm: 7.99(d,1H), 7.48(d,1H), 6.83-6.80(m,2H), 4.22-4.11(m,1H), 4.11-4.02(m,1H), 3.61(q,2H), 2.41(s,3H), 1.23(t,3H)

Preparation Example 37

5-Cyclopentyl-4-cyclopropyl-2-{2-fluoro-4-methyl-5-[(2,2,2-trifluoroethyl)sulphanyl]-phenyl}-2,4-dihydro-3H-1,2,4-triazole-3-thione (Ex. No. 497)

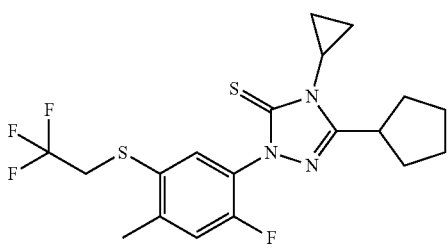 [SMILES: Cc1cc(F)c(-n2nc(C3CCCC3)n(C3CC3)c2=S)cc1SCC(F)(F)F]

To a solution of 100.0 mg (0.24 mmol) of 5-cyclopentyl-4-cyclopropyl-2-{2-fluoro-4-methyl-5-[(2,2,2-trifluoroethyl)sulphanyl]phenyl}-2,4-dihydro-3H-1,2,4-triazol-3-one in 10 ml of toluene are added 292 mg (0.72 mmol) of 2,4-bis(4-methoxyphenyl)-1,3,2,4-dithiadiphosphetane 2,4-disulphide (Lawesson's reagent). The reaction mixture is heated to reflux under argon overnight, then diluted with ethyl acetate, filtered through silica gel and concentrated. Purification by column chromatography on silica gel by means of MPLC with cyclohexane/ethyl acetate as eluent gives 51 mg (98% pure, 48% of theory) of the title compound as a colourless solid.

log P[a]: 4.68; log P[b]: 4.57; $^1$H NMR (D$^6$-DMSO, 400 MHz) δ ppm: 7.74(d,1H), 7.42(d,1H), 3.95(q,2H), 3.49-3.39 (m,1H), 3.11-3.02(m,1H), 2.45(s,3H), 2.15-2.05(m,2H), 1.89-1.75(m,2H), 1.73-1.60(m,4H), 1.20-1.11(m,4H)

Synthesis of Anilines of the Formula (IVa), (IVb) and Intermediates (X), (XI), (XII), (XIII), (XVI), (XVII), (XVIII), (XIX) and (XX)

2,2,2-Trifluoro-N-(2-fluoro-4-methylphenyl)acetamide (XIII-1)

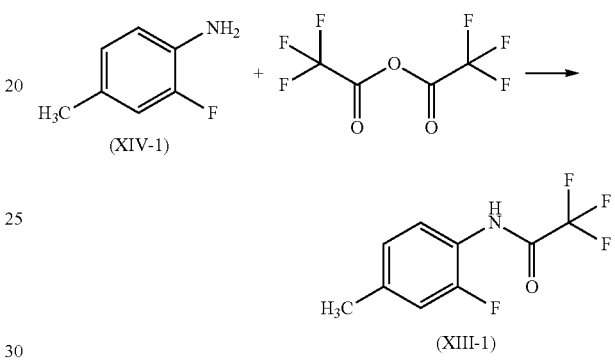

At 0° C., 27.5 g of 2-fluoro-4-methylaniline are initially charged in 300 ml of dichloromethane, 26.7 g of triethylamine are added and 50.8 g of trifluoroacetic anhydride are then added dropwise. The mixture is stirred at 0° C. for 2 h and then concentrated by rotary evaporation. The residue is taken up in water and extracted twice with ethyl acetate. The combined organic phases are dried over sodium sulphate and filtered, and the solvent is removed under reduced pressure. This gives 49.0 g (100% of theory) of the title compound.

log P[a]: 2.40

The following was obtained analogously:

N-(4-Chloro-2-fluorophenyl)-2,2,2-trifluoroacetamide (XIII-2)

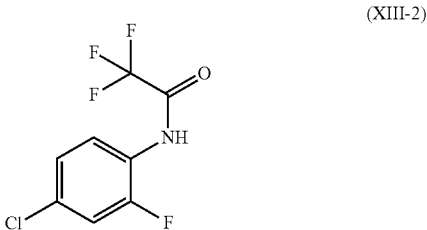 [SMILES: O=C(Nc1ccc(Cl)cc1F)C(F)(F)F]

log P[a]: 2.53; log P[b]: 2.40; 1H NMR (D6-DMSO, 400 MHz) δ ppm: 11.29(s,1H), 7.62(dd,1H), 7.55(dd,1H), 7.37(dd,1H)

4-Fluoro-2-methyl-5-[(trifluoroacetyl)amino]benzenesulphonyl chloride (XII-1)

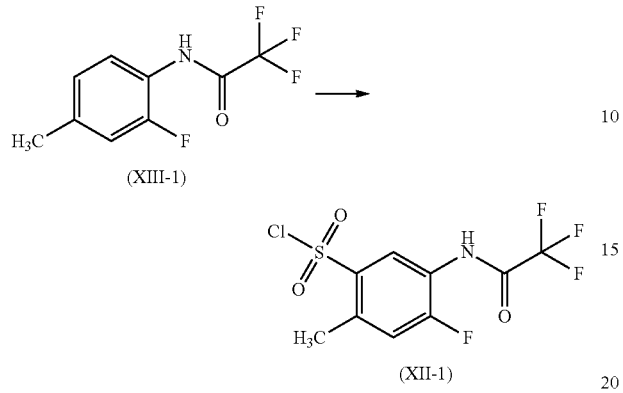

258 g of chlorosulphonic acid are initially charged, and 49 g of 2,2,2-trifluoro-N-(2-fluoro-4-methylphenyl)acetamide are added in portions at room temperature. The mixture is stirred at room temperature for another 16 h. The mixture is added to ice while stirring, and extracted twice with ethyl acetate. The combined organic phases are dried over sodium sulphate and filtered, and the solvent is removed under reduced pressure. This gives 70.8 g of the chlorosulphonyl (XII-1). The crude product is immediately converted further.

N,N'-[Disulphanediylbis(6-fluoro-4-methylbenzene-3,1-diyl)]bis(2,2,2-trifluoroacetamide) (XI-1)

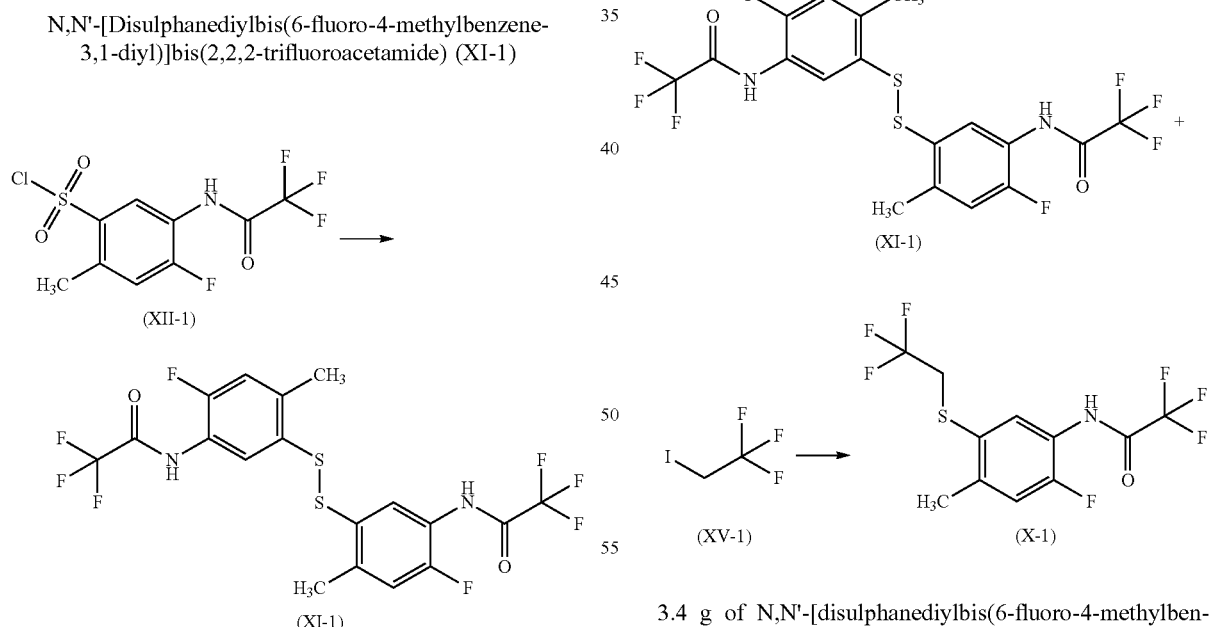

298.8 g of sodium iodide are dissolved in 1000 ml of trifluoroacetic acid, and 70.8 g of 4-fluoro-2-methyl-5-[(trifluoroacetyl)amino]benzenesulphonyl chloride are added at room temperature. The mixture is stirred at room temperature for 16 h and the solvent is then removed under reduced pressure. The residue is stirred with water and filtered off with suction. This gives 62.3 g (86% of theory) of the title compound as a solid.

log P[a]: 4.41

The following was obtained analogously:

N,N'-[Disulphanediylbis(4-chloro-6-fluorobenzene-3,1-diyl)]bis(2,2,2-trifluoroacetamide) (XI-2)

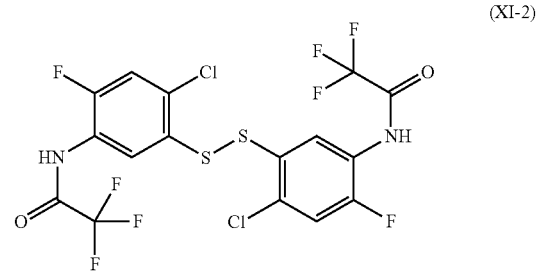 [SMILES: O=C(Nc1cc(SSc2cc(NC(=O)C(F)(F)F)c(F)cc2Cl)c(Cl)cc1F)C(F)(F)F]

log P[a]: 4.60; log P[b]: 3.82; 1H NMR (D6-DMSO, 400 MHz) δ ppm: 11.44(s,2H), 7.95(d,2H), 7.83(d,2H)

2,2,2-Trifluoro-N-{2-fluoro-4-methyl-5-[(2,2,2-trifluoroethyl)sulphanyl]phenyl}acetamide (X-1)

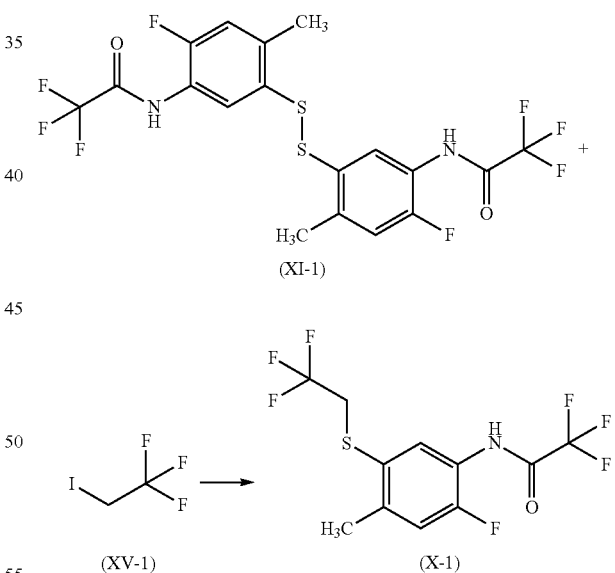

3.4 g of N,N'-[disulphanediylbis(6-fluoro-4-methylbenzene-3,1-diyl)]bis(2,2,2-trifluoroacetamide) are dissolved in 150 ml of N,N-dimethylformamide, and 1.86 g of potassium carbonate, 3.11 g of 1,1,1-trifluoroiodoethane, 2.39 g of Rongalit and a few drops of water are added. The reaction mixture is stirred at room temperature for 16 h. The majority of the N,N-dimethylformamide is distilled off under reduced pressure. The residue is taken up in water and extracted twice with ethyl acetate. The combined organic phases are dried over sodium sulphate and filtered, and the solvent is then removed under reduced pressure. This gives 4.48 g (90% of theory) of the title compound.

log P[a]: 3.31

The following was obtained analogously:

N-{4-Chloro-2-fluoro-5-[(2,2,2-trifluoroethyl)sulphanyl]phenyl}-2,2,2-trifluoroacetamide (X-2)

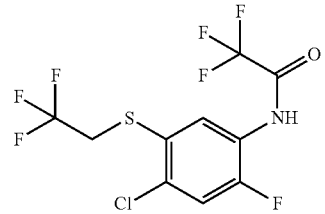

log P[a]: 3.34; log P[b]: 3.14; 1H NMR (D6-DMSO, 400 MHz) δ ppm: 11.47(bs,1H), 7.85(d,1H), 7.76(d,1H), 4.09 (q,2H)

4-Chloro-2-fluoro-5-[(2,2,2-trifluoroethyl)sulphanyl]aniline (IVa-2)

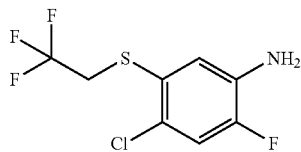 [SMILES: Nc1cc(SCC(F)(F)F)c(Cl)cc1F]

11.0 g (30.9 mmol) of N-{4-chloro-2-fluoro-5-[(2,2,2-trifluoroethyl)sulphanyl]phenyl}-2,2,2-trifluoroacetamide in 150 ml of dioxane are added cautiously to a solution of 10.3 ml (186 mmol) of sulphuric acid (96%) in 100 ml of water. The reaction mixture is then heated under reflux overnight. After cooling, the solution is adjusted to pH 7 using a saturated sodium bicarbonate solution and a little sodium carbonate and extracted three times with ethyl acetate. The combined organic phases are washed with a saturated sodium chloride solution, dried over sodium sulphate, filtered and concentrated. The residue comprises 8.27 g (96% pure, 99% of theory) of the title compound as a black oil/solid mixture.

log P[a]: 3.02; log P[b]: 3.00; 1H NMR (D6-DMSO, 400 MHz) δ ppm: 7.27(d,1H), 7.04(d,1H), 5.46(bs,2H), 3.85(q, 2H)

The following was obtained analogously:

4-Bromo-2-fluoro-5-[(2,2,2-trifluoroethyl)sulphanyl]aniline (IVa-14)

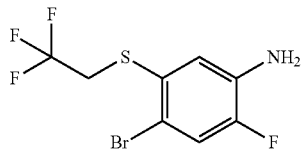

log P[a]: 3.15; log P[b]: 3.12; 1H NMR (D6-DMSO, 400 MHz) δ ppm: 7.37(d,1H), 7.05(d,1H), 5.48(broad,2H), 3.86 (q,2H)

S-(5-Acetamido-4-fluoro-2-methylphenyl)ethanethioate (XVII-1)

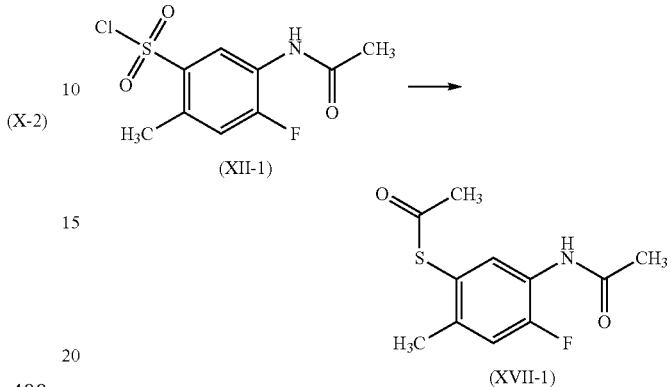

99.3 g of 5-acetamido-4-fluoro-2-methylbenzenesulphonyl chloride are suspended in 700 ml of glacial acetic acid, 0.9 g of iodine and 38.7 g of red phosphorus are added, and the mixture is stirred at reflux for 5 h. After cooling, the solid is filtered off and the filtrate is concentrated by rotary evaporation. The residue is stirred with water and filtered off with suction. This gives 57.6 g (67% of theory) of the title compound as a solid.

log P[a]: 1.78

5-Amino-4-fluoro-2-methylbenzenethiol (XVI-1)

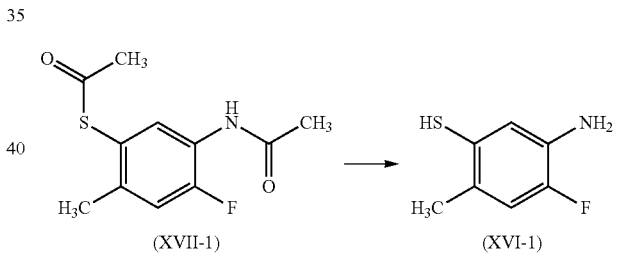

57.4 g of S-(5-acetamido-4-fluoro-2-methylphenyl)ethanethioate are dissolved in 750 ml of water and 96.6 g of potassium hydroxide. The reaction mixture is boiled at reflux for 16 hours. After cooling, the solution is adjusted to pH 2-3 with hydrochloric acid, and the precipitated solid is filtered off with suction. This gives 35.8 g (94% of theory) of the title compound as a solid.

log P[a]: 3.70

2-Fluoro-4-methyl-5-[(2,2,2-trifluoroethyl)sulphinyl]aniline (IVb-1)

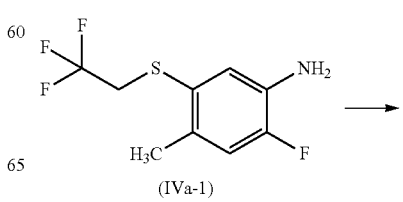

-continued

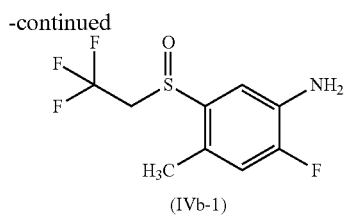

(IVb-1)

At 0-4° C., 5.00 g (0.21 mmol) of 2-fluoro-4-methyl-5-[(2,2,2-trifluoroethyl)sulphanyl]aniline are initially charged in 100 ml of dichloromethane, 6.18 g (0.25 mmol) of meta-chloroperbenzoic acid are added thereto and the reaction mixture is stirred at room temperature for 2 h. A 33% sodium thiosulphate solution is then added, and the mixture is extracted twice with dichloromethane. The combined organic phases are washed with a saturated sodium carbonate solution, dried over sodium sulphate and filtered, and the solvent is removed under reduced pressure. The residue comprises 5.10 g (90% pure, 86% of theory) of the title compound as a brown oil.

log P[a]: 1.77; log P[b]: 1.72; 1H NMR (D6-DMSO, 400 MHz) δ ppm: 7.26(d,1H), 7.02(d,1H), 5.45(bs,2H), 4.08-3.95(m,1H), 3.88-3.75(m,1H), 2.19(s,3H)

Synthesis of Bromides of the Formula (VIIa)

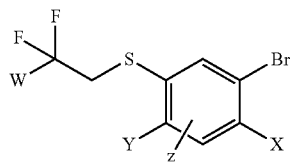

(VIIa)

5-Bromo-2-methylphenyl-2,2,2-trifluoroethyl sulphide (VIIa-7)

Stage 1: 5-Bromo-2-methylbenzenesulphonyl chloride

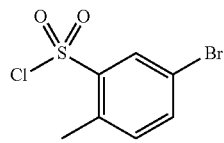

69.50 g (406.3 mmol) of 4-bromotoluene are initially charged in 250 ml of dichloromethane, and 175.33 g (1.50 mol) of chlorosulphonic acid are added dropwise at −5° C. With stirring, the reaction mixture is brought to room temperature overnight, 1000 ml of ice-water are added and the mixture is extracted with dichloromethane. The combined organic phases are washed with saturated aqueous sodium chloride solution, dried over magnesium sulphate, filtered and freed of the solvent under reduced pressure. This gives 89.54 g (95% pure, 78% of theory) of the title compound as a yellow liquid which is reacted further without further purification.

log P[a]: 3.73; log P[b]: 3.74; GC-MS: EI mass (m/z): 270 (1Cl,1Br) [M]+; ¹H NMR (CDCl₃, 400 MHz): 8.19(d,1H), 7.73-7.72(m,1H), 7.31(d,1H), 2.73(s,3H); ¹H NMR (CD₃CN, 400 MHz): 8.18(d,1H), 7.88-7.85(m,1H), 7.46(d,1H), 2.71(s,3H)

Stage 2: 4-Bromo-2-[(3-bromo-4-methylphenyl)disulphanyl]-1-methylbenzene

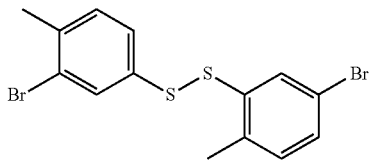 [SMILES: Cc1ccc(SSc2cc(Br)ccc2C)cc1Br]

25.00 g (92.7 mmol) of 5-bromo-2-methylbenzenesulphonyl chloride are admixed with 145.7 g of aqueous hydriodic acid (57%, 649.2 mmol) while stirring vigorously. The reaction mixture is stirred at room temperature for 3 days, then 40% aqueous sodium bisulphite solution is added. The solid is filtered off with suction, washed thoroughly with water and dried on a clay tile overnight. This gives 19.50 g (95% pure, 99% of theory) of the title compound as a yellow solid, which is converted further without further purification.

log P[a]: >7.36; log P[b]: >7.36; GC-MS: EI mass (m/z): 404 (2Br) [M]+

1H NMR (D6-DMSO): 7.56(d,2H), 7.46-7.43(m,2H), 7.26(d,2H), 2.35(s,6H)

Stage 3: 5-Bromo-2-methylphenyl-2,2,2-trifluoroethyl sulphide (VIIa-7)

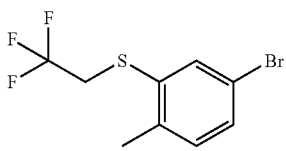

(VIIa-7)

27.70 g (68.5 mmol) of 4-bromo-2[(3-bromo-4-methylphenyl)disulphanyl]-1-methylbenzene are initially charged in 350 ml of N,N-dimethylformamide, 23.86 g (137.1 mmol) of sodium dithionite, 18.66 g (137.1 mmol) of Rongalit® and 18.94 g (137.1 mmol) of potassium carbonate are added and the mixture is cooled to 0° C. 31.65 g (150.8 mmol) of 1,1,1-trifluoro-2-iodoethane in 20 ml of N,N-dimethylformamide are added dropwise at 0° C. The reaction mixture is brought to room temperature overnight while stirring, 500 ml of water are added and the mixture is extracted with tert-butyl methyl ether. The combined organic phases are washed with water, saturated aqueous sodium bicarbonate solution and saturated aqueous sodium chloride solution, dried over magnesium sulphate, filtered and freed of the solvent under reduced pressure. Purification by column chromatography on silica gel by means of MPLC with cyclohexane/ethyl acetate as eluent gives 30.01 g (93% pure, 71% of theory) of the title compound as a colourless liquid.

log P[a]: 4.29; log P[b]: 4.26; GC-MS: EI mass (m/z): 286 (1Br) [M]+

1H NMR (D6-DMSO, 400 MHz) δ ppm: 7.70(d,1H), 7.39-7.36(m,1H), 7.21(d,1H), 4.09(q,2H), 2.30(s,3H)

The following were obtained analogously:

4-Bromo-1-methoxy-2-[(2,2,2-trifluoroethyl)sulphanyl]benzene (VIIa-8)

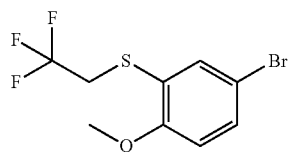
(VIIa-8)

log P[a]: 3.69; log P[b]: 3.81; GC-MS: EI mass (m/z): 302 (1Br) [M]$^+$
1H NMR (D6-DMSO, 400 MHz) δ ppm: 7.59(d,1H), 7.45-7.42(m,1H), 7.00(d,1H), 4.02(q,2H), 3.85(s,3H)

1,4-Dibromo-2-fluoro-5-[(2,2,2-trifluoroethyl)sulphanyl]benzene (VIIa-14)

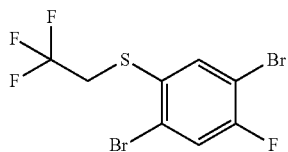 [SMILES: Fc1cc(Br)c(SCC(F)(F)F)cc1Br]

log P[a]: 4.39; log P[b]: 4.36; GC-MS: EI mass (m/z): 368 (2Br) [M]$^+$; $^1$H NMR (D6-DMSO, 400 MHz): 8.00(d,1H), 7.87(d,1H), 4.21(q,2H)

4-Bromo-2-[(2,2,2-trifluoroethyl)sulphanyl]benzonitrile (VIIa-9)

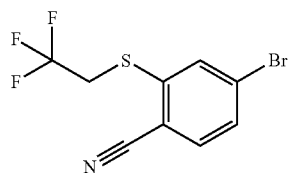
(VIIa-9)

24.0 g (86.4 mmol) of sodium hydride (60% in mineral oil) are initially charged in 300 ml of N,N-dimethylformamide, and 10.0 g (86.4 mmol) of 2,2,2-trifluoroethanethiol are added dropwise at 0° C. At 0° C., the reaction mixture is added dropwise to a solution of 14.4 g (72.0 mmol) of 4-bromo-2-fluorobenzonitrile in 100 ml of N,N-dimethylformamide, and the mixture is brought to room temperature overnight while stirring. The reaction mixture is poured into water, neutralized with saturated aqueous ammonium chloride solution and extracted with tert-butyl methyl ether. The combined organic phases are washed successively with water and saturated aqueous sodium chloride solution, dried over magnesium sulphate, filtered and freed of the solvent under reduced pressure. The residue is stirred with petroleum ether, filtered off and recrystallized from diethyl ether. This gives 17.6 g (99% pure, 82% of theory) of the title compound as a colourless solid.

log P[a]: 3.21; log P[b]: 3.16; 1H NMR (D6-DMSO, 400 MHz) δ ppm: 8.12(d,1H), 7.83(d,1H), 7.72-7.69(m,1H), 4.33(q,2H)

The following was obtained analogously:

4-Bromo-2-[(2,2,2-trifluoroethyl)sulphanyl]-1-(trifluoromethyl)benzene (VIIa-10)

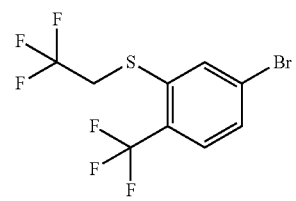
(VIIa-10)

log P[a]: 4.22; log P[b]: 4.20; $^1$H NMR (D6-DMSO, 400 MHz): 8.18(s,1H), 7.73-7.68(m,2H), 4.30(q,2H)

4-Bromo-5-fluoro-2-[(2,2,2-trifluoroethyl)sulphanyl]benzonitrile (VIIa-18)

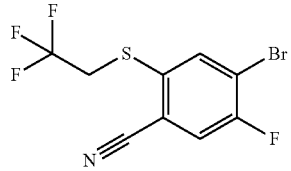 [SMILES: N#Cc1cc(F)c(Br)cc1SCC(F)(F)F]

log P[a]: 3.32; log P[b]: 3.26; GC-MS: EI mass (m/z): 315 [M]$^+$; $^1$H NMR (D6-DMSO, 400 MHz): 8.29(d,1H), 8.12 (d,1H), 4.26(q,2H)

Synthesis of Iodides of the Formula (VIIa)

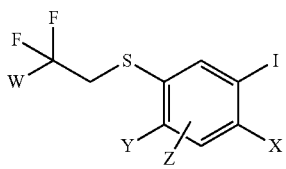
(VIIa)

1-Fluoro-2-iodo-5-methyl-4-[(2,2,2-trifluoroethyl)sulphanyl]benzene (VIIa-1-I)

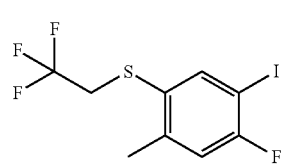
(VIIa-1-I)

10.0 g (33.0 mmol) of 5-bromo-2-methylphenyl-2,2,2-trifluoroethyl sulphide, 9.89 g (66.0 mmol) of sodium iodide, 314 mg (1.65 mmol) of copper(I) iodide and 469 mg (3.3 mmol) of trans-N,N'-dimethylcyclohexane-1,2-diamine (racemic) were stirred in 33 ml of degassed dioxane at 110° C. overnight. Another 9.89 g (66.0 mmol) of sodium iodide, 314 mg (1.65 mmol) of copper(I) iodide and 234 mg (1.65 mmol) of trans-N,N'-dimethylcyclohexane-1,2-diamine (racemic) were added, and the mixture was stirred at 110° C. overnight. Another 9.89 g (66.0 mmol) of sodium iodide and 314 mg (1.65 mmol) of copper(I) iodide and 20 ml of dioxane were added, and the mixture was stirred at 110° C. overnight. After cooling to room temperature, the mixture was diluted with ethyl acetate, filtered through kieselguhr and concentrated. Purification by column chromatography on silica gel by means of MPLC with cyclohexane/ethyl acetate as eluent gives 8.77 g (97% pure, 74% of theory) of the title compound as a colourless oil.

log P[a]: 4.44; log P[b]: 4.44; GC-MS: EI mass (m/z): 350 [M]$^+$

1H NMR (D6-DMSO, 400 MHz): 7.97(d,1H), 7.24(d, 1H), 3.96(q,2H), 2.35(s,3H)

The following was obtained analogously:

4-Iodo-1-methyl-2-[(2,2,2-trifluoroethyl)sulphanyl]benzene (VIIa-7-I)

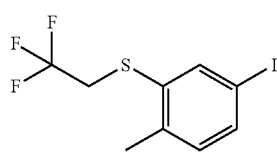

(VIIa-7-I)

log P[a]: 4.49; log P[b]: 4.48; GC-MS: EI mass (m/z): 332 [M]$^+$

1H NMR (D6-DMSO, 400 MHz): 7.83(d,1H), 7.55-7.53 (m,1H), 7.05(d,1H), 4.05(q,2H), 2.30(s,3H)

Synthesis of Boronic Acids of the Formula (VIII)

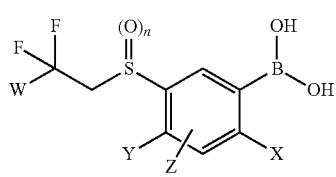

(VIII)

{4-Methyl-3-[(2,2,2-trifluoroethyl)sulphanyl]phenyl}boronic acid (VIIIa-7)

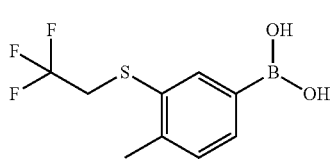

(VIIIa-7)

Stage 1: 4,4,5,5-Tetramethyl-2-{4-methyl-3-[(2,2,2-trifluoroethyl)sulphanyl]phenyl}-1,3,2-dioxaborolane

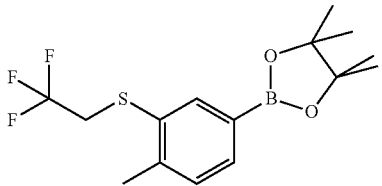 [SMILES: Cc1ccc(B2OC(C)(C)C(C)(C)O2)cc1SCC(F)(F)F]

15.0 g (52.6 mmol) of 5-bromo-2-methylphenyl-2,2,2-trifluoroethyl sulphide, 14.7 g (57.9 mmol) of 4,4,4',4',5,5,5',5'-octamethyl-2,2'-bis-1,2,3-dioxaborolane, 10.3 g (105.2 mmol) of potassium acetate and 2.15 g (2.63 mmol) of 1,1'-bis(diphenylphosphino)ferrocenepalladium(II) dichloride/methylene chloride adduct are initially charged in 78 ml of dry degassed dioxane and stirred under microwave irradiation (Anton Paar Multiwave) at 160° C. for 40 min. The reaction mixture is filtered through silica gel with ethyl acetate, and the filtrate is freed of the solvent under reduced pressure. Purification by column chromatography on silica gel by means of MPLC with cyclohexane/ethyl acetate as eluent gives 14.07 g (90% pure, 72% of theory) of the title compound as a green oil.

log P[a]: 3.73; log P[b]: 3.74; ESI mass (m/z): 333 [M+1]$^+$; GC-MS: EI mass (m/z): 332 [M]$^+$ 1H NMR (D6-DMSO, 400 MHz) δ ppm: 7.77(s,1H), 7.52(d,1H), 7.30(d,1H), 3.87(q,2H), 2.42(s,3H), 1.29(s, 12H)

Stage 2: {4-Methyl-3-[(2,2,2-trifluoroethyl)sulphanyl]phenyl}boronic acid (VIIIa-7) and {4-methyl-3-[(2,2,2-trifluoroethyl)sulphinyl]phenyl}boronic acid (VIIIb-7)

730 mg (2.2 mmol) of 4,4,5,5-tetramethyl-2-{4-methyl-3-[(2,2,2-trifluoroethyl)sulphanyl]phenyl}-1,3,2-dioxaborolane are initially charged in 20 ml of acetone and 20 ml of water, and 381 mg (4.9 mmol) of ammonium acetate and 1.06 g (4.9 mmol) of sodium periodate are added at 0° C. The reaction mixture is stirred at room temperature overnight and then freed from acetone under reduced pressure. The acidic aqueous phase is extracted with ethyl acetate, and the combined organic phases are washed successively with water and saturated aqueous sodium chloride solution, dried over magnesium sulphate, filtered and freed of the solvent under reduced pressure. Purification by column chromatography on silica gel by means of MPLC with cyclohexane/ethyl acetate as eluent gives 105 mg (96% pure, 18% of theory) of {4-methyl-3-[(2,2,2-trifluoroethyl)sulphanyl]phenyl}boronic acid and 138 mg (97% pure, 23% of theory) of {4-methyl-3-[(2,2,2-trifluoroethyl)sulphinyl]phenyl}boronic acid as colourless solids.

{4-Methyl-3-[(2,2,2-trifluoroethyl)sulphanyl]phenyl}boronic acid (VIIIa-7)

log P[a]: 2.30; log P[b]: 2.24; ESI mass (m/z): pos.[a]: 251 [M+1]$^+$, neg.[b]: 249 [M−1]$^−$ 1H NMR (D6-DMSO, 400 MHz): 8.08(s,2H), 7.92(s,1H), 7.61-7.59(m,1H), 7.23(d,1H), 3.90(q,2H), 2.38(s,3H)

{4-Methyl-3-[(2,2,2-trifluoroethyl)sulphinyl]phenyl}boronic acid (VIIIb-7)

log P[a]: 1.41; log P[b]: 1.36; ESI mass (m/z): pos.[a]: 267 [M+1]$^+$;

1H NMR (D6-DMSO, 400 MHz): 8.31(s,1H), 8.24(s,2H), 7.89-7.87(m,1H), 7.31(d,1H), 4.12-4.02(m,1H), 3.94-3.82(m,1H), 2.39(s,3H)

The following were obtained analogously:

2-{4-Chloro-3-[(2,2,2-trifluoroethyl)sulphanyl]phenyl}-4,4,5,5-tetramethyl-1,3,2-dioxaborolane

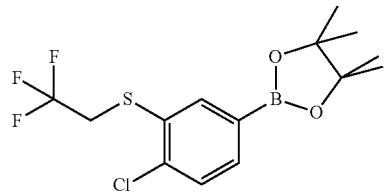 [SMILES: CC1(C)OB(c2ccc(Cl)c(SCC(F)(F)F)c2)OC1(C)C]

log P[a]: 5.27; log P[b]: 5.16; ESI mass (m/z): pos.[a]: 353 [M+1]$^+$; GC-MS: EI mass (m/z): 352[M]$^+$; 1H NMR (D6-DMSO, 400 MHz): 7.87(d,1H), 7.62-7.60(m,1H), 7.50(d,1H), 3.71(q,2H), 1.33(s,12H)

{4-Chloro-3-[(2,2,2-trifluoroethyl)sulphanyl]phenyl}boronic acid (VIIIa-3)

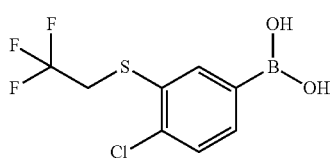
(VIIIa-3)

log P[a]: 2.40; log P[b]: 2.41; ESI mass (m/z): neg.[a]: 315 [M+HCOO$^−$]$^−$, 1H NMR (D6-DMSO, 400 MHz): 8.30 (broad,2H), 8.00(d,1H), 7.67-7.64(m,1H), 7.49(d,1H), 4.07(q,2H)

2-{2,4-Dichloro-5-[(2,2,2-trifluoroethyl)sulphanyl]phenyl}-4,4,5,5-tetramethyl-1,3,2-dioxaborolane

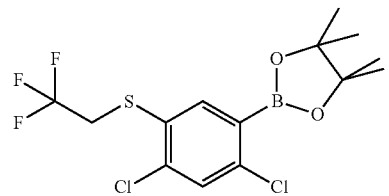 [SMILES: CC1(C)OB(c2cc(SCC(F)(F)F)c(Cl)cc2Cl)OC1(C)C]

log P[a]: 5.68; log P[b]: 5.31; ESI mass (m/z): pos.[a]: 387 [M+1]$^+$; GC-MS: EI mass (m/z): 386[M]$^+$; 1H NMR (D6-DMSO, 400 MHz): 7.79(s,1H), 7.72(s,1H), 4.08(q,2H), 1.32(s,12H)

{2,4-Dichloro-5-[(2,2,2-trifluoroethyl)sulphanyl]phenyl}boronic acid (VIIIa-6)

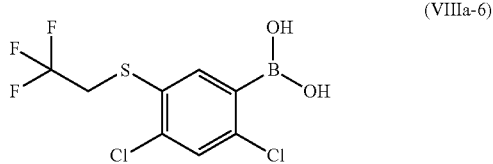 [SMILES: OB(O)c1cc(SCC(F)(F)F)c(Cl)cc1Cl]
(VIIIa-6)

log P[a]: 2.61; log P[b]: 2.52; ESI mass (m/z): neg.[a]: 348 [M+HCOO$^−$]$^−$, 1H NMR (D6-DMSO, 400 MHz): 8.50 (broad,2H), 7.68(s,1H), 7.60(s,1H), 4.11(q,2H)

2-{4-Methoxy-3-[(2,2,2-trifluoroethyl)sulphanyl]phenyl}-4,4,5,5-tetramethyl-1,3,2-dioxaborolane

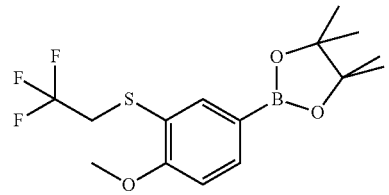 [SMILES: COc1ccc(B2OC(C)(C)C(C)(C)O2)cc1SCC(F)(F)F]

log P[a]: 4.54; log P[b]: 4.46; ESI mass (m/z): pos.[a]: 349 [M+1]$^+$; GC-MS: EI mass (m/z): 348[M]$^+$; 1H NMR (D6-DMSO, 400 MHz): 7.67(d,1H), 7.64-7.62(m,1H), 7.07(d,1H), 3.89(s,3H), 3.83(q,2H), 1.29(s,12H)

{4-Methoxy-3-[(2,2,2-trifluoroethyl)sulphanyl]phenyl}boronic acid (VIIIa-8)

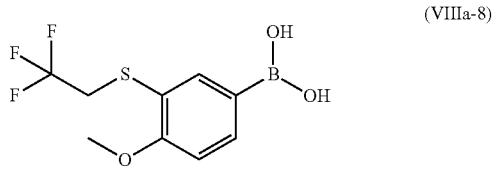 [SMILES: COc1ccc(B(O)O)cc1SCC(F)(F)F]
(VIIIa-8)

log P[a]: 1.94; log P[b]: 1.93; ESI mass (m/z): neg.[a]: 311 [M+HCOO⁻]⁻, ¹H NMR (D6-DMSO, 400 MHz): 7.98 (broad,2H), 7.86(d,1H), 7.74-7.71(m,1H), 7.02(d,1H), 3.87 (s,3H), 3.84(q,2H)

{2,4-Dimethyl-5-[(2,2,2-trifluoroethyl)sulphanyl]phenyl}boronic acid (VIIIa-11)

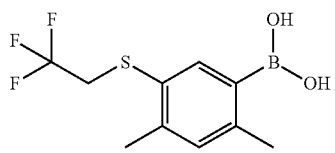
(VIIIa-11)

log P[a]: 2.58; log P[b]: 2.57; ESI mass (m/z): neg.[a]: 309 [M+HCOO⁻]⁻, ¹H NMR (D6-DMSO, 400 MHz): 8.02 (broad,2H), 7.61(s,1H), 7.03(s,1H), 3.81(q,2H), 2.36(s,3H), 2.34(s,3H)

{2-Fluoro-4-methyl-5-[(2,2,2-trifluoroethyl)sulphinyl]phenyl}boronic acid (VIIIb-1)

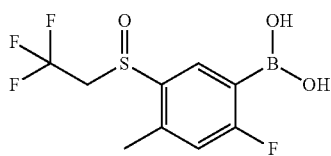
(VIIIb-1)

300 mg (1.12 mmol) of {2-fluoro-4-methyl-5-[(2,2,2-trifluoroethyl)sulphanyl]phenyl}boronic acid are dissolved in acetonitrile, 396.4 g (1.12 mmol) of Selectfluor® are added and the mixture is stirred at room temperature overnight. A further 39.8 mg (0.12 mmol) of Selectfluor® are added and the reaction mixture is stirred for 2 h, then diluted with ethyl acetate and washed with 1N hydrochloric acid. The organic phase is dried over magnesium sulphate, filtered and freed of the solvent under reduced pressure. Purification by column chromatography on silica gel by means of MPLC with cyclohexane/ethyl acetate as eluent gives 102 mg (97% pure, 31% of theory) of the title compound as a colourless oil which crystallizes gradually in the course of storage to give a colourless solid.

log P[a]: 1.38; log P[b]: 1.11; ESI mass (m/z): pos.[a]: 285 [M+1]⁺, neg.[a]: 329 [M+HCOO⁻]⁻

¹H NMR (D6-DMSO, 400 MHz): 8.36(s,2H), 8.08(d,1H), 7.15(d,1H), 4.14-3.92(m,2H), 2.39(s,3H)

The following were obtained analogously:

{4-Chloro-3-[(2,2,2-trifluoroethyl)sulphinyl]phenyl}boronic acid (VIIIb-3)

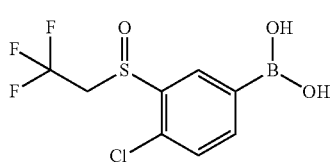
(VIIIb-3)

log P[a]: 1.74; log P[b]: 1.68; ESI mass (m/z): pos.[a]: 287 [M+1]⁺; ¹H NMR (D6-DMSO, 400 MHz): 8.45(broad, 2H), 8.33(d,1H), 8.01-7.99(m,1H), 7.62(d,1H), 4.24-4.12 (m,1H), 4.08-3.96(m,1H)

{2,4-Dichloro-5-[(2,2,2-trifluoroethyl)sulphinyl]phenyl}boronic acid (VIIIb-6)

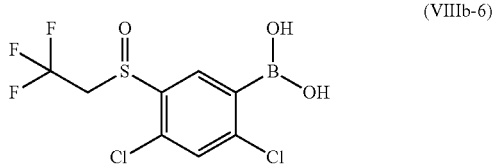 [SMILES: O=S(CC(F)(F)F)c1cc(B(O)O)c(Cl)cc1Cl]
(VIIIb-6)

log P[a]: 1.86; log P[b]: 1.51; ESI mass (m/z): pos.[a]: 321 [M+1]⁺; ¹H NMR (D6-DMSO, 400 MHz): 8.64(broad, 2H), 7.92(s,1H), 7.79(s,1H), 4.29-4.04(m,2H)

{4-Methoxy-3-[(2,2,2-trifluoroethyl)sulphanyl]phenyl}boronic acid (VIIIb-8)

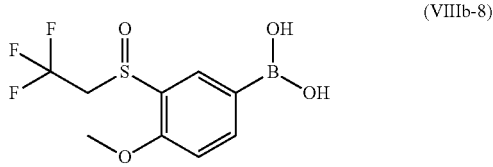 [SMILES: COc1ccc(B(O)O)cc1S(=O)CC(F)(F)F]
(VIIIb-8)

log P[a]: 1.36; log P[b]: 1.37; ESI mass (m/z): pos.[a]: 283 [M+1]⁺; ¹H NMR (D6-DMSO, 400 MHz): 8.15(s,1H), 8.13(s,2H), 8.02-8.00(m,1H), 7.17(d,1H), 4.08-3.99(m,1H), 3.90(s,3H), 3.87-3.78(m,1H)

{2,4-Dimethyl-5-[(2,2,2-trifluoroethyl)sulphinyl]phenyl}boronic acid (VIIIb-11)

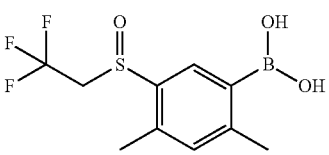
(VIIIb-11)

log P[a]: 1.61; log P[b]: 1.61; ESI mass (m/z): pos.[a]: 281 [M+1]⁺; ¹H NMR (D6-DMSO, 400 MHz): 8.15(s,2H), 7.96(s,1H), 7.09(s,1H), 4.05-3.85(m,2H), 2.44(s,3H), 2.33 (s,3H)

Synthesis of Thioureas of the Formula (IIa) and (IIb)

1-{2-Fluoro-4-methyl-5-[(2,2,2-trifluoroethyl)sulphanyl]phenyl}-3-(2,2,2-trifluoroethyl)thiourea (IIa-1)

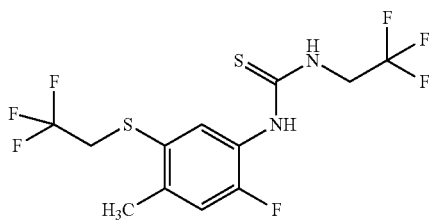 [SMILES: Cc1cc(F)c(NC(=S)NCC(F)(F)F)cc1SCC(F)(F)F]

1.00 g (4.18 mmol) of 2-fluoro-4-methyl-5-[(2,2,2-trifluoroethyl)sulphanyl]aniline is initially charged in 5 ml of dichloromethane, and 0.006 ml (0.042 mmol) of triethylamine is added thereto. After the addition of 0.59 g (4.18 mmol) of 1,1,1-trifluoro-2-isothiocyanatoethane, the reaction mixture is stirred at room temperature overnight. The solvent is removed under reduced pressure, the residue is stirred with a little toluene and the insoluble fraction is filtered off with suction and dried. This gives 0.31 g (100% pure, 20% of theory) of the title compound as a white solid. The filtrate is freed of the solvent under reduced pressure. The residue of 1.30 g comprises the title compound in a purity of 77%.

log P[a]: 3.32; log P[b]: 3.24; 1H NMR (D6-DMSO, 400 MHz) δ ppm: 9.62(bs,1H), 8.34(bs,1H), 7.76(d,1H), 7.26(d,1H), 4.46-4.40(m,2H), 3.87(q,2H), 2.38(s,3H)

The following was obtained analogously:

1-{2-Fluoro-4-methyl-5-[(2,2,2-trifluoroethyl)sulphinyl]phenyl}-3-(2,2,2-trifluoroethyl)thiourea (IIb-1)

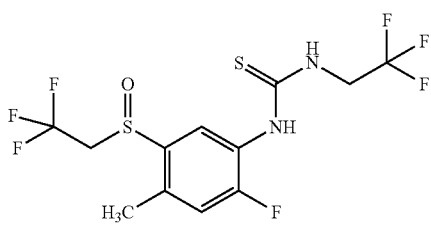 [SMILES: Cc1cc(F)c(NC(=S)NCC(F)(F)F)cc1S(=O)CC(F)(F)F]

log P[a]: 2.34; log P[b]: 2.3; 1H NMR (D6-DMSO, 400 MHz) δ ppm: 9.75(bs,1H), 8.50(bs,1H), 8.12(bd,1H), 7.36 (d,1H), 4.52-4.40(m,1H), 4.21-4.15(m,1H), 4.05-3.95(m,1H), 2.36(s,3H)

Synthesis of Isocyanates of the Formula (IIIa)

4-Fluoro-5-isocyanato-2-methylphenyl-2,2,2-trifluoroethyl sulphide (IIIa-1)

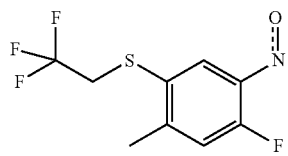

A solution of 5.00 g (20.9 mmol) of 2-fluoro-4-methyl-5-[(2,2,2-trifluoroethyl)sulphanyl]aniline in 50 ml of toluene is admixed at room temperature with 3.10 g (15.68 mmol) of trichloromethyl chlorocarbonate (diphosgene), and heated to reflux in an apparatus having wash bottles containing ammonia/isopropanol mixture for 2 h. Toluene is distilled off using a water separator, fresh toluene is added and the operation is repeated several times. Drying under reduced pressure gives 5.15 g (90% pure, 84% of theory) of the title compound as a yellow oil.

GC-MS EI mass (m/z): 265 [M]+, GC-MS index 1392; 1H NMR (CDCl3, 400 MHz) δ ppm: 7.24(d 1H), 7.03(d,1H), 3.31(q,2H), 2.45(s,3H)

The following were obtained analogously:

2-Chloro-5-isocyanatophenyl-2,2,2-trifluoroethyl sulphide (IIIa-3)

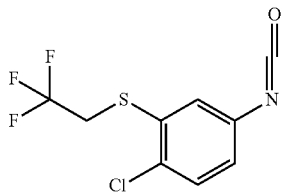

GC-MS EI mass (m/z): 267 [M]+, GC-MS index 1452

5-Isocyanato-2,4-dimethylphenyl-2,2,2-trifluoroethyl sulphide (IIIc-11)

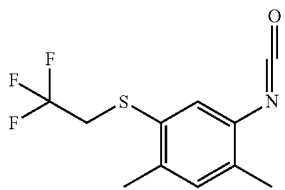

GC-MS EI mass (m/z): 261 [M]+, GC-MS index 1500; 1H NMR (CDCl3, 400 MHz) δ ppm: 7.19(s,1H), 7.05(s,1H), 3.34(q,2H), 2.40(s,3H), 2.28(s,3H)

Synthesis of Compounds of the General Formula (XXIV)

4-[4-Cyclopropyl-5-oxo-3-(trifluoromethyl)-4,5-dihydro-1H-1,2,4-triazol-1-yl]-2,5-difluorobenzonitrile (XXIV-1)

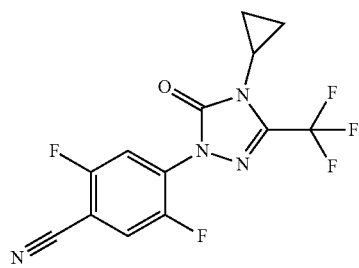 [SMILES: N#Cc1cc(F)c(-n2nc(C(F)(F)F)n(C3CC3)c2=O)cc1F]

To a solution of 202 mg (5.0 mmol) of sodium hydride (60% in mineral oil) in 30 ml of N,N-dimethylformamide are added, at 0° C., 974 mg (5.0 mmol) of 4-cyclopropyl-5-(trifluoromethyl)-2,4-dihydro-3H-1,2,4-triazol-3-one (prepared according to EP 657437 A1; DE 4339412 A1). After stirring at 0° C. for 30 minutes, 660 mg (4.2 mmol) of 2,4,5-trifluorobenzonitrile are added. The reaction mixture is stirred at room temperature for 3 d, then poured into water, neutralized and extracted with tert-butyl methyl ether. The combined organic phases are washed successively with water and saturated aqueous sodium chloride solution, dried over magnesium sulphate, filtered and freed of the solvent under reduced pressure. Purification by column chromatography on silica gel by means of MPLC with cyclohexane/ ethyl acetate as eluent gives 539 mg (100% pure, 39% of theory) of the title compound as a yellow solid.

log P[a]: 2.91; log P[a]: 2.90; 1H NMR (D6-DMSO): 8.29(dd,1H), 7.84(dd,1H), 3.10-3.04(m,1H), 1.23-1.01(m, 4H)

Synthesis of Compounds of the General Formula (XXVII) and (XXVIII)

Methyl 1-[5-(chlorosulphonyl)-2-fluoro-4-methylphenyl]-4-isopropyl-5-oxo-4,5-dihydro-1H-1,2,4-triazole-3-carboxylate (XXVII-1)

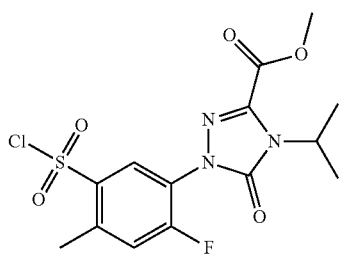 [SMILES: COC(=O)c1nn(-c2cc(S(=O)(=O)Cl)c(C)cc2F)c(=O)n1C(C)C]

330 mg (1.13 mmol) of methyl-1-(2-fluoro-4-methylphenyl)-4-isopropyl-5-oxo-4,5-dihydro-1H-1,2,4-triazole-3-carboxylate (synthesis according to DE2725148) in 30 ml of dichloromethane are admixed with 5 g (42.91 mmol) of chlorosulphonic acid in portions and stirred under reflux for 12 h. After cooling, ice-water is added dropwise and extracted with dichloromethane. The combined organic phases are washed with water, dried over sodium sulphate and filtered. Removal of the solvent under reduced pressure gives 350 mg (85% pure by 1H NMR, 79% of theory) of product.

1H NMR (D6-DMSO): 7.84-7.82(m,1H), 7.27-7.25(m, 1H), 4.99-4.95(sept,1H), 3.89(s,3H), 2.57(s,3H), 1.48-1.47 (d,6H)

Dimethyl 1,1'-[disulphanediylbis(6-fluoro-4-methylbenzene-3,1-diyl)]bis(4-isopropyl-5-oxo-4,5-dihydro-1H-1,2,4-triazole-3-carboxylate) (XXVIII-1)

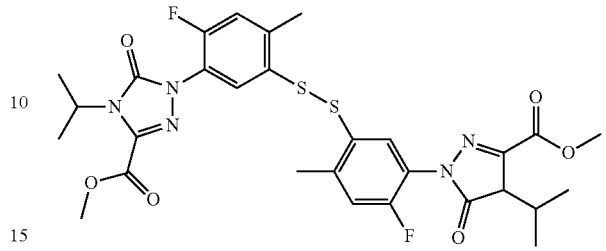

5.50 g (14.04 mmol) of methyl-1-[5-(chlorosulphonyl)-2-fluoro-4-methylphenyl]-4-isopropyl-5-oxo-4,5-dihydro-1H-1,2,4-triazole-3-carboxylate are heated together with 4.10 g (73.42 mmol) of iron powder in 200 ml of ethanol and 7.6 g of concentrated hydrochloric acid under reflux for 12 h. After removal of the solvent under reduced pressure, the residue is stirred with water and filtered off with suction to obtain 4.50 g of crude product (49% of theory) as a light brown solid.

log P[a]: 4.11

By the above-described processes, the following compounds of the general formula (I) were prepared:

(I) with (I-A)

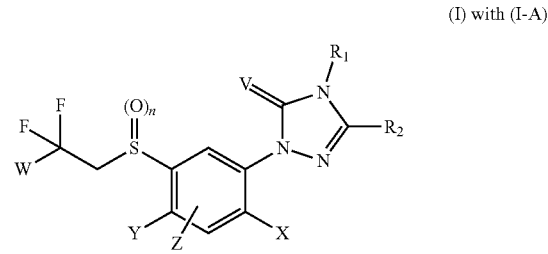

(compound of the general formula (I) with (I-A) with Z=H)

| Example No. | $R^1$ | $R^2$ | W | n | Y | X | V |
|---|---|---|---|---|---|---|---|
| 1 | $CH_3$ | $CH_3$ | F | 1 | CN | F | O |
| 2 | H | $CH_3$ | F | 0 | CN | F | O |
| 3 | $CH(CH_3)_2$ | COOH | H | 0 | $CH_3$ | F | O |
| 4 | $CH(CH_3)_2$ | H | F | 0 | $CH_3$ | F | O |
| 5 | $CH(CH_3)_2$ | H | H | 0 | $CH_3$ | F | O |
| 6 | $CH(CH_3)_2$ | H | F | 1 | $CH_3$ | F | O |
| 7 | H | H | F | 0 | $CH_3$ | F | O |
| 8 | $CH(CH_3)_2$ | H | H | 1 | $CH_3$ | F | O |
| 9 | $CH_3$ | $CF_3$ | F | 0 | $CH_3$ | F | O |
| 10 | $CH_3$ | $CH_3$ | F | 0 | $CH_3$ | F | O |
| 11 | $CH_3$ | $CH_3$ | F | 1 | $CH_3$ | F | O |
| 12 | $CH_3$ | $CF_3$ | F | 1 | $CH_3$ | F | O |
| 13 | $CH_3$ | 2-fluoro-4-chlorophenyl | F | 0 | $OCH_3$ | H | O |
| 14 | $CH_3$ | $CH_3$ | F | 0 | $CH_3$ | H | O |
| 15 | $CH_3$ | phenyl | F | 0 | $CH_3$ | F | O |
| 16 | $CH_3$ | 2-fluoro-4-chlorophenyl | F | 0 | $CH_3$ | H | O |
| 17 | cyclopropyl | $CH_3$ | F | 0 | $CH_3$ | H | O |
| 18 | cyclopropyl | $CH(CH_3)_2$ | F | 0 | $CH_3$ | H | O |
| 19 | cyclopropyl | $CH_2OCH_3$ | F | 0 | $CH_3$ | H | O |
| 20 | cyclopropyl | H | F | 0 | $CH_3$ | H | O |
| 21 | $CH_3$ | $CF_3$ | F | 0 | $CH_3$ | H | O |
| 22 | $C(CH_3)_3$ | $CF_3$ | F | 0 | $CH_3$ | H | O |
| 23 | $CH_3$ | phenyl | F | 1 | $CH_3$ | F | O |

-continued

| Example No. | R¹ | R² | W | n | Y | X | V |
|---|---|---|---|---|---|---|---|
| 24 | CH₃ | phenyl | F | 1 | CH₃ | CH₃ | O |
| 25 | CH₃ | 2-fluoro-4-chlorophenyl | F | 1 | CH₃ | H | O |
| 26 | cyclopropyl | CH₃ | F | 1 | CH₃ | H | O |
| 27 | cyclopropyl | CH₂OCH₃ | F | 1 | CH₃ | H | O |
| 28 | cyclopropyl | H | F | 1 | CH₃ | H | O |
| 29 | CH₃ | CF₃ | F | 1 | CH₃ | H | O |
| 30 | C(CH₃)₃ | CF₃ | F | 1 | CH₃ | H | O |
| 31 | 4-methyl-3-(2,2,2-trifluoroethyl-sulphanyl)phenyl | CH₃ | F | 0 | CH₃ | H | O |
| 32 | cyclopropyl | CF₃ | F | 0 | CH₃ | H | O |
| 33 | cyclopropyl | CH(CH₃)₂ | F | 0 | Cl | H | O |
| 34 | cyclopropyl | CF₃ | F | 1 | CH₃ | H | O |
| 35 | phenyl | CF₃ | F | 0 | CH₃ | H | O |
| 36 | phenyl | CF₃ | F | 0 | CH₃ | F | O |
| 37 | phenyl | CF₃ | F | 1 | CH₃ | F | O |
| 38 | CH₃ | CF₃ | F | 0 | CN | F | O |
| 39 | CH₃ | 2-fluoro-4-chlorophenyl | F | 1 | CH₃ | F | O |
| 40 | CH₃ | 2-fluoro-4-chlorophenyl | F | 0 | CH₃ | F | O |
| 41 | cyclopropyl | CH₃ | F | 1 | CH₃ | F | O |
| 42 | cyclopropyl | CH₃ | F | 0 | CH₃ | F | O |
| 43 | cyclopropyl | CH(CH₃)₂ | F | 1 | CH₃ | F | O |
| 44 | cyclopropyl | CH(CH₃)₂ | F | 0 | CH₃ | F | O |
| 45 | cyclopropyl | CH₂OCH₃ | F | 1 | CH₃ | F | O |
| 46 | cyclopropyl | CH₂OCH₃ | F | 0 | CH₃ | F | O |
| 47 | cyclopropyl | CF₃ | F | 1 | CN | F | O |
| 48 | cyclopropyl | CF₃ | F | 0 | CH₃ | CH₃ | O |
| 49 | C(CH₃)₃ | CF₃ | F | 0 | CH₃ | CH₃ | O |
| 50 | CH₂CH₃ | CF₃ | F | 0 | CH₃ | Cl | O |
| 51 | cyclopropyl | CF₃ | F | 0 | Cl | H | O |
| 52 | cyclopropyl | CF₃ | F | 0 | OCH₃ | H | O |
| 53 | cyclopropyl | CF₃ | F | 1 | OCH₃ | H | O |
| 54 | CH₂CH₃ | CF₃ | F | 0 | CH₃ | H | O |
| 55 | CH₂CF₃ | CF₃ | F | 0 | CH₃ | F | O |
| 56 | CH₂CF₃ | CF₃ | F | 1 | CH₃ | F | O |
| 57 | CH₂CH₃ | CF₃ | F | 0 | CH₃ | F | O |
| 58 | CH₂CH₃ | CF₃ | F | 1 | CH₃ | F | O |
| 59 | cyclopropyl | CF₃ | F | 0 | CH₃ | F | O |
| 60 | cyclopropyl | CF₃ | F | 1 | CH₃ | F | O |
| 61 | cyclopropyl | H | F | 0 | CH₃ | F | O |
| 62 | cyclopropyl | H | F | 1 | CH₃ | F | O |
| 63 | cyclopropyl | C(CH₃)₃ | F | 0 | CH₃ | F | O |
| 64 | cyclopropyl | C(CH₃)₃ | F | 1 | CH₃ | F | O |
| 65 | cyclopropyl | cyclopropyl | F | 0 | CH₃ | F | O |
| 66 | cyclopropyl | cyclopropyl | F | 1 | CH₃ | F | O |
| 67 | C(CH₃)₃ | CF₃ | F | 0 | CH₃ | F | O |
| 68 | C(CH₃)₃ | CF₃ | F | 1 | CH₃ | F | O |
| 69 | cyclopropyl | 3-fluorophenyl | F | 0 | CH₃ | F | O |
| 70 | cyclopropyl | 3-fluorophenyl | F | 1 | CH₃ | F | O |
| 71 | cyclopropyl | CH₂CH₂CH₂CH₃ | F | 0 | CH₃ | F | O |
| 72 | cyclopropyl | CH₂CH₂CH₂CH₃ | F | 1 | CH₃ | F | O |
| 73 | cyclopropyl | CH₂OCH₂CH₃ | F | 0 | CH₃ | F | O |
| 74 | cyclopropyl | CH₂OCH₂CH₃ | F | 1 | CH₃ | F | O |
| 75 | cyclopropyl | CH₂CH₂OCH₃ | F | 0 | CH₃ | F | O |
| 76 | cyclopropyl | CH₂CH₂OCH₃ | F | 1 | CH₃ | F | O |
| 77 | cyclopropyl | CH₂CH₃ | F | 0 | CH₃ | F | O |
| 78 | cyclopropyl | CH₂CH₃ | F | 1 | CH₃ | F | O |
| 79 | cyclopropyl | CH₂CH₂CH₃ | F | 0 | CH₃ | F | O |
| 80 | cyclopropyl | CH₂CH₂CH₃ | F | 1 | CH₃ | F | O |
| 81 | cyclopropyl | CH=CHCH₃ | F | 0 | CH₃ | F | O |
| 82 | cyclopropyl | CH=CHCH₃ | F | 1 | CH₃ | F | O |
| 83 | cyclopropyl | CH₂CH(CH₃)₂ | F | 0 | CH₃ | F | O |
| 84 | cyclopropyl | CH₂CH(CH₃)₂ | F | 1 | CH₃ | F | O |
| 85 | cyclopropyl | CH(CH₃)CH₂CH₃ | F | 0 | CH₃ | F | O |
| 86 | cyclopropyl | CH(CH₃)CH₂CH₃ | F | 1 | CH₃ | F | O |
| 87 | cyclopropyl | cyclobutyl | F | 0 | CH₃ | F | O |
| 88 | cyclopropyl | cyclobutyl | F | 1 | CH₃ | F | O |
| 89 | CH₂CH₂OCH₃ | CF₃ | F | 0 | CH₃ | F | O |
| 90 | cyclopropyl | OCH₃ | F | 0 | CH₃ | H | O |
| 91 | cyclopropyl | OCH(CH₃)₂ | F | 0 | CH₃ | H | O |
| 92 | cyclopropyl | OCH₂CF₃ | F | 0 | CH₃ | H | O |
| 93 | CH₃ | OCH₃ | F | 0 | CH₃ | F | O |
| 94 | CH₃ | OCH₃ | F | 1 | CH₃ | F | O |

-continued

| Example No. | R¹ | R² | W | n | Y | X | V |
|---|---|---|---|---|---|---|---|
| 95 | CH₃ | OCH₃ | F | 0 | CF₃ | H | O |
| 96 | CH₃ | OCH₃ | F | 1 | CF₃ | H | O |
| 97 | CH₃ | OCH₃ | F | 1 | Cl | Cl | O |
| 98 | CH₃ | OCH₃ | F | 1 | Cl | F | O |
| 99 | CH₃ | OCH₃ | F | 1 | Cl | H | O |
| 100 | cyclopropyl | OCH(CH₃)₂ | F | 1 | CH₃ | F | O |
| 101 | cyclopropyl | OCH(CH₃)₂ | F | 0 | CH₃ | F | O |
| 102 | cyclopropyl | OCH₂CF₃ | F | 1 | CH₃ | F | O |
| 103 | cyclopropyl | OCH₂CF₃ | F | 0 | CH₃ | F | O |
| 104 | cyclopropyl | OCH₃ | F | 1 | CH₃ | F | O |
| 105 | cyclopropyl | OCH₃ | F | 0 | CH₃ | F | O |
| 106 | cyclopropyl | OCH₃ | F | 1 | Cl | Cl | O |
| 107 | cyclopropyl | OCH₃ | F | 0 | Cl | Cl | O |
| 108 | cyclopropyl | OCH₃ | F | 0 | Cl | H | O |
| 109 | cyclopropyl | OCH₃ | F | 1 | OCH₃ | H | O |
| 110 | cyclopropyl | OCH₃ | F | 1 | Br | H | O |
| 111 | cyclopropyl | OCH₃ | F | 0 | Br | H | O |
| 112 | cyclopropyl | OCH₂CH₂CH₃ | F | 1 | CH₃ | F | O |
| 113 | cyclopropyl | OCH₂CH₂CH₃ | F | 0 | CH₃ | F | O |
| 114 | cyclopropyl | OCH₃ | F | 0 | Cl | F | O |
| 115 | cyclopropyl | OCH₃ | F | 1 | Cl | F | O |
| 116 | cyclopropyl | OCH₃ | F | 0 | CH₃ | Cl | O |
| 117 | cyclopropyl | OCH₃ | F | 1 | CH₃ | Cl | O |
| 118 | cyclopropyl | OCH₃ | F | 1 | CN | H | O |
| 119 | cyclopropyl | OCH₃ | F | 1 | CH₃ | CH₃ | O |
| 120 | cyclopropyl | OCH₂CH₃ | F | 0 | CH₃ | F | O |
| 121 | cyclopropyl | OCH₂CH₃ | F | 1 | CH₃ | F | O |
| 122 | cyclopropyl | OCH₂CH₃ | F | 0 | CH₃ | H | O |
| 123 | cyclopropyl | OCH₂CH₂CH₃ | F | 0 | CH₃ | H | O |
| 124 | cyclopropyl | OCH₂CH₂CH₂CH₃ | F | 1 | CH₃ | F | O |
| 125 | cyclopropyl | OCH₂CH₂CH₂CH₃ | F | 0 | CH₃ | F | O |
| 126 | cyclopropyl | OCH₂CH₂CH₂CH₃ | F | 0 | CH₃ | H | O |
| 127 | CH₃ | OCH₂CH₂CH₃ | F | 0 | CH₃ | F | O |
| 128 | CH₃ | OCH₂CH₂CH₂CH₃ | F | 0 | CH₃ | F | O |
| 129 | CH₃ | OCH₂CH₃ | F | 0 | CH₃ | F | O |
| 130 | CH₃ | OCH₂CH₃ | F | 0 | CH₃ | H | O |
| 131 | CH₃ | OCH₂CH₃ | F | 1 | CH₃ | F | O |
| 132 | CH₃ | OCH₂CH₂CH₃ | F | 1 | CH₃ | F | O |
| 133 | CH₃ | OCH₂CH₂CH₃ | F | 1 | CH₃ | H | O |
| 134 | cyclopropyl | OCH₂-cyclopropyl | F | 0 | CH₃ | F | O |
| 135 | cyclopropyl | OCH₂-cyclopropyl | F | 0 | CH₃ | H | O |
| 136 | cyclopropyl | OCH₂CH₂C(=CH₂)CH₃ | F | 0 | CH₃ | F | O |
| 137 | cyclopropyl | OCH₂CH₂C(=CH₂)CH₃ | F | 1 | CH₃ | F | O |
| 138 | cyclopropyl | OCH₂CH₂C(=CH₂)CH₃ | F | 0 | CH₃ | H | O |
| 139 | cyclopropyl | OCH₂CH₂C(=CH₂)CH₃ | F | 1 | CH₃ | H | O |
| 140 | cyclopropyl | OCH(CH₃)CH₂CH₃ | F | 0 | CH₃ | F | O |
| 141 | cyclopropyl | OCH(CH₃)CH₂CH₃ | F | 1 | CH₃ | F | O |
| 142 | cyclopropyl | OCH(CH₃)CH₂CH₃ | F | 0 | CH₃ | H | O |
| 143 | CH₃ | OCH₂-cyclopropyl | F | 0 | CH₃ | F | O |
| 144 | cyclopropyl | OCH₃ | F | 0 | CF₃ | H | O |
| 145 | CH₃ | OCH₂-cyclopropyl | F | 0 | CH₃ | H | O |
| 146 | CH₃ | OCH₂CH₂CH₃ | F | 1 | CH₃ | H | O |
| 147 | cyclopropyl | OCH₃ | F | 1 | CF₃ | H | O |
| 148 | CH₃ | OCH₂CH(CH₃)₂ | F | 0 | CH₃ | F | O |
| 149 | CH₃ | OCH₂CH₂OCH₃ | F | 0 | CH₃ | F | O |
| 150 | CH₃ | OCH₂C(CH₃)₃ | F | 0 | CH₃ | F | O |
| 151 | CH₃ | OCH(CH₃)₂ | F | 0 | CH₃ | F | O |
| 152 | CH₃ | OCH₂CH(CH₃)₂ | F | 1 | CH₃ | F | O |
| 153 | CH₃ | O-cyclohexyl | F | 0 | CH₃ | F | O |
| 154 | CH₃ | OC(CH₃)₃ | F | 0 | CH₃ | H | O |
| 155 | CH₃ | O-cyclohexyl | F | 0 | CH₃ | H | O |
| 156 | CH₃ | O-3-tetrahydrofuryl | F | 0 | CH₃ | H | O |
| 157 | CH₃ | OC(CH₃)₃ | F | 0 | CH₃ | F | O |
| 158 | CH₃ | O-phenyl | F | 0 | CH₃ | F | O |
| 159 | CH₃ | O-phenyl | F | 1 | CH₃ | F | O |
| 160 | CH₃ | OCH₂CF₃ | F | 1 | CH₃ | F | O |
| 161 | CH₃ | O-3-tetrahydrofuryl | F | 1 | CH₃ | F | O |
| 162 | CH₃ | OCH₂C(CH₃)₃ | F | 1 | CH₃ | H | O |
| 163 | CH₃ | OCH(CH₃)₂ | F | 1 | CH₃ | H | O |
| 164 | CH₃ | O-cyclohexyl | F | 1 | CH₃ | F | O |
| 165 | CH₃ | OCH₂C(CH₃)₃ | F | 1 | CH₃ | F | O |
| 166 | CH₃ | OCH(CH₃)₂ | F | 1 | CH₃ | F | O |
| 167 | CH₃ | OCH₂CH(CH₃)₂ | F | 1 | CH₃ | H | O |
| 168 | CH₃ | OCH₃ | F | 0 | Br | H | O |
| 169 | CH₃ | OCH₃ | F | 1 | F | F | O |
| 170 | cyclopropyl | OCH₃ | F | 1 | F | F | O |

-continued

| Example No. | R¹ | R² | W | n | Y | X | V |
|---|---|---|---|---|---|---|---|
| 171 | cyclopropyl | OCH₃ | F | 0 | F | F | O |
| 172 | cyclopropyl | OCH₃ | F | 1 | Br | F | O |
| 173 | cyclopropyl | OCH₃ | F | 0 | Br | F | O |
| 174 | CH₃ | OCH₃ | F | 1 | Br | F | O |
| 175 | CH₃ | OCH₃ | F | 0 | Br | F | O |
| 176 | CH₂CH=CH₂ | OCH₃ | F | 0 | CH₃ | H | O |
| 177 | CH₃ | O-benzyl | F | 1 | CH₃ | F | O |
| 178 | CH₃ | O-benzyl | F | 1 | CH₃ | H | O |
| 179 | CH₂CH=CH₂ | OCH₃ | F | 1 | CH₃ | H | O |
| 180 | CH₂CH₃ | OCH₃ | F | 0 | CH₃ | F | O |
| 181 | CH₂CH₃ | OCH₃ | F | 1 | CH₃ | F | O |
| 182 | CH₂CH=CH₂ | OCH₃ | F | 0 | CH₃ | F | O |
| 183 | CH₂CH=CH₂ | OCH₃ | F | 1 | CH₃ | F | O |
| 184 | CH₃ | OC(CH₃)₃ | F | 1 | CH₃ | F | O |
| 185 | cyclopropyl | OCH₂CF₃ | F | 0 | Cl | Cl | O |
| 186 | cyclopropyl | OCH₂CF₃ | F | 0 | Cl | F | O |
| 187 | cyclopropyl | OCH₂CF₃ | F | 0 | CH₃ | Cl | O |
| 188 | cyclopropyl | OCH₂CF₃ | F | 0 | OCH₃ | F | O |
| 189 | cyclopropyl | OCH₂CF₃ | F | 0 | CF₃ | H | O |
| 190 | CH₃ | N(CH₃)₂ | F | 0 | CH₃ | F | O |
| 191 | CH₃ | N(CH₃)₂ | F | 1 | CH₃ | F | O |
| 192 | CH₃ | (4-methyl-5-oxo-3-phenoxy-1.2.4-triazol-1-yl) | F | 0 | CH₃ | H | O |
| 193 | cyclopropyl | N(CH₃)₂ | F | 0 | CH₃ | F | O |
| 194 | cyclopropyl | N(CH₃)₂ | F | 1 | CH₃ | F | O |
| 195 | N(CH₃)₂ | cyclopropyl | F | 0 | CH₃ | F | O |
| 196 | NH₂ | cyclopropyl | F | 0 | CH₃ | F | O |
| 197 | N(CH₃)₂ | cyclopropyl | F | 1 | CH₃ | F | O |
| 198 | NH₂ | CH₂OCH₃ | F | 0 | CH₃ | F | O |
| 199 | NHCH₃ | cyclopropyl | F | 0 | CH₃ | F | O |
| 200 | NH₂ | CH₃ | F | 0 | CH₃ | F | O |
| 201 | N(CH₃)₂ | CH₃ | F | 0 | CH₃ | F | O |
| 202 | N=C(CH₃)CH₂CH(CH₃)₂ | CH₃ | F | 0 | CH₃ | F | O |
| 203 | NHCH₃ | H | F | 0 | CH₃ | F | O |
| 204 | NH₂ | CH(CH₃)₂ | F | 1 | CH₃ | F | O |
| 205 | NH₂ | CF₃ | F | 0 | CH₃ | F | O |
| 206 | NH₂ | cyclopropyl | F | 1 | CH₃ | F | O |
| 207 | NH₂ | CH₂OCH₃ | F | 1 | CH₃ | F | O |
| 208 | NHCH₃ | cyclopropyl | F | 1 | CH₃ | F | O |
| 209 | NH₂ | CH₃ | F | 1 | CH₃ | F | O |
| 210 | N(CH₃)₂ | CH₃ | F | 1 | CH₃ | F | O |
| 211 | NH₂ | H | F | 0 | CH₃ | F | O |
| 212 | NH₂ | CF₃ | F | 0 | CH₃ | H | O |
| 213 | N(CH₃)₂ | CF₃ | F | 1 | CH₃ | F | O |
| 214 | N(CH₃)₂ | CF₃ | F | 0 | CH₃ | F | O |
| 215 | NH₂ | CF₃ | F | 1 | CH₃ | F | O |
| 216 | NHCH₃ | N(CH₃)₂ | F | 0 | CH₃ | F | O |
| 217 | NHCH₃ | N(CH₃)₂ | F | 1 | CH₃ | F | O |
| 218 | NH₂ | NHCH₃ | F | 0 | CH₃ | F | O |
| 219 | NH₂ | NHCH₃ | F | 1 | CH₃ | F | O |
| 220 | NH₂ | N(CH₃)₂ | F | 0 | CH₃ | F | O |
| 221 | NH₂ | N(CH₃)₂ | F | 1 | CH₃ | F | O |
| 222 | NH₂ | N(CH₂CH₃)₂ | F | 0 | CH₃ | F | O |
| 223 | NH₂ | N(CH₂CH₃)₂ | F | 1 | CH₃ | F | O |
| 224 | NH₂ | NHCH(CH₃)₂ | F | 0 | CH₃ | F | O |
| 225 | NH₂ | NHCH(CH₃)₂ | F | 1 | CH₃ | F | O |
| 226 | OCH₃ | CH₃ | F | 1 | CH₃ | F | O |
| 227 | OCH₃ | OCH₂CH₃ | F | 0 | CH₃ | H | O |
| 228 | cyclopropyl | S(=O)₂CH₃ | F | 1 | CH₃ | F | O |
| 229 | cyclopropyl | S(=O)CH₂CHF₂ | F | 1 | CH₃ | F | O |
| 230 | cyclopropyl | S(=O)CH₃ | F | 0 | CH₃ | F | O |
| 231 | cyclopropyl | S(=O)CH₃ | F | 1 | CH₃ | F | O |
| 232 | CH₃ | S(=O)CH₃ | F | 0 | CH₃ | F | O |
| 233 | CH₃ | S(=O)CH₃ | F | 1 | CH₃ | F | O |
| 234 | cyclopropyl | S(=O)CH₂CH₃ | F | 0 | CH₃ | F | O |
| 235 | cyclopropyl | S(=O)CH₂CH₃ | F | 1 | CH₃ | F | O |
| 236 | cyclopropyl | S(=O)CH₂CH₂CH₃ | F | 0 | CH₃ | F | O |
| 237 | cyclopropyl | S(=O)CH₂CH₂CH₃ | F | 1 | CH₃ | F | O |
| 238 | cyclopropyl | S(=O)CH(CH₃)₂ | F | 0 | CH₃ | F | O |
| 239 | cyclopropyl | S(=O)CH(CH₃)₂ | F | 1 | CH₃ | F | O |
| 240 | CH₂CH₃ | S(=O)CH₃ | F | 0 | CH₃ | F | O |
| 241 | CH₂CH₃ | S(=O)CH₃ | F | 1 | CH₃ | F | O |
| 242 | CH₃CH=CH₃ | S(=O)CH₃ | F | 1 | CH₃ | F | O |
| 243 | CH₃ | S(=O)CH₂CH₃ | F | 0 | CH₃ | F | O |
| 244 | CH₃ | S(=O)CH₂CH₃ | F | 1 | CH₃ | F | O |

-continued

| Example No. | R¹ | R² | W | n | Y | X | V |
|---|---|---|---|---|---|---|---|
| 245 | $CH_3$ | $S(=O)CH(CH_3)_2$ | F | 1 | $CH_3$ | F | O |
| 246 | $CH_3$ | $S(=O)CH_2CH_2CH_3$ | F | 1 | $CH_3$ | F | O |
| 247 | $CH_3$ | $S(=O)CH_2$-cyclopropyl | F | 0 | $CH_3$ | F | O |
| 248 | $CH_3$ | $S(=O)CH_2$-cyclopropyl | F | 1 | $CH_3$ | F | O |
| 249 | $CH_2CH=CH_2$ | $S(=O)CH(CH_3)_2$ | F | 1 | $CH_3$ | F | O |
| 250 | $CH_3$ | $S(=O)$-benzyl | F | 1 | $CH_3$ | F | O |
| 251 | $CH_2CH_3$ | $S(=O)CH_2CH_2CH_3$ | F | 1 | $CH_3$ | F | O |
| 252 | $CH_2CH_3$ | $S(=O)CH_2CH_3$ | F | 1 | $CH_3$ | F | O |
| 253 | $CH_2CH_3$ | $S(=O)CH_2CH_3$ | F | 0 | $CH_3$ | F | O |
| 254 | cyclopropyl | $SCH_2CF_3$ | F | 0 | $CH_3$ | F | O |
| 255 | cyclopropyl | $SCH_2CF_3$ | F | 1 | $CH_3$ | F | O |
| 256 | cyclopropyl | $SCH_2CHF_2$ | F | 1 | $CH_3$ | F | O |
| 257 | cyclopropyl | $SCH_3$ | F | 1 | $CH_3$ | F | O |
| 258 | cyclopropyl | $SCH_2CHF_2$ | F | 0 | $CH_3$ | F | O |
| 259 | cyclopropyl | $SCH_3$ | F | 0 | $CH_3$ | F | O |
| 260 | $CH_3$ | $SCH_3$ | F | 1 | $CH_3$ | F | O |
| 261 | cyclopropyl | $SCH_2CH_3$ | F | 0 | $CH_3$ | F | O |
| 262 | cyclopropyl | $SCH_2CH_3$ | F | 1 | $CH_3$ | F | O |
| 263 | cyclopropyl | $SCF_3$ | F | 0 | $CH_3$ | F | O |
| 264 | cyclopropyl | $SCF_3$ | F | 1 | $CH_3$ | F | O |
| 265 | cyclopropyl | $SCH_2CH_2CH_3$ | F | 0 | $CH_3$ | F | O |
| 266 | cyclopropyl | $SCH_2CH_2CH_3$ | F | 1 | $CH_3$ | F | O |
| 267 | cyclopropyl | $SCH(CH_3)_2$ | F | 1 | $CH_3$ | F | O |
| 268 | cyclopropyl | $SCH(CH_3)_2$ | F | 0 | $CH_3$ | F | O |
| 269 | $CH_2CH_3$ | $SCH_3$ | F | 0 | $CH_3$ | F | O |
| 270 | $CH_2CH_3$ | $SCH_3$ | F | 1 | $CH_3$ | F | O |
| 271 | $CH_2CH=CH_2$ | $SCH_3$ | F | 0 | $CH_3$ | F | O |
| 272 | $CH_2CH=CH_2$ | $SCH_3$ | F | 1 | $CH_3$ | F | O |
| 273 | $CH_3$ | $SCH_2CH_3$ | F | 0 | $CH_3$ | F | O |
| 274 | $CH_3$ | $SCH_2CH_3$ | F | 1 | $CH_3$ | F | O |
| 275 | $CH_3$ | $SCH(CH_3)_2$ | F | 1 | $CH_3$ | F | O |
| 276 | $CH_3$ | $SCH(CH_3)_2$ | F | 0 | $CH_3$ | F | O |
| 277 | $CH_3$ | $SCH_2CH_2CH_3$ | F | 0 | $CH_3$ | F | O |
| 278 | $CH_3$ | $SCH_2CH_2CH_3$ | F | 1 | $CH_3$ | F | O |
| 279 | $CH_3$ | $SCH_2$-cyclopropyl | F | 0 | $CH_3$ | F | O |
| 280 | $CH_3$ | $SCH_2$-cyclopropyl | F | 1 | $CH_3$ | F | O |
| 281 | $CH_3$ | $SCH_2CF_3$ | F | 0 | $CH_3$ | F | O |
| 282 | $CH_3$ | $SCH_2CF_3$ | F | 1 | $CH_3$ | F | O |
| 283 | $CH_3$ | $SCF_3$ | F | 0 | $CH_3$ | F | O |
| 284 | $CH_3$ | $SCF_3$ | F | 1 | $CH_3$ | F | O |
| 285 | $CH_2CH=CH_2$ | $SCH(CH_3)_2$ | F | 1 | $CH_3$ | F | O |
| 286 | $CH_3$ | S-benzyl | F | 0 | $CH_3$ | F | O |
| 287 | $CH_3$ | S-benzyl | F | 1 | $CH_3$ | F | O |
| 288 | $CH_2CH_3$ | $SCH_2CH_2CH_3$ | F | 0 | $CH_3$ | F | O |
| 289 | $CH_3$ | $SCH_2CHF_2$ | F | 1 | $CH_3$ | F | O |
| 290 | $CH_3$ | $SCH_2CH=CH_2$ | F | 0 | $CH_3$ | F | O |
| 291 | $CH_3$ | $SCH_2CH=CH_2$ | F | 1 | $CH_3$ | F | O |
| 292 | $CH_2CH_3$ | $SCH_2CH_3$ | F | 0 | $CH_3$ | F | O |
| 293 | $CH_2CH_3$ | $SCH_2CH_3$ | F | 1 | $CH_3$ | F | O |
| 294 | cyclopropyl | Br | F | 0 | $CH_3$ | F | O |
| 295 | cyclopropyl | Br | F | 1 | $CH_3$ | F | O |

(compound of the general formula (I) with (I-A) with Z=H and W=F)

| Example No. | R¹ | R² | n | Y | X | V |
|---|---|---|---|---|---|---|
| 345 | $CH_2CH=CH_2$ | $CF_3$ | 0 | $CH_3$ | F | O |
| 346 | $CH_3$ | cyclopropyl | 0 | $CH_3$ | F | O |
| 347 | $CH(CH_3)_2$ | cyclopropyl | 0 | $CH_3$ | F | O |
| 348 | 3-pyridyl | $CH_2CH_3$ | 0 | $CH_3$ | F | O |
| 349 | 4-fluorophenyl | H | 0 | $CH_3$ | F | O |
| 350 | phenyl | $CH_3$ | 0 | $CH_3$ | F | O |
| 351 | phenyl | H | 0 | $CH_3$ | F | O |
| 352 | $CH_3$ | cyclopropyl | 1 | $CH_3$ | F | O |
| 353 | $CH(CH_3)_2$ | cyclopropyl | 1 | $CH_3$ | F | O |
| 354 | 3-pyridyl | $CH_2CH_3$ | 1 | $CH_3$ | F | O |
| 355 | 4-fluorophenyl | H | 1 | $CH_3$ | F | O |
| 356 | phenyl | $CH_3$ | 1 | $CH_3$ | F | O |
| 357 | phenyl | H | 1 | $CH_3$ | F | O |
| 358 | cyclopropyl | cyclopentyl | 0 | $CH_3$ | F | O |
| 359 | cyclopropyl | $CH_2CH_2OCH(CH_3)_2$ | 0 | $CH_3$ | F | O |
| 360 | cyclopropyl | cyclopentyl | 1 | $CH_3$ | F | O |
| 361 | cyclopropyl | cyclohexyl | 1 | $CH_3$ | F | O |
| 362 | cyclopropyl | $CH_2CH_2OCH(CH_3)_2$ | 1 | $CH_3$ | F | O |
| 363 | $CH(CH_3)_2$ | $CF_3$ | 1 | $CH_3$ | F | O |
| 364 | $CH_2CH=CH_2$ | $CF_3$ | 1 | $CH_3$ | F | O |
| 365 | $CH_2CH_2CH_2CH_3$ | $CF_3$ | 1 | $CH_3$ | F | O |
| 366 | cyclopropyl | 2-methoxyphenyl | 0 | $CH_3$ | F | O |
| 367 | $C(CH_3)_3$ | H | 0 | $CH_3$ | F | O |
| 368 | benzyl | H | 0 | $CH_3$ | F | O |
| 369 | $C(CH_3)_3$ | H | 1 | $CH_3$ | F | O |
| 370 | benzyl | H | 1 | $CH_3$ | F | O |
| 371 | $C(CH_3)_3$ | H | 0 | $CH_3$ | $CH_3$ | O |
| 372 | $C(CH_3)_3$ | H | 1 | $CH_3$ | $CH_3$ | O |
| 373 | benzyl | H | 0 | $CH_3$ | $CH_3$ | O |
| 374 | benzyl | H | 1 | $CH_3$ | $CH_3$ | O |
| 375 | cyclopropyl | $OCH_2CH=CH_2$ | 0 | $CH_3$ | F | O |
| 376 | $CH_3$ | $OCH_2CCl_3$ | 0 | $CH_3$ | F | O |

-continued

| Example No. | R¹ | R² | n | Y | X | V |
|---|---|---|---|---|---|---|
| 377 | cyclopropyl | OCH₂CF₃ | 0 | CH₃ | CH₃ | O |
| 378 | cyclopropyl | OCH₂CF₃ | 0 | Br | H | O |
| 379 | cyclopropyl | OCH₃ | 1 | CH₃ | F | O |
| 380 | cyclopropyl | OCH₃ | 1 | CH₃ | F | O |
| 381 | cyclopropyl | OCH₂CF₃ | 1 | CH₃ | CH₃ | O |
| 382 | cyclopropyl | OCH₂CF₃ | 1 | Cl | F | O |
| 383 | cyclopropyl | OCH₂CF₃ | 1 | Br | F | O |
| 384 | cyclopropyl | OCH₂CF₃ | 1 | Cl | CH₃ | O |
| 385 | cyclopropyl | OCH₂CF₃ | 1 | OCH₃ | F | O |
| 386 | cyclopropyl | OCH₂C(CH₃)₃ | 0 | CH₃ | F | O |
| 387 | cyclopropyl | OCH₂C(CH₃)₃ | 1 | CH₃ | F | O |
| 388 | CH₂CH₂CH₂OCH₃ | OCH₃ | 0 | CH₃ | F | O |
| 389 | CH₂CH₂CH₃ | OCH₃ | 0 | CH₃ | F | O |
| 390 | CH₂-cyclopropyl | OCH₃ | 0 | CH₃ | F | O |
| 391 | cyclopropyl | OCH₂CH=CH₂ | 1 | CH₃ | F | O |
| 392 | CH₃ | OCH₂CCl₃ | 1 | CH₃ | F | O |
| 393 | CH₂CF₃ | OCH₃ | 0 | CH₃ | F | O |
| 394 | cyclopropyl | OCH₂C(CH₃)₃ | 0 | Cl | F | O |
| 395 | cyclopropyl | OCH₂C(CH₃)₃ | 0 | OCH₃ | F | O |
| 396 | cyclopropyl | OCH₂C(CH₃)₃ | 0 | CH₃ | Cl | O |
| 397 | cyclopropyl | OCH₂C(CH₃)₃ | 0 | Cl | Cl | O |
| 398 | CH₂CH₃ | OCH₂CF₃ | 0 | CH₃ | F | O |
| 399 | CH₂CH=CH₂ | OCH₂CF₃ | 0 | CH₃ | F | O |
| 400 | CH₂CH₃ | OCH₂CH₂CH₃ | 0 | CH₃ | F | O |
| 401 | CH₂CH₃ | OCH₂CH₃ | 0 | CH₃ | F | O |
| 402 | cyclopropyl | OCH₂C(CH₃)₃ | 1 | Cl | F | O |
| 403 | cyclopropyl | OCH₂C(CH₃)₃ | 1 | OCH₃ | F | O |
| 404 | cyclopropyl | OCH₂C(CH₃)₃ | 1 | CH₃ | Cl | O |
| 405 | cyclopropyl | OCH₂C(CH₃)₃ | 1 | Cl | Cl | O |
| 406 | CH₂CH₃ | OCH₂CF₃ | 1 | CH₃ | F | O |
| 407 | CH₂CH=CH₂ | OCH₂CF₃ | 1 | CH₃ | F | O |
| 408 | CH₂CH₃ | OCH₂CH₂CH₃ | 1 | CH₃ | F | O |
| 409 | CH₂CH₃ | OCH₂CH₃ | 1 | CH₃ | F | O |
| 410 | cyclopropyl | OCH₂phenyl | 0 | CH₃ | F | O |
| 411 | CH₂CH₂CH₃ | OCH₃ | 1 | CH₃ | F | O |
| 412 | CH₂-cyclopropyl | OCH₃ | 1 | CH₃ | F | O |
| 413 | CH(CH₃)₂ | OCH₃ | 1 | CH₃ | F | O |
| 414 | cyclopropyl | OCH₂phenyl | 1 | CH₃ | F | O |
| 415 | CH₂CF₃ | OCH₃ | 1 | CH₃ | F | O |
| 416 | cyclopropyl | N(CH₃)₂ | 0 | CH₃ | F | O |
| 417 | NH₂ | CH(CH₃)₂ | 2 | CH₃ | F | O |
| 418 | OCH₃ | CH(CH₃)₂ | 0 | CH₃ | F | O |
| 419 | OCH₃ | CH(CH₃)₂ | 1 | CH₃ | F | O |
| 420 | CH₃ | SO₂CH₃ | 0 | CH₃ | F | O |
| 421 | CH₃ | SO₂CH₃ | 1 | CH₃ | F | O |
| 422 | CH₂CH₃ | SO₂CH₃ | 1 | CH₃ | F | O |
| 423 | CH₂CH=CH₂ | SOCH₂CH₃ | 1 | CH₃ | F | O |
| 424 | CH₂CH=CH₂ | SOCH₂CH₃ | 1 | CH₃ | F | O |
| 425 | cyclopropyl | SCH₂CH=CH₂ | 0 | CH₃ | F | O |
| 426 | CH₂CH₃ | SCH₂CH₂CH₃ | 0 | CH₃ | F | O |
| 427 | CH₂CH=CH₂ | SCH₂CH₂CH₃ | 0 | CH₃ | F | O |
| 428 | CH₂CH=CH₂ | SCH₂CH₃ | 0 | CH₃ | F | O |
| 429 | CH₂CH=CH₂ | SCH₂CH=CH₂ | 0 | CH₃ | F | O |
| 430 | CH₂CH=CH₂ | SCH₂CH₂CH₃ | 1 | CH₃ | F | O |
| 431 | CH₂CH=CH₂ | SCH₂CH₃ | 1 | CH₃ | F | O |
| 432 | CH₂CH=CH₂ | SCH₂CH=CH₂ | 1 | CH₃ | F | O |
| 433 | CH₃ | Br | 1 | CH₃ | F | O |
| 434 | CH₂CH₃ | Cl | 0 | CH₃ | F | O |
| 435 | CH₃ | Cl | 0 | CH₃ | F | O |
| 436 | CH₂CH₃ | Cl | 1 | CH₃ | F | O |
| 437 | CH₃ | Cl | 1 | CH₃ | F | O |
| 438 | C(CH₃)₃ | Br | 0 | CH₃ | F | O |
| 439 | CH(CH₃)₂ | Br | 0 | CH₃ | F | O |
| 440 | benzyl | Br | 0 | CH₃ | F | O |
| 441 | C(CH₃)₃ | Br | 1 | CH₃ | F | O |
| 442 | CH(CH₃)₂ | Br | 1 | CH₃ | F | O |
| 443 | benzyl | Br | 1 | CH₃ | F | O |
| 492 | cyclopropyl | CH₂OCH₃ | 0 | CH₃ | F | S |
| 493 | cyclopropyl | CH₂CH(CH₃)₂ | 0 | CH₃ | F | S |
| 494 | cyclopropyl | CH(CH₃)₂ | 0 | CH₃ | F | S |
| 495 | cyclopropyl | CH₂CH₂CH₂CH₃ | 0 | CH₃ | F | S |
| 496 | cyclopropyl | cyclohexyl | 0 | CH₃ | F | S |
| 497 | cyclopropyl | cyclopentyl | 0 | CH₃ | F | S |
| 498 | CH(CH3)2 | cyclopropyl | 0 | CH₃ | F | S |
| 499 | cyclopropyl | CH(CH₃)CH₂CH₃ | 0 | CH₃ | F | S |
| 500 | cyclopropyl | CH₂OCH₂CH₃ | 0 | CH₃ | F | S |
| 501 | cyclopropyl | CH=CHCH₃ | 0 | CH₃ | F | S |
| 502 | cyclopropyl | CH₂CH₃ | 0 | CH₃ | F | S |
| 503 | cyclopropyl | CH₂CH₂CH₃ | 0 | CH₃ | F | S |
| 504 | cyclopropyl | cyclopropyl | 0 | CH₃ | F | S |
| 505 | cyclopropyl | cyclobutyl | 0 | CH₃ | F | S |
| 506 | cyclopropyl | 2-methoxyphenyl | 0 | CH₃ | F | S |
| 507 | CH₂CH₃ | CF₃ | 0 | OCH3 | H | S |
| 508 | CH₂CF₃ | OCH₃ | 1 | CH₃ | F | O |
| 509 | CH₂CF₃ | OCH₃ | 1 | CH₃ | F | O |

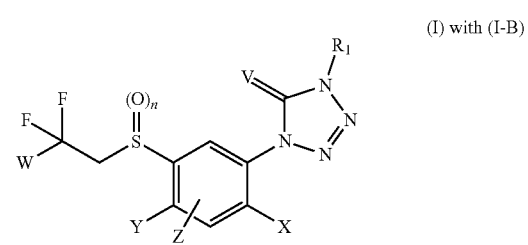

(I) with (I-B)

(compound of the general formula (I) with (I-B) with Z=H)

| Example No. | R¹ | W | n | Y | X | V |
|---|---|---|---|---|---|---|
| 296 | CH₃ | F | 0 | CH₃ | H | O |
| 297 | CH₃ | F | 1 | CH₃ | CH₃ | O |
| 298 | CH(CH₃)₂ | F | 0 | CH₃ | CH₃ | O |
| 299 | H | F | 0 | CH₃ | F | O |
| 300 | CH(CH₃)₂ | F | 1 | CH₃ | CH₃ | O |
| 301 | CH₃ | F | 1 | CH₃ | F | O |
| 302 | CH₃ | F | 0 | CH₃ | F | O |
| 303 | H | F | 1 | CH₃ | F | O |
| 304 | CH₂CF₃ | F | 0 | CH₃ | F | O |
| 305 | CH₂CF₃ | F | 1 | CH₃ | F | O |
| 306 | 4-chlorophenyl | F | 0 | CH₃ | F | O |
| 307 | 4-chlorophenyl | F | 1 | CH₃ | F | O |

(compound of the general formula (I) with (I-B) with Z=H and W=F)

| Example No. | R¹ | n | Y | X | V |
|---|---|---|---|---|---|
| 444 | CH₂CF₂CF₃ | 0 | CH₃ | F | O |
| 445 | 4-trifluoromethylphenyl | 1 | CH₃ | F | O |
| 446 | CH₂CF₂CF₃ | 1 | CH₃ | F | O |
| 447 | CH₃ | 0 | CH₃ | F | S |

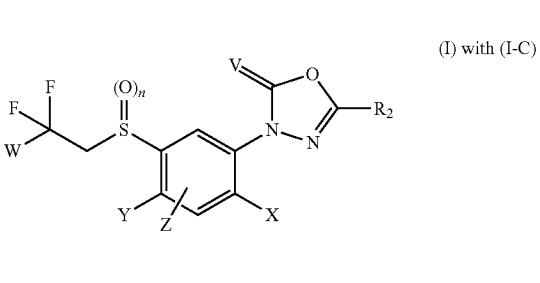

(I) with (I-C)

(compound of the general formula (I) with (I-C) with Z=H)

| Example No. | R² | W | n | Y | X | V |
|---|---|---|---|---|---|---|
| 308 | CF₃ | F | 0 | CN | F | O |
| 309 | CF₃ | F | 1 | CN | F | O |

(compound of the general formula (I) with (I-C) with Z=H and W=F)

| Example No. | R² | n | Y | X | V |
|---|---|---|---|---|---|
| 448 | CH₃ | 0 | CH₃ | F | O |
| 449 | C(CH₃)₃ | 0 | CH₃ | F | O |
| 450 | CH₂OCH₃ | 0 | CH₃ | F | O |
| 451 | CH₃ | 1 | CH₃ | F | O |
| 452 | C(CH₃)₃ | 1 | CH₃ | F | O |
| 453 | CH₂OCH₃ | 1 | CH₃ | F | O |
| 454 | H | 0 | CH₃ | F | O |
| 455 | CH₂CH₃ | 0 | CH₃ | F | O |
| 456 | cyclopropyl | 0 | CH₃ | F | O |
| 457 | phenyl | 0 | CH₃ | F | O |
| 458 | 4-chlorophenyl | 0 | CH₃ | F | O |
| 459 | 4-pyridyl | 0 | CH₃ | F | O |
| 460 | CH₂CH₂CH₃ | 0 | CH₃ | F | O |
| 461 | CH₂CH₂CH₂CH₃ | 0 | CH₃ | F | O |
| 462 | CH(CH₃)₂ | 0 | CH₃ | F | O |
| 463 | CH₂OCH₂CH₃ | 0 | CH₃ | F | O |
| 464 | 3-fluorophenyl | 0 | CH₃ | F | O |
| 465 | cyclopropyl | 1 | CH₃ | F | O |
| 466 | 4-methoxyphenyl | 0 | CH₃ | F | O |
| 467 | 4-nitrophenyl | 0 | CH₃ | F | O |
| 468 | 2-thienyl | 0 | CH₃ | F | O |
| 469 | 2-furyl | 0 | CH₃ | F | O |
| 470 | CH₂CH₂CH₃ | 1 | CH₃ | F | O |
| 471 | CH₂CH₂CH₂CH₃ | 1 | CH₃ | F | O |
| 472 | CH(CH₃)₂ | 1 | CH₃ | F | O |
| 473 | CH₂OCH₂CH₃ | 1 | CH₃ | F | O |
| 474 | 4-methoxyphenyl | 1 | CH₃ | F | O |
| 475 | 4-nitrophenyl | 1 | CH₃ | F | O |
| 476 | 2-thienyl | 1 | CH₃ | F | O |
| 477 | 2-furyl | 1 | CH₃ | F | O |
| 478 | benzyl | 1 | CH₃ | F | O |
| 479 | CH₂CH₂CH₂Cl | 0 | CH₃ | F | O |
| 480 | CH₂CH₂CH₂Cl | 1 | CH₃ | F | O |
| 481 | H | 1 | CH₃ | F | O |
| 482 | cyclopropyl | 0 | CH₃ | CH₃ | O |
| 483 | C(CH₃)₃ | 0 | CH₃ | CH₃ | O |
| 484 | cyclopropyl | 1 | CH₃ | CH₃ | O |
| 485 | C(CH₃)₃ | 1 | CH₃ | CH₃ | O |

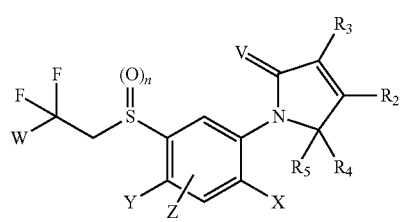

(I) with (I-D)

(compound of the general formula (I) with (I-D) with Z=H)

| Example No. | R² | W | n | Y | X | V | R³ | R⁴ | R⁵ |
|---|---|---|---|---|---|---|---|---|---|
| 310 | OCH₃ | F | 0 | CH₃ | F | O | H | H | H |
| 311 | OCH₃ | F | 1 | CH₃ | F | O | H | H | H |
| 312 | OCH₃ | F | 0 | CH₃ | CH₃ | O | H | H | H |
| 313 | OCH₃ | F | 1 | CH₃ | CH₃ | O | H | H | H |
| 314 | OCH₃ | F | 1 | Cl | Cl | O | H | H | H |
| 315 | OCH₃ | F | 1 | Cl | H | O | H | H | H |
| 316 | OCH₃ | F | 0 | CH₃ | H | O | H | H | H |
| 317 | OCH₃ | F | 1 | CH₃ | H | O | H | H | H |
| 318 | OCH₃ | F | 1 | CH₃ | Cl | O | H | H | H |
| 319 | OCH₃ | F | 0 | CH₃ | Cl | O | H | H | H |
| 320 | OCH₃ | F | 0 | CN | H | O | H | H | H |
| 321 | OCH₃ | F | 1 | CF₃ | H | O | H | H | H |
| 322 | OCH₃ | F | 0 | CF₃ | H | O | H | H | H |
| 323 | O-benzyl | F | 1 | CH₃ | F | O | H | H | H |
| 324 | OCH₃ | F | 1 | Cl | F | O | H | H | H |
| 325 | OCH(CH₃)₂ | F | 1 | CH₃ | F | O | H | H | H |
| 326 | OCH₂CH₂CH₃ | F | 1 | CH₃ | F | O | H | H | H |
| 327 | OCH₃ | F | 0 | Cl | F | O | H | H | H |
| 328 | OCH₂CH₂OCH₃ | F | 0 | CH₃ | F | O | H | H | H |
| 329 | O-cyclopentyl | F | 0 | CH₃ | F | O | H | H | H |
| 330 | OCH₂CH₃ | F | 0 | CH₃ | F | O | H | H | H |
| 331 | OCH₂-cyclopropyl | F | 0 | CH₃ | F | O | H | H | H |
| 332 | OCH₂-cyclopropyl | F | 1 | CH₃ | F | O | H | H | H |
| 333 | OCH₂CH₂CH₃ | F | 1 | CH₃ | F | O | H | H | H |
| 334 | OCH₃ | F | 1 | CH₃ | F | O | H | H | H |
| 335 | OCH₂CH₂OCH₃ | F | 1 | CH₃ | F | O | H | H | H |
| 336 | O-cyclopentyl | F | 1 | CH₃ | F | O | H | H | H |

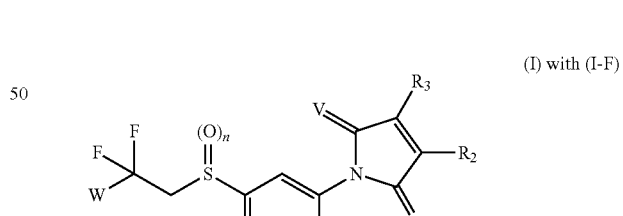

(I) with (I-E)

(compound of the general formula (I) with (I-E) with Z=H and W=F)

| Example No. | R¹ | R² | R³ | n | Y | X | V |
|---|---|---|---|---|---|---|---|
| 486 | CH₂CH₃ | H | H | 0 | CH₃ | F | O |
| 487 | CH₂CH₃ | H | H | 1 | CH₃ | F | O |
| 488 | C(CH₃)₃ | H | H | 0 | CH₃ | F | O |
| 489 | C(CH₃)₃ | H | H | 1 | CH₃ | F | O |

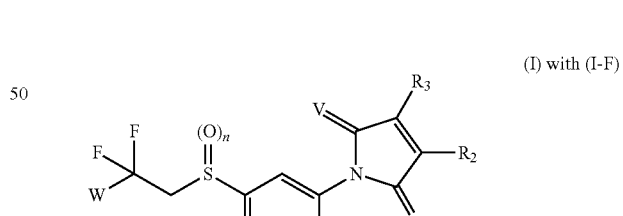

(I) with (I-F)

(compound of the general formula (I) with (I-F) with Z=H)

| Example No. | R² | W | n | Y | X | V | R³ | V' |
|---|---|---|---|---|---|---|---|---|
| 337 | Br | F | 0 | CH₃ | F | O | H | O |
| 338 | Cl | F | 0 | CH₃ | F | O | Cl | O |
| 339 | CH₃ | F | 0 | CH₃ | F | O | CH₃ | O |

-continued

| Example No. | $R^2$ | W | n | Y | X | V | $R^3$ | V' |
|---|---|---|---|---|---|---|---|---|
| 340 | $CH_3$ | F | 0 | $CH_3$ | F | O | H | O |
| 341 | $CH_3$ | F | 1 | $CH_3$ | F | O | $CH_3$ | O |
| 342 | $CH_3$ | F | 0 | $CH_3$ | $CH_3$ | O | $CH_3$ | O |

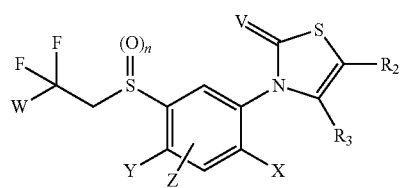

(I) with (I-G)

(compound of the general formula (I) with (I-G) with Z=H)

when V=NR$^{15}$

| Example No. | $R^2$ | W | n | Y | X | V | $R^3$ | $R^{15}$ |
|---|---|---|---|---|---|---|---|---|
| 343 | $CH_3$ | F | 0 | $CH_3$ | F | N | $CH_3$ | $CH_2CF_3$ |
| 344 | $CH_3$ | F | 1 | $CH_3$ | F | N | $CH_3$ | $CH_3CF_3$ |

(compound of the general formula (I) with (I-G) with Z=H and W=F)

when V=NR$^{15}$

| Example No. | $R^2$ | n | Y | X | V | $R^3$ | $R^{15}$ |
|---|---|---|---|---|---|---|---|
| 490 | H | 0 | $CH_3$ | F | N | H | $CH_2CF_3$ |
| 491 | H | 1 | $CH_3$ | F | N | H | $CH_2CF_3$ |

Spectroscopic Data of Selected Examples:

| Ex. No. | logP[a] | logP[b] | $^1$H NMR(D6-DMSO, 400 MHz) δ ppm |
|---|---|---|---|
| 1 | 1.61 | 1.59 | 8.37(d, 1H), 8.28(d, 1H), 4.49-4.26(m, 2H), 3.23(s, 3H), 2.31(s, 3H) |
| 2 | 1.88 | 1.74 | 11.99(s, 1H), 8.14(d, 1H), 8.07(d, 1H), 4.16(q, 2H), 2.18(s, 3H) |
| 3 | 1.95 | 2.50 | 7.70-7.68(m, 1H), 7.41(m, 1H), 6.20(tt, 1H), 5.05-4.98(sept, 1H), 3.44(dt, 2H), 2.33(s, 3H), 1.48-1.46(d, 6H) |
| 4 | 2.82 | 2.97 | 8.36(s, 1H), 7.73-7.71(m, 1H), 7.41-7.38(m, 1H), 4.17(sept, 1H), 3.99-3.91(q, 2H), 2.43(s, 3H), 1.38-1.36(d, 6H) |
| 5 | 2.55 | 2.50 | 8.35(s, 1H), 7.64-7.62(m, 1H), 7.38-7.35(m, 1H), 6.19(tt, 1H), 4.20-4.13(sept, 1H), 3.51-3.42(dt, 2H), 2.41(s, 3H), 1.38-1.36(d, 6H) |
| 6 | 1.88 | 2.02 | 8.42(s, 1H), 7.99-7.97(m, 1H), 7.53-7.50(m, 1H), 4.26-4.02(m, 3H), 2.42(s, 3H), 1.39-1.37(d, 6H) |
| 7 | 2.00 | 2.16 | 11.89(s, 1H), 8.10(s, 1H), 7.71-7.70(m, 1H), 7.40-7.37(m, 1H), 3.99-3.91(q, 2H), 2.43(s, 3H) |
| 8 | 1.58 | 1.60 | 8.40(s, 1H), 7.95-7.93(m, 1H), 7.50-7.47(m, 1H), 6.44(tt, 1H), 4.21-4.14(sept, 1H), 3.73-3.65(m, 1H), 3.54-3.41(m, 1H), 2.39(s, 3H), 1.39-1.37(d, 6H) |
| 9 | 3.58 | 3.53 | 7.79(d, 1H), 7.47(d, 1H), 3.95(q, 2H), 3.38(s, 3H), 2.45(s, 3H) |
| 10 | 2.42 | 2.38 | 7.68(d, 1H), 7.38(d, 1H), 3.93(q, 2H), 3.20(s, 3H), 2.43(s, 3H), 2.25(s, 3H) |
| 11 | 1.57 | 1.50 | 7.94(d, 1H), 7.49(d, 1H), 4.28-4.16(m, 1H), 4.10-3.98(m, 1H), 3.21(s, 3H), 2.41(s, 3H), 2.27(s, 3H) |
| 12 | 2.52 | 2.46 | 8.04(d, 1H), 7.58(d, 1H), 4.32-4.20(m, 1H), 4.09-3.98(m, 1H), 3.38(s, 3H), 2.44(s, 3H) |
| 13 | 4.07 | 3.99 | 7.98(d, 1H), 7.85-7.81(m, 1H), 7.80-7.75(m, 2H), 7.57-7.53(m, 1H), 7.19(d, 1H), 3.89(s, 3H), 3.89(q, 2H), 3.19(s, 3H) |
| 14 | 2.81 | 2.77 | 8.05(d, 1H), 7.76-7.72(m, 1H), 7.34(d, 1H), 3.89(q, 2H), 3.20(s, 3H), 2.38(s, 3H), 2.28(s, 3H) |
| 15 | 3.53 | 3.46 | 7.82-7.76(m, 3H), 7.61-7.56(m, 3H), 7.44(d, 1H), 3.96(q, 2H), 3.37(s, 3H), 2.45(s, 3H) |
| 16 | 4.60 | 4.52 | 8.10(d, 1H), 7.80-7.74(m, 3H), 7.58-7.54(m, 1H), 7.39(d, 1H), 3.93(q, 2H), 3.19(s, 3H), 2.40(s, 3H) |
| 17 | 3.28 | 3.22 | 8.03(d, 1H), 7.73-7.69(m, 1H), 7.33(d, 1H), 3.88(q, 2H), 2.90-2.83(m, 1H), 2.37(s, 3H), 2.32(s, 3H), 0.99-0.94(m, 4H) |
| 18 | 4.29 | 4.22 | 8.07(d, 1H), 7.72-7.68(m, 1H), 7.33(d, 1H), 3.88(q, 2H), 3.20-3.11(m, 1H), 2.94-2.88(m, 1H), 2.38(s, 3H), 1.30(d, 6H), 1.02-0.97(m, 4H) |
| 19 | 3.38 | 3.31 | 8.04(d, 1H), 7.73-7.69(m, 1H), 7.36(d, 1H), 4.47(s, 2H), 3.90(q, 2H), 3.36(s, 3H), 2.92-2.85(m, 1H), 2.38(s, 3H), 1.07-1.00(m, 2H), 0.99-0.92(m, 2H) |
| 20 | 3.02 | 2.96 | 8.20(s, 1H), 8.03(d, 1H), 7.75-7.71(m, 1H), 7.35(d, 1H), 3.92(q, 2H), 3.08-3.00(m, 1H), 2.38(s, 3H), 0.95-0.91(m, 4H) |
| 21 | 3.96 | 3.90 | 8.02(d, 1H), 7.67-7.70(m, 1H), 7.42(d, 1H), 3.94(q, 2H), 3.36(s, 3H), 2.41(s, 3H) |
| 22 | 5.30 | 5.24 | 8.00(d, 1H), 7.67-7.70(m, 1H), 7.42(d, 1H), 3.94(q, 2H), 2.41(s, 3H), 1.67(s, 9H) |
| 23 | 2.48 | 2.43 | 8.06(d, 1H), 7.78-7.80(m, 2H), 7.53-7.61(m, 4H), 4.19-4.28(m, 1H), 4.02-4.13(m, 1H), 3.37(s, 3H), 2.44(s, 3H) |
| 24 | 2.59 | 2.53 | 7.85(s, 1H), 7.78-7.80(m, 2H), 7.57-7.61(m, 3H), 7.40(s, 1H), 4.13-4.22(m, 1H), 3.96-4.05(m, 1H), 3.38(s, 3H), 2.39(s, 3H), 2.34(s, 3H) |
| 25 | 3.30 | 3.26 | 8.41(d, 1H), 8.12-8.14(m, 1H), 7.77-7.81(m, 2H), 7.55-7.57(m, 1H), 7.49(d, 1H), 4.11-4.21(m, 1H), 3.96-4.05(m, 1H), 3.21(s, 3H), 2.38(s, 3H) |
| 26 | 2.13 | 2.12 | 8.34(d, 1H), 8.02-8.05(m, 1H), 7.42(d, 1H), 4.11-4.18(m, 1H), 3.90-3.97(m, 1H), 2.88-2.91(m, 1H), 2.35(s, 3H), 2.34(s, 3H), 0.97-0.99(m, 4H) |

-continued

| Ex. No. | logP[a] | logP[b] | $^1$H NMR(D6-DMSO, 400 MHz) δ ppm |
|---|---|---|---|
| 27 | 2.22 | 2.21 | 8.35(d, 1H), 8.04-8.06(m, 1H), 7.44(d, 1H), 4.50(s, 2H), 4.10-4.19(m, 1H), 3.93-4.02(m, 1H), 3.37(s, 3H), 2.88-2.93(m, 1H), 2.35(s, 3H), 0.94-1.07(m, 4H) |
| 28 | 1.94 | 1.92 | 8.38(d, 1H), 8.25(s, 1H), 8.02-8.05(m, 1H), 7.45(d, 1H), 4.10-4.19(m, 1H), 3.92-4.01(m, 1H), 3.03-3.09(m, 1H), 2.36(s, 3H), 0.93-0.95(m, 4H) |
| 29 | 2.70 | 2.68 | 8.33(d, 1H), 8.04-8.06(m, 1H), 7.51(d, 1H), 4.13-4.23(m, 1H), 3.96-4.07(m, 1H), 3.38(s, 3H), 2.38(s, 3H) |
| 30 | 3.87 | 3.82 | 8.37(d, 1H), 7.99-8.01(m, 1H), 7.51(d, 1H), 4.15-4.19(m, 1H), 3.98-4.05(m, 1H), 2.39(s, 3H), 1.68(s, 9H) |
| 31 | 4.88 | 4.80 | 8.09(d, 1H), 7.81-7.77(m, 1H), 7.72(d, 1H), 7.44(d, 1H), 7.38(d, 1H), 7.35-7.31(m, 1H), 4.08(q, 2H), 3.90(q, 2H), 2.41(s, 3H), 2.40(s, 3H), 2.15(s, 3H) |
| 32 | 4.35 | 4.30 | 7.99(d, 1H), 7.65-7.68(m, 1H), 7.41(d, 1H), 3.89-3.96(q, 2H), 3.01-3.07(m, 1H), 2.40(s, 3H), 1.00-1.09(m, 4H) |
| 33 | 4.42 | 4.47 | 8.19(d, 1H), 7.78-7.81(m, 1H), 7.60(d, 1H), 4.00-4.08(q, 2H), 3.13-3.19(m, 1H), 2.89-2.94(m, 1H), 1.31(d, 6H), 0.99-1.01(m, 4H) |
| 34 | 3.10 | 3.01 | 8.31(d, 1H), 8.02-8.00(m, 1H), 7.50(d, 1H), 4.22-4.13(m, 1H), 4.05-3.96(m, 1H), 3.08-3.03(m, 1H), 2.38(s, 3H), 1.13-1.01(m, 4H) |
| 35 | 4.63 | 4.55 | 8.08(d, 1H), 7.76-7.74(m, 1H), 7.63-7.59(m, 5H), 7.45(d, 1H), 3.95(q, 2H), 2.43(s, 3H) |
| 36 | 4.33 | 4.24 | 7.90(d, 1H), 7.61(s, 5H), 7.51(d, 1H), 3.95(q, 2H), 2.48(s, 3H) |
| 37 | 3.29 | 3.25 | 8.16(d, 1H), 7.65-7.60(m, 6H), 4.33-4.24(m, 1H), 4.08-3.96(m, 1H), 2.45(s, 3H) |
| 38 | 3.09 | 3.08 | 8.27(d, 1H), 8.14(d, 1H), 4.17(q, 2H), 3.32(s, 3H) |
| 39 | 2.97 | 2.91 | 8.05(d, 1H), 7.80-7.75(m, 2H), 7.57-7.54(m, 2H), 4.28-4.19(m, 1H), 4.13-4.02(m, 1H), 3.21(s, 3H), 2.43(s, 3H) |
| 40 | 4.06 | 3.96 | 7.81-7.74(m, 3H), 7.56-7.53(m, 1H), 7.44(d, 1H), 3.96(q, 2H), 3.21(s, 3H), 2.45(s, 3H) |
| 41 | 1.85 | 1.79 | 7.93(d, 1H), 7.48(d, 1H), 4.25-4.19(m, 1H), 4.06-3.99(m, 1H), 2.91-2.88(m, 1H), 2.40(s, 3H), 2.32(s, 3H), 0.99-0.95(m, 4H) |
| 42 | 2.76 | 2.73 | 7.66(d, 1H), 7.37(d, 1H), 3.92(q, 2H), 2.90-2.87(m, 1H), 2.42(s, 3H), 2.30(s, 3H), 0.97-0.95(m, 4H) |
| 43 | 2.52 | 2.47 | 7.92(d, 1H), 7.48(d, 1H), 4.24-4.12(m, 1H), 4.10-4.00(m, 1H), 3.21-3.14(m, 1H), 2.97-2.92(m, 1H), 2.40(s, 3H), 1.30-1.28(m, 6H), 1.04-0.99(m, 4H) |
| 44 | 3.59 | 3.52 | 7.67(d, 1H), 7.37(d, 1H), 3.92(q, 2H), 3.19-3.12(m, 1H), 2.94-2.91(m, 1H), 2.43(s, 3H), 1.27(d, 6H), 1.00-0.98(m, 4H) |
| 45 | 1.99 | 1.96 | 7.96(d, 1H), 7.51(d, 1H), 4.47(s, 2H), 4.26-4.17(m, 1H), 4.10-4.01(m, 1H), 3.36(s, 3H), 2.94-2.88(m, 1H), 2.41(s, 3H), 1.06-1.02(m, 1H), 1.00-0.93(m, 2H) |
| 46 | 2.91 | 2.90 | 7.70(d, 1H), 7.39(d, 1H), 4.44(s, 2H), 3.94(q, 2H), 3.36(s, 3H), 2.92-2.87(m, 1H), 2.43(s, 3H), 1.05-0.93(m, 4H) |
| 47 | 2.92 | 2.84 | 8.46(d, 1H), 8.24(d, 1H), 4.52-4.40(m, 1H), 4.33-4.22(m, 1H), 3.10-3.05(m, 1H), 1.15-1.02(m, 4H) |
| 48 | 4.13 | 4.09 | 7.54(s, 1H), 7.30(s, 1H), 3.90(q, 2H), 3.10-3.04(m, 1H), 2.40(s, 3H), 2.14(s, 3H), 1.11-1.01(s, 4H) |
| 49 | 4.95 | 4.88 | 7.59(s, 1H), 7.31(s, 1H), 3.95(q, 2H), 2.40(s, 3H), 2.11(s, 3H), 1.67(s, 9H) |
| 50 | 4.14 | 4.07 | 7.85(s, 1H), 7.66(s, 1H), 4.07(q, 2H), 3.85(q, 2H), 2.42(s, 3H), 1.29(t, 3H) |
| 51 | 4.43 | 4.39 | 8.12(d, 1H), 7.78-7.76(m, 1), 7.71-7.65(m, 1H), 4.09(q, 2H), 3.07-3.02(m, 1H), 1.12-1.01(m, 4H) |
| 52 | 3.84 | 3.79 | 7.86(d, 1H), 7.72-7.69(m, 1H), 7.18(d, 1H), 3.93-3.83(m, 5H), 3.05-3.01(m, 1H), 1.11-0.99(m, 4H) |
| 53 | 3.03 | 2.93 | 8.10(d, 1H), 8.05-8.02(m, 1H), 7.35(d, 1H), 4.20-4.10(m, 1H), 3.98-3.90(m, 1H), 3.92(s, 3H), 3.07-3.02(m, 1H), 1.12-1.00(m, 4H) |
| 54 | 4.38 | 4.32 | 8.02(d, 1H), 7.70-7.68(m, 1H), 7.41(d, 1H), 3.95(q, 2H), 3.83(q, 2H), 2.41(s, 3H), 1.28(t, 3H) |
| 55 | 4.22 | 4.11 | 7.84(d, 1H), 7.50(d, 1H), 4.79(q, 2H), 3.97(q, 2H), 2.46(s, 3H) |
| 56 | 3.20 | 3.09 | 8.10(d, 1H), 7.61(d, 1H), 4.78(q, 2H), 4.32-4.20(m, 1H), 4.11-3.99(m, 1H), 2.45(s, 3H) |
| 57 | 3.96 | 3.88 | 7.83(d, 1H), 7.47(d, 1H), 3.96(q, 2H), 3.84(q, 2H), 2.46(s, 3H), 1.29(t, 3H) |
| 58 | 2.88 | 2.77 | 8.07(d, 1H), 7.58(d, 1H), 4.31-4.20(m, 1H), 4.10-3.98(m, 1H), 3.84(q, 2H), 2.44(s, 3H), 1.29(t, 3H) |
| 59 | 3.97 | 3.91 | 7.77(d, 1H), 7.46(d, 1H), 3.93(q, 2H), 3.11-3.05(m, 1H), 2.45(s, 3H), 1.11-1.01(m, 4H) |
| 60 | 2.93 | 2.82 | 8.02(d, 1H), 7.57(d, 1H), 4.31-4.21(m, 1H), 4.05-3.95(m, 1H), 3.10-3.0(m, 1H), 2.43(s, 3H), 1.10-1.02(m, 4H) |
| 61 | 2.62 | 2.59 | 8.19(s, 1H), 7.70(d, 1H), 7.39(d, 1H), 3.94(q, 2H), 3.07-3.02(m, 1H), 2.43(s, 3H), 0.94-0.92(m, 4H) |
| 62 | 1.69 | 1.69 | 8.24(s, 1H), 7.96(d, 1H), 7.51(d, 1H), 4.26-4.17(m, 1H), 4.10-4.00(m, 1H), 3.08-3.03(m, 1H), 2.41(s, 3H), 0.94-0.92(m, 4H) |
| 63 | 4.17 | 4.11 | 7.68(d, 1H), 7.37(d, 1H), 3.92(q, 2H), 3.10-3.03(m, 1H), 2.43(s, 3H), 1.43(s, 9H), 1.27-1.22(m, 2H), 1.08-1.02(m, 2H) |
| 64 | 2.95 | 2.97 | 7.92(d, 1H), 7.48(d, 1H), 4.27-4.15(m, 1H), 4.12-4.00(m, 1H), 3.10-3.04(m, 1H), 2.40(s, 3H), 1.44(s, 9H), 1.28-1.24(m, 2H), 1.08-1.02(m, 2H) |

| Ex. No. | logP[a] | logP[b] | 1H NMR(D6-DMSO, 400 MHz) δ ppm |
| --- | --- | --- | --- |
| 65 | 3.39 | 3.33 | 7.63(d, 1H), 7.35(d, 1H), 3.92(q, 2H), 2.99-2.94(m, 1H), 2.42(s, 3H), 2.09-2.02(m, 1H), 1.02-0.98(m, 6H), 0.91-0.87(m, 2H) |
| 66 | 2.31 | 2.33 | 7.89(d, 1H), 7.46(d, 1H), 4.26-4.14(m, 1H), 4.09-3.98(m, 1H), 3.01-2.95(m, 1H), 2.39(s, 3H), 2.11-2.03(m, 1H), 1.05-0.98(m, 6H), 0.95-0.88(m, 2H) |
| 67 | 4.78 | 4.66 | 7.82(d, 1H), 7.46(d, 1H), 3.97(q, 2H), 2.45(s, 3H), 1.66(s, 9H) |
| 68 | 3.54 | 3.49 | 8.07(d, 1H), 7.57(d, 1H), 4.26-4.22(m, 1H), 4.09-4.02(m, 1H), 2.44(s, 3H), 1.67(s, 9H) |
| 69 | 3.98 | 3.89 | 7.79(d, 1H), 7.71-7.69(m, 2H), 7.64-7.59(m, 1H), 7.47-7.42(m, 2H), 3.95(q, 2H), 3.32-3.27(m, 1H), 2.45(s, 3H), 0.95-0.90(m, 2H), 0.68-0.64(m, 2H) |
| 70 | 2.94 | 2.87 | 8.04(d, 1H), 7.71(d, 2H), 7.65-7.59(m, 1H), 7.54(d, 1H), 7.47-7.42(m, 1H), 4.28-4.19(m, 1H), 4.11-4.02(m, 1H), 3.31-3.26(m, 1H), 2.43(s, 3H), 0.95-0.89(m, 2H), 0.72-0.66(m, 2H) |
| 71 | 4.05 | 3.96 | 7.66(d, 1H), 7.37(d, 1H), 3.92(q, 2H), 2.91-2.85(m, 1H), 2.70-2.66(m, 2H), 2.43(s, 3H), 1.71-1.64(m, 2H), 1.46-1.37(m, 2H), 0.98-0.95(m, 4H), 0.93(t, 3H) |
| 72 | 2.94 | 2.88 | 7.92(d, 1H), 7.48(d, 1H), 4.25-4.16(m, 1H), 4.10-4.01(m, 1H), 2.93-2.87(m, 1H), 2.70(t, 2H), 2.40(s, 3H), 1.73-1.65(m, 2H), 1.47-1.38(m, 2H), 1.01-0.92(m, 7H) |
| 73 | 3.33 | 3.27 | 7.70(d, 1H), 7.39(d, 1H), 4.47(s, 2H), 3.94(q, 2H), 3.56(q, 2H), 2.93-2.88(m, 1H), 2.43(s, 3H), 1.17(t, 3H), 1.06-1.00(m, 2H), 0.99-0.93(m, 2H) |
| 74 | 2.31 | 2.25 | 7.96(d, 1H), 7.50(d, 1H), 4.49(s, 2H), 4.26-4.17(m, 1H), 4.11-4.00(m, 1H), 3.57(q, 2H), 2.95-2.89(m, 1H), 2.41(s, 3H), 1.19-1.15(m, 3H), 1.07-0.93(m, 4H) |
| 75 | 2.97 | 2.89 | 7.66(d, 1H), 7.38(d, 1H), 3.92(q, 2H), 3.71(t, 2H), 3.29(s, 3H), 2.96(t, 2H), 2.91-2.86(m, 1H), 2.43(s, 3H), 0.99-0.96(m, 4H) |
| 76 | 2.03 | 1.97 | 7.92(d, 1H), 7.49(d, 1H), 4.25-4.16(m, 1H), 4.11-4.02(m, 1H), 3.72(t, 2H), 3.29(s, 3H), 2.97(t, 2H), 2.93-2.88(m, 1H), 2.40(s, 3H), 1.02-0.98(m, 4H) |
| 77 | 3.24 | 3.18 | 7.67(d, 1H), 7.37(d, 1H), 3.92(q, 2H), 2.91-2.86(m, 1H), 2.72(q, 2H), 2.43(s, 3H), 1.23(t, 3H), 0.99-0.95(m, 4H) |
| 78 | 2.20 | 2.15 | 7.92(d, 1H), 7.48(d, 1H), 4.25-4.16(m, 1H), 4.10-4.00(m, 1H), 2.92-2.87(m, 1H), 2.72(q, 2H), 2.40(s, 3H), 1.24(t, 3H), 1.01-0.96(m, 4H) |
| 79 | 3.64 | 3.56 | 7.66(d, 1H), 7.37(d, 1H), 3.92(q, 2H), 2.90-2.85(m, 1H), 2.68-2.64(m, 2H), 2.43(s, 3H), 1.76-1.67(m, 2H), 1.02-0.96(m, 7H) |
| 80 | 2.56 | 2.49 | 7.92(d, 1H), 7.48(d, 1H), 4.25-4.15(m, 1H), 4.10-4.00(m, 1H), 2.92-2.87(m, 1H), 2.68(t, 2H), 2.40(s, 3H), 1.78-1.69(m, 2H), 1.02-0.97(m, 7H) |
| 81 | 3.55 | 3.49 | 7.70(d, 1H), 7.38(d, 1H), 6.73-6.64(m, 1H), 6.42-6.64(m, 1H), 3.93(q, 2H), 2.95-2.90(m, 1H), 2.43(s, 3H), 1.94-1.92(m, 3H), 1.06-1.01(m, 2H), 0.93-0.89(m, 2H) |
| 82 | 2.48 | 2.42 | 7.96(d, 1H), 7.49(d, 1H), 6.75-6.66(m, 1H), 6.43-6.37(m, 1H), 4.25-4.16(m, 1H), 4.10-3.98(m, 1H), 2.97-2.91(m, 1H), 2.41(s, 3H), 1.95-1.93(m, 3H), 1.06-0.99(m, 2H), 0.95-0.91(m, 2H) |
| 83 | 3.99 | 3.93 | 7.66(d, 1H), 7.37(d, 1H), 3.92(q, 2H), 2.88-2.84(m, 1H), 2.56(d, 2H), 2.43(s, 3H), 2.18-2.11(m, 1H), 1.01-0.97(m, 10H) |
| 84 | 2.86 | 2.80 | 7.93(d, 1H), 7.48(d, 1H), 4.25-4.18(m, 1H), 4.08-4.01(m, 1H), 2.90-2.86(m, 1H), 2.55(d, 2H), 2.40(s, 3H), 2.20-2.13(m, 1H), 1.02-0.98(m, 10H) |
| 85 | 4.01 | 3.94 | 7.67(d, 1H), 7.37(d, 1H), 3.92(q, 2H), 3.02-2.97(m, 1H), 2.93-2.88(m, 1H), 2.43(s, 3H), 1.83-1.76(m, 1H), 1.61-1.54(m, 1H), 1.24(d, 3H), 1.03-0.91(m, 7H) |
| 86 | 2.86 | 2.79 | 7.92(d, 1H), 7.48(d, 1H), 4.24-4.18(m, 1H), 4.10-4.02(m, 1H), 3.04-2.99(m, 1H), 2.95-2.89(m, 1H), 2.41(s, 3H), 1.85-1.77(m, 1H), 1.63-1.55(m, 1H), 1.27-1.24(m, 3H), 1.03-0.91(m, 7H) |
| 87 | 3.85 | 3.77 | 7.69(d, 1H), 7.38(d, 1H), 3.93(q, 2H), 3.74-3.65(m, 1H), 2.83-2.77(m, 1H), 2.43(s, 3H), 2.35-2.27(m, 4H), 2.12-2.00(m, 1H), 1.91-1.82(m, 1H), 0.96-0.90(m, 4H) |
| 88 | 2.72 | 2.66 | 7.94(d, 1H), 7.48(d, 1H), 4.25-4.16(m, 1H), 4.12-4.00(m, 1H), 3.74-3.67(m, 1H), 2.84-2.79(m, 1H), 2.41(s, 3H), 2.37-2.30(m, 4H), 2.11-2.03(m, 1H), 1.91-1.86(m, 1H), 0.94(d, 4H) |
| 89 | 3.80 | 3.73 | 7.83(d, 1H), 7.48(d, 1H), 4.01-3.94(m, 4H), 3.61(t, 2H), 3.27(s, 3H), 2.45(s, 3H) |
| 90 | 3.74 | 3.67 | 8.02(d, 1H), 7.68-7.65(m, 1H), 7.32(d, 1H), 4.02(s, 3H), 3.87(q, 2H), 2.79-2.75(m, 1H), 2.37(s, 3H), 0.93-0.87(m, 4H) |
| 91 | 4.59 | 4.54 | 7.99(d, 1H), 7.66-7.63(m, 1H), 7.31(d, 1H), 5.08-5.01(m, 1H), 3.87(q, 2H), 2.76-2.74(m, 1H), 2.36(s, 3H), 1.41(d, 6H), 0.92-0.90(m, 4H) |
| 92 | 4.29 | 4.20 | 8.00(d, 1H), 7.68-7.66(m, 1H), 7.34(d, 1H), 5.11(q, 2H), 3.89(q, 2H), 2.86-2.81(m, 1H), 2.37(s, 3H), 0.95-0.93(m, 4H) |
| 93 | 2.78 | 2.73 | 7.70(d, 1H), 7.38(d, 1H), 3.97(s, 3H), 3.92(q, 2H), 3.10(s, 3H), 2.43(s, 3H) |
| 94 | 1.77 | 1.77 | 7.96(d, 1H), 7.48(d, 1H), 4.25-4.19(m, 1H), 4.07-4.00(m, 1H), 3.99(s, 3H), 3.11(s, 3H), 2.40(s, 3H) |

| Ex. No. | logP[a] | logP[b] | ¹H NMR(D6-DMSO, 400 MHz) δ ppm |
|---|---|---|---|
| 95 | 3.74 | 3.64 | 8.34(d, 1H), 7.94-7.92(m, 1H), 7.87-7.84(m, 1H), 4.11-4.04(m, 5H), 3.11(s, 3H) |
| 96 | 2.89 | 2.83 | 8.70(d, 1H), 8.32-8.29(m, 1H), 8.03(d, 1H), 4.15(q, 2H), 4.09(s, 3H), 3.13(s, 3H) |
| 97 | 2.26 | 2.24 | 8.11(s, 1H), 7.94(s, 1H), 4.37-4.28(m, 1H), 4.20-4.13(m, 1H), 3.99(s, 3H), 3.11(s, 3H) |
| 98 | 2.12 | 2.10 | 8.01(d, 1H), 7.96(d, 1H), 4.34-4.28(m, 1H), 4.18-4.12(m, 1H), 4.00(s, 3H), 3.11(s, 3H) |
| 99 | 2.54 | 2.52 | 8.35(d, 1H), 8.17-8.14(m, 1H), 7.72(d, 1H), 4.26-4.09(m, 2H), 4.07(s, 3H), 3.11(s, 3H) |
| 100 | 2.82 | 2.79 | 7.94(d, 1H), 7.46(d, 1H), 4.99-4.93(m, 1H), 4.24-4.15(m, 1H), 4.09-4.00(m, 1H), 2.81-2.75(m, 1H), 2.39(s, 3H), 1.40-1.37(m, 6H), 0.92-0.91(m, 4H) |
| 101 | 3.93 | 3.85 | 7.68(d, 1H), 7.35(d, 1H), 4.96-4.90(m, 1H), 3.92(q, 2H), 2.78-2.75(m, 1H), 2.49(s, 3H), 1.38(d, 6H), 0.92-0.90(m, 4H) |
| 102 | 2.83 | 2.77 | 7.95(d, 1H), 7.49(d, 1H), 5.08-5.01(m, 2H), 4.26-4.17(m, 1H), 4.06-3.94(m, 1H), 2.89-2.84(m, 1H), 2.40(s, 3H), 0.96-0.93(m, 4H) |
| 103 | 3.80 | 3.72 | 7.69(d, 1H), 7.38(d, 1H), 5.02(q, 2H), 3.91(q, 2H), 2.88-2.83(m, 1H), 2.43(s, 3H), 0.96-0.90(m, 4H) |
| 104 | 2.13 | 2.08 | 7.95(d, 1H), 7.47(d, 1H), 4.25-4.18(m, 1H), 4.06-4.00(m, 1H), 3.97(s, 3H), 2.82-2.77(m, 1H), 2.40(s, 3H), 0.94-0.91(m, 4H) |
| 105 | 3.16 | 3.11 | 7.69(d, 1H), 7.36(d, 1H), 3.95(s, 3H), 3.91(q, 2H), 2.80-2.78(m, 1H), 2.42(s, 3H), 0.92-0.89(m, 4H) |
| 106 | 2.65 | 2.61 | 8.09(s, 1H), 7.94(s, 1H), 4.40-4.28(m, 1H), 4.21-4.09(m, 1H), 3.97(s, 3H), 2.85-2.78(m, 1H), 0.94-0.91(m, 4H) |
| 107 | 3.46 | 3.42 | 7.91(s, 1H), 7.83(s, 1H), 4.19(q, 2H), 3.95(s, 3H), 2.82-2.78(m, 1H), 0.94-0.89(m, 4H) |
| 108 | 3.91 | 3.84 | 8.13(d, 1H), 7.77-7.74(m, 1H), 7.58(d, 1H), 4.07-3.99(m, 5H), 2.79-2.75(m, 1H), 0.94-0.90(m, 4H) |
| 109 | 2.34 | 2.30 | 8.11(d, 1H), 8.05-8.02(m, 1H), 7.28(d, 1H), 4.13-4.04(m, 1H), 4.03(s, 3H), 3.95-3.90(m, 1H), 3.89(s, 3H), 2.80-2.76(m, 1H), 0.94-0.91(m, 4H) |
| 110 | 3.00 | 2.95 | 8.35(d, 1H), 8.07-8.04(m, 1H), 7.84(d, 1H), 4.21-4.03(m, 2H), 4.05(s, 3H), 2.81-2.77(m, 1H), 0.95-0.92(m, 4H) |
| 111 | 4.01 | 3.93 | 8.12(d, 1H), 7.72(d, 1H), 7.67-7.64(m, 1H), 4.08-4.00(m, 5H), 2.79-2.75(m, 1H), 0.93-0.90(m, 4H) |
| 112 | 2.83 | 2.79 | 7.94(d, 1H), 7.46(d, 1H), 4.25(t, 2H), 4.24-4.18(m, 1H), 4.06-4.02(m, 1H), 2.82-2.80(m, 1H), 2.40(s, 3H), 1.80-1.75(m, 2H), 0.99(t, 3H), 0.94-0.92(m, 4H) |
| 113 | 4.00 | 3.92 | 7.68(d, 1H), 7.35(d, 1H), 4.23(t, 2H), 3.91(q, 2H), 2.82-2.77(m, 1H), 2.43(s, 3H), 1.82-1.72(m, 2H), 0.98(t, 3H), 0.93-0.91(m, 4H) |
| 114 | 3.32 | 3.27 | 7.84(d, 1H), 7.78(d, 1H), 4.08(q, 2H), 3.97(s, 3H), 2.81-2.78(m, 1H), 0.93-0.91(m, 4H) |
| 115 | 2.45 | 2.43 | 8.00(d, 1H), 7.95(d, 1H), 4.34-4.24(m, 1H), 4.20-4.10(m, 1H), 3.99(s, 3H), 2.83-2.77(m, 1H), 0.94-0.91(m, 4H) |
| 116 | 3.20 | 3.30 | 7.68(s, 1H), 7.56(s, 1H), 4.04(q, 2H), 3.94(s, 3H), 2.81-2.78(m, 1H), 2.39(s, 3H), 0.94-0.89(m, 4H) |
| 117 | 2.28 | 2.30 | 7.90(s, 1H), 7.69(s, 1H), 4.28-4.22(m, 1H), 4.08-4.01(m, 1H), 3.96(s, 3H), 2.82-2.80(m, 1H), 2.40(s, 3H), 0.93-0.91(m, 4H) |
| 118 | 2.47 | 2.43 | 8.50(d, 1H), 8.24-8.21(m, 1H), 8.12(d, 1H), 4.40-4.20(m, 2H), 4.07(s, 3H), 2.85-2.78(m, 1H), 0.96-0.93(m, 4H) |
| 119 | 2.21 | 2.17 | 7.76(s, 1H), 7.33(s, 1H), 4.19-4.12(m, 1H), 3.98-3.92(m, 1H), 3.96(s, 3H), 2.82-2.78(m, 1H), 2.36(s, 3H), 2.27(s, 3H), 0.94-0.90(m, 4H) |
| 120 | 3.58 | 3.44 | 7.68(d, 1H), 7.35(d, 1H), 4.32(q, 2H), 3.91(q, 2H), 2.81-2.76(m, 1H), 2.42(s, 3H), 1.37(t, 3H), 0.92-0.87(m, 4H) |
| 121 | 2.47 | 2.43 | 7.94(d, 1H), 7.46(d, 1H), 4.35(q, 2H), 4.24-4.18(m, 1H), 4.06-3.99(m, 1H), 2.81-2.78(m, 1H), 2.39(s, 3H), 1.38(t, 3H), 0.94-0.91(m, 4H) |
| 122 | 4.19 | 4.04 | 8.00(d, 1H), 7.67-7.64(m, 1H), 7.31(d, 1H), 4.40(q, 2H), 3.87(q, 2H), 2.80-2.74(m, 1H), 2.37(s, 3H), 1.38(t, 3H), 0.94-0.88(m, 4H) |
| 123 | 4.66 | 4.57 | 8.00(d, 1H), 7.67-7.64(m, 1H), 7.31(d, 1H), 4.31(t, 2H), 3.87(q, 2H), 2.81-2.75(m, 1H), 2.37(s, 3H), 1.84-1.76(m, 2H), 1.00(t, 3H), 0.93-0.91(m, 4H) |
| 124 | 3.24 | 3.20 | 7.94(d, 1H), 7.46(d, 1H), 4.29(t, 2H), 4.24-4.15(m, 1H), 4.08-3.99(m, 1H), 2.83-2.77(m, 1H), 2.39(s, 3H), 1.78-1.71(m, 2H), 1.49-1.40(m, 2H), 0.96-0.92(m, 7H) |
| 125 | 4.41 | 4.35 | 7.68(d, 1H), 7.35(d, 1H), 4.27(t, 2H), 3.91(q, 2H), 2.82-2.76(m, 1H), 2.42(s, 3H), 1.77-1.70(m, 2H), 1.48-1.39(m, 2H), 0.96-0.89(m, 7H) |
| 126 | 5.11 | 5.02 | 8.00(d, 1H), 7.67-7.64(m, 1H), 7.31(d, 1H), 4.35(t, 2H), 3.87(q, 2H), 2.80-2.74(m, 1H), 2.36(s, 3H), 1.80-1.73(m, 2H), 1.50-1.41(m, 2H), 0.97-0.90(m, 7H) |
| 127 | 3.61 | 3.57 | 7.69(d, 1H), 7.37(d, 1H), 4.25(t, 2H), 3.92(q, 2H), 3.10(s, 3H), 2.43(s, 3H), 1.80-1.73(m, 2H), 0.97(q, 3H) |
| 128 | 4.11 | 3.95 | 7.68(d, 1H), 7.37(d, 1H), 4.29(t, 2H), 3.92(q, 2H), 3.09(s, 3H), 2.43(s, 3H), 1.77-1.70(m, 2H), 1.46-1.40(m, 2H), 0.93(t, 3H) |
| 129 | 3.19 | 3.14 | 7.69(d, 1H), 7.37(d, 1H), 4.35(q, 2H), 3.92(q, 2H), 3.09(s, 3H), 2.42(s, 3H), 1.38(t, 3H) |

-continued

| Ex. No. | logP[a] | logP[b] | ¹H NMR(D6-DMSO, 400 MHz) δ ppm |
|---|---|---|---|
| 130 | 3.77 | 3.74 | 8.02(d, 1H), 7.69-7.66(m, 1H), 7.32(d, 1H), 4.42(q, 2H), 3.88(q, 2H), 3.08(s, 3H), 2.37(s, 3H), 1.40(t, 3H) |
| 131 | 2.13 | 2.09 | 7.95(d, 1H), 7.47(d, 1H), 4.27(t, 2H), 4.25-4.20(m, 1H), 4.04-4.01(m, 1H), 3.11(s, 3H), 2.40(s, 3H), 1.78(q, 2H), 0.98(t, 3H) |
| 132 | 2.52 | 2.47 | 7.95(d, 1H), 7.47(d, 1H), 4.27(t, 2H), 4.25-4.20(m, 1H), 4.04-4.01(m, 1H), 3.11(s, 3H), 2.40(s, 3H), 1.78(q, 2H), 0.98(t, 3H) |
| 133 | 2.93 | 2.86 | 8.30(d, 1H), 8.02-8.00(m, 1H), 7.41(d, 1H), 4.35(t, 2H), 4.17-4.11(m, 1H), 3.98-3.92(m, 1H), 3.11(s, 3H), 2.40(s, 3H), 1.84-1.76(m, 2H), 1.00(t, 3H) |
| 134 | 3.99 | 3.90 | 7.67(d, 1H), 7.35(d, 1H), 4.12(d, 2H), 3.91(q, 2H), 2.84-2.78(m, 1H), 2.42(s, 3H), 1.33-1.27(m, 1H), 0.94-0.93(m, 4H), 0.62-0.60(m, 2H), 0.42-0.38(m, 2H) |
| 135 | 4.60 | 4.56 | 7.99(d, 1H), 7.66-7.64(m, 1H), 7.31(d, 1H), 4.20(d, 2H), 3.87(q, 2H), 2.82-2.77(m, 1H), 2.36(s, 3H), 1.36-1.30(m, 1H), 0.95-0.92(m, 4H), 0.64-0.61(m, 2H), 0.42-0.41(m, 2H) |
| 136 | 4.37 | 4.33 | 7.68(d, 1H), 7.36(d, 1H), 4.84-4.80(m, 2H), 4.38(t, 2H), 3.91(q, 2H), 2.80-2.74(m, 1H), 2.49-2.47(m, 2H), 2.42(s, 3H), 1.77(s, 3H), 0.90-0.85(m, 4H) |
| 137 | 3.25 | 3.17 | 7.94(d, 1H), 7.46(d, 1H), 4.85-4.81(m, 2H), 4.40(t, 2H), 4.24-4.15(m, 1H), 4.08-3.96(m, 1H), 2.81-2.75(m, 1H), 2.50-2.47(m, 2H), 2.40(s, 3H), 1.78(s, 3H), 0.93-0.89(m, 4H) |
| 138 | 5.01 | 4.96 | 8.00(d, 1H), 7.68-7.65(m, 1H), 7.32(d, 1H), 4.85-4.82(m, 2H), 4.46(t, 2H), 3.87(q, 2H), 2.78-2.73(m, 1H), 2.53-2.52(m, 2H), 2.33(s, 3H), 1.79(s, 3H), 0.93-0.88(m, 4H) |
| 139 | 3.67 | 3.60 | 8.30(d, 1H), 7.99-7.96(m, 1H), 7.41(d, 1H), 4.85-4.82(m, 2H), 4.48(t, 2H), 4.17-4.10(m, 1H), 3.97-3.90(m, 1H), 2.79-2.76(m, 1H), 2.53-2.52(m, 2H), 2.34(s, 3H), 1.79(s, 3H), 0.93-0.89(m, 4H) |
| 140 | 4.36 | 4.30 | 7.68(d, 1H), 7.35(d, 1H), 4.78-4.74(m, 1H), 3.92(q, 2H), 2.80-2.75(m, 1H), 2.42(s, 3H), 1.76-1.67(m, 2H), 1.35(d, 3H), 0.96-0.89(m, 7H) |
| 141 | 3.18 | 3.12 | 7.94(d, 1H), 7.46(d, 1H), 4.81-4.77(m, 1H), 4.24-4.15(m, 1H), 4.09-4.00(m, 1H), 2.82-2.76(m, 1H), 2.39(s, 3H), 1.76-1.70(m, 2H), 1.36(t, 3H), 0.98-0.91(m, 7H) |
| 142 | 5.01 | 4.96 | 7.99(d, 1H), 7.66-7.63(m, 1H), 7.31(d, 1H), 4.90-4.85(m, 1H), 3.88(q, 2H), 2.79-2.73(m, 1H), 2.36(s, 3H), 1.78-1.70(m, 2H), 1.39(d, 3H), 0.96(t, 3H), 0.92-0.91(m, 4H) |
| 143 | 3.66 | 3.58 | 7.69(d, 1H), 7.36(d, 1H), 4.14(d, 2H), 3.91(q, 2H), 3.11(s, 3H), 2.43(s, 3H), 1.35-1.24(m, 1H), 0.63-0.56(m, 2H), 0.43-0.35(m, 2H) |
| 144 | 4.14 | 3.85 | 8.33(d, 1H), 7.93-1.90(m, 1H), 7.84(d, 1H), 4.10-4.03(m, 5H), 2.81-2.78(m, 1H), 0.95-0.92(m, 4H) |
| 145 | 4.20 | 4.19 | 8.01(d, 1H), 7.68-7.65(m, 1H), 7.32(d, 1H), 4.22(d, 2H), 3.88(q, 2H), 3.10(s, 3H), 2.37(s, 3H), 1.36-1.28(m, 1H), 0.65-0.59(m, 2H), 0.47-0.40(m, 2H) |
| 146 | 2.90 | 2.85 | 7.95(d, 1H), 7.45(d, 1H), 4.31(t, 2H), 4.25-4.15(m, 1H), 4.07-4.00(m, 1H), 3.10(s, 3H), 2.40(s, 3H), 1.78-1.71(m, 2H), 1.48-1.41(m, 2H), 0.94(t, 3H) |
| 147 | 3.27 | 3.19 | 8.71(d, 1H), 8.28-8.26(m, 1H), 8.02(d, 1H), 4.17-4.10(m, 2H), 4.08(s, 3H), 2.84-2.80(m, 1H), 0.97-0.93(m, 4H) |
| 148 | 4.03 | 3.92 | 7.69(d, 1H), 7.37(d, 1H), 4.07(d, 2H), 3.92(q, 2H), 3.11(s, 3H), 2.43(s, 3H), 2.12-2.05(m, 1H), 0.98(d, 6H) |
| 149 | 2.83 | 2.76 | 7.69(d, 1H), 7.37(d, 1H), 4.42-4.40(m, 2H), 3.92(q, 2H), 3.70-3.68(m, 2H), 3.33(s, 3H), 3.10(s, 3H), 2.43(s, 3H) |
| 150 | 4.35 | 4.29 | 7.69(d, 1H), 7.37(d, 1H), 3.97(s, 2H), 3.92(q, 2H), 3.13(s, 3H), 2.43(s, 3H), 1.00(s, 9H) |
| 151 | 3.61 | 3.53 | 7.69(d, 1H), 7.36(d, 1H), 4.99-4.92(m, 1H), 3.92(q, 2H), 3.07(s, 3H), 2.43(s, 3H), 1.39(d, 6H) |
| 152 | 2.90 | 2.83 | 7.95(d, 1H), 7.47(d, 1H), 4.29-4.12(m, 1H), 4.09(d, 2H), 4.07-3.99(m, 1H), 3.12(s, 3H), 2.40(s, 3H), 2.12-2.06(m, 1H), 0.99(d, 6H) |
| 153 | 4.50 | 4.44 | 7.68(d, 1H), 7.36(d, 1H), 4.76-4.72(m, 1H), 3.92(q, 2H), 3.09(s, 3H), 2.41(s, 3H), 2.00-1.97(m, 2H), 1.74-1.70(m, 2H), 1.64-1.56(m, 2H), 1.49-1.41(m, 1H), 1.25-1.40(m, 3H) |
| 154 | 4.55 | 4.45 | 7.98(d, 1H), 7.69-7.66(m, 1H), 7.32(d, 1H), 3.90(q, 2H), 3.05(s, 3H), 2.36(s, 3H), 1.59(s, 9H) |
| 155 | 5.22 | 5.17 | 8.01(d, 1H), 7.66-7.63(m, 1H), 7.31(d, 1H), 4.87-4.83(m, 1H), 3.89(q, 2H), 3.08(s, 3H), 2.36(s, 3H), 2.09-2.01(m, 2H), 1.76-1.71(m, 2H), 1.68-1.58(m, 2H), 1.53-1.45(m, 1H), 1.43-1.34(m, 3H) |
| 156 | 3.27 | 3.27 | 8.01(d, 1H), 7.68-7.65(m, 1H), 7.32(d, 1H), 5.43-5.42(m, 1H), 3.98(d, 1H), 3.93-3.85(m, 4H), 3.80-3.74(m, 1H), 3.07(s, 3H), 2.37(s, 3H), 2.32-2.25(m, 1H), 2.20-2.09(m, 1H) |
| 157 | 3.98 | 3.88 | 7.68(d, 1H), 7.36(d, 1H), 3.92(q, 2H), 3.05(s, 3H), 2.42(s, 3H), 1.55(s, 9H) |
| 158 | 3.70 | 3.66 | 7.66(d, 1H), 7.49-7.42(m, 4H), 7.36(d, 1H), 7.32-7.28(m, 1H), 3.90(q, 2H), 3.25(s, 3H), 2.41(s, 3H) |
| 159 | 2.70 | 2.65 | 7.89(d, 1H), 7.51-7.43(m, 5H), 7.33-7.28(m, 1H), 4.23-4.14(m, 1H), 4.08-3.99(m, 1H), 3.26(s, 3H), 2.39(s, 3H) |
| 160 | 2.52 | 2.38 | 7.96(d, 1H), 7.50(d, 1H), 5.11-5.04(m, 2H), 4.26-4.20(m, 1H), 4.05-3.98(m, 1H), 3.15(s, 3H), 2.41(s, 3H) |

-continued

| Ex. No. | logP[a] | logP[b] | ¹H NMR(D6-DMSO, 400 MHz) δ ppm |
|---|---|---|---|
| 161 | 1.89 | 1.84 | 7.95(d, 1H), 7.48(d, 1H), 5.37-5.35(m, 1H), 4.25-4.03(m, 1H), 4.02-3.95(m, 2H), 3.91-3.81(m, 2H), 3.78-3.73(m, 1H), 3.09(s, 3H), 2.40(s, 3H), 2.27-2.15(m, 2H) |
| 162 | 3.67 | 3.57 | 8.29(d, 1H), 8.03-8.01(m, 1H), 7.41(d, 1H), 4.14-4.11(m, 1H), 4.07(s, 2H), 3.99-3.94(m, 1H), 3.14(s, 3H), 2.34(s, 3H), 1.03(s, 9H) |
| 163 | 2.87 | 2.80 | 8.30(d, 1H), 8.01-7.98(m, 1H), 7.41(d, 1H), 5.13-5.06(m, 1H), 4.17-4.10(m, 1H), 3.99-3.92(m, 1H), 3.08(s, 3H), 2.34(s, 3H), 1.43-1.40(m, 6H) |
| 164 | 3.29 | 3.22 | 7.93(d, 1H), 7.47(d, 1H), 4.79-4.75(m, 1H), 4.24-4.16(m, 1H), 4.08-4.02(m, 1H), 3.10(s, 3H), 2.40(s, 3H), 2.01-1.98(m, 2H), 1.73-1.59(m, 4H), 1.51-1.48(m, 1H), 1.42-1.26(m, 3H) |
| 165 | 3.21 | 3.15 | 7.94(d, 1H), 7.47(d, 1H), 4.20-4.18(m, 1H), 4.07-4.04(m, 1H), 3.99(s, 2H), 3.14(s, 3H), 2.40(s, 3H), 1.01(s, 9H) |
| 166 | 2.48 | 2.44 | 7.95(d, 1H), 7.47(d, 1H), 5.01-4.95(m, 1H), 4.24-4.18(m, 1H), 4.08-4.01(m, 1H), 3.08(s, 3H), 2.40(s, 3H), 1.40-1.38(m, 6H) |
| 167 | 3.31 | 3.26 | 8.29(d, 1H), 8.02-8.00(m, 1H), 7.41(d, 1H), 4.16(d, 2H), 4.15-4.11(m, 1H), 3.98-3.92(m, 1H), 3.12(s, 3H), 2.34(s, 3H), 2.14-2.08(m, 1H), 1.00(d, 6H) |
| 168 | 3.60 | 3.54 | 8.13(d, 1H), 7.73(d, 1H), 7.68-7.66(m, 1H), 4.05(s, 3H), 4.04(q, 2H), 3.09(s, 3H) |
| 169 | 1.81 | 1.77 | 7.95(t, 1H), 7.81(t, 1H), 4.39-4.28(m, 2H), 3.99(s, 3H), 3.11(s, 3H) |
| 170 | 2.15 | 2.11 | 7.94(t, 1H), 7.80(t, 1H), 4.41-4.27(m, 2H), 3.98(s, 3H), 2.82-2.79(m, 1H), 0.94-0.91(m, 4H) |
| 171 | 2.97 | 2.92 | 7.83(t, 1H), 7.62(t, 1H), 3.96(q, 2H), 3.96(s, 3H), 2.81-2.78(m, 1H), 0.92-0.91(m, 4H) |
| 172 | 2.57 | 2.53 | 8.05(d, 1H), 7.99(d, 1H), 4.31-4.20(m, 1H), 4.15-4.03(m, 1H), 3.99(s, 3H), 2.87-2.79(m, 1H), 0.94-0.91(m, 4H) |
| 173 | 3.43 | 3.36 | 7.89(d, 1H), 7.82(d, 1H), 4.08(q, 2H), 3.97(s, 3H), 2.81-2.78(m, 1H), 0.93-0.91(m, 4H) |
| 174 | 2.21 | 2.15 | 8.07(d, 1H), 8.00(d, 1H), 4.29-4.23(m, 1H), 4.14-4.07(m, 1H), 4.00(s, 3H), 3.11(s, 3H) |
| 175 | 3.04 | 2.98 | 7.90(d, 1H), 7.83(d, 1H), 4.09(q, 2H), 3.98(s, 3H), 3.10(s, 3H) |
| 176 | 3.87 | 3.81 | 8.04(d, 1H), 7.70-7.67(m, 1H), 7.34(d, 1H), 5.92-5.84(m, 1H), 5.20-5.10(m, 2H), 4.18(d, 2H), 4.04(s, 3H), 3.89(q, 2H), 2.38(s, 3H) |
| 177 | 2.92 | 2.85 | 7.98(d, 1H), 7.55-7.48(m, 3H), 7.46-7.40(m, 3H), 5.37(s, 2H), 4.26-4.20(m, 1H), 4.07-4.01(m, 1H), 3.12(s, 3H), 2.41(s, 3H) |
| 178 | 3.23 | 3.18 | 8.34(d, 1H), 8.03-8.01(m, 1H), 7.57-7.55(m, 2H), 7.46-7.40(m, 4H), 5.45(s, 2H), 4.19-4.12(m, 1H), 3.98-3.92(m, 1H), 3.12(s, 3H), 2.35(s, 3H) |
| 179 | 2.61 | 2.57 | 8.33(d, 1H), 8.03-8.00(m, 1H), 7.41(d, 1H), 5.93-5.85(m, 1H), 5.21-5.11(m, 2H), 4.20(d, 2H), 4.18-4.08(m, 1H), 4.06(s, 3H), 4.00-3.94(m, 1H), 2.35(s, 3H) |
| 180 | 3.16 | 3.10 | 7.72(d, 1H), 7.37(d, 1H), 3.97(s, 3H), 3.93(q, 2H), 3.59(q, 2H), 2.43(s, 3H), 1.20(t, 3H) |
| 181 | 2.11 | 2.07 | 7.97(d, 1H), 7.48(d, 1H), 4.25-4.18(m, 1H), 4.09-4.02(m, 1H), 4.00(s, 3H), 3.60(q, 2H), 2.41(s, 3H), 1.21(t, 3H) |
| 182 | 3.30 | 3.24 | 7.73(d, 1H), 7.38(d, 1H), 5.93-5.85(m, 1H), 5.22-5.19(m, 1H), 5.15-5.11(m, 1H), 4.19-4.17(m, 2H), 3.97(s, 3H), 3.93(q, 2H), 2.43(s, 3H) |
| 183 | 2.24 | 2.21 | 7.99(d, 1H), 7.49(d, 1H), 5.95-5.83(m, 1H), 5.22-5.19(m, 1H), 5.16-5.11(m, 1H), 4.25-4.15(m, 3H), 4.10-4.04(m, 1H), 3.99(s, 3H), 2.41(s, 3H) |
| 184 | 2.82 | 2.76 | 7.96(d, 1H), 7.47(d, 1H), 4.20-4.18(m, 1H), 4.10-4.05(m, 1H), 3.06(s, 3H), 2.40(s, 3H), 1.56(s, 9H) |
| 185 | 4.14 | 4.10 | 7.93(s, 1H), 7.84(s, 1H), 5.03(q, 2H), 4.17(q, 2H), 2.90-2.85(m, 1H), 0.98-0.89(m, 4H) |
| 186 | 3.96 | 3.89 | 7.85(d, 1H), 7.81(d, 1H), 5.04(q, 2H), 4.07(q, 2H), 2.90-2.83(m, 1H), 0.99-0.89(m, 4H) |
| 187 | 3.98 | 3.93 | 7.70(s, 1H), 7.57(d, 1H), 5.02(q, 2H), 4.02(q, 2H), 2.90-2.84(m, 1H), 2.40(s, 3H), 1.00-0.90(m, 4H) |
| 188 | 3.49 | 3.46 | 7.58(d, 1H), 7.20(d, 1H), 5.01(q, 2H), 3.92(s, 3H), 3.86(q, 2H), 2.87-2.82(m, 1H), 0.97-0.90(m, 4H) |
| 189 | 4.55 | 4.48 | 8.30(d, 1H), 7.96-7.93(m, 1H), 7.86(d, 1H), 5.17(q, 2H), 4.10(q, 2H), 2.88-2.83(m, 1H), 0.98-0.94(m, 4H) |
| 190 | 2.84 | 2.81 | 7.68(d, 1H), 7.35(d, 1H), 3.92(q, 2H), 3.20(s, 3H), 2.78(s, 6H), 2.42(s, 3H) |
| 191 | 1.86 | 1.84 | 7.94(d, 1H), 7.46(d, 1H), 4.21-4.17(m, 1H), 4.09-4.02(m, 1H), 3.21(s, 3H), 2.80(s, 6H), 2.40(s, 3H) |
| 192 | 3.76 | 3.68 | 7.98(d, 1H), 7.67-7.64(m, 1H), 7.52-7.46(m, 4H), 7.38-7.31(m, 2H), 3.91(q, 2H), 3.28(s, 3H), 3.21(s, 3H), 2.38(s, 3H) |
| 193 | 3.20 | 3.15 | 7.67(d, 1H), 7.34(d, 1H), 3.91(q, 2H), 2.95-2.93(m, 1H), 2.85(s, 6H), 2.42(s, 3H), 1.02-0.99(m, 2H), 0.93-0.90(m, 2H) |
| 194 | 2.17 | 2.12 | 7.93(d, 1H), 7.44(d, 1H), 4.25-4.14(m, 1H), 4.10-4.00(m, 1H), 2.99-2.92(m, 1H), 2.87(s, 6H), 2.39(s, 3H), 1.05-1.00(m, 2H), 0.98-0.90(m, 2H) |
| 195 | 3.75 | 3.73 | 7.67(d, 1H), 7.37(d, 1H), 3.94(q, 2H), 2.95(s, 6H), 2.43(s, 3H), 2.04-1.97(m, 1H), 0.99-0.93(m, 2H), 0.91-0.85(m, 2H) |
| 196 | 2.67 | 2.61 | 7.63(d, 1H), 7.37(d, 1H), 5.47(breit, 2H), 3.93(q, 2H), 2.43(s, 3H), 2.09-2.01(m, 1H), 1.01-0.95(m, 2H), 0.94-0.89(m, 2H) |

-continued

| Ex. No. | logP[a] | logP[b] | ¹H NMR(D6-DMSO, 400 MHz) δ ppm |
|---|---|---|---|
| 197 | 2.60 | 2.59 | 7.91(d, 1H), 7.49(d, 1H), 4.27-4.00(m, 2H), 2.96(s, 3H), 2.50(s, 6H), 2.40(s, 3H), 2.06-1.98(m, 1H), 1.00-0.95(m, 2H), 0.94-0.87(m, 2H) |
| 198 | 2.28 | 2.22 | 7.70(d, 1H), 7.41(s, 1H), 5.49(s, 2H), 4.38(s, 2H), 3.96(q, 2H), 3.32(s, 3H), 2.44(s, 3H) |
| 199 | 3.15 | 3.07 | 7.67(d, 1H), 7.37(d, 1H), 6.19(q, 1H), 3.95(q, 2H), 2.71(d, 3H), 2.42(s, 3H), 2.06-1.99(m, 1H), 1.02-0.95(m, 2H), 0.94-0.88(m, 2H) |
| 200 | 2.18 | 2.13 | 7.66(d, 1H), 7.39(d, 1H), 5.41(s, 2H), 3.94(q, 2H), 2.43(s, 3H), 2.21(s, 3H) |
| 201 | 3.17 | 3.14 | 7.69(d, 1H), 7.39(d, 1H), 3.94(q, 2H), 2.92(s, 3H), 2.43(s, 3H), 2.20(s, 6H) |
| 202 | 4.06 | 3.98 | 7.75(d, 1H), 7.40(d, 1H), 3.96(q, 2H), 2.43(s, 3H), 2.37(d, 2H), 2.17(s, 3H), 2.12-2.02(m, 1H), 1.98(s, 3H), 0.96(d, 6H) |
| 203 | 2.32 | 2.27 | 8.29(s, 1H), 7.71(d, 1H), 7.41(d, 1H), 6.24(q, 1H), 3.97(q, 2H), 2.71(d, 3H), 2.42(s, 3H) |
| 204 | 1.96 | 1.95 | 7.92(d, 1H), 7.50(d, 1H), 5.46(s, 2H), 4.27-4.05(m, 2H), 3.11-3.02(m, 1H), 2.41(s, 3H), 1.28-1.22(m, 6H) |
| 205 | 3.15 | 3.08 | 7.79(d, 1H), 7.47(d, 1H), 5.85(breit, 2H), 3.98(q, 2H), 2.45(s, 3H) |
| 206 | 1.75 | 1.72 | 7.89(d, 1H), 7.48(d, 1H), 5.49(breit, 2H), 4.25-4.00(m, 2H), 2.40(s, 3H), 2.12-2.03(m, 1H), 1.04-0.98(m, 2H), 0.97-0.90(m, 2H) |
| 207 | 1.47 | 1.45 | 7.96(d, 1H), 7.53(d, 1H), 5.50(breit, 2H), 4.40(s, 2H), 4.30-4.16(m, 1H), 4.14-4.02(m, 1H), 3.35(s, 3H), 2.42(s, 3H) |
| 208 | 2.09 | 2.05 | 7.91(d, 1H), 7.49(d, 1H), 6.22(q, 1H), 4.27-4.01(m, 2H), 2.73(d, 3H), 2.41(s, 3H), 2.09-2.00(m, 1H), 1.03-0.97(m, 2H), 0.96-0.89(m, 2H) |
| 209 | 1.36 | 1.34 | 7.93(d, 1H), 7.50(d, 1H), 5.43(s, 2H), 4.29-4.16(m, 1H), 4.12-4.00(m, 1H), 2.41(s, 3H), 2.23(s, 3H) |
| 210 | 2.09 | 2.09 | 7.95(d, 1H), 7.50(d, 1H), 4.29-4.17(m, 1H), 4.11-4.00(m, 1H), 2.93(s, 3H), 2.41(s, 3H), 2.22(s, 6H) |
| 211 | 2.02 | 2.01 | 8.23(s, 1H), 7.68(d, 1H), 7.41(d, 1H), 5.58(breit, 2H), 3.96(q, 2H), 2.43(s, 3H) |
| 212 | 3.38 | 3.37 | 8.00(d, 1H), 7.70-7.67(m, 1H), 7.42(d, 1H), 5.79(breit, 2H), 3.95(q, 2H), 2.41(s, 3H) |
| 213 | 3.16 | 3.09 | 8.08(d, 1H), 7.58(d, 1H), 4.30-4.23(m, 1H), 4.04-3.98(m, 1H), 2.97(s, 6H), 2.44(s, 3H) |
| 214 | 4.24 | 4.15 | 7.82(d, 1H), 7.48(d, 1H), 3.95(q, 2H), 2.97(s, 6H), 2.46(s, 3H) |
| 215 | 2.19 | 2.17 | 8.03(d, 1H), 7.59(d, 1H), 5.83(breit, 2H), 4.31-4.20(m, 1H), 4.15-4.03(m, 1H), 2.44(s, 3H) |
| 216 | 3.03 | 2.99 | 7.68(d, 1H), 7.35(d, 1H), 6.08(q, 1H), 3.93(q, 2H), 2.90(s, 6H), 2.67(d, 3H), 2.42(s, 3H) |
| 217 | 2.02 | 1.98 | 7.95(d, 1H), 7.46(d, 1H), 6.11(q, 1H), 4.25-4.00(m, 2H), 2.92(s, 6H), 2.68(d, 3H), 2.40(s, 3H) |
| 218 | 2.06 | 2.04 | 7.64(d, 1H), 7.32(d, 1H), 6.19-6.15(m, 1H), 5.27(breit, 2H), 3.90(q, 2H), 2.69(d, 3H), 2.42(s, 3H) |
| 219 | 1.32 | 1.29 | 7.93(d, 1H), 7.42(d, 1H), 6.25(q, 1H), 5.31(breit, 2H), 4.22-4.12(m, 1H), 4.09-4.00(m, 1H), 2.71(d, 3H), 2.39(s, 3H) |
| 220 | 2.51 | 2.48 | 7.65(d, 1H), 7.35(d, 1H), 5.37(breit, 2H), 3.92(q, 2H), 2.89(s, 6H), 2.43(s, 3H) |
| 221 | 1.63 | 1.60 | 7.93(d, 1H), 7.46(d, 1H), 5.40(breit, 2H), 4.26-4.12(m, 1H), 4.11-4.00(m, 1H), 2.91(s, 6H), 2.40(s, 3H) |
| 222 | 3.22 | 3.17 | 7.64(d, 1H), 7.34(d, 1H), 5.34(breit, 2H), 3.91(q, 2H), 3.36(q, 4H), 2.42(s, 3H), 1.10(t, 6H) |
| 223 | 2.23 | 2.18 | 7.92(d, 1H), 7.45(d, 1H), 5.37(breit, 2H), 4.25-4.12(m, 1H), 4.11-4.00(m, 1H), 3.38(q, 4H), 2.39(s, 3H), 1.12(t, 6H) |
| 224 | 2.74 | 2.71 | 7.63(d, 1H), 7.32(d, 1H), 5.84(d, 1H), 5.26(breit, 2H), 3.90(q, 2H), 3.69-3.63(m, 1H), 2.42(s, 3H), 1.18(d, 6H) |
| 225 | 1.87 | 1.83 | 7.92(d, 1H), 7.42(d, 1H), 5.93(d, 1H), 5.30(breit, 2H), 4.24-4.13(m, 1H), 4.11-4.00(m, 1H), 3.72-3.67(m, 1H), 2.39(s, 3H), 1.18(t, 6H) |
| 226 | 1.76 | 1.74 | 7.97(d, 1H), 7.52(d, 1H), 4.30-4.19(m, 1H), 4.10-4.00(m, 1H), 4.04(s, 3H), 2.42(s, 3H), 2.35(s, 3H) |
| 227 | 3.76 | 3.70 | 7.96(d, 1H), 7.66-7.62(m, 1H), 7.35(d, 1H), 4.48(q, 2H), 3.99(s, 3H), 3.90(q, 2H), 2.38(s, 3H), 1.43(t, 3H) |
| 228 | 2.12 | 2.08 | 8.03(d, 1H), 7.57(d, 1H), 4.30-4.23(m, 1H), 4.06-3.97(m, 1H), 3.59(s, 3H), 3.14-3.11(m, 1H), 2.43(s, 3H), 1.21-1.16(m, 2H), 1.07-1.03(m, 2H) |
| 229 | 2.10 | 2.07 | 8.02-8.00(m, 1H), 7.57(d, 1H), 6.77-6.48(m, 1H), 4.32-4.20(m, 1H), 4.19-3.96(m, 3H), 3.11-3.06(m, 1H), 2.43(s, 3H), 1.20-1.04(m, 4H) |
| 230 | 2.45 | 2.40 | 7.76(d, 1H), 7.45(d, 1H), 3.95(q, 2H), 3.10(s, 3H), 3.09-3.05(m, 1H), 2.45(s, 3H), 1.11-1.05(m, 4H) |
| 231 | 1.61 | 1.58 | 8.02-7.99(m, 1H), 7.56(d, 1H), 4.29-4.19(m, 1H), 4.08-4.01(m, 1H), 3.12(s, 3H), 3.10-3.05(m, 1H), 2.43(s, 3H), 1.19-1.05(m, 4H) |
| 232 | 2.25 | 2.21 | 7.78(d, 1H), 7.45(d, 1H), 3.96(q, 2H), 3.47(s, 3H), 3.14(s, 3H), 2.45(s, 3H) |
| 233 | 1.47 | 1.44 | 8.03-8.01(m, 1H), 7.57(d, 1H), 4.29-4.22(m, 1H), 4.08-4.02(m, 1H), 3.47(s, 3H), 3.15(s, 3H), 2.43(s, 3H) |
| 234 | 2.68 | 2.65 | 7.75(d, 1H), 7.44(d, 1H), 3.95(q, 2H), 3.44-3.33(m, 2H), 3.09-3.04(m, 1H), 2.45(s, 3H), 1.29(t, 3H), 1.15-1.03(m, 4H) |

-continued

| Ex. No. | logP[a] | logP[b] | ¹H NMR(D6-DMSO, 400 MHz) δ ppm |
|---|---|---|---|
| 235 | 1.85 | 1.80 | 8.01-7.99(m, 1H), 7.55(d, 1H), 4.28-4.19(m, 1H), 4.07-4.00(m, 1H), 3.45-4.35(m, 2H), 3.09-3.04(m, 1H), 2.43(s, 3H), 1.32-1.28(m, 3H), 1.19-1.04(m, 4H) |
| 236 | 3.05 | 2.98 | 7.75(d, 1H), 7.60(d, 1H), 3.95(q, 2H), 3.39-3.34(m, 2H), 3.10-3.04(m, 1H), 2.45(s, 3H), 1.83-1.74(m, 2H), 1.16-1.03(m, 7H) |
| 237 | 2.14 | 2.08 | 8.00(d, 1H), 7.56(d, 1H), 4.29-4.19(m, 1H), 4.07-4.00(m, 1H), 3.40-3.34(m, 2H), 3.10-3.05(m, 1H), 2.43(s, 3H), 1.82-1.75(m, 2H), 1.19-1.03(m, 7H) |
| 238 | 2.99 | 2.92 | 7.75(d, 1H), 7.44(d, 1H), 3.94(q, 2H), 3.76-3.69(m, 1H), 3.09-3.04(m, 1H), 2.45(s, 3H), 1.33(d, 3H), 1.30(d, 3H), 1.14 1.04(m, 4H) |
| 239 | 2.08 | 2.03 | 8.01(d, 1H), 7.55(d, 1H), 4.28-4.19(m, 1H), 4.06-4.00(m, 1H), 3.75-3.68(m, 1H), 3.09-3.04(m, 1H), 2.43(s, 3H), 1.34-1.30(m, 6H), 1.13-1.02 m, 4H) |
| 240 | 2.53 | 2.46 | 7.80(d, 1H), 7.45(d, 1H), 4.01-3.92(m, 4H), 3.14(s, 3H), 2.45(s, 3H), 1.33(t, 3H) |
| 241 | 1.65 | 1.61 | 8.05-8.02(m, 1H), 7.57(d, 1H), 4.28-4.22(m, 1H), 4.11-4.02(m, 1H), 3.98-3.93(m, 2H), 3.15(s, 3H), 2.44(s, 3H), 1.33(t, 3H) |
| 242 | 1.79 | 1.75 | 8.06(d, 1H), 7.57(d, 1H), 6.05-5.95(m, 1H), 5.31-5.22(m, 2H), 4.60-4.50(m, 2H), 4.29-4.19(m, 1H), 4.10-4.02(m, 1H), 3.13(s, 3H), 2.44(s, 3H) |
| 243 | 2.55 | 2.51 | 7.77(d, 1H), 7.45(d, 1H), 3.96(q, 2H), 3.45(s, 3H), 3.43-3.35(m, 2H), 2.45(s, 3H), 1.27(t, 3H) |
| 244 | 1.69 | 1.65 | 8.02(d, 1H), 7.56(d, 1H), 4.28-4.19(m, 1H), 4.08-4.00(m, 1H), 3.45(s, 3H), 3.43-3.34(m, 2H), 2.43(s, 3H), 1.29-1.25(m, 3H) |
| 245 | 1.94 | 1.90 | 8.03(d, 1H), 7.56(d, 1H), 4.28-4.19(m, 1H), 4.07-4.00(m, 1H), 3.68-3.61(m, 1H), 3.44(s, 3H), 2.43(s, 3H), 1.36-1.34(m, 3H), 1.26(d, 3H) |
| 246 | 1.99 | 1.95 | 8.02(d, 1H), 7.56(d, 1H), 4.29-4.19(m, 1H), 4.08-4.01(m, 1H), 3.46(s, 3H), 3.43-3.35(m, 2H), 2.43(s, 3H), 1.78-1.73(m, 2H), 1.06(t, 3H) |
| 247 | 2.94 | 2.85 | 7.77(d, 1H), 7.45(d, 1H), 3.96(q, 2H), 3.47(s, 3H), 3.46-3.41(m, 2H), 2.45(s, 3H), 1.06-1.02(m, 1H), 0.65-0.58(m, 2H), 0.49-0.34(m, 2H) |
| 248 | 2.03 | 1.98 | 8.01(d, 1H), 7.56(d, 1H), 4.28-4.19(m, 1H), 4.08-4.00(m, 1H), 3.47(s, 3H), 3.45-3.41(m, 2H), 2.43(s, 3H), 1.07-1.02(m, 1H), 0.66-0.60(m, 2H), 0.49-0.35(m, 2H) |
| 249 | 2.32 | 2.26 | 8.07(d, 1H), 7.57(d, 1H), 6.03-5.94(m, 1H), 5.29-5.19(m, 2H), 4.54(d, 2H), 4.28-4.19(m, 1H), 4.09-4.02(m, 1H), 3.64-3.57(m, 1H), 2.44(s, 3H), 1.40-1.33(m, 3H), 1.26(d, 3H) |
| 250 | 2.34 | 2.29 | 7.95-7.92(m, 1H), 7.56(d, 1H), 7.39-7.33(m, 5H), 4.76-4.69(m, 2H), 4.29-4.20(m, 1H), 4.08-4.00(m, 1H), 3.25(d, 3H), 2.43(s, 3H) |
| 251 | 2.22 | 2.18 | 8.04(d, 1H), 7.57(d, 1H), 4.28-4.19(m, 1H), 4.10-4.03(m, 1H), 3.95(q, 2H), 3.45-3.35(m, 2H), 2.43(s, 3H), 1.80-1.74(m, 2H), 1.32(t, 3H), 1.06(t, 3H) |
| 252 | 1.90 | 1.87 | 8.04(d, 1H), 7.56(d, 1H), 4.28-4.19(m, 1H), 4.10-4.00(m, 1H), 3.94(q, 2H), 3.45-3.35(m, 2H), 2.43(s, 3H), 1.34-1.25(m, 6H) |
| 253 | 2.84 | 2.81 | 7.80(d, 1H), 7.45(d, 1H), 4.07-3.91(m, 4H), 3.45-3.34(m, 2H), 2.45(s, 3H), 1.37-1.23(m, 6H) |
| 254 | 3.89 | 3.84 | 7.68(d, 1H), 7.40(d, 1H), 4.17(q, 2H), 3.93(q, 2H), 2.96-2.90(m, 1H), 2.43(s, 3H), 1.05-0.95(m, 4H) |
| 255 | 2.93 | 2.89 | 7.95(d, 1H), 7.51(d, 1H), 4.26-4.14(m, 1H), 4.17(q, 2H), 4.07-3.95(m, 1H), 2.96-2.94(m, 1H), 2.41(s, 3H), 1.02-1.00(m, 4H) |
| 256 | 2.73 | 2.69 | 7.78(d, 1H), 7.51(d, 1H), 6.48-6.18(m, 1H), 4.30-4.17(m, 1H), 4.08-3.96(m, 1H), 3.71-3.62(m, 2H), 2.93-2.88(m, 1H), 2.41(s, 3H), 1.04-0.96(m, 4H) |
| 257 | 2.45 | 2.40 | 7.96(d, 1H), 7.50(d, 1H), 4.26-4.16(m, 1H), 4.10-4.01(m, 1H), 2.89-2.84(m, 1H), 2.53(s, 3H), 2.41(s, 3H), 0.99-0.97(m, 4H) |
| 258 | 3.71 | 3.75 | 7.71(d, 1H), 7.39(d, 1H), 6.49-6.18(m, 1H), 3.94(q, 2H), 3.70-3.61(m, 2H), 2.92-2.86(m, 1H), 2.42(s, 3H), 1.04-0.94(m, 4H) |
| 259 | 3.56 | 3.60 | 7.71(d, 1H), 7.39(d, 1H), 3.94(q, 2H), 2.87-2.82(m, 1H), 2.52(s, 3H), 2.43(s, 3H), 1.01-0.93(m, 4H) |
| 260 | 2.07 | 2.03 | 7.98(d, 1H), 7.51(d, 1H), 4.26-4.20(m, 1H), 4.09-4.02(m, 1H), 3.19(s, 3H), 2.58(s, 3H), 2.42(s, 3H) |
| 261 | 3.99 | 4.03 | 7.70(d, 1H), 7.38(d, 1H), 3.94(q, 2H), 3.11(q, 2H), 2.86-2.81(m, 1H), 2.42(s, 3H), 1.36(t, 3H), 1.01-0.93(m, 4H) |
| 262 | 2.81 | 2.76 | 7.96(d, 1H), 7.50(d, 1H), 4.26-4.16(m, 1H), 4.10-4.01(m, 1H), 3.12(q, 2H), 2.88-2.82(m, 1H), 2.41(s, 3H), 1.36(t, 3H), 0.98-0.94(m, 4H |
| 263 | 4.08 | 4.01 | 7.73(d, 1H), 7.45(d, 1H), 3.96(q, 2H), 2.97-2.92(m, 1H), 2.45(s, 3H), 1.12-1.02(m, 4H) |
| 264 | 3.05 | 2.98 | 7.99(d, 1H), 7.57(d, 1H), 4.28-4.19(m, 1H), 4.14-4.04(m, 1H), 2.98-2.93(m, 1H), 2.43(s, 3H), 1.13-1.02(m, 4H) |
| 265 | 4.41 | 4.32 | 7.69(d, 1H), 7.38(d, 1H), 3.94(q, 2H), 3.08(t, 2H), 2.86-2.81(m, 1H), 2.42(s, 3H), 1.78-1.69(m, 2H), 1.01-0.93(m, 7H) |
| 266 | 3.24 | 3.17 | 7.97(d, 1H), 7.50(d, 1H), 4.25-4.21(m, 1H), 4.06-4.02(m, 1H), 3.11(t, 2H), 2.88-2.85(m, 1H), 2.42(s, 3H), 1.78-1.72(m, 2H), 1.01-0.97(m, 7H) |
| 267 | 3.19 | 3.12 | 7.97(d, 1H), 7.50(d, 1H), 4.26-4.17(m, 1H), 4.09-4.00(m, 1H), 3.80-3.73(m, 1H), 2.87-2.82(m, 1H), 2.41(s, 3H), 1.43-1.40(m, 6H), 0.98-0.96(m, 4H) |

| Ex. No. | logP[a] | logP[b] | $^1$H NMR(D6-DMSO, 400 MHz) δ ppm |
|---|---|---|---|
| 268 | 4.37 | 4.28 | 7.71(d, 1H), 7.39(d, 1H), 3.94(q, 2H), 3.78-3.71(m, 1H), 2.86-2.79(m, 1H), 2.43(s, 3H), 1.41(d, 6H), 0.99-0.94(m, 4H) |
| 269 | 3.53 | 3.44 | 7.75(d, 1H), 7.40(d, 1H), 3.96(q, 2H), 3.65(q, 2H), 2.57(s, 3H), 2.43(s, 3H), 1.23(s, 3H) |
| 270 | 2.39 | 2.33 | 7.99(d, 1H), 7.51(d, 1H), 4.26-4.19(m, 1H), 4.11-4.02(m, 1H), 3.66(q, 2H), 2.59(s, 3H), 2.42(s, 3H), 1.24(t, 3H) |
| 271 | 3.61 | 3.58 | 7.76(d, 1H), 7.41(d, 1H), 5.93-5.94(m, 1H), 5.27-2.24(m, 1H), 5.18-5.14(m, 1H), 4.25(d, 2H), 3.96(q, 2H), 2.55(s, 3H), 2.44(s, 3H) |
| 272 | 2.54 | 2.48 | 8.01(d, 1H), 7.52(d, 1H), 5.93-5.86(m, 1H), 5.27-5.24(m, 1H), 5.19-5.14(m, 1H), 4.27(d, 2H), 4.23-4.20(m, 1H), 4.11-4.05(m, 1H), 2.56(s, 3H), 2.42(s, 3H) |
| 273 | 3.51 | 3.44 | 7.72(d, 1H), 7.40(d, 1H), 3.95(q, 2H), 3.18(s, 3H), 3.11(q, 2H), 2.43(s, 3H), 1.34(t, 3H) |
| 274 | 2.42 | 2.36 | 7.98(d, 1H), 7.52(d, 1H), 4.26-4.20(m, 1H), 4.09-4.03(m, 1H), 3.19(s, 3H), 3.12(q, 2H), 2.42(s, 3H), 1.34(t, 3H) |
| 275 | 2.73 | 2.68 | 7.99(d, 1H), 7.52(d, 1H), 4.27-4.20(m, 1H), 4.09-4.02(m, 1H), 3.72-3.66(m, 1H), 3.21(s, 3H), 2.42(s, 3H), 1.40-1.37(m, 6H) |
| 276 | 3.86 | 3.80 | 7.73(d, 1H), 7.41(d, 1H), 3.95(q, 2H), 3.71-3.64(m, 1H), 3.20(s, 3H), 2.43(s, 3H), 1.37(d, 6H) |
| 277 | 3.90 | 3.86 | 7.71(d, 1H), 7.40(d, 1H), 3.95(q, 2H), 3.19(s, 3H), 3.08(t, 2H), 2.43(s, 3H), 1.74-1.67(m, 2H), 0.97(t, 3H) |
| 278 | 2.80 | 2.74 | 7.97(d, 1H), 7.51(d, 1H), 4.26-4.20(m, 1H), 4.09-4.02(m, 1H), 3.20(s, 3H), 3.10(t, 2H), 2.42(s, 3H), 1.74-1.67(m, 2H), 0.98(t, 3H) |
| 279 | 3.91 | 3.83 | 7.71(d, 1H), 7.40(d, 1H), 3.97(q, 2H), 3.20(s, 3H), 3.06(t, 2H), 2.43(s, 3H), 1.20-1.14(m, 1H), 0.58-0.51(m, 2H), 0.32-0.26(m, 2H) |
| 280 | 2.82 | 2.75 | 7.97(d, 1H), 7.52(d, 1H), 4.26-4.20(m, 1H), 4.09-4.02(m, 1H), 3.21(s, 3H), 3.07(d, 2H), 2.42(s, 3H), 1.39-1.32(m, 1H), 0.59-0.55(m, 2H), 0.33-0.29(m, 2H) |
| 281 | 3.53 | 3.45 | 7.69(d, 1H), 7.42(d, 1H), 4.12(q, 2H), 3.94(q, 2H), 3.26(s, 3H), 2.44(s, 3H) |
| 282 | 2.57 | 2.52 | 7.96(d, 1H), 7.53(d, 1H), 4.29-4.17(m, 1H), 4.12(q, 2H), 4.11-3.99(m, 1H), 3.27(s, 3H), 2.42(s, 3H) |
| 283 | 3.71 | 3.64 | 7.75(d, 1H), 7.47(d, 1H), 3.97(q, 2H), 2.45(s, 3H) |
| 284 | 2.65 | 2.60 | 8.00(d, 1H), 7.58(d, 1H), 4.32-4.19(m, 1H), 4.16-4.04(m, 1H), 3.32(s, 3H), 2.44(s, 3H) |
| 285 | 3.24 | 3.17 | 8.03(d, 1H), 7.53(d, 1H), 5.92-5.85(m, 1H), 5.25-5.22(m, 1H), 5.14-5.10(m, 1H), 4.29-4.28(m, 2H), 4.28-4.20(m, 1H), 4.17-4.05(m, 1H), 3.74-3.61(m, 1H), 2.43(s, 3H), 1.40-4.35(m, 6H) |
| 286 | 4.12 | 4.03 | 7.67(d, 1H), 7.43-7.38(m, 3H), 7.35-7.27(m, 3H), 4.33(s, 2H), 3.95(q, 2H), 3.09(s, 3H), 2.44(s, 3H) |
| 287 | 3.08 | 3.02 | 7.97(d, 1H), 7.53(d, 1H), 7.42-7.27(m, 5H), 4.35(s, 2H), 4.28-4.22(m, 1H), 4.07-4.00(m, 1H), 3.10(s, 3H), 2.42(s, 3H) |
| 288 | 3.18 | 3.13 | 7.99(d, 1H), 7.48(d, 1H), 4.26-4.17(m, 1H), 4.10-4.01(m, 1H), 3.67(q, 2H), 3.12(t, 2H), 2.42(s, 3H), 1.77-1.68(m, 2H), 1.23(t, 3H), 0.98(t, 3H) |
| 289 | 3.30 | 3.25 | 7.72(d, 1H), 7.41(d, 1H), 6.46-6.18(m, 1H), 3.94(q, 2H), 3.68-3.59(m, 2H), 3.23(s, 3H), 2.43(s, 3H) |
| 290 | 3.62 | 3.56 | 7.70(d, 1H), 7.41(d, 1H), 5.98-5.90(m, 1H), 5.30-5.25(m, 1H), 5.17-5.14(m, 1H), 3.95(q, 2H), 3.76(d, 2H), 3.20(s, 3H), 2.43(s, 3H) |
| 291 | 2.55 | 2.51 | 7.97(d, 1H), 7.52(d, 1H), 6.00-5.90(m, 1H), 5.31-5.26(m, 1H), 5.18-5.15(m, 1H), 4.27-4.20(m, 1H), 4.09-4.02(m, 1H), 3.77(d, 2H), 3.21(s, 3H), 2.42(s, 3H) |
| 292 | 3.91 | 3.86 | 7.74(d, 1H), 7.40(d, 1H), 3.96(q, 2H), 3.65(q, 2H), 3.13(q, 2H), 2.43(s, 3H), 1.35(t, 3H), 1.22(t, 3H) |
| 293 | 2.76 | 2.72 | 8.00(d, 1H), 7.51(d, 1H), 4.25-4.16(m, 1H), 4.13-4.04(m, 1H), 3.66(q, 2H), 3.14(q, 2H), 2.42(s, 3H), 1.35(t, 3H), 1.23(t, 3H) |
| 294 | 3.48 | 3.38 | 7.71(d, 1H), 7.41(d, 1H), 3.94(q, 2H), 2.96-2.91(m, 1H), 2.43(s, 3H), 1.04-1.00(m, 4H) |
| 295 | 2.39 | 2.34 | 7.96(d, 1H), 7.52(d, 1H), 4.27-4.18(m, 1H), 4.07-3.98(m, 1H), 2.96-2.91(m, 1H), 2.41(s, 3H), 1.05-1.00(m, 4H) |
| 296 | 3.07 | 3.04 | 7.98(d, 1H), 7.69-7.66(m, 1H), 7.47(d, 1H), 4.02(q, 2H), 3.62(s, 3H), 2.42(s, 3H) |
| 297 | 1.96 | 1.96 | 7.88(s, 1H), 7.48(s, 1H), 4.26-4.19(m, 1H), 4.02-3.96(m, 1H), 3.63(s, 3H), 2.41(s, 3H), 2.27(s, 3H) |
| 298 | 3.81 | 3.78 | 7.66(s, 1H), 7.36(s, 1H), 4.51-4.43(m, 1H), 3.98(q, 2H), 2.41(s, 3H), 2.13(s, 3H), 1.47(d, 6H) |
| 299 | 2.45 | 0.90 | 14.78(s, 1H), 7.89(d, 1H), 7.52(d, 1H), 4.00(q, 2H), 2.46(s, 3H) |
| 300 | 2.63 | 2.61 | 7.91(s, 1H), 7.48(s, 1H), 4.51-4.44(m, 1H), 4.31-4.16(m, 1H), 4.12-3.96(m, 1H), 2.42(s, 3H), 2.26(s, 3H), 1.48(d, 6H) |
| 301 | 1.87 | 1.82 | 8.13(d, 1H), 7.65(d, 1H), 4.32-4.22(m, 1H), 4.08-4.01(m, 1H), 3.61(s, 3H), 2.46(s, 3H) |
| 302 | 2.89 | 2.86 | 7.88(s, 1H), 7.54(s, 1H), 3.99(q, 2H), 3.63(s, 3H), 2.46(s, 3H) |
| 303 | 1.59 | 0.37 | 8.13(d, 1H), 7.64(d, 1H), 4.30-4.21(m, 1H), 4.12-4.01(m, 1H), 2.46(s, 3H) |
| 304 | 3.61 | 3.48 | 7.95(d, 1H), 7.56(d, 1H), 5.14(q, 2H), 4.01(q, 2H), 2.47(s, 3H) |
| 305 | 2.57 | 2.51 | 8.20(d, 1H), 7.67(d, 1H), 5.12(q, 2H), 4.32-4.23(m, 1H), 4.11-4.00(m, 1H), 2.47(s, 3H) |

| Ex. No. | logP[a] | logP[b] | $^1$H NMR(D6-DMSO, 400 MHz) δ ppm |
|---|---|---|---|
| 306 | 4.75 | 4.59 | 7.98-7.93(m, 3H), 7.72-7.69(m, 2H), 7.59(d, 1H), 3.98(q, 2H), s, 3H unter DMSO-Signal |
| 307 | 3.53 | 3.49 | 8.25(d, 1H), 7.96-7.92(m, 2H), 7.72-7.68(m, 3H), 4.35-4.26(m, 1H), 4.08-3.96(m, 1H), 2.48(s, 3H) |
| 308 | 3.47 | 3.40 | 8.32(d, 1H), 8.10(d, 1H), 4.14(q, 2H) |
| 309 | 2.86 | 2.80 | 8.53(d, 1H), 8.30(d, 1H), 4.55-4.43(m, 1H), 4.32-4.20(m, 1H) |
| 310 | 2.87 | 2.81 | 7.73(d, 1H), 7.26(d, 1H), 5.34(s, 1H), 4.42(s, 2H), 3.90(q, 2H), 3.85(s, 3H), 2.38(s, 3H) |
| 311 | 1.83 | 1.84 | 8.06(d, 1H), 7.37(d, 1H), 5.38(s, 1H), 4.48-4.44(m, 2H), 4.20-4.13(m, 1H), 4.06-3.94(m, 1H), 3.86(s, 3H), 2.38(s, 3H) |
| 312 | 2.88 | 2.81 | 7.42(s, 1H), 7.16(s, 1H), 5.28(s, 1H), 4.36(s, 2H), 3.93(q, 2H), 3.84(s, 3H), 2.32(s, 3H), 2.08(s, 3H) |
| 313 | 1.83 | 1.83 | 7.70(s, 1H), 7.27(s, 1H), 5.31(s, 1H), 4.44-4.33(m, 2H), 4.14-3.93(m, 2H), 3.85(s, 3H), 2.35(s, 3H), 2.18(s, 3H) |
| 314 | 2.24 | 2.23 | 8.03(s, 1H), 7.93(s, 1H), 5.39(s, 1H), 4.48-4.38(m, 2H), 4.33-4.24(m, 1H), 4.14-4.05(m, 1H), 3.87(s, 3H) |
| 315 | 2.24 | 2.23 | 8.36(d, 1H), 7.84-8.81(m, 1H), 7.60(d, 1H), 5.41(s, 1H), 4.62-4.52(m, 2H), 4.20-4.00(m, 2H), 3.87(s, 3H) |
| 316 | 2.98 | 2.95 | 7.78(d, 1H), 7.58-7.55(m, 1H), 7.21(d, 1H), 5.32(s, 1H), 4.49(s, 2H), 3.92(q, 2H), 3.85(s, 3H), 2.32(s, 3H) |
| 317 | 1.90 | 1.90 | 8.22(d, 1H), 7.77-7.74(m, 1H), 7.31(d, 1H), 5.37(s, 1H), 4.54(q, 2H), 4.11-4.02(m, 1H), 3.96-3.90(m, 1H), 3.86(s, 3H), 2.32(s, 3H) |
| 318 | 1.99 | 1.94 | 7.87(s, 1H), 7.63(s, 1H), 5.37(s, 1H), 4.38(s, 2H), 4.24-4.17(m, 1H), 4.04-3.98(m, 1H), 3.87(s, 3H), 2.38(s, 3H) |
| 319 | 3.02 | 2.98 | 7.62(s, 1H), 7.48(s, 1H), 5.33(s, 1H), 4.33(s, 2H), 4.03(q, 2H), 3.86(s, 3H), 2.35(s, 3H) |
| 320 | 2.45 | 2.43 | 7.99(d, 1H), 7.91-7.88(m, 1H), 7.82(d, 1H), 5.42(s, 1H), 4.58(s, 2H), 4.16(q, 2H), 3.88(s, 3H) |
| 321 | 2.61 | 2.55 | 8.56(d, 1H), 8.12-8.09(m, 1H), 7.89(d, 1H), 5.46(s, 1H), 4.74-4.59(m, 2H), 4.19-4.02(m, 2H), 3.90(s, 3H) |
| 322 | 3.31 | 3.25 | 7.97-7.93(m, 2H), 7.71(d, 1H), 5.41(s, 1H), 4.60(s, 2H), 4.13(q, 2H), 3.88(s, 3H) |
| 323 | 2.87 | 2.81 | 8.07(d, 1H), 7.50-7.36(m, 6H), 5.49(s, 1H), 5.17(s, 2H), 4.56-4.46(m, 2H), 4.20-4.10(m, 1H), 4.04-3.94(m, 1H), 2.38(s, 3H) |
| 324 | 2.13 | 2.11 | 8.21(d, 1H), 7.85(d, 1H), 5.42(s, 1H), 4.57-4.47(m, 2H), 4.28-4.22(m, 1H), 4.11-4.05(m, 1H), 3.87(s, 3H) |
| 325 | 2.46 | 2.43 | 8.07(d, 1H), 7.37(d, 1H), 5.37(s, 1H), 4.60-4.53(m, 1H), 4.45-4.35(m, 2H), 4.19-4.13(m, 1H), 4.00-3.89(m, 1H), 2.37(s, 3H), 1.32(d, 6H) |
| 326 | 2.91 | 2.88 | 8.07(d, 1H), 7.37(d, 1H), 5.37(s, 1H), 4.50-4.40(m, 2H), 4.20-4.4.10(m, 1H), 4.07(t, 2H), 4.03-3.91(m, 1H), 2.38(s, 3H), 1.74-1.67(m, 2H), 1.46-1.37(m, 2H), 0.93(t, 3H) |
| 327 | 2.97 | 2.92 | 7.90(d, 1H), 7.67(d, 1H), 5.37(s, 1H), 4.48(s, 2H), 4.07(q, 2H), 3.86(s, 3H) |
| 328 | 2.86 | 2.82 | 7.72(d, 1H), 7.25(d, 1H), 5.35(s, 1H), 4.43(s, 2H), 4.19-4.17(m, 2H), 3.91(q, 2H), 3.67-3.64(m, 2H), 3.30(s, 3H), 2.37(s, 3H) |
| 329 | 4.20 | 4.06 | 7.72(d, 1H), 7.71(d, 1H), 5.28(s, 1H), 4.80-4.76(m, 1H), 4.37(s, 2H), 3.91(q, 2H), 2.37(s, 3H), 1.96-1.89(m, 2H), 1.80-1.58(m, 6H) |
| 330 | 3.29 | 3.21 | 7.72(d, 1H), 7.25(d, 1H), 4.41(s, 2H), 4.11(q, 2H), 3.91(q, 3H), 2.37(s, 3H), 1.34(t, 3H) |
| 331 | 3.64 | 3.58 | 7.72(d, 1H), 7.25(d, 1H), 5.29(s, 1H), 4.42(s, 2H), 3.95-3.87(m, 4H), 2.37(s, 3H), 1.25-1.21(m, 1H), 0.61-0.58(m, 2H), 0.37-0.34(m, 2H) |
| 332 | 2.55 | 2.50 | 8.06(d, 1H), 7.37(d, 1H), 5.34(s, 1H), 4.48-4.44(m, 2H), 4.20-4.11(m, 1H), 4.03-3.91(m, 3H), 2.38(s, 3H), 1.26-1.22(m, 1H), 0.61-0.58(m, 2H), 0.37-0.33(m, 2H) |
| 333 | 2.57 | 2.52 | 8.07(d, 1H), 7.37(d, 1H), 5.36(s, 1H), 4.57-4.55(m, 2H), 4.20-4.13(m, 1H), 4.03(t, 2H), 4.01-3.94(m, 1H), 2.38(s, 3H), 1.79-1.70(m, 2H), 0.96(t, 3H) |
| 334 | 2.19 | 2.14 | 8.07(d, 1H), 7.37(d, 1H), 5.36(s, 1H), 4.45(d, 2H), 4.20-4.10(m, 3H), 4.03-3.94(m, 1H), 2.37(s, 3H), 1.35(t, 3H) |
| 335 | 1.92 | 1.86 | 8.06(d, 1H), 7.37(d, 1H), 5.40(s, 1H), 4.49-4.45(m, 2H), 4.22-4.18(m, 3H), 4.02-3.91(m, 1H), 3.67-3.65(m, 2H), 3.30(s, 3H), 2.38(s, 3H) |
| 336 | 2.97 | 2.91 | 8.07(d, 1H), 7.36(d, 1H), 5.33(s, 1H), 4.81-4.77(m, 1H), 4.04(s, 2H), 4.19-4.10(m, 1H), 4.00-3.91(m, 1H), 2.37(s, 3H), 1.98-1.90(m, 2H), 1.81-1.76(m, 2H), 1.73-1.58(m, 4H) |
| 337 | 3.91 | 3.50 | 7.72(s, 1H), 7.71-7.69(m, 1H), 7.44-7.42(m, 1H), 3.93-3.86(q, 2H), 2.44(s, 3H) |
| 338 | 3.99 | 4.00 | 7.71-7.70(m, 1H), 7.47-7.45(m, 1H), 3.89-3.84(q, 2H), 2.46(s, 3H) |
| 339 | 3.60 | 3.61 | 7.63-7.62(m, 1H), 7.41-7.38(m, 1H), 3.95-3.88(q, 2H), 2.43(s, 3H), 2.00(s, 6H) |
| 340 | 3.37 | 3.39 | 7.65-7.63(m, 1H), 7.41-7.39(m, 1H), 6.90-6.88(q, 1H), 3.95-3.88(q, 2H), 2.43(s, 3H), 2.10(d, 3H) |
| 341 | 2.52 | 2.49 | 7.90-7.88(m, 1H), 7.53-7.50(m, 1H), 4.30-4.24(m, 1H), 3.97-3.90(m, 1H), 2.43(s, 3H), 2.01(s, 6H) |
| 342 | 3.73 | 3.70 | 7.39(s, 1H), 7.26(s, 1H), 3.93-3.85(q, 2H), 2.37(s, 3H), 2.01(s, 3H), 1.99(s, 6H) |

| Ex. No. | logP[a] | logP[b] | $^1$H NMR(D6-DMSO, 400 MHz) δ ppm |
|---|---|---|---|
| 343 | 3.02 | 4.91 | 7.63(d, 1H), 7.37(d, 1H), 4.08-4.02(m, 1H), 3.95-3.90(m, 1H), 3.64-3.59(m, 2H), 2.41(s, 3H), 2.11(s, 3H), 1.71(s, 3H) |
| 344 | 2.17 | 3.68 | 7.81(m, 1H), 7.52(d, 1H), 4.36-4.17(m, 2H), 3.89-3.56(m, 2H), 2.45-2.44(m, 3H), 2.13-2.12(m, 3H), 1.77-1.74(m, 3H) |
| 345 | 4.02 | 4.04 | 7.85(d, 1H), 7.48(d, 1H), 5.99-5.89(m, 1H), 5.29-5.18(m, 2H), 4.44(d, 2H), 3.97(q, 2H), 2.46(s, 3H) |
| 346 | 2.97 | 2.92 | 7.65(d, 1H), 7.37(d, 1H), 3.92(q, 2H), 3.30(s, 3H), 2.42(s, 3H), 2.00-1.93(m, 1H), 0.99-0.95(m, 2H), 0.91-0.85(m, 2H) |
| 347 | 3.70 | 3.63 | 7.67(d, 1H), 7.36(d, 1H), 4.50-4.43(m, 1H), 3.93(q, 2H), 2.42(s, 3H), 2.05-1.99(m, 1H), 1.49(d, 6H), 0.99-0.94(m, 2H), 0.89-0.85(m, 2H) |
| 348 | 2.91 | 2.87 | 8.77(d, 1H), 8.73-8.71(m, 1H), 8.06-8.03(m, 1H), 7.81(d, 1H), 7.66-7.63(m, 1H), 7.44(d, 1H), 3.95(q, 2H), 2.56(q, 2H), 2.46(s, 3H), 1.09(t, 3H) |
| 349 | 3.48 | 3.40 | 8.73(s, 1H), 7.82-7.75(m, 3H), 7.46-7.40(m, 3H), 3.97(q, 2H), 2.45(s, 3H) |
| 350 | 3.40 | 3.34 | 7.80(d, 1H), 7.60-7.50(m, 5H), 7.42(d, 1H), 3.96(q, 2H), 2.45(s, 3H), 2.17(s, 3H) |
| 351 | 3.43 | 3.36 | 8.76(s, 1H), 7.82(d, 1H), 7.74(d, 2H), 7.56(t, 2H), 7.46-7.41(m, 2H), 3.98(q, 2H), 2.45(s, 3H) |
| 352 | 1.99 | 1.96 | 7.91(d, 1H), 7.48(d, 1H), 4.24-4.15(m, 1H), 4.11-4.02(m, 1H), 3.32(s, 3H), 2.40(s, 3H), 2.02-1.95(m, 1H), 1.01-0.95(m, 2H), 0.91-0.87(m, 2H) |
| 353 | 2.58 | 2.55 | 7.92(d, 1H), 7.47(d, 1H), 4.52-4.45(m, 1H), 4.23-4.17(m, 1H), 4.14-4.04(m, 1H), 2.40(s, 3H), 2.07-2.01(m, 1H), 1.51-1.48(m, 6H), 1.00-0.88(m, 4H) |
| 354 | 1.98 | 1.97 | 8.79(d, 1H), 8.73-8.72(m, 1H), 8.07(d, 2H), 7.66-7.63(m, 1H), 7.55(d, 1H), 4.30-4.20(m, 1H), 4.12-4.00(m, 1H), 2.56(q, 2H), 2.43(s, 3H), 1.10(t, 3H) |
| 355 | 2.45 | 2.41 | 8.76(s, 1H), 8.07(d, 1H), 7.80-7.75(m, 2H), 7.56(d, 1H), 7.45-7.40(m, 2H), 4.30-4.20(m, 1H), 4.12-4.00(m, 1H), 2.44(s, 3H) |
| 356 | 2.38 | 2.35 | 8.06(d, 1H), 7.61-7.51(m, 6H), 4.29-4.22(m, 1H), 4.09-4.02(m, 1H), 2.43(s, 3H), 2.18(s, 3H) |
| 357 | 2.38 | 2.36 | 8.80(s, 1H), 8.08(d, 1H), 7.75-7.73(m, 2H), 7.59-7.55(m, 3H), 7.46-7.41(m, 1H), 4.29-4.20(m, 1H), 4.13-4.01(m, 1H), 2.44(s, 3H) |
| 358 | 4.18 | 4.20 | 7.66(d, 1H), 7.36(d, 1H), 3.92(q, 2H), 3.31-3.23(m, 1H), 2.91-2.86(m, 1H), 2.42(s, 3H), 2.08-2.00(m, 2H), 1.86-1.77(m, 2H), 1.75-1.60(m, 4H), 1.02-0.98(m, 4H) |
| 359 | 3.63 | 3.66 | 7.65(d, 1H), 7.38(d, 1H), 3.92(q, 2H), 3.74(t, 2H), 3.64-3.57(m, 1H), 2.93-2.87(m, 3H), 2.43(s, 3H), 1.09(d, 6H), 0.98-0.96(m, 4H) |
| 360 | 3.06 | 3.03 | 7.92(d, 1H), 7.47(d, 1H), 4.24-4.15(m, 1H), 4.11-4.02(m, 1H), 3.31-2.25(m, 1H), 2.93-2.88(m, 1H), 2.40(s, 3H), 2.08-2.01(m, 2H), 1.88-1.79(m, 2H), 1.75-1.61(m, 4H), 1.05-0.96(m, 4H) |
| 361 | 3.34 | 3.31 | 7.91(d, 1H), 7.47(d, 1H), 4.24-4.15(m, 1H), 4.12-4.03(m, 1H), 2.95-2.83(m, 2H), 2.40(s, 3H), 2.04(m, 2H), 1.81-1.78(m, 2H), 1.70-1.67(m, 1H), 1.49-1.22(m, 5H), 1.01-0.99(m, 4H) |
| 362 | 2.63 | 2.61 | 7.92(d, 1H), 7.48(d, 1H), 4.25-4.16(m, 1H), 4.09-4.00(m, 1H), 3.75(t, 2H), 3.64-3.58(m, 1H), 2.95-2.88(m, 3H), 2.40(s, 3H), 1.09(d, 6H), 1.02-0.98(m, 4H) |
| 363 | 3.22 | 3.18 | 8.08(d, 1H), 7.57(d, 1H), 4.38-4.31(m, 1H), 4.29-4.20(m, 1H), 4.10-4.01(m, 1H), 2.44(s, 3H), 1.53-1.50(m, 6H) |
| 364 | 3.00 | 2.96 | 8.10(d, 1H), 7.59(d, 1H), 6.00-5.90(m, 1H), 5.29-5.20(m, 2H), 4.44(d, 2H), 4.30-4.21(m, 1H), 4.10-4.01(m, 1H), 2.44(s, 3H) |
| 365 | 3.61 | 3.54 | 8.08(d, 1H), 7.58(d, 1H), 4.29-4.20(m, 1H), 4.10-3.98(m, 1H), 3.78(t, 2H), 2.44(s, 3H), 1.72-1.64(m, 2H), 1.41-1.31(m, 2H), 0.92(t, 3H) |
| 366 | 3.77 | 3.71 | 7.77(d, 1H), 7.61-7.57(m, 1H), 7.46-7.40(m, 2H), 7.23(d, 1H), 7.12-7.08(m, 1H), 3.96(q, 2H), 3.89(s, 3H), 2.95-2.91(m, 1H), 2.44(s, 3H), 0.72-0.67(m, 2H), 0.55-0.51(m, 2H) |
| 367 | 3.27 | 3.23 | 8.22(s, 1H), 7.70(d, 1H), 7.39(d, 1H), 3.94(t, 2H), 2.43(s, 3H), 1.54(s, 9H) |
| 368 | 3.38 | 3.34 | 8.36(s, 1H), 7.74(d, 1H), 7.42-7.32(m, 6H), 4.87(s, 2H), 3.96(q, 2H), 2.43(s, 3H) |
| 369 | 2.21 | 2.16 | 8.27(s, 1H), 7.97(d, 1H), 7.50(d, 1H), 4.29-4.16(m, 1H), 4.14-4.02(m, 1H), 2.42(s, 3H), 1.55(s, 9H) |
| 370 | 2.35 | 2.36 | 8.41(s, 1H), 8.00(d, 1H), 7.51(d, 1H), 7.43-7.32(m, 5H), 4.89(s, 2H), 4.25-4.16(m, 1H), 4.13-4.04(m, 1H), 2.42(s, 3H) |
| 371 | 3.46 | 3.39 | 8.16(s, 1H), 7.46(s, 1H), 7.26(s, 1H), 3.96-3.88(m, 2H), 2.39(s, 3H), 2.11(s, 3H), 1.54(s, 9H) |
| 372 | 2.34 | 2.28 | 8.22(s, 1H), 7.75(s, 1H), 7.36(s, 1H), 4.16-4.13(m, 1H), 4.04-4.01(m, 1H), 2.37(s, 3H), 2.24(s, 3H), 1.55(s, 9H) |
| 373 | 3.55 | 3.47 | 8.30(s, 1H), 7.50(s, 1H), 7.42-7.32(m, 5H), 7.27(s, 1H), 4.88(s, 2H), 3.92(q, 2H), 2.39(s, 3H), 2.13(s, 3H) |
| 374 | 2.50 | 2.47 | 8.35(s, 1H), 7.78(s, 1H), 7.43-7.32(m, 6H), 4.89(s, 2H), 4.20-4.10(m, 1H), 4.07-3.97(m, 1H), 2.38(s, 3H), 2.25(s, 3H) |
| 375 | 3.74 | 3.70 | 7.68(d, 1H), 7.36(d, 1H), 6.13-6.03(m, 1H), 5.52-5.46(m, 1H), 5.37-5.32(m, 1H), 4.82-4.79(m, 2H), 3.91(q, 2H), 2.84-2.78(m, 1H), 2.42(s, 3H), 0.95-0.90(m, 4H) |
| 376 | 4.23 | 4.18 | 7.72(d, 1H), 7.39(d, 1H), 5.14(s, 2H), 3.93(q, 2H), 3.19(s, 3H), 2.43(s, 3H) |

| Ex. No. | logP[a] | logP[b] | ¹H NMR(D6-DMSO, 400 MHz) δ ppm |
|---|---|---|---|
| 377 | 4.01 | 3.92 | 7.48(s, 1H), 7.25(s, 1H), 5.01(q, 2H), 3.88(q, 2H), 2.89-2.82(m, 1H), 2.38(s, 3H), 2.16(s, 3H), 0.98-0.90(m, 4H) |
| 378 | 4.43 | 4.48 | 7.69(d, 1H), 7.38(d, 1H), 5.02(q, 2H), 3.91(q, 2H), 2.88-2.83(m, 1H), 2.43(s, 3H), 0.96-0.90(m, 4H) |
| 379 | 2.14 | 2.09 | 7.95(d, 1H), 7.47(d, 1H), 4.25-4.18(m, 1H), 4.06-4.00(m, 1H), 3.97(s, 3H), 2.82-2.77(m, 1H), 2.40(s, 3H), 0.94-0.91(m, 4H) |
| 380 | 2.14 | 2.09 | 7.95(d, 1H), 7.47(d, 1H), 4.25-4.18(m, 1H), 4.06-4.00(m, 1H), 3.97(s, 3H), 2.82-2.77(m, 1H), 2.40(s, 3H), 0.94-0.91(m, 4H) |
| 381 | 2.88 | 2.94 | 7.77(s, 1H), 7.35(d, 1H), 5.06-4.99(m, 2H), 4.20-4.11(m, 1H), 3.96-3.86(m, 1H), 2.89-2.84(m, 1H), 2.36(s, 3H), 2.27(s, 3H), 0.95-0.94(m, 4H) |
| 382 | 3.22 | 3.13 | 8.01-7.97(m, 2H), 5.09-5.02(m, 2H), 4.35-4.26(m, 1H), 4.14-4.02(m, 1H), 2.89-2.84(m, 1H), 0.96-0.94(m, 4H) |
| 383 | 3.27 | 3.26 | 8.08(d, 1H), 7.99(d, 1H), 5.05(q, 2H), 4.31-4.24(m, 1H), 4.09-4.03(m, 1H), 2.88-2.85(m, 1H), 0.96-0.94(m, 4H) |
| 384 | 3.06 | 2.97 | 7.92(s, 1H), 7.71(s, 1H), 5.06-4.99(m, 2H), 4.29-4.20(m, 1H), 4.07-3.96(m, 1H), 2.90-2.85(m, 1H), 2.40(s, 3H), 0.96-0.92(m, 4H) |
| 385 | 2.80 | 2.74 | 7.72(d, 1H), 7.40(d, 1H), 5.02(q, 2H), 4.23-4.16(m, 1H), 4.06-3.91(m, 1H), 3.92(s, 3H), 2.88-2.83(m, 1H), 0.94-0.93(m, 4H) |
| 386 | 4.77 | 4.71 | 7.68(d, 1H), 7.36(d, 1H), 3.94(s, 2H), 3.91(q, 2H), 2.86-2.79(m, 1H), 2.42(s, 3H), 1.01(s, 9H), 0.96-0.90(m, 4H) |
| 387 | 3.60 | 3.52 | 7.93(d, 1H), 7.46(d, 1H), 4.24-4.14(m, 1H), 4.10-3.99(m, 1H), 3.96(s, 2H), 2.89-2.80(m, 1H), 2.40(s, 3H), 1.02(s, 9H), 0.97-0.92(m, 4H) |
| 388 | 3.16 | 3.15 | 7.71(d, 1H), 7.37(d, 1H), 3.97(s, 3H), 3.92(q, 2H), 3.60(t, 2H), 3.35(t, 2H), 3.22(s, 3H), 2.43(s, 3H), 1.86-1.80(m, 2H) |
| 389 | 3.53 | 3.46 | 7.72(d, 1H), 7.37(d, 1H), 3.97(s, 3H), 3.93(q, 2H), 3.51(t, 2H), 2.43(s, 3H), 1.67-1.58(m, 2H), 0.88(t, 3H) |
| 390 | 3.64 | 3.58 | 7.73(d, 1H), 7.38(d, 1H), 3.98(s, 3H), 3.94(q, 2H), 3.42(d, 2H), 2.43(s, 3H), 1.16-1.08(m, 1H), 0.54-0.48(m, 2H), 0.36-0.30(m, 2H) |
| 391 | 2.68 | 2.65 | 7.94(d, 1H), 7.47(d, 1H), 6.13-6.03(m, 1H), 5.51-5.46(m, 1H), 5.36-5.33(m, 1H), 4.83-4.81(m, 2H), 4.24-4.15(m, 1H), 4.08-3.99(m, 1H), 2.85-2.80(m, 1H), 2.40(s, 3H), 0.94-0.91(m, 4H) |
| 392 | 3.13 | 3.09 | 7.97(d, 1H), 7.50(d, 1H), 5.19-5.13(m, 2H), 4.26-4.20(m, 1H), 4.07-4.01(m, 1H), 3.20(s, 3H), 2.41(s, 3H) |
| 393 | 3.50 | 3.47 | 7.75(d, 1H), 7.41(d, 1H), 4.49(q, 2H), 4.01(s, 3H), 3.95(q, 2H), 2.42(s, 3H) |
| 394 | 4.95 | 4.89 | 7.84(d, 1H), 7.78(d, 1H), 4.07(q, 2H), 3.95(s, 2H), 2.87-2.79(m, 1H), 1.01(s, 9H), 0.96-0.92(m, 4H) |
| 395 | 4.38 | 4.32 | 7.56(d, 1H), 7.18(d, 1H), 3.95-3.80(m, 7H), 2.84-2.77(m, 1H), 1.01(s, 9H), 0.96-0.90(m, 4H) |
| 396 | 4.92 | 4.85 | 7.68(s, 1H), 7.55(s, 1H), 4.02(q, 2H), 3.92(s, 2H), 2.86-2.81(m, 1H), 2.39(s, 3H), 1.01(s, 9H), 0.96-0.92(m, 4H) |
| 397 | 5.12 | 5.04 | 7.91(s, 1H), 7.83(s, 1H), 4.17(q, 2H), 3.93(s, 2H), 2.87-2.81(m, 1H), 1.01(s, 9H), 0.99-0.88(m, 4H) |
| 398 | 3.84 | 3.79 | 7.72(d, 1H), 7.39(d, 1H), 5.07(q, 2H), 3.93(q, 2H), 3.63(q, 2H), 2.43(s, 3H), 1.23(t, 3H) |
| 399 | 3.94 | 3.89 | 7.74(d, 1H), 7.40(d, 1H), 5.95-5.85(m, 1H), 5.25-5.22(m, 1H), 5.17-5.13(m, 1H), 5.06(q, 2H), 4.23-4.22(m, 2H), 3.93(q, 2H), 2.44(s, 3H) |
| 400 | 4.06 | 3.96 | 7.71(d, 1H), 7.36(d, 1H), 4.26(t, 2H), 3.93(q, 2H), 3.59(q, 2H), 2.43(s, 3H), 1.82-1.73(m, 2H), 1.21(t, 3H), 0.97(t, 3H) |
| 401 | 3.62 | 3.53 | 7.71(d, 1H), 7.37(d, 1H), 4.35(q, 2H), 3.93(q, 2H), 3.58(q, 2H), 2.43(s, 3H), 1.38(t, 3H), 1.20(t, 3H) |
| 402 | 4.13 | 3.98 | 7.98(d, 1H), 7.94(d, 1H), 4.33-4.22(m, 1H), 4.19-4.08(m, 1H), 3.97(s, 2H), 2.87-2.79(m, 1H), 1.02(s, 9H), 0.97-0.90(m, 4H) |
| 403 | 3.50 | 3.44 | 7.70(d, 1H), 7.37(d, 1H), 4.22-4.11(m, 1H), 4.02-3.91(m, 1H), 3.94(s, 2H), 3.93(s, 3H), 2.86-2.79(m, 1H), 1.01(s, 9H), 0.96-0.92(m, 4H) |
| 404 | 3.79 | 3.71 | 7.90(s, 1H), 7.68(s, 1H), 4.31-4.20(m, 1H), 4.11-4.00(m, 1H), 3.94(s, 2H), 2.89-2.80(m, 1H), 2.40(s, 3H), 1.01(s, 9H), 0.97-0.92(m, 4H) |
| 405 | 4.36 | 4.18 | 8.09(s, 1H), 7.93(s, 1H), 4.37-4.27(m, 1H), 4.20-4.10(m, 1H), 3.95(s, 2H), 2.87-2.80(m, 1H), 1.02(s, 9H), 0.98-0.91(m, 4H) |
| 406 | 2.82 | 2.78 | 7.98(d, 1H), 7.50(d, 1H), 5.13-5.05(m, 2H), 4.27-4.15(m, 1H), 4.10-3.98(m, 1H), 3.64(q, 2H), 2.41(s, 3H), 1.24(t, 3H) |
| 407 | 2.94 | 2.90 | 8.00(d, 1H), 7.51(d, 1H), 5.97-5.74(m, 1H), 5.26-5.22(m, 1H), 5.18-5.13(m, 1H), 5.12-5.04(m, 2H), 4.27-4.16(m, 3H), 4.11-4.00(m, 1H), 2.42(s, 3H) |
| 408 | 2.86 | 2.81 | 7.96(d, 1H), 7.47(d, 1H), 4.28(t, 2H), 4.25-4.14(m, 1H), 4.12-4.02(m, 1H), 3.60(q, 2H), 2.40(s, 3H), 1.83-1.73(m, 2H), 1.22(t, 3H), 0.98(t, 3H) |
| 409 | 2.44 | 2.44 | 7.96(d, 1H), 7.47(d, 1H), 4.37(q, 2H), 4.24-4.15(m, 1H), 4.11-4.02(m, 1H), 3.59(q, 2H), 2.40(s, 3H), 1.38(t, 3H), 1.21(t, 3H) |
| 410 | 4.32 | 4.25 | 7.69(d, 1H), 7.53-7.51(m, 2H), 7.46-7.36(m, 4H), 5.33(s, 2H), 3.92(q, 2H), 2.84-2.79(m, 1H), 2.43(s, 3H), 0.95-0.88(m, 4H) |
| 411 | 2.44 | 2.41 | 7.97(d, 1H), 7.48(d, 1H), 4.30-4.15(m, 1H), 4.15-4.02(m, 1H), 3.99(s, 3H), 3.52(t, 2H), 2.41(s, 3H), 1.70-1.59(m, 2H), 0.88(t, 3H) |
| 412 | 2.54 | 2.52 | 7.98(d, 1H), 7.49(d, 1H), 4.39-4.15(m, 1H), 4.15-4.01(m, 1H), 4.01(s, 3H), 3.44(d, 2H), 2.41(s, 3H), 1.19-1.09(m, 1H), 0.55-0.49(m, 2H), 0.45-39(m, 2H) |

| Ex. No. | logP[a] | logP[b] | $^1$H NMR(D6-DMSO, 400 MHz) δ ppm |
|---|---|---|---|
| 413 | 2.44 | 2.40 | 7.97(d, 1H), 7.48(d, 1H), 4.30-4.15(m, 2H), 4.15-4.02(m, 1H), 3.99(s, 3H), 2.40(s, 3H), 1.39(d, 6H) |
| 414 | 3.24 | 3.19 | 7.97(d, 1H), 7.58-7.39(m, 6H), 5.35(s, 2H), 4.26-4.16(m, 1H), 4.08-3.99(m, 1H), 2.85-2.80(m, 1H), 2.40(s, 3H), 0.98-0.88(m, 4H) |
| 415 | 2.48 | 2.45 | 8.00(d, 1H), 7.51(d, 1H), 4.50(q, 2H), 4.30-4.15(m, 1H), 4.15-4.03(m, 1H), 4.03(s, 3H), 2.42(s, 3H) |
| 416 | 3.86 | 3.80 | 8.04(d, 1H), 7.70-7.68(m, 1H), 7.30(d, 1H), 3.87(q, 2H), 2.95-2.91(m, 1H), 2.90(s, 6H), 2.36(s, 3H), 1.04-1.00(m, 2H), 0.95-0.90(m, 2H) |
| 417 | 2.25 | 2.21 | 8.02(d, 1H), 7.67(d, 1H), 5.45(s, 2H), 4.98(q, 2H), 3.10-3.20(m, 1H), 2.69(s, 3H), 1.25(d, 6H) |
| 418 | 3.52 | 3.49 | 7.73(d, 1H), 7.41(d, 1H), 4.06(s, 3H), 3.95(q, 2H), 3.11-3.04(m, 1H), 2.44(s, 3H), 1.27(d, 6H) |
| 419 | 2.46 | 2.42 | 7.97(d, 1H), 7.52(d, 1H), 4.26-4.19(m, 1H), 4.11-4.05(m, 1H), 4.07(s, 3H), 3.13-3.06(m, 1H), 2.42(s, 3H), 1.30-1.28(m, 6H) |
| 420 | 2.70 | 2.77 | 7.80(d, 1H), 7.48(d, 1H), 3.95(q, 2H), 3.57(s, 3H), 3.47(s, 3H), 2.46(s, 3H) |
| 421 | 1.88 | 1.84 | 8.05(d, 1H), 7.59(d, 1H), 4.30-4.24(m, 1H), 4.06-4.00(m, 1H), 3.57(s, 3H), 3.47(s, 3H), 2.44(s, 3H) |
| 422 | 2.12 | 2.11 | 8.08(d, 1H), 7.59(d, 1H), 4.29-4.23(m, 1H), 4.08-4.01(m, 1H), 3.96(q, 2H), 3.60(s, 3H), 2.44(s, 3H), 1.31(t, 3H) |
| 423 | 2.34 | 2.37 | 8.06(d, 1H), 7.57(d, 1H), 6.04-5.95(m, 1H), 5.30-5.28(m, 1H), 5.25-5.21(m, 1H), 4.56-4.53(m, 2H), 4.28-4.19(m, 1H), 4.10-4.03(m, 1H), 3.42-3.27(m, 2H), 2.44(s, 3H), 1.77-1.72(m, 2H), 1.04(t, 3H) |
| 424 | 2.05 | 2.04 | 8.07(d, 1H), 7.57(d, 1H), 6.04-5.95(m, 1H), 5.30-5.27(m, 1H), 5.25-5.20(m, 1H), 4.56-4.48(m, 2H), 4.30-4.18(m, 1H), 4.12-4.00(m, 1H), 3.45-3.30(m, 2H), 2.44(s, 3H), 1.29-1.25(m, 3H) |
| 425 | 4.10 | 4.01 | 7.69(d, 1H), 7.39(d, 1H), 6.03-5.93(m, 1H), 5.35-5.31(m, 1H), 5.19-5.16(m, 1H), 3.94(q, 2H), 3.78(d, 2H), 2.88-2.83(m, 1H), 2.43(s, 3H), 1.01-0.92(m, 4H) |
| 426 | 4.37 | 4.29 | 7.73(d, 1H), 7.40(d, 1H), 3.96(q, 2H), 3.66(q, 2H), 3.10(t, 2H), 2.43(s, 3H), 1.77-1.68(m, 2H), 1.22(t, 3H), 0.97(t, 3H) |
| 427 | 4.45 | 4.37 | 7.75(d, 1H), 7.41(d, 1H), 5.93-5.84(m, 1H), 5.26-5.23(m, 1H), 5.16-5.11(m, 1H), 4.26-4.25(m, 2H), 3.96(q, 2H), 3.08(t, 2H), 2.43(s, 3H), 1.75-1.66(m, 2H), 0.96(t, 3H) |
| 428 | 4.03 | 3.96 | 7.76(d, 1H), 7.41(d, 1H), 5.93-5.84(m, 1H), 5.26-5.23(m, 1H), 5.16-5.11(m, 1H), 4.26-4.25(m, 2H), 3.96(q, 2H), 3.10(q, 2H), 2.44(s, 3H), 1.33(t, 3H) |
| 429 | 4.13 | 4.07 | 7.74(d, 1H), 7.41(d, 1H), 5.99-5.87(m, 2H), 5.25-5.23(m, 2H), 5.17-5.11(m, 2H), 4.28-4.26(m, 2H), 3.96(q, 2H), 3.76(d, 2H), 2.44(s, 3H) |
| 430 | 3.18 | 3.33 | 8.01(d, 1H), 7.52(d, 1H), 5.95-5.86(m, 1H), 5.26-5.23(m, 1H), 5.16-5.12(m, 1H), 4.28-4.27(m, 2H), 4.27-4.17(m, 1H), 4.14-4.03(m, 1H), 3.09(t, 2H), 2.42(s, 3H), 1.75-1.66(m, 2H), 0.96(t, 3H) |
| 431 | 2.83 | 2.92 | 8.02(d, 1H), 7.52(d, 1H), 5.95-5.85(m, 1H), 5.26-5.23(m, 1H), 5.16-5.12(m, 1H), 4.29-4.26(m, 2H), 4.26-4.17(m, 1H), 4.14-4.05(m, 1H), 3.12(q, 2H), 2.42(s, 3H), 1.34(t, 3H) |
| 432 | 2.94 | 3.05 | 8.01(d, 1H), 7.53(d, 1H), 5.99-5.87(m, 2H), 5.27-5.23(m, 2H), 5.18-5.12(m, 2H), 4.29-4.28(m, 2H), 4.28-4.17(m, 1H), 4.13-4.04(m, 1H), 3.78(d, 2H), 2.42(s, 3H) |
| 433 | 2.02 | 1.99 | 7.98(d, 1H), 7.53(d, 1H), 4.27-4.18(m, 1H), 4.10-4.01(m, 1H), 3.25(s, 3H), 2.42(s, 3H) |
| 434 | 3.45 | 3.40 | 7.76(d, 1H), 7.43(d, 1H), 3.96(q, 2H), 3.75(q, 2H), 2.44(s, 3H), 1.25(t, 3H) |
| 435 | 3.07 | 3.04 | 7.73(d, 1H), 7.43(d, 1H), 3.95(q, 2H), 3.26(s, 3H), 2.44(s, 3H) |
| 436 | 2.34 | 2.30 | 8.01(d, 1H), 7.54(d, 1H), 4.31-4.16(m, 1H), 4.16-3.98(m, 1H), 4.04(q, 2H), 2.42(s, 3H), 1.26(t, 3H) |
| 437 | 2.00 | 1.98 | 7.99(d, 1H), 7.54(d, 1H), 4.31-4.19(m, 1H), 4.10-3.98(m, 1H), 3.26(s, 3H), 2.42(s, 3H) |
| 438 | 4.24 | 4.17 | 7.74(d, 1H), 7.41(d, 1H), 3.96(q, 2H), 2.43(s, 3H), 1.70(s, 9H) |
| 439 | 3.83 | 3.80 | 7.75(d, 1H), 7.41(d, 1H), 4.43-4.31(m, 1H), 3.96(q, 2H), 2.43(s, 3H), 1.47(d, 6H) |
| 440 | 4.18 | 4.13 | 7.81(d, 1H), 7.48-7.39(m, 4H), 7.38-7.31(m, 2H), 4.93(s, 2H), 3.97(q, 2H), 2.44(s, 3H) |
| 441 | 3.02 | 2.98 | 7.98(d, 1H), 7.52(d, 1H), 4.31-4.18(m, 1H), 4.15-4.00(m, 1H), 2.42(s, 3H), 1.71(s, 9H) |
| 442 | 2.68 | 2.62 | 8.00(d, 1H), 7.53(d, 1H), 4.40-4.31(m, 1H), 4.30-4.19(m, 1H), 4.12-4.00(m, 1H), 2.42(s, 3H), 1.49-1.47(m, 6H) |
| 443 | 3.08 | 3.00 | 8.05(d, 1H), 7.55(d, 1H), 7.44-7.40(m, 2H), 7.36-7.33(m, 3H), 5.76(s, 2H), 4.31-4.19(m, 1H), 4.18-3.98(m, 1H), 2.43(s, 3H) |
| 444 | 4.09 | 4.04 | 7.95(d, 1H), 7.56(d, 1H), 5.18(t, 2H), 4.02(q, 2H), 2.47(s, 3H) |
| 445 | 3.75 | 3.72 | 8.23(d, 1H), 8.18(d, 2H), 8.02(d, 2H), 7.71(d, 1H), 4.39-4.27(m, 1H), 4.08-3.96(m, 1H), 2.48(s, 3H) |
| 446 | 3.05 | 3.01 | 8.19(d, 1H), 7.68(d, 1H), 5.16(t, 2H), 4.32-4.23(m, 1H), 4.13-4.01(m, 1H), 2.47(s, 3H) |
| 447 | 3.51 | 3.49 | 7.96(d, 1H), 7.58(d, 1H), 3.99(q, 2H), 3.93(s, 3H), 2.49(s, 3H) |
| 448 | 3.11 | 3.09 | 7.80(d, 1H), 7.45(d, 1H), 3.95(q, 2H), 2.44(s, 3H), 2.34(s, 3H) |
| 449 | 4.30 | 4.25 | 7.84(d, 1H), 7.45(d, 1H), 3.94(q, 2H), 2.44(s, 3H), 1.31(s, 9H) |

| Ex. No. | logP[a] | logP[b] | $^1$H NMR(D6-DMSO, 400 MHz) δ ppm |
|---|---|---|---|
| 450 | 3.18 | 3.15 | 7.85(d, 1H), 7.47(d, 1H), 4.45(s, 2H), 3.95(q, 2H), 3.39(s, 3H), 2.45(s, 3H) |
| 451 | 1.99 | 2.02 | 8.05(d, 1H), 7.56(d, 1H), 4.31-4.19(m, 1H), 4.07-3.94(m, 1H), 2.42(s, 3H), 2.35(s, 3H) |
| 452 | 3.10 | 3.09 | 8.08(d, 1H), 7.56(d, 1H), 4.31-4.20(m, 1H), 4.10-3.98(m, 1H), 2.42(s, 3H), 1.32(s, 9H) |
| 453 | 2.08 | 2.10 | 8.11(d, 1H), 7.58(d, 1H), 4.46(s, 2H), 4.30-4.21(m, 1H), 4.06-3.97(m, 1H), 3.39(s, 3H), 2.43(s, 3H) |
| 454 | 2.85 | 2.83 | 8.69(s, 1H), 7.83(d, 1H), 7.47(d, 1H), 3.96(q, 2H), 2.44(s, 3H) |
| 455 | 3.53 | 3.46 | 7.81(d, 1H), 7.45(d, 1H), 3.95(q, 2H), 2.69(q, 2H), 2.44(s, 3H), 1.20(s, 3H) |
| 456 | 3.62 | 3.55 | 7.80(d, 1H), 7.44(d, 1H), 3.95(q, 2H), 2.43(s, 3H), 2.09-2.02(m, 1H), 1.11-1.04(m, 2H), 1.02-0.98(m, 2H) |
| 457 | 4.35 | 4.29 | 7.93-7.88(m, 3H), 7.67-7.58(m, 3H), 7.50(d, 1H), 3.96(q, 2H), 2.47(s, 3H) |
| 458 | 4.85 | 4.78 | 7.92-7.89(m, 3H), 7.68(d, 2H), 7.50(d, 1H), 3.95(q, 2H), 2.47(s, 3H) |
| 459 | 3.20 | 3.20 | 8.83-8.82(m, 2H), 7.92(d, 1H), 7.83-7.81(m, 2H), 7.52(d, 1H), 3.95(q, 2H), 2.47(s, 3H) |
| 460 | 3.94 | 3.92 | 7.82(d, 1H), 7.45(d, 1H), 3.95(q, 2H), 2.67(t, 2H), 2.44(s, 3H), 1.72-1.61(m, 2H), 0.98(t, 3H) |
| 461 | 4.35 | 4.33 | 7.81(d, 1H), 7.45(d, 1H), 3.95(q, 2H), 2.67(t, 2H), 2.44(s, 3H), 1.70-1.60(m, 2H), 1.45-1.35(m, 2H), 0.91(t, 3H) |
| 462 | 3.93 | 3.84 | 7.82(d, 1H), 7.45(d, 1H), 3.95(q, 2H), 3.05-2.95(m, 1H), 2.44(s, 3H), 1.25(d, 6H) |
| 463 | 3.53 | 3.52 | 7.85(d, 1H), 7.47(d, 1H), 4.48(s, 2H), 3.95(q, 2H), 3.59(q, 2H), 2.44(s, 3H), 1.16(t, 3H) |
| 464 | 4.44 | 4.34 | 7.92(d, 1H), 7.75(d, 1H), 7.70-7.64(m, 2H), 7.54-7.49(m, 2H), 3.95(q, 2H), 2.47(s, 3H) |
| 465 | 2.50 | 2.48 | 8.08(d, 1H), 7.55(d, 1H), 4.28-4.19(m, 1H), 4.06-3.94(m, 1H), 2.42(s, 3H), 2.09-2.03(m, 1H), 1.11-1.05(m, 2H), 1.05-0.99(m, 2H) |
| 466 | 4.35 | 4.27 | 7.91(d, 1H), 7.84-7.81(m, 2H), 7.49(d, 1H), 7.16-7.13(m, 2H), 3.96(q, 2H), 3.86(s, 3H), 2.46(s, 3H) |
| 467 | 4.23 | 4.11 | 8.43-8.40(m, 2H), 8.16-8.13(m, 2H), 7.93(d, 1H), 7.52(d, 1H), 3.95(q, 2H), 2.48(s, 3H) |
| 468 | 4.13 | 4.09 | 7.97-7.86(m, 1H), 7.90(d, 1H), 7.80-7.79(m, 1H), 7.49(d, 1H), 7.30-7.28(m, 1H), 3.95(q, 2H), 2.46(s, 3H) |
| 469 | 3.74 | 3.65 | 8.06(s, 1H), 7.89(d, 1H), 7.49(d, 1H), 7.34-7.33(m, 1H), 6.81-6.80(m, 1H), 3.95(q, 2H), 2.46(s, 3H) |
| 470 | 2.77 | 2.63 | 8.07(d, 1H), 7.56(d, 1H), 4.32-4.20(m, 1H), 4.09-3.95(m, 1H), 2.65(t, 2H), 2.42(s, 3H), 1.75-1.65(m, 2H), 0.99(t, 3H) |
| 471 | 3.17 | 3.11 | 8.06(d, 1H), 7.56(d, 1H), 4.31-4.19(m, 1H), 4.10-3.98(m, 1H), 2.67(t, 2H), 2.42(s, 3H), 1.70-1.60(m, 2H), 1.45-1.35(m, 2H), 0.92(t, 3H) |
| 472 | 2.75 | 2.71 | 8.07(d, 1H), 7.56(d, 1H), 4.31-4.20(m, 1H), 4.08-3.98(m, 1H), 3.07-2.98(m, 1H), 2.42(s, 3H), 1.26(d, 6H) |
| 473 | 2.45 | 2.40 | 8.10(d, 1H), 7.58(d, 1H), 4.49(s, 2H), 4.31-4.20(m, 1H), 4.09-3.95(m, 1H), 3.60(q, 2H), 2.43(s, 3H), 1.17(t, 3H) |
| 474 | 3.21 | 3.18 | 8.17(d, 1H), 7.85-7.82(m, 2H), 7.60(d, 1H), 7.16-7.13(m, 2H), 4.35-4.21(m, 1H), 4.10-3.98(m, 1H), 3.86(s, 3H), 2.45(s, 3H) |
| 475 | 3.13 | 3.10 | 8.44-8.40(m, 2H), 8.20-8.13(m, 3H), 7.63(d, 1H), 4.38-4.22(m, 1H), 4.10-3.98(m, 1H), 2.45(s, 3H) |
| 476 | 2.96 | 2.93 | 8.15(d, 1H), 7.98-7.97(m, 1H), 7.80-7.79(m, 1H), 7.60(d, 1H), 7.31-7.29(m, 1H), 4.35-4.22(m, 1H), 4.10-3.99(m, 1H), 2.44(s, 3H) |
| 477 | 2.66 | 2.62 | 8.15(d, 1H), 8.07-8.06(m, 1H), 7.60(d, 1H), 7.35-7.34(m, 1H), 6.81-6.80(m, 1H), 4.33-4.22(m, 1H), 4.09-3.92(m, 1H), 2.44(s, 3H) |
| 478 | 3.09 | 3.06 | 8.08(d, 1H), 7.56(d, 1H), 7.39(d, 4H), 7.35-7.29(m, 1H), 4.30-4.19(m, 1H), 4.10(s, 2H), 4.09-3.95(m, 1H), 2.42(s, 3H) |
| 479 | 3.83 | 3.82 | 7.81(d, 1H), 7.46(d, 1H), 3.94(q, 2H), 3.77(t, 2H), 2.82(t, 2H), 2.44(s, 3H), 2.15-2.08(m, 2H) |
| 480 | 2.76 | 2.76 | 8.07(d, 1H), 7.56(d, 1H), 4.31-4.19(m, 1H), 4.08-3.95(m, 1H), 3.78(t, 2H), 2.82(t, 2H), 2.42(s, 3H), 2.18-2.09(m, 2H) |
| 481 | 1.80 | 1.79 | 8.71(s, 1H), 8.09(d, 1H), 7.58(d, 1H), 4.31-4.19(m, 1H), 4.09-3.92(m, 1H), 2.42(s, 3H) |
| 482 | 3.83 | 3.78 | 7.60(s, 1H), 7.28(s, 1H), 3.93(q, 2H), 2.38(s, 3H), 2.18(s, 3H), 2.09-2.00(m, 1H), 1.11-1.02(m, 2H), 1.02-0.92(m, 2H) |
| 483 | 4.52 | 4.47 | 7.63(s, 1H), 7.29(s, 1H), 3.93(q, 2H), 2.39(s, 3H), 2.18(s, 3H), 1.31(s, 9H) |
| 484 | 2.66 | 2.59 | 7.87(s, 1H), 7.39(s, 1H), 4.28-4.11(m, 1H), 4.02-3.89(m, 1H), 2.37(s, 3H), 2.29(s, 3H), 2.09-1.99(m, 1H), 1.10-1.01(m, 2H), 1.00-0.95(m, 2H) |
| 485 | 3.27 | 3.20 | 7.90(s, 1H), 7.40(s, 1H), 4.25-4.11(m, 1H), 4.05-3.92(m, 1H), 2.38(s, 3H), 2.30(s, 3H), 1.32(s, 9H) |
| 486 | 2.84 | 2.79 | 7.72(d, 1H), 7.36(d, 1H), 6.77(d, 1H), 6.73-6.72(m, 1H), 3.94(q, 2H), 3.60(q, 2H), 2.41(s, 3H), 1.22(t, 3H) |
| 487 | 1.83 | 1.81 | 7.99(d, 1H), 7.48(d, 1H), 6.83-6.80(m, 2H), 4.22-4.11(m, 1H), 4.11-4.02(m, 1H), 3.61(q, 2H), 2.41(s, 3H), 1.23(t, 3H) |
| 488 | 3.69 | 3.63 | 7.70(d, 1H), 7.35(d, 1H), 6.74(d, 1H), 6.68(t, 1H), 3.99-3.90(m, 2H), 2.42(s, 3H), 1.49(s, 9H) |

-continued

| Ex. No. | logP[a] | logP[b] | $^1$H NMR(D6-DMSO, 400 MHz) δ ppm |
|---|---|---|---|
| 489 | 2.50 | 2.47 | 8.00(d, 1H), 7.47(d, 1H), 6.79-6.77(m, 2H), 4.17-4.07(m, 2H), 2.40(s, 3H), 1.50(s, 9H) |
| 490 | 3.66 | 4.29 | 7.70(d, 1H), 7.37(d, 1H), 7.11(d, 1H), 6.50(d, 1H), 3.95(q, 2H), 3.65(q, 2H), 2.41(s, 3H) |
| 491 | 2.46 | 3.10 | 7.93(d, 1H), 7.49(d, 1H), 7.18(d, 1H), 6.56(d, 1H), 4.28-3.92(m, 2H), 3.68(q, 2H), 2.43(s, 3H) |
| 492 | 3.49 | 3.43 | 7.78(d, 1H), 7.45(d, 1H), 4.60(s, 2H), 3.96(q, 2H), 3.37(s, 3H), 3.09-3.05(m, 1H), 2.46(s, 3H), 1.20-1.15(m, 2H), 1.13-1.09(m, 2H) |
| 493 | 4.44 | 4.35 | 7.74(d, 1H), 7.43(d, 1H), 3.94(q, 2H), 3.07-3.05(m, 1H), 2.71(d, 2H), 2.45(s, 3H), 2.19-2.15(m, 1H), 1.15-1.14(m, 4H), 1.00(d, 6H) |
| 494 | 4.1 | 4.02 | 7.74(d, 1H), 7.43(d, 1H), 3.95(q, 2H), 3.36-3.29(m, 1H), 3.13-3.10(m, 1H), 2.46(s, 3H), 1.30(s, 6H), 1.17-1.15(m, 4H) |
| 495 | 4.52 | 4.43 | 7.73(d, 1H), 7.43(d, 1H), 3.95(q, 2H), 3.10-3.04(m, 1H), 2.83(t, 2H), 2.45(s, 3H), 1.74-1.67(m, 2H), 1.46-1.37(m, 2H), 1.17-1.12(m, 4H), 0.93(t, 3H) |
| 496 | 5.00 | 4.88 | 7.74(d, 1H), 7.42(d, 1H), 3.95(q, 2H), 3.12-3.07(m, 1H), 3.05-2.99(m, 1H), 2.45(s, 3H), 2.08-2.02(m, 2H), 1.82-1.75(m, 2H), 1.71-1.62(m, 1H), 1.45-1.30(m, 4H), 1.29-1.20(m, 1H), 1.17-1.16(m, 4H) |
| 497 | 4.68 | 4.57 | 7.74(d, 1H), 7.42(d, 1H), 3.95(q, 2H), 3.49-3.3, 39(m, 1H), 3.11-3.02(m, 1H), 2.45(s, 3H), 2.15-2.05(m, 2H), 1.89-1.75(m, 2H), 1.73-1.60(m, 4H), 1.20-1.11(m, 4H) |
| 498 | 4.24 | 4.14 | 7.75(d, 1H), 7.42(d, 1H), 5.20-5.10(m, 1H), 3.96(q, 2H), 2.45(s, 3H), 2.28-2.18(m, 1H), 1.59(d, 6H), 1.10-1.01(m, 2H), 1.00-0.95(m, 2H) |
| 499 | 4.46 | 4.39 | 7.75(d, 1H), 7.43(d, 1H), 3.95(q, 2H), 3.21-3.164(m, 1H), 3.12-3.06(m, 1H), 2.46(s, 3H), 1.85-1.78(m, 1H), 1.64-1.57(m, 1H), 1.27(d, 3H), 1.20-1.11(m, 4H), 0.92(t, 3H) |
| 500 | 3.82 | 3.77 | 7.78(d, 1H), 7.44(d, 1H), 4.62(s, 2H), 3.96(q, 2H), 3.58(q, 2H), 3.11-3.04(m, 1H), 2.45(s, 3H), 1.23-1.19(m, 2H), 1.17(t, 3H), 1.13-1.08(m, 2H) |
| 501 | 4.00 | 3.94 | |
| 502 | 3.69 | 3.65 | 7.73(d, 1H), 7.43(d, 1H), 3.94(q, 2H), 3.10-3.04(m, 1H), 2.86(q, 2H), 2.46(s, 3H), 1.26(t, 3H), 1.17-1.08(m, 4H) |
| 503 | 4.09 | 4.04 | 7.73(d, 1H), 7.43(d, 1H), 3.95(q, 2H), 3.10-3.04(m, 1H), 2.83-2.78(m, 2H), 2.45(s, 3H), 1.80-1.70(m, 2H), 1.17-1.11(m, 4H), 1.00(t, 3H) |
| 504 | 3.89 | 3.82 | 7.71(d, 1H), 7.41(d, 1H), 3.94(q, 2H), 3.20-3.10(m, 1H), 2.44(s, 3H), 2.21-2.11(m, 1H), 1.21-1.12(m, 4H), 1.11-1.03(m, 2H), 0.98-0.89(m, 2H) |
| 505 | 4.32 | 4.25 | 7.76(d, 1H), 7.43(d, 1H), 3.95(q, 2H), 3.90-3.80(m, 1H), 3.05-2.98(m, 1H), 2.46(s, 3H), 2.40-2.30(m, 4H), 2.15-2.01(m, 1H), 1.95-1.82(m, 1H), 1.11-1.09(m, 4H) |
| 506 | 4.23 | 4.18 | 7.86(d, 1H), 7.65-7.61(m, 1H), 7.49-7.45(m, 2H), 7.26(d, 1H), 7.14-7.10(m, 1H), 3.98(q, 2H), 3.91(s, 3H), 3.16-3.12(m, 1H), 2.47(s, 3H), 0.84-0.82(m, 2H), 0.61-0.51(m, 2H) |
| 507 | 4.24 | 4.17 | 7.88(d, 1H), 7.73-7.70(m, 1H), 7.23(d, 1H), 4.17(q, 2H), 3.94(q, 2H), 3.94(s, 3H), 1.34(t, 3H) |
| 508 | 2.49 | 2.43 | 8.00(d, 1H), 7.51(d, 1H), 4.50(q, 2H), 4.30-4.15(m, 1H), 4.15-4.03(m, 1H), 4.03(s, 3H), 2.42(s, 3H) |
| 509 | 2.49 | 2.43 | 8.00(d, 1H), 7.51(d, 1H), 4.50(q, 2H), 4.30-4.15(m, 1H), 4.15-4.03(m, 1H), 4.03(s, 3H), 2.42(s, 3H) |

The optical rotations were determined on a Perkin Elmer 341, serial number 9123, at a wavelength of 589 nm and a temperature of 20° C., by the following formula:

$$(\text{specific rotation} \alpha)_D^{°C.} = \frac{\text{angle of rotation} * \text{volume of solution(ml)}}{\text{cell path length(dm)} * \text{initial mass(g)}}$$

The specific rotations below should be understood as an average from 5 different measurements:

| | |
|---|---|
| 379 | −103.2 in CHCl$_3$ (c = 0.009) |
| 380 | 103.9 in CHCl$_3$ (c = 0.009) |
| 508 | 86.7 in CHCl$_3$ (c = 0.009) |
| 509 | −87.6 in CHCl$_3$ (c = 0.009) |

Use Examples
*Boophilus microplus* Injection Test (BOOPMI Inj)
Solvent: dimethyl sulphoxide To prepare an appropriate active ingredient formulation, 10 mg of active ingredient are mixed with 0.5 ml of solvent and the concentrate is diluted with solvent to the desired concentration.

1 µl of the active ingredient solution is injected into the abdomen of 5 engorged adult female cattle ticks (*Boophilus microplus*). The animals are transferred into dishes and kept in a climate-controlled room.

The efficacy is assessed after 7 days by laying of fertile eggs. Eggs which are not visibly fertile are stored in a climate-controlled cabinet until the larvae hatch after about 42 days.

An efficacy of 100% means that none of the ticks has laid any fertile eggs; 0% means that all the eggs are fertile.

In this test, for example, the following compounds from the preparation examples show an efficacy of 100% at an application rate of 20 µg/animal 5, 36, 37, 38, 45, 60, 92, 99, 101, 102, 103, 104, 105, 106, 115, 116, 117, 119, 157, 160, 215, 228, 231, 241, 245, 253, 257, 270, 295, 301, 302, 305, 311, 321, 381, 384, 385, 390, 392, 393, 406, 411, 415, 423, 439, 442, 504

*Lucilia cuprina* Test (LUCICU)

Solvent: dimethyl sulphoxide

To prepare an appropriate active ingredient formulation, 10 mg of active ingredient are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active ingredient preparation of the desired concentration.

After 2 days, the kill in % is determined 100% means that all the larvae have been killed; 0% means that none of the larvae have been killed.

In this test, for example, the following compounds from the preparation examples show an efficacy of 80% at an application rate of 100 ppm: 4

*Myzus persicae*—Spray Test (MYZUPE)

Solvent: 78 parts by weight of acetone
1.5 parts by weight of dimethylformamide
Emulsifier: 0.5 part by weight of alkylaryl polyglycol ether To produce an appropriate active ingredient formulation, 1 part by weight of active ingredient is mixed with the specified amounts of solvent and emulsifier, and the concentrate is diluted to the desired concentration with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 6 days, the activity in % is determined 100% means that all the aphids have been killed; 0% means that none of the aphids have been killed.

In this test, for example, the following compounds from the preparation examples show an efficacy of 90% at an application rate of 500 g/ha: 311, 320, 423

In this test, for example, the following compounds from the preparation examples show an efficacy of 90% at an application rate of 100 g/ha: 411

*Phaedon cochleariae*—Spray Test (PHAECO)

Solvent: 78.0 parts by weight of acetone
1.5 parts by weight of dimethylformamide
Emulsifier: 0.5 part by weight of alkylaryl polyglycol ether To produce an appropriate active ingredient formulation, 1 part by weight of active ingredient is mixed with the specified amounts of solvent and emulsifier, and the concentrate is diluted to the desired concentration with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, the efficacy in % is determined 100% means that all beetle larvae have been killed; 0% means that none of the beetle larvae have been killed.

In this test, for example, the following compounds from the preparation examples show an efficacy of 100% at an application rate of 500 g/ha: 2, 8, 10, 11, 93, 106, 109, 176, 179, 183, 219, 223, 225, 303, 311, 320, 321, 322, 328, 329, 330, 349, 351, 376, 390, 392, 392, 411, 447, 490, 504, 506

In this test, for example, the following compounds from the preparation examples show an efficacy of 83% at an application rate of 500 g/ha: 1, 94, 95, 154, 209, 272, 331, 332, 336, 350, 355, 394, 435, 437, 502

In this test, for example, the following compound from the preparation examples shows an efficacy of 83% at an application rate of 100 g/ha: 98

*Spodoptera frugiperda*—Spray Test (SPODFR)

Solvent: 78.0 parts by weight of acetone
1.5 parts by weight of dimethylformamide
Emulsifier: alkylaryl polyglycol ether To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active ingredient formulation of the desired concentration and, after drying, populated with caterpillars of the armyworm (*Spodoptera frugiperda*).

After 7 days, the activity in % is determined 100% means that all caterpillars have been killed; 0% means that none of the caterpillars have been killed.

In this test, for example, the following compounds from the preparation examples show an efficacy of 100% at an application rate of 500 g/ha: 411, 504

*Tetranychus urticae*—Spray Test, OP-Resistant (TETRUR)

Solvent: 78.0 parts by weight of acetone
1.5 parts by weight of dimethylformamide
Emulsifier: 0.5 part by weight of alkylaryl polyglycol ether To produce an appropriate active ingredient formulation, 1 part by weight of active ingredient is mixed with the specified amounts of solvent and emulsifier, and the concentrate is diluted to the desired concentration with emulsifier-containing water.

Discs of bean leaves (*Phaseolus vulgaris*) infested by all stages of the greenhouse red spider mite (*Tetranychus urticae*) are sprayed with an active ingredient formulation of the desired concentration.

After 6 days, the efficacy in % is determined 100% means that all the spider mites have been killed; 0% means that none of the spider mites have been killed.

In this test, for example, the following compounds from the preparation examples show an efficacy of 100% at an application rate of 500 g/ha: 5, 9, 11, 12, 15, 17, 18, 19, 21, 29, 32, 36, 37, 38, 40, 43, 44, 45, 48, 50, 59, 61, 63, 64, 65, 66, 68, 74, 75, 76, 77, 78, 79, 80, 82, 83, 84, 85, 86, 87, 88, 89, 90, 91, 92, 98, 100, 101, 102, 103, 104, 105, 106, 114, 115, 120, 121, 122, 123, 127, 132, 140, 146, 149, 150, 151, 153, 154, 155, 157, 158, 159, 160, 165, 170, 171, 172, 173, 180, 182, 183, 184, 189, 193, 194, 195, 196, 197, 198, 199, 200, 201, 202, 203, 204, 205, 206, 207, 208, 209, 210, 211, 215, 216, 221, 225, 226, 230, 231, 233, 234, 235, 237, 238, 239, 240, 241, 242, 243, 244, 245, 246, 247, 248, 250, 251, 252, 253, 255, 257, 259, 260, 261, 262, 264, 265, 266, 267, 268, 269, 270, 271, 272, 273, 274, 275, 276, 277, 278, 279, 280, 281, 282, 283, 284, 285, 286, 287, 288, 289, 290, 291, 292, 294, 295, 298, 300, 301, 302, 304, 305, 306, 307, 310, 311, 314, 324, 325, 343, 344, 345, 347, 350, 351, 353, 356, 358, 359, 361, 363, 365, 366, 367, 368, 369, 370, 371, 372, 375, 376, 377, 380, 382, 383, 384, 386, 390, 391, 393, 394, 395, 396, 397, 398, 400, 401, 403, 404, 408, 410, 411, 412, 414, 417, 419, 421, 422, 425, 426, 428, 433, 434, 435, 436, 438, 439, 440, 441, 442, 444, 447, 448, 450, 452, 453, 455, 456, 458, 460, 462, 464, 466, 467, 468, 470, 472, 475, 478, 479, 480, 482, 483, 484, 485, 486, 488, 490, 491, 492, 493, 494, 495, 498, 500, 503, 504, 505, 508

In this test, for example, the following compounds from the preparation examples show an efficacy of 90% at an application rate of 500 g/ha: 3, 4, 10, 14, 16, 20, 22, 23, 24, 25, 28, 30, 33, 34, 35, 39, 41, 42, 46, 49, 51, 52, 54, 55, 57, 58, 60, 67, 70, 71, 72, 73, 93, 97, 99, 112, 113, 116, 117, 119, 125, 126, 128, 129, 130, 131, 133, 134, 136, 137, 141, 143, 144, 148, 152, 162, 164, 166, 169, 176, 178, 179, 185, 187, 190, 191, 192, 212, 213, 217, 218, 219, 220, 222, 223, 224, 228, 229, 232, 236, 249, 254, 256, 258, 293, 296, 302, 312, 313, 315, 316, 317, 318, 326, 327, 328, 329, 330, 331, 332, 335, 336, 337, 338, 339, 340, 341, 342, 346, 348, 349, 352, 355, 357, 360, 362, 364, 374, 378, 379, 381, 387, 388, 389, 392, 399, 402, 405, 406, 407, 409, 413, 415, 416, 418, 420, 423, 424, 427, 429, 430, 431, 437, 446, 449, 451, 454, 457, 459, 461, 463, 465, 469, 474, 487, 489, 496, 497, 499, 501, 502, 506, 507

In this test, for example, the following compound from the preparation examples shows an efficacy of 80% at an application rate of 500 g/ha: 6

In this test, for example, the following compounds from the preparation examples show an efficacy of 100% at an application rate of 100 g/ha: 62, 69, 175, 177, 263

In this test, for example, the following compounds from the preparation examples show an efficacy of 90% at an application rate of 100 g/ha: 56, 124, 188, 476

In this test, for example, the following compound from the preparation examples shows an efficacy of 90% at an application rate of 20 g/ha: 334

*Meloidogyne Incognita* Test (MELGIN)

Solvent: 125.0 parts by weight of acetone

To produce an appropriate active ingredient formulation, 1 part by weight of active ingredient is mixed with the specified amounts of solvent and the concentrate is diluted to the desired concentration with water.

Vessels are filled with sand, active ingredient solution, an egg/larvae suspension of the southern root-knot nematode (*Meloidogyne incognita*) and lettuce seeds. The lettuce seeds germinate and the plants develop. The galls develop on the roots After 14 days, the nematicidal efficacy in % is determined by the formation of galls. 100% means that no galls have been found; 0% means that the number of galls on the treated plants corresponds to the untreated control.

In this test, for example, the following compounds from the preparation examples show an efficacy of 100% at an application rate of 20 ppm: 7, 40, 61, 102, 103, 110, 111, 116, 117, 118, 145, 160, 202, 304, 305, 415, 446, 491

In this test, for example, the following compounds from the preparation examples show an efficacy of 90% at an application rate of 20 ppm: 4, 39, 99, 104, 105, 106, 107, 108, 115, 135, 138, 139, 140, 142, 146, 150, 213, 214, 323, 331, 332, 444, 502

The invention claimed is:

1. A compound of formula (I)

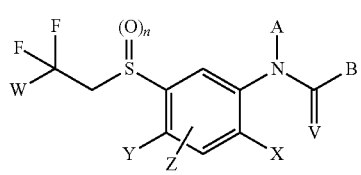

(I)

in which

A and B together with the atoms to which they are bonded are a substructure selected from the group consisting of

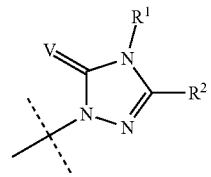

(I-A)

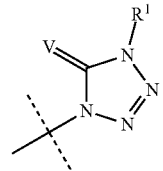

(I-B)

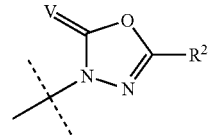

(I-C)

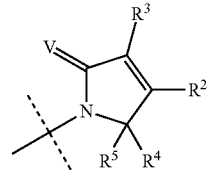

(I-D)

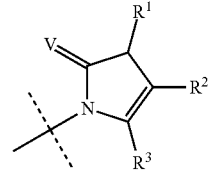

(I-E)

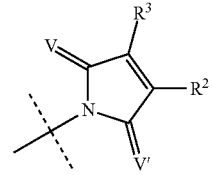

(I-F)

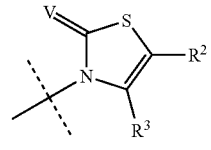

(I-G)

where $R^1$ is hydrogen, cyano or nitro; or is alkyl, cycloalkylalkyl, haloalkyl, cyanoalkyl, hydroxyalkyl, alkoxyalkyl, aminoalkyl, alkoxycarbonylalkyl, alkylsulphanylalkyl, alkylsulphinylalkyl, alkylsulphonylalkyl, haloalkylsulphanylalkyl, haloalkylsulphinylalkyl, haloalkylsulphonylalkyl, alkoxyalkylsulphonylalkyl, alkoxyalkylsulphinylalkyl, alkoxyalkylsulphonylalkyl, phenylalkyl, phenoxyalkyl, phenylsulphanylalkyl, phenylsulphinylalkyl, phenylsulphonylalkyl, hetarylalkyl, hetaryloxyalkyl, hetarylthioalkyl, where the aforementioned radicals may each be saturated or unsaturated and/or optionally substituted; or is optionally substituted saturated or unsaturated cycloalkyl which may optionally be interrupted by one or more heteroatoms; or is alkylcarbonyl, haloalkylcarbonyl, hydroxyalkylcarbonyl, alkoxyalkylcarbonyl, phenylcarbonyl, hetarylcarbonyl, alkoxycarbonyl, haloalkoxycarbonyl, aryloxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl(aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or is carbonyl or carboxyl; or is optionally substituted phenyl or optionally substituted hetaryl; or is alkoxy, haloalkoxy, cycloalkyloxy, aryloxy, arylalkyloxy or carbonyloxy, where the aforementioned radicals may optionally be substituted, or is hydroxyl; or is alkylamino, haloalkylamino, dihaloalkylamino, dialkylamino, cycloalkylamino, dicycloalkylamino, cycloalkyl(alkyl)amino, arylamino, diarylamino, hetarylamino, dihetarylamino, alkyl(aryl)amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulphonylamino, or arylsulphonylamino, where the aforementioned radicals may each be saturated or unsaturated and/or optionally substituted, or is amino; or is alkylsulphanyl, alkylsulphinyl, alkylsulphonyl, haloalkylsulphanyl, haloalkylsulphinyl, haloalkylsulphanyl, cycloalkylsulphanyl, cycloalkylsulphinyl, cycloalkylsulphonyl, cycloalkylalkylsulphanyl, cycloalkylalkylsulphinyl, cycloalkylalkylsulphonyl, arylsulphanyl, arylsulphinyl, arylsulphonyl, arylalkylsulphanyl, arylalkylsulphinyl, arylalkylsulphonyl, aminosulphonyl, alkylaminosulphonyl, dialkylaminosulphonyl or arylaminosulphonyl, where the aforementioned radicals may each be saturated or unsaturated and/or optionally substituted, or is sulphanyl; and $R^2$, $R^3$, $R^4$ and $R^5$ each independently are hydrogen, cyano, halogen or nitro; or are alkyl, cycloalkylalkyl, haloalkyl, cyanoalkyl, hydroxyalkyl, alkoxyalkyl, aminoalkyl, alkoxycarbonylalkyl, alkylsulphanylalkyl, alkylsulphinylalkyl, alkylsulphonylalkyl, haloalkylsulphanylalkyl, haloalkylsulphinylalkyl, haloalkylsulphonylalkyl, alkoxyalkylsulphonylalkyl, alkoxyalkylsulphinylalkyl, alkoxyalkylsulphonylalkyl, phenylalkyl, phenoxyalkyl, phenylsulphanylalkyl, phenylsulphinylalkyl, phenylsulphonylalkyl, hetarylalkyl, hetaryloxyalkyl, hetarylthioalkyl, where the aforementioned radicals may each be saturated or unsaturated and/or optionally substituted; or are optionally substituted saturated or unsaturated cycloalkyl which may optionally be interrupted by one or more heteroatoms; or are alkylcarbonyl, haloalkylcarbonyl, hydroxyalkylcarbonyl, alkoxyalkylcarbonyl, phenylcarbonyl, hetarylcarbonyl, alkoxycarbonyl, haloalkoxycarbonyl, aryloxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, di arylaminoc arbonyl, alkyl(aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or are carbonyl or carboxyl; or are optionally substituted phenyl or optionally substituted hetaryl; or are alkoxy, haloalkoxy, alkoxyalkoxy, aryloxy, arylalkyloxy, cycloalkyloxy, cycloalkylalkyloxy or carbonyloxy, where the aforementioned radicals may be saturated or unsaturated and/or optionally substituted, or are hydroxyl; or are alkylamino, dialkylamino, haloalkylamino, dihaloalkylamino, cycloalkylamino, dicycloalkylamino, cycloalkyl(alkyl)amino, arylamino, diarylamino, hetarylamino, dihetarylamino, alkyl(aryl)amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulphonylamino, or arylsulphonylamino, where the aforementioned radicals may each be saturated or unsaturated and/or optionally substituted, or are amino; or are alkylsulphanyl, alkylsulphinyl, alkylsulphonyl, haloalkylsulphanyl, haloalkylsulphinyl, haloalkylsulphonyl, cycloalkylsulphanyl, cycloalkylsulphinyl, cycloalkylsulphonyl, cycloalkylalkylsulphanyl, cycloalkylalkylsulphinyl, cycloalkylalkylsulphonyl, arylsulphanyl, arylsulphinyl, arylsulphonyl, arylalkylsulphanyl, arylalkylsulphinyl, arylalkylsulphonyl, aminosulphonyl, alkylaminosulphonyl, dialkylaminosulphonyl or arylaminosulphonyl, where the aforementioned radicals may each be saturated or unsaturated and/or optionally substituted, or are sulphanyl; or $R^4$ and $R^5$ together with the atom to which they are bonded may form an optionally substituted, saturated or unsaturated three- to eight-membered ring optionally interrupted by one or more heteroatoms which are selected independently from the group consisting of O, S and N; or $R^2$ is a saturated or unsaturated cycle optionally interrupted by one or more heteroatoms which are each selected from the group consisting of O, S and N, which may optionally be substituted;

where in substructures of formula (I-B), (I-C), (I-D), (I-E), (I-F) or (I-G) V and V' are each independently oxygen, sulphur or an optionally substituted nitrogen; and wherein in substructure of formula (I-A), V and V' each independently are oxygen or sulphur, W is hydrogen or halogen;

X, Y and Z, each independently, are hydrogen, halogen, hydroxyl, amino, cyano, nitro, OCN, SCN, $SF_5$; or are trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulphinyl, haloalkylsulphinyl, alkoxyalkylsulphinyl, alkylsulphinylalkyl, alkylsulphonyl, haloalkylsulphonyl, alkoxyalkylsulphonyl, alkylsulphonylalkyl, alkylsulphonyloxy, alkylcarbonyl, haloalkylcarbonyl, carboxyl, alkylcarbonyloxy, alkoxycarbonyl, haloalkoxycarbonyl, aminocarbonyl, alkylaminocarbonyl, dialkylaminocarbonyl, alkenylaminocarbonyl, dialkenylaminocarbonyl, cycloalkylaminocarbonyl, alkylsulphonylamino, aminosulphonyl, alkylaminosulphonyl, dialkylaminosulphonyl, alkylsulphoximino, aminothiocarbonyl, alkylaminothiocarbonyl or dialkylaminothiocarbonyl, where all the aforementioned radicals may optionally be substituted; or are phenylalkyl, phenoxy, phenylalkyloxy, phenoxyalkyl, phenylthio, phenylthioalkyl, phenylsulphinyl, phenylsulphonyl, hetarylalkyl, hetaryloxy, hetarylalkyloxy, hetarylthio, hetarylsulphinyl or hetarylsulphonyl, where all the aforementioned radicals may optionally be substituted; or are cycloalkylalkyl, cycloalkyloxy, cycloalkylalkoxy, cycloalkylthio, cycloalkylalkylthio, cycloalkylsulphinyl, cycloalkylalkylsulphinyl, cycloalkylsulphonyl, cycloalkylalkylsulphonyl or cycloalkenyl, where all the aforementioned radicals may each optionally be substituted; or are NR'R''
where R' and R'' each independently
are hydrogen, cyano, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl; or R' and R'' together with the nitrogen atom to which they are bonded may form an optionally substituted, saturated or unsaturated five- to eight-membered ring optionally interrupted by one or more heteroatoms which are selected independently from the group consisting of O, S and N; or are a 3- to 6-membered saturated, partly saturated or aromatic ring which may optionally contain one to three heteroatoms which are selected independently from the group consisting of O, S and N, and which may optionally be substituted;

or X and Z, or Y and Z, together with the carbon atoms to which they are bonded, form a 5- or 6-membered ring which is optionally substituted and optionally interrupted by one or more heteroatoms which are selected independently from the group consisting of O, S, N and CO;

n is the number 0, 1 or 2.

2. A compound according to claim 1 in which
$R^1$ is hydrogen, cyano or nitro; or
is $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylsulphanyl$(C_1-C_6)$alkyl, hetarylsulphinyl$(C_1-C_6)$alkyl, hetarylsulphonyl$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or is optionally substituted saturated or unsaturated $(C_3-C_6)$cycloalkyl which may optionally be interrupted by one or more heteroatoms; or is $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$(C_1-C_6)$alkylaminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or is optionally substituted phenyl or optionally substituted hetaryl; or is $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or is hydroxyl; or is $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$(C_1-C_6)$alkylamino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or is $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphanyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; and $R^2$, $R^3$, $R^4$ and $R^5$ each independently
are hydrogen, cyano, halogen or nitro; or
are $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$ alkyl, $(C_1-C_6)$alkoxy$(C_1-C_6)$alkyl, amino$(C_1-C_6)$ alkyl, $(C_1-C_6)$alkoxycarbonyl$(C_1-C_6)$alkyl, $(C_1-C_6)$ alkylsulphanyl$(C_1-C_6)$alkyl, $(C_1-C_6)$alkylsulphinyl $(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$ alkylsulphinyl$(C_1-C_6)$alkyl, $(C_1-C_6)$alkoxy$(C_1-C_6)$ alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$ alkyl, hetarylthio$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or are optionally substituted saturated or unsaturated $(C_3-C_6)$cycloalkyl which may optionally be interrupted by one or more heteroatoms; or are $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$ cycloalkylaminocarbonyl, $(C_3-C_6)$cycloalkyl$(C_1-C_6)$ alkylaminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or are carbonyl or carboxyl; or are optionally substituted phenyl or optionally substituted hetaryl; or are $(C_1-C_6)$alkoxy, halo$(C_1-C_6)$alkoxy, $(C_1-C_6)$alkoxy $(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or are hydroxyl; or are $(C_1-C_6)$alkylamino, di$(C_1-C_6)$alkylamino, halo$(C_1-C_6)$alkylamino, dihalo$(C_1-C_6)$alkylamino, $(C_3-C_6)$ cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$ alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or are amino; or are $(C_1-C_6)$alkylsulphanyl, $(C_1-C_6)$alkylsulphinyl, $(C_1-C_6)$alkylsulphonyl, halo$(C_1-C_6)$alkylsulphanyl, halo $(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl $(C_1-C_6)$alkylsulphinyl, $(C_3-C_6)$cycloalkyl$(C_1-C_6)$ alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or are sulphanyl; or $R^4$ and $R^5$ together with the atom to which they are bonded may form an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$ alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N; or $R^2$ is an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$ alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$ alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

and n is the number 0 or 1.

3. A compound according to claim 2 in which

X, Y and Z each independently are hydrogen, halogen, hydroxyl, amino, cyano, nitro, OCN, SCN, $SF_5$; or are tri$(C_1-C_6)$alkylsilyl, $(C_1-C_6)$alkyl, halo$(C_1-C_6)$ alkyl, cyano$(C_1-C_6)$alkyl, hydroxy$(C_1-C_6)$alkyl, $(C_1-C_6)$alkoxycarbonyl$(C_1-C_6)$alkyl, $(C_1-C_6)$alkoxy $(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$ alkynyl, cyano$(C_2-C_6)$alkynyl, $(C_1-C_6)$alkoxy, halo $(C_1-C_6)$alkoxy, cyano$(C_1-C_6)$alkoxy, hydroxycarbonyl$(C_1-C_6)$alkoxy, $(C_1-C_6)$alkoxycarbonyl$(C_1-C_6)$ alkoxy, $(C_1-C_6)$alkoxy$(C_1-C_6)$alkoxy, $(C_1-C_6)$ alkylhydroxyimino, $(C_1-C_6)$alkoxyimino, $(C_1-C_6)$ alkyl$(C_1-C_6)$alkoxyimino, halo$(C_1-C_6)$alkyl$(C_1-C_6)$ alkoxyimino, $(C_1-C_6)$alkylthio, halo$(C_1-C_6)$ alkylthio, $(C_1-C_6)$alkoxy$(C_1-C_6)$alkylthio, $(C_1-C_6)$ alkylthio$(C_1-C_6)$alkyl, $(C_1-C_6)$alkylsulphinyl, halo $(C_1-C_6)$alkylsulphinyl, $(C_1-C_6)$alkoxy$(C_1-C_6)$ alkylsulphinyl, $(C_1-C_6)$alkoxysulphinyl$(C_1-C_6)$alkyl, $(C_1-C_6)$alkylsulphonyl, halo$(C_1-C_6)$alkylsulphonyl, $(C_1-C_6)$alkoxy$(C_1-C_6)$alkylsulphonyl, $(C_1-C_6)$alkylsulphonyl(C₁-C₆)alkyl, (C₁-C₆)alkylsulphonyloxy, (C₁-C₆)alkylcarbonyl, halo(C₁-C₆)alkylcarbonyl, carboxyl, (C₁-C₆)alkylcarbonyloxy, (C₁-C₆)alkoxycarbonyl, halo(C₁-C₆)alkoxycarbonyl, aminocarbonyl, (C₁-C₆)alkylaminocarbonyl, di(C₁-C₆)alkylaminocarbonyl, (C₂-C₆)alkenylaminocarbonyl, di(C₂-C₆)alkenylaminocarbonyl, (C₃-C₆)cycloalkylaminocarbonyl, (C₁-C₆)alkylsulphonylamino, aminosulphonyl, (C₁-C₆)alkylaminosulphonyl, di(C₁-C₆)alkylaminosulphonyl, (C₁-C₆)alkylsulphoximino, aminothiocarbonyl, (C₁-C₆)alkylaminothiocarbonyl or di(C₁-C₆)alkylaminothiocarbonyl, where all the aforementioned radicals may optionally be substituted by halogen; or are phenyl(C₁-C₃)alkyl, phenoxy, phenyl(C₁-C₃)alkyloxy, phenoxy(C₁-C₃)alkyl, phenylthio, phenylthio(C₁-C₃)alkyl, phenylsulphinyl, phenylsulphonyl, hetaryl(C₁-C₃)alkyl, hetaryloxy, hetaryl(C₁-C₃)alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are (C₃-C₆)cycloalkyl(C₁-C₃)alkyl, (C₃-C₆)cycloalkyloxy, (C₃-C₆)cycloalkyl(C₁-C₃)alkoxy, (C₃-C₆)cycloalkylthio, (C₃-C₆)cycloalkyl(C₁-C₃)alkylthio, (C₃-C₆)cycloalkylsulphinyl, (C₃-C₆)cycloalkyl(C₁-C₃)alkylsulphinyl, (C₃-C₆)cycloalkylsulphonyl, (C₃-C₆)cycloalkyl(C₁-C₃)alkylsulphonyl or (C₃-C₈)cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"
where R' and R" each independently
are hydrogen, cyano, (C₁-C₆)alkyl, halo(C₁-C₆)alkyl, cyano(C₁-C₆)alkyl, hydroxy(C₁-C₆)alkyl, (C₁-C₆)alkoxy(C₁-C₆)alkyl, (C₁-C₆)alkylthio(C₁-C₆)alkyl, (C₂-C₆)alkenyl, halo(C₂-C₆)alkenyl, cyano(C₂-C₆)alkenyl, (C₂-C₆)alkynyl, halo(C₂-C₆)alkynyl, cyano(C₂-C₆)alkynyl, acyl or (C₁-C₆)alkoxycarbonyl; or
R' and R" together with the nitrogen atom to which they are bonded may form an optionally identically or differently halogen-, cyano-, nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or
are a (C₃-C₆)cycloalkyl, oxetanyl, oxolanyl, oxanyl, (C₃-C₈)cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

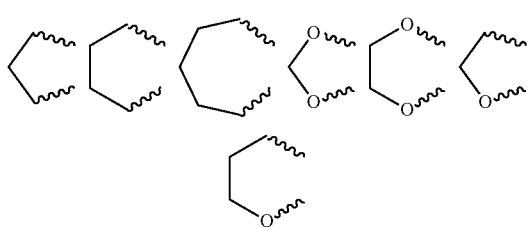

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

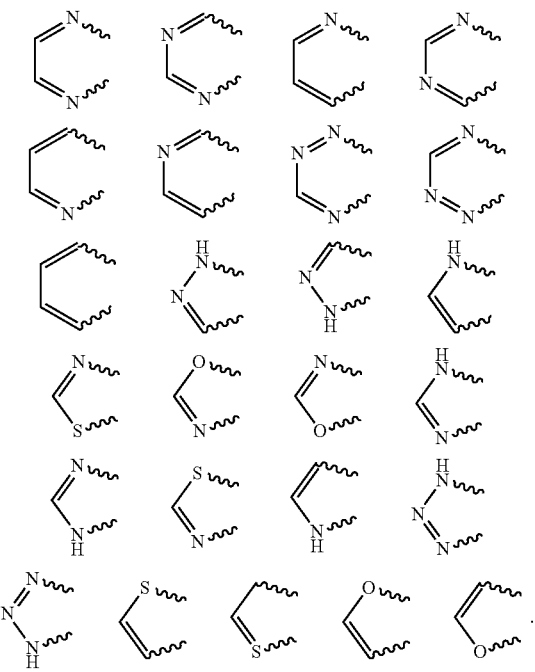

4. A compound according to claim 1, in which
A and B together with the atoms to which they are bonded are a substructure of the formula (I-A)

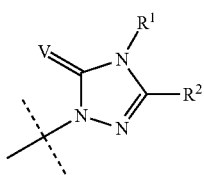
(I-A)

where
R[1] is hydrogen, cyano or nitro; or
  is ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylsulphanyl($C_1$-$C_6$)alkyl, ($C_1$-$C_6$)alkylsulphinyl($C_1$-$C_6$)alkyl, ($C_1$-$C_6$)alkylsulphonyl($C_1$-$C_6$)alkyl, halo($C_1$-$C_6$)alkylsulphanyl($C_1$-$C_6$)alkyl, halo($C_1$-$C_6$)alkylsulphinyl($C_1$-$C_6$)alkyl, halo($C_1$-$C_6$)alkylsulphonyl($C_1$-$C_6$)alkyl, ($C_1$-$C_6$)alkoxy($C_1$-$C_6$)alkylsulphanyl($C_1$-$C_6$)alkyl, ($C_1$-$C_6$)alkoxy($C_1$-$C_6$)alkylsulphinyl($C_1$-$C_6$)alkyl, ($C_1$-$C_6$)alkoxy($C_1$-$C_6$)alkylsulphonyl($C_1$-$C_6$)alkyl, phenyl($C_1$-$C_6$)alkyl, phenoxy($C_1$-$C_6$)alkyl, phenylsulphanyl($C_1$-$C_6$)alkyl, phenylsulphinyl($C_1$-$C_6$)alkyl, phenylsulphonyl($C_1$-$C_6$)alkyl, hetaryl($C_1$-$C_6$)alkyl, hetaryloxy($C_1$-$C_6$)alkyl, hetarylsulphanyl($C_1$-$C_6$)alkyl, hetarylsulphinyl($C_1$-$C_6$)alkyl, hetarylsulphonyl($C_1$-$C_6$)alkyl, where the aforementioned radicals may each optionally be substituted and/or, under the condition that, in the case of an unsaturated radical, the defined minimum number of carbon atoms is 2, the radicals may be saturated or unsaturated; or
  is optionally substituted saturated or unsaturated ($C_3$-$C_6$)cycloalkyl which may optionally be interrupted by one or more heteroatoms; or
  is ($C_1$-$C_6$)alkylcarbonyl, halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, ($C_1$-$C_6$)alkoxycarbonyl, halo($C_1$-$C_6$)alkoxycarbonyl, aryloxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or
  is optionally substituted phenyl or optionally substituted hetaryl; or
  is ($C_1$-$C_6$)alkoxy, halo($C_1$-$C_6$)alkoxy, ($C_3$-$C_6$)cycloalkyloxy, aryloxy, aryl($C_1$-$C_6$)alkyloxy or carbonyloxy, where the aforementioned radicals may each optionally be substituted, or is hydroxyl; or
  is ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_3$-$C_6$)cycloalkyl(($C_1$-$C_6$)alkyl)amino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or
  is ($C_1$-$C_6$)alkylsulphanyl, ($C_1$-$C_6$)alkylsulphinyl, ($C_1$-$C_6$)alkylsulphonyl, halo($C_1$-$C_6$)alkylsulphanyl, halo($C_1$-$C_6$)alkylsulphinyl, halo($C_1$-$C_6$)alkylsulphanyl, ($C_3$-$C_6$)cycloalkylsulphanyl, ($C_3$-$C_6$)cycloalkylsulphinyl, ($C_3$-$C_6$)cycloalkylsulphonyl, ($C_3$-$C_6$)cycloalkyl($C_1$-$C_6$)alkylsulphanyl, ($C_3$-$C_6$)cycloalkyl($C_1$-$C_6$)alkylsulphinyl, ($C_3$-$C_6$)cycloalkyl($C_1$-$C_6$)alkylsulphonyl, arylsulphanyl, arylsulphinyl, arylsulphonyl, aryl($C_1$-$C_6$)alkylsulphanyl, aryl($C_1$-$C_6$)alkylsulphinyl, aryl($C_1$-$C_6$)alkylsulphonyl, aminosulphonyl, ($C_1$-$C_6$)alkylaminosulphonyl, di($C_1$-$C_6$)alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; and
R[2] is hydrogen, cyano, halogen or nitro; or
  is ($C_1$-$C_6$)alkyl, ($C_3$-$C_6$)cycloalkyl($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylsulphanyl($C_1$-$C_6$)alkyl, ($C_1$-$C_6$)alkylsulphinyl($C_1$-$C_6$)alkyl, ($C_1$-$C_6$)alkylsulphonyl($C_1$-$C_6$)alkyl, halo($C_1$-$C_6$)alkylsulphanyl($C_1$-$C_6$)alkyl, halo($C_1$-$C_6$)alkylsulphinyl($C_1$-$C_6$)alkyl, halo($C_1$-$C_6$)alkylsulphonyl($C_1$-$C_6$)alkyl, ($C_1$-$C_6$)alkoxy($C_1$-$C_6$)alkylsulphanyl($C_1$-$C_6$)alkyl, ($C_1$-$C_6$)alkoxy($C_1$-$C_6$)alkylsulphinyl($C_1$-$C_6$)alkyl, ($C_1$-$C_6$)alkoxy($C_1$-$C_6$)alkylsulphonyl($C_1$-$C_6$)alkyl, phenyl($C_1$-$C_6$)alkyl, phenoxy($C_1$-$C_6$)alkyl, phenylsulphanyl($C_1$-$C_6$)alkyl, phenylsulphinyl($C_1$-$C_6$)alkyl, phenylsulphonyl($C_1$-$C_6$)alkyl, hetaryl($C_1$-$C_6$)alkyl, hetaryloxy($C_1$-$C_6$)alkyl, hetarylthio($C_1$-$C_6$)alkyl, where the aforementioned radicals may each optionally be substituted and/or, under the condition that, in the case of an unsaturated radical, the defined minimum number of carbon atoms is 2, the radicals may be saturated or unsaturated; or
  is optionally substituted saturated or unsaturated ($C_3$-$C_6$)cycloalkyl which may optionally be interrupted by one or more heteroatoms; or
  is ($C_1$-$C_6$)alkylcarbonyl, halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, ($C_1$-$C_6$)alkoxycarbonyl, halo($C_1$-$C_6$)alkoxycarbonyl, aryloxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or is optionally substituted phenyl or optionally substituted hetaryl; or is $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or is hydroxyl; or is $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or is $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; or is an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

W is hydrogen or halogen;

X, Y and Z each independently are hydrogen, halogen, hydroxyl, amino, cyano, nitro, OCN, SCN, $SF_5$; or are tri$(C_1-C_6)$alkylsilyl, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxycarbonyl$(C_1-C_6)$alkyl, $(C_1-C_6)$alkoxy$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, $(C_1-C_6)$alkoxy, halo$(C_1-C_6)$alkoxy, cyano$(C_1-C_6)$alkoxy, hydroxycarbonyl$(C_1-C_6)$alkoxy, $(C_1-C_6)$alkoxycarbonyl$(C_1-C_6)$alkoxy, $(C_1-C_6)$alkoxy$(C_1-C_6)$alkoxy, $(C_1-C_6)$alkylhydroxyimino, $(C_1-C_6)$alkoxyimino, $(C_1-C_6)$alkyl$(C_1-C_6)$alkoxyimino, halo$(C_1-C_6)$alkyl$(C_1-C_6)$alkoxyimino, $(C_1-C_6)$alkylthio, halo$(C_1-C_6)$alkylthio, $(C_1-C_6)$alkoxy$(C_1-C_6)$alkylthio, $(C_1-C_6)$alkylthio$(C_1-C_6)$alkyl, $(C_1-C_6)$alkylsulphinyl, halo$(C_1-C_6)$alkylsulphinyl, $(C_1-C_6)$alkoxy$(C_1-C_6)$alkylsulphinyl, $(C_1-C_6)$alkylsulphinyl$(C_1-C_6)$alkyl, $(C_1-C_6)$alkylsulphonyl, halo$(C_1-C_6)$alkylsulphonyl, $(C_1-C_6)$alkoxy$(C_1-C_6)$alkylsulphonyl, $(C_1-C_6)$alkylsulphonyl$(C_1-C_6)$alkyl, $(C_1-C_6)$alkylsulphonyloxy, $(C_1-C_6)$alkylcarbonyl, halo$(C_1-C_6)$alkylcarbonyl, carboxyl, $(C_1-C_6)$alkylcarbonyloxy, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_2-C_6)$alkenylaminocarbonyl, di$(C_2-C_6)$alkenylaminocarbonyl, $(C_3-C_6)$cyclo$(C_1-C_6)$alkylaminocarbonyl, $(C_1-C_6)$alkylsulphonylamino, aminosulphonyl, $(C_1-C_6)$alkylaminosulphonyl, di$(C_1-C_6)$alkylaminosulphonyl, $(C_1-C_6)$alkylsulphoximino, aminothiocarbonyl, $(C_1-C_6)$alkylaminothiocarbonyl or di$(C_1-C_6)$alkylaminothiocarbonyl, where all the aforementioned radicals may optionally be substituted by halogen; or are phenyl$(C_1-C_3)$alkyl, phenoxy, phenyl$(C_1-C_3)$alkyloxy, phenoxy$(C_1-C_3)$alkyl, phenylthio, phenylthio$(C_1-C_3)$alkyl, phenylsulphinyl, phenylsulphonyl, hetaryl$(C_1-C_3)$alkyl, hetaryloxy, hetaryl$(C_1-C_3)$alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are $(C_3-C_6)$cycloalkyl$(C_1-C_3)$alkyl, $(C_3-C_6)$cycloalkyloxy, $(C_3-C_6)$cycloalkyl$(C_1-C_3)$alkoxy, $(C_3-C_6)$cycloalkylthio, $(C_3-C_6)$cycloalkyl$(C_1-C_3)$alkylthio, $(C_3-C_6)$cycloalkylsulphinyl, $(C_3-C_6)$cycloalkyl$(C_1-C_3)$alkylsulphinyl, $(C_3-C_6)$cycloalkylsulphonyl, $(C_3-C_6)$cycloalkyl$(C_1-C_3)$alkylsulphonyl or $(C_3-C_8)$cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"

where R' and R" each independently are hydrogen, cyano, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, $(C_1-C_6)$alkylthio$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, acyl or $(C_1-C_6)$alkoxycarbonyl; or R' and R" together with the nitrogen atom to which they are bonded may form an optionally identically or differently halogen-, cyano-nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a $(C_3-C_6)$cycloalkyl, oxetanyl, oxolanyl, oxanyl, $(C_3-C_8)$cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

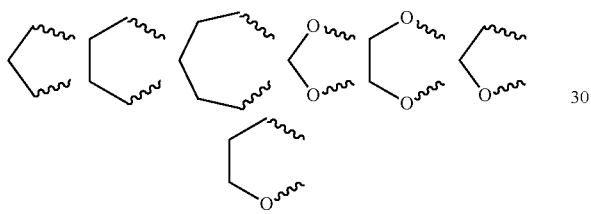

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

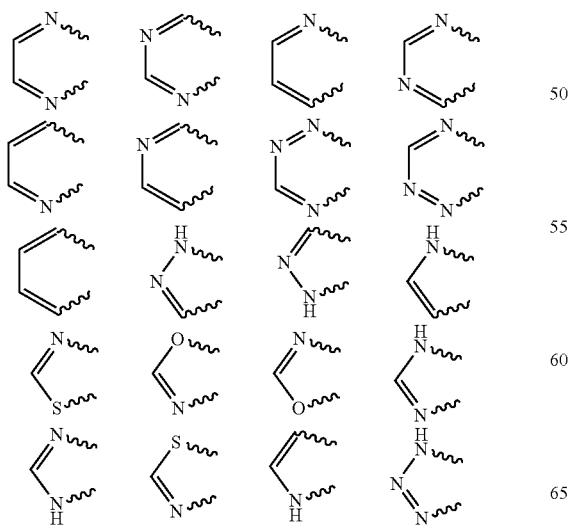

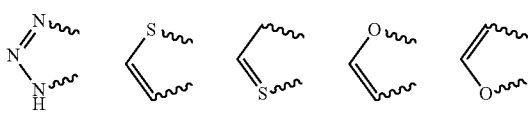

and n is the number 0 or 1.

5. A compound according to claim 4 in which the substructure of the formula (I-A) is a substructure which is selected from the group consisting of

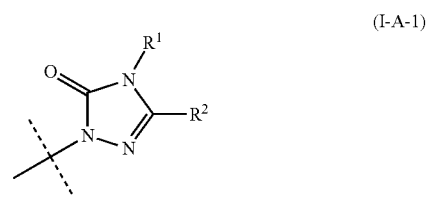

(I-A-1)

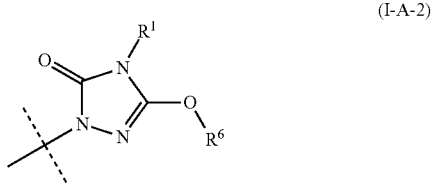

(I-A-2)

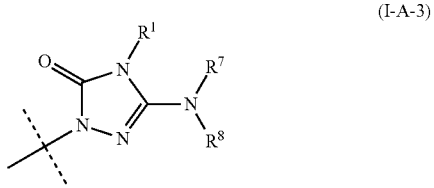

(I-A-3)

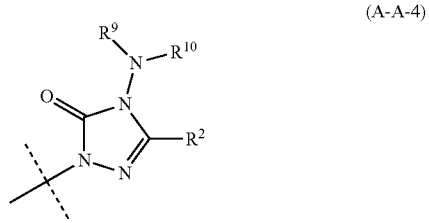

(A-A-4)

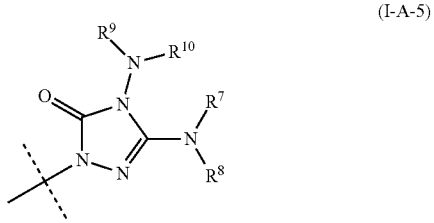

(I-A-5)

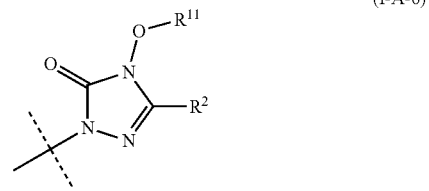

(I-A-6)

-continued

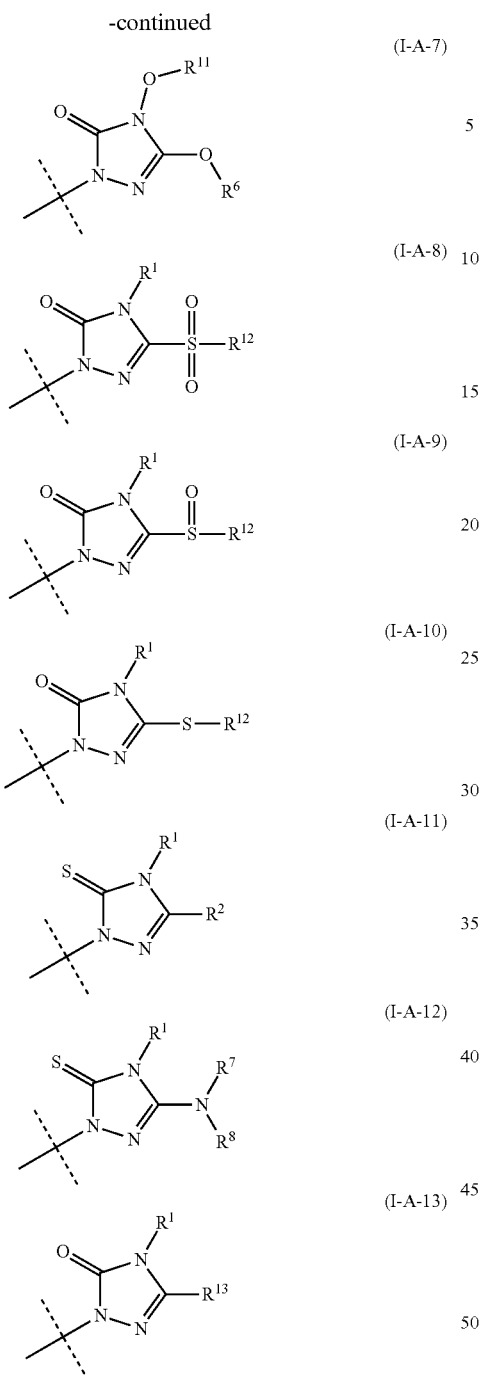

where
R¹ is hydrogen; or
is $(C_1-C_6)$alkyl, $(C_{3-5})$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is $(C_3-C_6)$cycloalkyl, $(C_3-C_6)$cycloalkenyl, oxetanyl, oxolanyl, oxanyl, phenyl, pyridyl, pyrimidyl, pyridazinyl, pyrazinyl, triazinyl, thiazolyl, thiazadiazolyl, oxazolyl, oxadiazolyl, pyrazolyl or triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

R² is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is carboxyl;

R⁶ is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo($C_1$-$C_6$)alkylsulphonyl or optionally methyl-, fluorine-, chlorine-, cyano-substituted cyclopropyl;

$R^7$ and $R^8$ are each independently hydrogen, ($C_1$-$C_6$)alkyl, halo($C_2$-$C_6$)alkyl, cyano($C_1$-$C_6$)alkyl or ($C_3$-$C_6$)cycloalkyl, where the aforementioned radicals may optionally each be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano- or cyclopropyl-substituted cyclopropyl;

or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^9$ and $R^{10}$ are each independently hydrogen, ($C_1$-$C_6$)alkyl, halo($C_2$-$C_6$)alkyl, cyano($C_1$-$C_6$)alkyl, ($C_3$-$C_6$)cycloalkyl, or together are ($C_2$-$C_6$)alkylidene, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano- or cyclopropyl-substituted cyclopropyl;

or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^{11}$ is hydrogen; or is ($C_1$-$C_6$)alkyl, ($C_3$-$C_6$)cycloalkyl($C_1$-$C_3$)alkyl, ($C_2$-$C_6$)alkenyl, ($C_2$-$C_6$)alkynyl, halo($C_1$-$C_6$)alkyl, cyano($C_1$-$C_6$)alkyl, ($C_1$-$C_6$)alkoxy($C_1$-$C_6$)alkyl or phenyl($C_1$-$C_3$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl; or is ($C_3$-$C_6$)cycloalkyl, ($C_3$-$C_6$)cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiadiazolyl, oxazolyl, oxadiazolyl, pyrazolyl, triazolyl, where the aforementioned radicals may each be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;

$R^{12}$ is ($C_1$-$C_6$)alkyl, ($C_3$-$C_6$)cycloalkyl, ($C_2$-$C_6$)alkenyl, halo($C_1$-$C_6$)alkyl, cyano($C_1$-$C_6$)alkyl, phenyl($C_1$-$C_3$)alkyl or ($C_3$-$C_6$)cycloalkyl($C_1$-$C_6$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;

$R^{13}$ is halogen;

W is hydrogen or halogen optionally comprising fluorine or chlorine;

X, Y and Z are each independently hydrogen, fluorine, chlorine, bromine, cyano, nitro, amino, hydroxyl, ($C_1$-$C_4$)alkyl, ($C_1$-$C_4$)haloalkyl, ($C_2$-$C_4$)alkenyl, ($C_2$-$C_4$)alkynyl, ($C_1$-$C_4$)alkoxy, ($C_1$-$C_4$)haloalkoxy or aminothiocarbonyl;

or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and n is the number 0 or 1.

6. A compound according to claim 4 in which the substructure of formula (I-A) is a substructure which is selected from the group consisting of

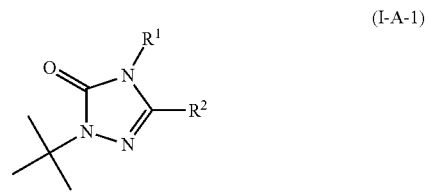

(I-A-1)

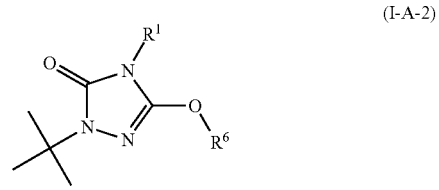

(I-A-2)

-continued (I-A-3) 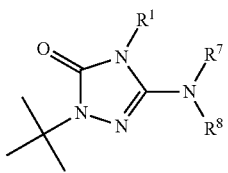

(I-A-4) 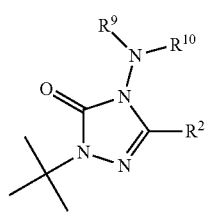

(I-A-5) 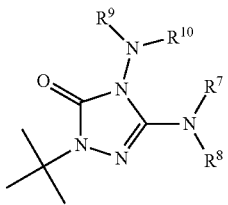

(I-A-6) 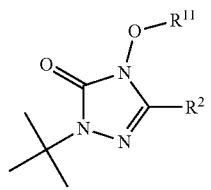

(I-A-8) 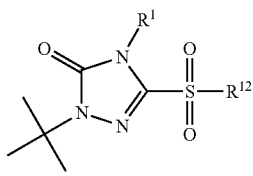

(I-A-9) 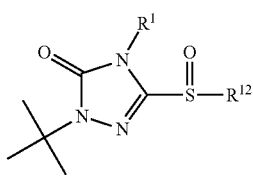

(I-A-10) 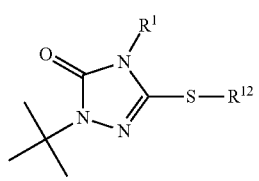

(I-A-11) 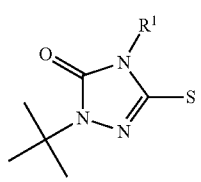

-continued (I-A-13) 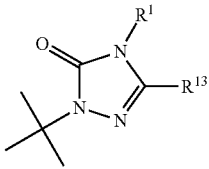

where $R^1$ is hydrogen; or is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyridyl, pyrimidyl, pyridazinyl, pyrazinyl, triazinyl, thiazolyl, thiazadiazolyl, oxazolyl, oxadiazolyl, pyrazolyl or triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

$R^2$ is hydrogen; or is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo($C_1$-$C_6$)alkylsulphonyl or optionally methyl-, fluorine-, chlorine-, cyano-substituted cyclopropyl; or
is carboxyl;

$R^6$ is hydrogen; or
is ($C_1$-$C_6$)alkyl, ($C_3$-$C_6$)cycloalkyl($C_1$-$C_3$)alkyl, ($C_2$-$C_6$)alkenyl, ($C_2$-$C_6$)alkynyl, halo($C_1$-$C_6$)alkyl, cyano($C_1$-$C_6$)alkyl, ($C_1$-$C_6$)alkoxy($C_1$-$C_6$)alkyl or phenyl($C_1$-$C_3$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl; or
is ($C_3$-$C_6$)cycloalkyl, ($C_3$-$C_6$)cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;

$R^7$ and $R^8$ are each independently hydrogen, ($C_1$-$C_6$)alkyl, halo($C_2$-$C_6$)alkyl, cyano($C_1$-$C_6$)alkyl or ($C_3$-$C_6$)cycloalkyl, where the aforementioned radicals may optionally each be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano- or cyclopropyl-substituted cyclopropyl;
or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^9$ and $R^{10}$ are each independently hydrogen, ($C_1$-$C_6$)alkyl, halo($C_2$-$C_6$)alkyl, cyano($C_1$-$C_6$)alkyl, ($C_3$-$C_6$)cycloalkyl, or together are ($C_2$-$C_6$)alkylidene, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano- or cyclopropyl-substituted cyclopropyl;
or both together with the nitrogen atom to which they are bonded are an optionally substituted triazolinone, triazolidinethione, tetrazolinone, tetrazolidinethione, oxadiazolinone, pyrrolidinone, pyrrolidinethione, imidazolinone, imidazolidinethione, pyrrolidinedione, thiazolidinone, thiazolidinethione, morpholine, thiomorpholine, thiomorpholine 1-oxide, thiomorpholine 1,1-dioxide, piperazine, N-methylpiperazine or N-ethylpiperazine;

$R^{11}$ is hydrogen; or
is ($C_1$-$C_6$)alkyl, ($C_3$-$C_6$)cycloalkyl($C_1$-$C_3$)alkyl, ($C_2$-$C_6$)alkenyl, ($C_2$-$C_6$)alkynyl, halo($C_1$-$C_6$)alkyl, cyano($C_1$-$C_6$)alkyl, ($C_1$-$C_6$)alkoxy($C_1$-$C_6$)alkyl or phenyl($C_1$-$C_3$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl; or
is ($C_3$-$C_6$)cycloalkyl, ($C_3$-$C_6$)cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;

$R^{12}$ is ($C_1$-$C_6$)alkyl, ($C_3$-$C_6$)cycloalkyl, ($C_2$-$C_6$)alkenyl, halo($C_1$-$C_6$)alkyl, cyano($C_1$-$C_6$)alkyl, phenyl($C_1$-$C_3$)alkyl or ($C_3$-$C_6$)cycloalkyl($C_1$-$C_6$)alkyl, where the aforementioned radicals may each optionally be mono- to trisubstituted by halogen, cyano, nitro, hydroxyl, amino, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylsulphinyl, ($C_1$-$C_6$)alkylsulphanyl, ($C_1$-$C_6$)alkylsulphonyl, halo($C_1$-$C_6$)alkylsulphinyl, halo($C_1$-$C_6$)alkylsulphanyl, halo($C_1$-$C_6$)alkylsulphonyl or optionally methyl-, fluorine-, chlorine-, cyano-substituted cyclopropyl;

$R^{13}$ is halogen;

W is hydrogen or halogen;

X, Y and Z are each independently hydrogen, fluorine, chlorine, bromine, cyano, nitro, amino, hydroxyl, ($C_1$-$C_4$)alkyl, ($C_1$-$C_4$)haloalkyl, ($C_2$-$C_4$)alkenyl, ($C_2$-$C_4$)alkynyl, ($C_1$-$C_4$)alkoxy, ($C_1$-$C_4$)haloalkoxy or aminothiocarbonyl;
or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and n is the number 0 or 1.

7. A compound according to claim 1, in which A and B together with the atoms to which they are bonded are a substructure of the formula (I-B)

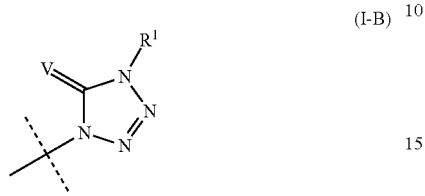

(I-B)

where

R$^1$ is hydrogen, cyano or nitro; or is (C$_1$-C$_6$)alkyl, (C$_3$-C$_6$)cycloalkyl(C$_1$-C$_6$)alkyl, halo(C$_2$-C$_6$)alkyl, cyano(C$_1$-C$_6$)alkyl, hydroxy(C$_1$-C$_6$)alkyl, (C$_1$-C$_6$)alkoxy(C$_1$-C$_6$)alkyl, amino(C$_1$-C$_6$)alkyl, (C$_1$-C$_6$)alkoxycarbonyl(C$_1$-C$_6$)alkyl, (C$_1$-C$_6$)alkylsulphanyl(C$_1$-C$_6$)alkyl, (C$_1$-C$_6$)alkylsulphinyl(C$_1$-C$_6$)alkyl, (C$_1$-C$_6$)alkylsulphonyl(C$_1$-C$_6$)alkyl, halo(C$_1$-C$_6$)alkylsulphanyl(C$_1$-C$_6$)alkyl, halo(C$_1$-C$_6$)alkylsulphinyl(C$_1$-C$_6$)alkyl, halo(C$_1$-C$_6$)alkylsulphonyl(C$_1$-C$_6$)alkyl, (C$_1$-C$_6$)alkoxy(C$_1$-C$_6$)alkylsulphanyl(C$_1$-C$_6$)alkyl, (C$_1$-C$_6$)alkoxy(C$_1$-C$_6$)alkylsulphinyl(C$_1$-C$_6$)alkyl, (C$_1$-C$_6$)alkoxy(C$_1$-C$_6$)alkylsulphonyl(C$_1$-C$_6$)alkyl, phenyl(C$_1$-C$_6$)alkyl, phenoxy(C$_1$-C$_6$)alkyl, phenylsulphanyl(C$_1$-C$_6$)alkyl, phenylsulphinyl(C$_1$-C$_6$)alkyl, phenylsulphonyl(C$_1$-C$_6$)alkyl, hetaryl(C$_1$-C$_6$)alkyl, hetaryloxy(C$_1$-C$_6$)alkyl, hetarylsulphanyl(C$_1$-C$_6$)alkyl, hetarylsulphinyl(C$_1$-C$_6$)alkyl, hetarylsulphonyl(C$_1$-C$_6$)alkyl, where the aforementioned radicals may each optionally be substituted and/or, under the condition that, in the case of an unsaturated radical, the defined minimum number of carbon atoms is 2, the radicals may be saturated or unsaturated; or is optionally substituted saturated or unsaturated (C$_3$-C$_6$)cycloalkyl which may optionally be interrupted by one or more heteroatoms; or is (C$_1$-C$_6$)alkylcarbonyl, halo(C$_1$-C$_6$)alkylcarbonyl, hydroxy(C$_1$-C$_6$)alkylcarbonyl, (C$_1$-C$_6$)alkoxy(C$_1$-C$_6$)alkylcarbonyl, phenylcarbonyl, hetarylcarbonyl, (C$_1$-C$_6$)alkoxycarbonyl, halo(C$_1$-C$_6$)alkoxycarbonyl, aryloxycarbonyl, aminocarbonyl, (C$_1$-C$_6$)alkylaminocarbonyl, di(C$_1$-C$_6$)alkylaminocarbonyl, (C$_3$-C$_6$)cycloalkylaminocarbonyl, di(C$_3$-C$_6$)cycloalkylaminocarbonyl, (C$_3$-C$_6$)cycloalkyl((C$_1$-C$_6$)alkyl)aminocarbonyl, arylaminocarbonyl, diarylaminocarbonyl, (C$_1$-C$_6$)alkyl(aryl)aminocarbonyl, (C$_3$-C$_6$)cycloalkyl(aryl)aminocarbonyl, (C$_1$-C$_6$)alkylaminothiocarbonyl, di(C$_1$-C$_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or is optionally substituted phenyl or optionally substituted hetaryl; or is (C$_1$-C$_6$)alkoxy, halo(C$_1$-C$_6$)alkoxy, (C$_3$-C$_6$)cycloalkyloxy, aryloxy, aryl(C$_1$-C$_6$)alkyloxy or carbonyloxy, where the aforementioned radicals may each optionally be substituted, or is hydroxyl; or is (C$_1$-C$_6$)alkylamino, halo(C$_1$-C$_6$)alkylamino, dihalo(C$_1$-C$_6$)alkylamino, di(C$_1$-C$_6$)alkylamino, (C$_3$-C$_6$)cycloalkylamino, di(C$_3$-C$_6$)cycloalkylamino, (C$_3$-C$_6$)cycloalkyl((C$_1$-C$_6$)alkyl)amino, arylamino, diarylamino, hetarylamino, dihetarylamino, (C$_1$-C$_6$)alkyl(aryl)amino, (C$_3$-C$_6$)cycloalkyl(aryl)amino, (C$_1$-C$_6$)alkylcarbonylamino, arylcarbonylamino, (C$_1$-C$_6$)alkoxycarbonylamino, aryloxycarbonylamino, (C$_1$-C$_6$)alkylcarbamoylamino, arylcarbamoylamino, (C$_1$-C$_6$)alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or is (C$_1$-C$_6$)alkylsulphanyl, (C$_1$-C$_6$)alkylsulphinyl, (C$_1$-C$_6$)alkylsulphonyl, halo(C$_1$-C$_6$)alkylsulphanyl, halo(C$_1$-C$_6$)alkylsulphinyl, halo(C$_1$-C$_6$)alkylsulphanyl, (C$_3$-C$_6$)cycloalkylsulphanyl, (C$_3$-C$_6$)cycloalkylsulphinyl, (C$_3$-C$_6$)cycloalkylsulphonyl, (C$_3$-C$_6$)cycloalkyl(C$_1$-C$_6$)alkylsulphanyl, (C$_3$-C$_6$)cycloalkyl(C$_1$-C$_6$)alkylsulphinyl, (C$_3$-C$_6$)cycloalkyl(C$_1$-C$_6$)alkylsulphonyl, arylsulphanyl, arylsulphinyl, arylsulphonyl, aryl(C$_1$-C$_6$)alkylsulphanyl, aryl(C$_1$-C$_6$)alkylsulphinyl, aryl(C$_1$-C$_6$)alkylsulphonyl, aminosulphonyl, (C$_1$-C$_6$)alkylaminosulphonyl, di(C$_1$-C$_6$)alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; and V is oxygen, sulphur or an optionally substituted nitrogen;

X, Y and Z each independently are hydrogen, halogen, hydroxyl, amino, cyano, nitro, OCN, SCN, SF$_5$; or are tri(C$_1$-C$_6$)alkylsilyl, (C$_1$-C$_6$)alkyl, halo(C$_1$-C$_6$)alkyl, cyano(C$_1$-C$_6$)alkyl, hydroxy(C$_1$-C$_6$)alkyl, (C$_1$-C$_6$)alkoxycarbonyl(C$_1$-C$_6$)alkyl, (C$_1$-C$_6$)alkoxy(C$_1$-C$_6$)alkyl, (C$_2$-C$_6$)alkenyl, halo(C$_2$-C$_6$)alkenyl, cyano(C$_2$-C$_6$)alkenyl, (C$_2$-C$_6$)alkynyl, halo(C$_2$-C$_6$)alkynyl, cyano(C$_2$-C$_6$)alkynyl, (C$_1$-C$_6$)alkoxy, halo(C$_1$-C$_6$)alkoxy, cyano(C$_1$-C$_6$)alkoxy, hydroxycarbonyl(C$_1$-C$_6$)alkoxy, (C$_1$-C$_6$)alkoxycarbonyl(C$_1$-C$_6$)alkoxy, (C$_1$-C$_6$)alkoxy(C$_1$-C$_6$)alkoxy, (C$_1$-C$_6$)alkylhydroxyimino, (C$_1$-C$_6$)alkoxyimino, (C$_1$-C$_6$)alkyl(C$_1$-C$_6$)alkoxyimino, halo(C$_1$-C$_6$)alkyl(C$_1$-C$_6$)alkoxyimino, (C$_1$-C$_6$)alkylthio, halo(C$_1$-C$_6$)alkylthio, (C$_1$-C$_6$)alkoxy(C$_1$-C$_6$)alkylthio, (C$_1$-C$_6$)alkylthio(C$_1$-C$_6$)alkyl, (C$_1$-C$_6$)alkylsulphinyl, halo(C$_1$-C$_6$)alkylsulphinyl, (C$_1$-C$_6$)alkoxy(C$_1$-C$_6$)alkylsulphinyl, (C$_1$-C$_6$)alkylsulphinyl(C$_1$-C$_6$)alkyl, (C$_1$-C$_6$)alkylsulphonyl, halo(C$_1$-C$_6$)alkylsulphonyl, (C$_1$-C$_6$)alkoxy(C$_1$-C$_6$)alkylsulphonyl, (C$_1$-C$_6$)alkylsulphonyl(C$_1$-C$_6$)alkyl, (C$_1$-C$_6$)alkylsulphonyloxy, (C$_1$-C$_6$)alkylcarbonyl, halo(C$_1$-C$_6$)alkylcarbonyl, carboxyl, (C$_1$-C$_6$)alkylcarbonyloxy, (C$_1$-C$_6$)alkoxycarbonyl, halo(C$_1$-C$_6$)alkoxycarbonyl, aminocarbonyl, (C$_1$-C$_6$)alkylaminocarbonyl, di(C$_1$-C$_6$)alkylaminocarbonyl, (C$_2$-C$_6$)alkenylaminocarbonyl, di(C$_2$-C$_6$)alkenylaminocarbonyl, (C$_3$-C$_6$)cyclo(C$_1$-C$_6$)alkylaminocarbonyl, (C$_1$-C$_6$)alkylsulphonylamino, aminosulphonyl, (C₁-C₆)alkylaminosulphonyl, di(C₁-C₆)alkylaminosulphonyl, (C₁-C₆)alkylsulphoximino, aminothiocarbonyl, (C₁-C₆)alkylaminothiocarbonyl or di(C₁-C₆)alkylaminothiocarbonyl, where all the aforementioned radicals may optionally be substituted by halogen; or are phenyl(C₁-C₃)alkyl, phenoxy, phenyl(C₁-C₃)alkyloxy, phenoxy(C₁-C₃)alkyl, phenylthio, phenylthio(C₁-C₃)alkyl, phenylsulphinyl, phenylsulphonyl, hetaryl(C₁-C₃)alkyl, hetaryloxy, hetaryl(C₁-C₃)alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are (C₃-C₆)cycloalkyl(C₁-C₃)alkyl, (C₃-C₆)cycloalkyloxy, (C₃-C₆)cycloalkyl(C₁-C₃)alkoxy, (C₃-C₆)cycloalkylthio, (C₃-C₆)cycloalkyl(C₁-C₃)alkylthio, (C₃-C₆)cycloalkylsulphinyl, (C₃-C₆)cycloalkyl(C₁-C₃)alkylsulphinyl, (C₃-C₆)cycloalkylsulphonyl, (C₃-C₆)cycloalkyl(C₁-C₃)alkylsulphonyl or (C₃-C₈)cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"

where R' and R" each independently are hydrogen, cyano, (C₁-C₆)alkyl, halo(C₁-C₆)alkyl, cyano(C₁-C₆)alkyl, hydroxy(C₁-C₆)alkyl, (C₁-C₆)alkoxy(C₁-C₆)alkyl, (C₁-C₆)alkylthio(C₁-C₆)alkyl, (C₂-C₆)alkenyl, halo(C₂-C₆)alkenyl, cyano(C₂-C₆)alkenyl, (C₂-C₆)alkynyl, halo(C₂-C₆)alkynyl, cyano(C₂-C₆)alkynyl, acyl or (C₁-C₆)alkoxycarbonyl; or R' and R" together with the nitrogen atom to which they are bonded may form an optionally identically or differently halogen-, cyano-, nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a (C₃-C₆)cycloalkyl, oxetanyl, oxolanyl, oxanyl, (C₃-C₈)cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

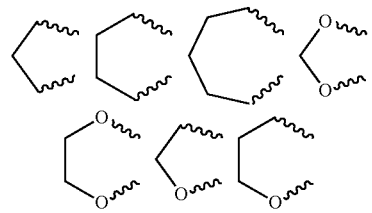

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

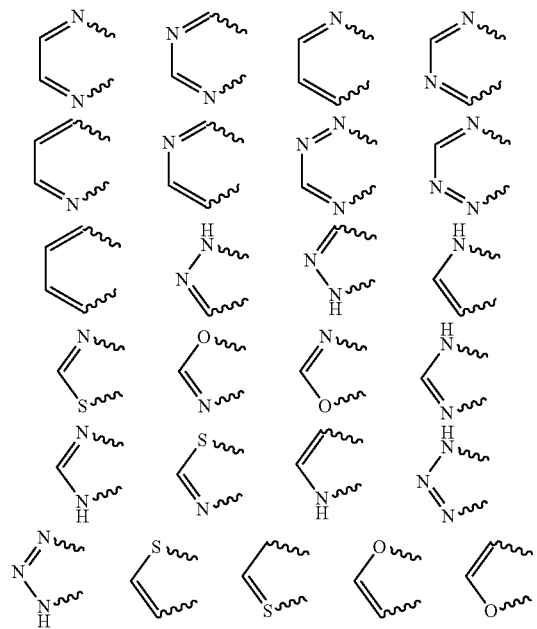

and n is the number 0 or 1.

8. A compound according to claim 7 in which the substructure of the formula (I-B) is a substructure which is selected from the group consisting of

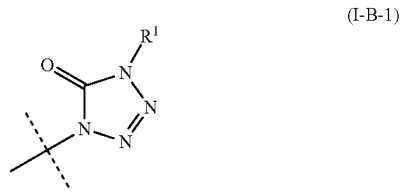

(I-B-1)

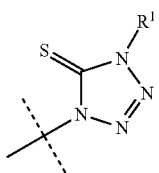

(I-B-2)

where
R¹ is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiadiazolyl, oxazolyl, oxadiazolyl, pyrazolyl or triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;
W is hydrogen or halogen, especially fluorine or chlorine;
X, Y and Z are each independently hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;
 or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
 or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and
n is the number 0 or 1.

9. A compound according to claim 1, in which A and B together with the atoms to which they are bonded are a substructure of the formula (I-C)

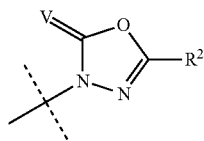

(I-C)

where
R² is hydrogen, cyano, halogen or nitro; or
is $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylthio$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or
is optionally substituted saturated or unsaturated $(C_3-C_6)$cycloalkyl which may optionally be interrupted by one or more heteroatoms; or
is $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or
is optionally substituted phenyl or optionally substituted hetaryl; or
is $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or is hydroxyl; or
is $(C_1-C_6)$alkylamino, di$(C_1-C_6)$alkylamino, halo$(C_1-C_6)$alkylamino, dihalo$(C_1-C_6)$alkylamino, $(C_3-C_6)$ cycloalkylamino, di($C_3$-$C_6$)cycloalkylamino, ($C_3$-$C_6$)cycloalkyl(($C_1$-$C_6$)alkyl)amino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or is ($C_1$-$C_6$)alkylsulphanyl, ($C_1$-$C_6$)alkylsulphinyl, ($C_1$-$C_6$)alkylsulphonyl, halo($C_1$-$C_6$)alkylsulphanyl, halo($C_1$-$C_6$)alkylsulphinyl, halo($C_1$-$C_6$)alkylsulphonyl, ($C_3$-$C_6$)cycloalkylsulphanyl, ($C_3$-$C_6$)cycloalkylsulphinyl, ($C_3$-$C_6$)cycloalkylsulphonyl, ($C_3$-$C_6$)cycloalkyl($C_1$-$C_6$)alkylsulphanyl, ($C_3$-$C_6$)cycloalkyl($C_1$-$C_6$)alkylsulphinyl, ($C_3$-$C_6$)cycloalkyl($C_1$-$C_6$)alkylsulphonyl, arylsulphanyl, arylsulphinyl, arylsulphonyl, aryl($C_1$-$C_6$)alkylsulphanyl, aryl($C_1$-$C_6$)alkylsulphinyl, aryl($C_1$-$C_6$)alkylsulphonyl, aminosulphonyl, ($C_1$-$C_6$)alkylaminosulphonyl, di($C_1$-$C_6$)alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; or is an optionally singly or multiply, identically or differently halogen-, cyano-, nitro-, hydroxyl-, amino-, ($C_1$-$C_6$)alkyl-, halo($C_1$-$C_6$)alkyl-, ($C_1$-$C_6$)alkoxy-, halo($C_1$-$C_6$)alkoxy-, ($C_1$-$C_6$)alkylsulphinyl-, ($C_1$-$C_6$)alkylsulphanyl-, ($C_1$-$C_6$)alkylsulphonyl-, halo($C_1$-$C_6$)alkylsulphinyl-, halo($C_1$-$C_6$)alkylsulphanyl-, halo($C_1$-$C_6$)alkylsulphonyl- or optionally substituted ($C_3$-$C_6$)cycloalkyl-substituted, saturated or unsaturated three- to six-membered ring optionally interrupted by heteroatoms from the group of O, S and N;

W is hydrogen or halogen;
V is oxygen, sulphur or an optionally substituted nitrogen;
X, Y and Z each independently
are hydrogen, halogen, hydroxyl, amino, cyano, nitro, OCN, SCN, $SF_5$; or
are tri($C_1$-$C_6$)alkylsilyl, ($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxycarbonyl($C_1$-$C_6$)alkyl, ($C_1$-$C_6$)alkoxy($C_1$-$C_6$)alkyl, ($C_2$-$C_6$)alkenyl, halo($C_2$-$C_6$)alkenyl, cyano($C_2$-$C_6$)alkenyl, ($C_2$-$C_6$)alkynyl, halo($C_2$-$C_6$)alkynyl, cyano($C_2$-$C_6$)alkynyl, ($C_1$-$C_6$)alkoxy, halo($C_1$-$C_6$)alkoxy, cyano($C_1$-$C_6$)alkoxy, hydroxycarbonyl($C_1$-$C_6$)alkoxy, ($C_1$-$C_6$)alkoxycarbonyl($C_1$-$C_6$)alkoxy, ($C_1$-$C_6$)alkoxy($C_1$-$C_6$)alkoxy, ($C_1$-$C_6$)alkylhydroxyimino, ($C_1$-$C_6$)alkoxyimino, ($C_1$-$C_6$)alkyl($C_1$-$C_6$)alkoxyimino, halo($C_1$-$C_6$)alkyl($C_1$-$C_6$)alkoxyimino, ($C_1$-$C_6$)alkylthio, halo($C_1$-$C_6$)alkylthio, ($C_1$-$C_6$)alkoxy($C_1$-$C_6$)alkylthio, ($C_1$-$C_6$)alkylthio($C_1$-$C_6$)alkyl, ($C_1$-$C_6$)alkylsulphinyl, halo($C_1$-$C_6$)alkylsulphinyl, ($C_1$-$C_6$)alkoxy($C_1$-$C_6$)alkylsulphinyl, ($C_1$-$C_6$)alkylsulphinyl($C_1$-$C_6$)alkyl, ($C_1$-$C_6$)alkylsulphonyl, halo($C_1$-$C_6$)alkylsulphonyl, ($C_1$-$C_6$)alkoxy($C_1$-$C_6$)alkylsulphonyl, ($C_1$-$C_6$)alkylsulphonyl($C_1$-$C_6$)alkyl, ($C_1$-$C_6$)alkylsulphonyloxy, ($C_1$-$C_6$)alkylcarbonyl, halo($C_1$-$C_6$)alkylcarbonyl, carboxyl, ($C_1$-$C_6$)alkylcarbonyloxy, ($C_1$-$C_6$)alkoxycarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_6$)cycloalkylaminocarbonyl, ($C_1$-$C_6$)alkylsulphonylamino, aminosulphonyl, ($C_1$-$C_6$)alkylaminosulphonyl, di($C_1$-$C_6$)alkylaminosulphonyl, ($C_1$-$C_6$)alkylsulphoximino, aminothiocarbonyl, ($C_1$-$C_6$)alkylaminothiocarbonyl or di($C_1$-$C_6$)alkylaminothiocarbonyl, where all the aforementioned radicals may optionally be substituted by halogen; or are phenyl($C_1$-$C_3$)alkyl, phenoxy, phenyl($C_1$-$C_3$)alkyloxy, phenoxy($C_1$-$C_3$)alkyl, phenylthio, phenylthio($C_1$-$C_3$)alkyl, phenylsulphinyl, phenylsulphonyl, hetaryl($C_1$-$C_3$)alkyl, hetaryloxy, hetaryl($C_1$-$C_3$)alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are ($C_3$-$C_6$)cycloalkyl($C_1$-$C_3$)alkyl, ($C_3$-$C_6$)cycloalkyloxy, ($C_3$-$C_6$)cycloalkyl($C_1$-$C_3$)alkoxy, ($C_3$-$C_6$)cycloalkylthio, ($C_3$-$C_6$)cycloalkyl($C_1$-$C_3$)alkylthio, ($C_3$-$C_6$)cycloalkylsulphinyl, ($C_3$-$C_6$)cycloalkyl($C_1$-$C_3$)alkylsulphinyl, ($C_3$-$C_6$)cycloalkylsulphonyl, ($C_3$-$C_6$)cycloalkyl($C_1$-$C_3$)alkylsulphonyl or ($C_3$-$C_8$)cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"
where R' and R" each independently
are hydrogen, cyano, ($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, ($C_1$-$C_6$)alkylthio($C_1$-$C_6$)alkyl, ($C_2$-$C_6$)alkenyl, halo($C_2$-$C_6$)alkenyl, cyano($C_2$-$C_6$)alkenyl, ($C_2$-$C_6$)alkynyl, halo($C_2$-$C_6$)alkynyl, cyano($C_2$-$C_6$)alkynyl, acyl or ($C_1$-$C_6$)alkoxycarbonyl; or
R' and R" together with the nitrogen atom to which they are bonded may form an optionally identically or differently halogen-, cyano-, nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a ($C_3$-$C_6$)cycloalkyl, oxetanyl, oxolanyl, oxanyl, ($C_3$-$C_8$)cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

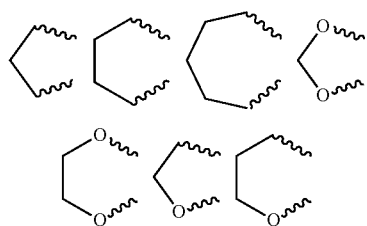

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

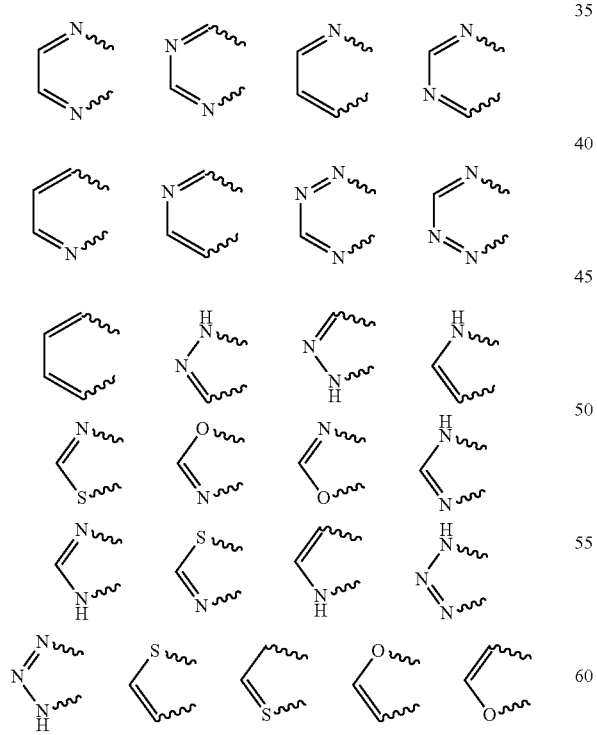

n is the number 0 or 1.

10. A compound according to claim 9 in which the substructure of formula (I-C) is the substructure (I-C-1)

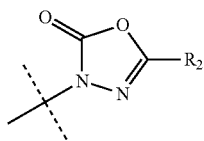

(I-C-1)

where
R² is hydrogen; or
  is (C₁-C₆)alkyl, (C₃-C₆)cycloalkyl(C₁-C₆)alkyl, (C₂-C₆)alkenyl, (C₂-C₆)alkynyl, halo(C₁-C₆)alkyl, cyano(C₁-C₆)alkyl, (C₁-C₆)alkoxy(C₁-C₆)alkyl or phenyl(C₁-C₃)alkyl, where the aforementioned radicals may each optionally be substituted; or
  is (C₃-C₆)cycloalkyl, (C₃-C₆)cycloalkenyl, phenyl, pyridyl, pyrimidyl, pyridazinyl, pyrazinyl, furyl, thienyl, triazinyl, thiazolyl, thiadiazolyl, oxazolyl, oxadiazolyl, pyrazolyl or triazolyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo(C₁-C₃)alkylsulphanyl or optionally methyl-, fluorine-, chlorine-, cyano-substituted cyclopropyl;
W is hydrogen or halogen, especially F or Cl;
X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;
Z is hydrogen; and
n is the number 0 or 1.

11. A compound according to claim 1, in which
A and B together with the atoms to which they are bonded are a substructure of the formula (I-D)

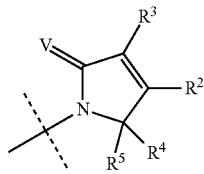

(I-D)

where
R², R³, R⁴ and R⁵ each independently
  are hydrogen, cyano, halogen or nitro; or
  are (C₁-C₆)alkyl, (C₃-C₆)cycloalkyl(C₁-C₆)alkyl, halo(C₁-C₆)alkyl, cyano(C₁-C₆)alkyl, hydroxy(C₁-C₆)alkyl, (C₁-C₆)alkoxy(C₁-C₆)alkyl, amino(C₁-C₆)alkyl, (C₁-C₆)alkoxycarbonyl(C₁-C₆)alkyl, (C₁-C₆)alkylsulphanyl(C₁-C₆)alkyl, (C₁-C₆)alkylsulphinyl(C₁-C₆)alkyl, (C₁-C₆)alkylsulphonyl(C₁-C₆)alkyl, halo(C₁-C₆)alkylsulphanyl(C₁-C₆)alkyl, halo(C₁-C₆)alkylsulphinyl(C₁-C₆)alkyl, halo(C₁-C₆)alkylsulphonyl(C₁-C₆)alkyl, (C₁-C₆)alkoxy(C₁-C₆)alkylsulphanyl(C₁-C₆)alkyl, (C₁-C₆)alkoxy(C₁-C₆)alkylsulphinyl(C₁-C₆)alkyl, (C₁-C₆)alkoxy(C₁-C₆)alkylsulphonyl(C₁-C₆)alkyl, phenyl(C₁-C₆)alkyl, phenoxy(C₁-C₆)alkyl, phenylsulphanyl(C₁-C₆)alkyl, phenylsulphinyl(C₁-C₆)alkyl, phenylsulphonyl(C₁-C₆)alkyl, hetaryl(C₁-C₆)alkyl, hetaryloxy(C₁-C₆)alkyl, hetarylthio(C₁-C₆)alkyl, where the aforementioned radicals may each optionally be substituted and/or, under the condition that, in the case of an unsaturated radical, the defined minimum number of carbon atoms is 2, the radicals may be saturated or unsaturated; or are optionally substituted saturated or unsaturated $(C_3-C_6)$cycloalkyl which may optionally be interrupted by one or more heteroatoms; or are $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or are carbonyl or carboxyl; or are optionally substituted phenyl or optionally substituted hetaryl; or are $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or are hydroxyl; or are $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or are amino; or are $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or are sulphanyl; or $R^4$ and $R^5$ together with the atom to which they are bonded may form an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N; or $R^2$ is an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

W is hydrogen or halogen;

V is oxygen, sulphur or an optionally substituted nitrogen;

W is hydrogen or halogen;

X, Y and Z each independently are hydrogen, halogen, hydroxyl, amino, cyano, nitro, OCN, SCN, $SF_5$; or are tri$(C_1-C_6)$alkylsilyl, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxycarbonyl$(C_1-C_6)$alkyl, $(C_1-C_6)$alkoxy$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, $(C_1-C_6)$alkoxy, halo$(C_1-C_6)$alkoxy, cyano$(C_1-C_6)$alkoxy, hydroxycarbonyl$(C_1-C_6)$alkoxy, $(C_1-C_6)$alkoxycarbonyl$(C_1-C_6)$alkoxy, $(C_1-C_6)$alkoxy$(C_1-C_6)$alkoxy, $(C_1-C_6)$alkylhydroxyimino, $(C_1-C_6)$alkoxyimino, $(C_1-C_6)$alkyl$(C_1-C_6)$alkoxyimino, halo$(C_1-C_6)$alkyl$(C_1-C_6)$alkoxyimino, $(C_1-C_6)$alkylthio, halo$(C_1-C_6)$alkylthio, $(C_1-C_6)$alkoxy$(C_1-C_6)$alkylthio, $(C_1-C_6)$alkylthio$(C_1-C_6)$alkyl, $(C_1-C_6)$alkylsulphinyl, halo$(C_1-C_6)$alkylsulphinyl, $(C_1-C_6)$alkoxy$(C_1-C_6)$alkylsulphinyl, $(C_1-C_6)$alkylsulphinyl$(C_1-C_6)$alkyl, $(C_1-C_6)$alkylsulphonyl, halo$(C_1-C_6)$alkylsulphonyl, $(C_1-C_6)$alkoxy$(C_1-C_6)$alkylsulphonyl, $(C_1-C_6)$alkylsulphonyl$(C_1-C_6)$alkyl, $(C_1-C_6)$alkylsulphonyloxy, $(C_1-C_6)$alkylcarbonyl, halo$(C_1-C_6)$alkylcarbonyl, carboxyl, $(C_1-C_6)$alkylcarbonyloxy, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_2-C_6)$alkenylaminocarbonyl, di$(C_2-C_6)$alkenylaminocarbonyl, $(C_3-C_6)$cycloalkylaminocarbonyl, $(C_1-C_6)$alkylsulphonylamino, aminosulphonyl, $(C_1-C_6)$alkylaminosulphonyl, di$(C_1-C_6)$alkylaminosulphonyl, $(C_1-C_6)$alkylsulphoximino, aminothiocarbonyl, $(C_1-C_6)$alkylaminothiocarbonyl or di$(C_1-C_6)$alkylaminothiocarbonyl, where all the aforementioned radicals may optionally be substituted by halogen; or are phenyl$(C_1-C_3)$alkyl, phenoxy, phenyl$(C_1-C_3)$alkyloxy, phenoxy$(C_1-C_3)$alkyl, phenylthio, phenylthio ($C_1$-$C_3$)alkyl, phenylsulphinyl, phenylsulphonyl, hetaryl($C_1$-$C_3$)alkyl, hetaryloxy, hetaryl($C_1$-$C_3$)alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are ($C_3$-$C_6$)cycloalkyl($C_1$-$C_3$)alkyl, ($C_3$-$C_6$)cycloalkyloxy, ($C_3$-$C_6$)cycloalkyl($C_1$-$C_3$)alkoxy, ($C_3$-$C_6$)cycloalkylthio, ($C_3$-$C_6$)cycloalkyl($C_1$-$C_3$)alkylthio, ($C_3$-$C_6$)cycloalkylsulphinyl, ($C_3$-$C_6$)cycloalkyl($C_1$-$C_3$)alkylsulphinyl, ($C_3$-$C_6$)cycloalkylsulphonyl, ($C_3$-$C_6$)cycloalkyl($C_1$-$C_3$)alkylsulphonyl or ($C_3$-$C_8$)cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"

where R' and R" each independently are hydrogen, cyano, ($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, ($C_1$-$C_6$)alkylthio($C_1$-$C_6$)alkyl, ($C_2$-$C_6$)alkenyl, halo($C_2$-$C_6$)alkenyl, cyano($C_2$-$C_6$)alkenyl, ($C_2$-$C_6$)alkynyl, halo($C_2$-$C_6$)alkynyl, cyano($C_2$-$C_6$)alkynyl, acyl or ($C_1$-$C_6$)alkoxycarbonyl; or R' and R" together with the nitrogen atom to which they are bonded may form an optionally identically or differently halogen-, cyano- nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a ($C_3$-$C_6$)cycloalkyl, oxetanyl, oxolanyl, oxanyl, ($C_3$-$C_8$)cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

-continued

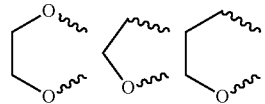

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

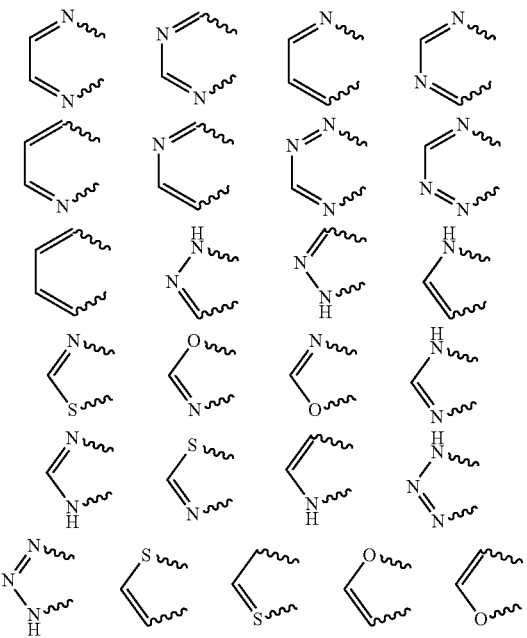

n is the number 0 or 1.

12. A compound according to claim 11 in which the substructure of formula (I-D) is a substructure which is selected from the group consisting of

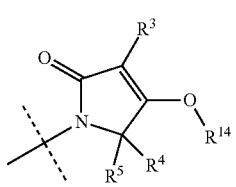

(I-D-1)

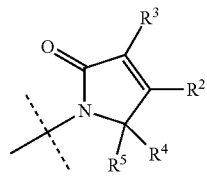

(I-D-2)

where
R², R³, R⁴ and R⁵ each independently
- are hydrogen; or
- are $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
- are $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
- are carboxyl; or
- R⁴ and R⁵ together with the atom to which they are bonded may form an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

R¹⁴ is $(C_1-C_6)$alkyl, halo$(C_1-C_6)$alkyl, cyano$(C_1-C_6)$alkyl, $(C_1-C_6)$alkoxy$(C_1-C_3)$alkyl, phenyl$(C_1-C_3)$alkyl, $(C_3-C_6)$cycloalkyl or $(C_3-C_6)$cycloalkyl$(C_1-C_3)$alkyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

X, Y and Z are each independently hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;
- or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
- or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;

n is the number 0 or 1.

13. A compound according to claim 1, in which
A and B together with the atoms to which they are bonded are a substructure of the formula (I-E)

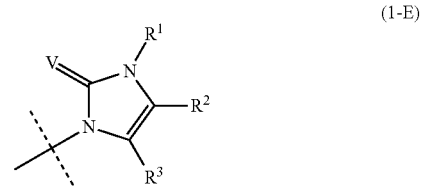

(1-E)

R¹ is hydrogen, cyano or nitro; or
- is $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylsulphanyl$(C_1-C_6)$alkyl, hetarylsulphinyl$(C_1-C_6)$alkyl, hetarylsulphonyl$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or
- is optionally substituted saturated or unsaturated $(C_3-C_6)$cycloalkyl which may optionally be interrupted by one or more heteroatoms; or
- is $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or is optionally substituted phenyl or optionally substituted hetaryl; or is $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or is hydroxyl; or is $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or is amino; or is $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or is sulphanyl; and $R^2$ and $R^3$ each independently are hydrogen, cyano, halogen or nitro; or are $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylthio$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or are optionally substituted saturated or unsaturated $(C_3-C_6)$cycloalkyl which may optionally be interrupted by one or more heteroatoms; or are $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or are carbonyl or carboxyl; or are optionally substituted phenyl or optionally substituted hetaryl; or are $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or are hydroxyl; or are $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or are amino; or are $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or are sulphanyl; or are an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$ alkylsulphanyl-, halo($C_1$-$C_6$)alkylsulphonyl- or optionally substituted ($C_3$-$C_6$)cycloalkyl-substituted, saturated or unsaturated three- to six-membered ring optionally interrupted by heteroatoms from the group of O, S and N;

W is hydrogen or halogen;

V is oxygen, sulphur or an optionally substituted nitrogen;

X, Y and Z each independently are hydrogen, halogen, hydroxyl, amino, cyano, nitro, OCN, SCN, $SF_5$; or are tri($C_1$-$C_6$)alkylsilyl, ($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxycarbonyl($C_1$-$C_6$)alkyl, ($C_1$-$C_6$)alkoxy($C_1$-$C_6$)alkyl, ($C_2$-$C_6$)alkenyl, halo($C_2$-$C_6$)alkenyl, cyano($C_2$-$C_6$)alkenyl, ($C_2$-$C_6$)alkynyl, halo($C_2$-$C_6$)alkynyl, cyano($C_2$-$C_6$)alkynyl, ($C_1$-$C_6$)alkoxy, halo($C_1$-$C_6$)alkoxy, cyano($C_1$-$C_6$)alkoxy, hydroxycarbonyl($C_1$-$C_6$)alkoxy, ($C_1$-$C_6$)alkoxycarbonyl($C_1$-$C_6$)alkoxy, ($C_1$-$C_6$)alkoxy($C_1$-$C_6$)alkoxy, ($C_1$-$C_6$)alkylhydroxyimino, ($C_1$-$C_6$)alkoxyimino, ($C_1$-$C_6$)alkyl($C_1$-$C_6$)alkoxyimino, halo($C_1$-$C_6$)alkyl($C_1$-$C_6$)alkoxyimino, ($C_1$-$C_6$)alkylthio, halo($C_1$-$C_6$)alkylthio, ($C_1$-$C_6$)alkoxy($C_1$-$C_6$)alkylthio, ($C_1$-$C_6$)alkylthio($C_1$-$C_6$)alkyl, ($C_1$-$C_6$)alkylsulphinyl, halo($C_1$-$C_6$)alkylsulphinyl, ($C_1$-$C_6$)alkoxy($C_1$-$C_6$)alkylsulphinyl, ($C_1$-$C_6$)alkylsulphinyl($C_1$-$C_6$)alkyl, ($C_1$-$C_6$)alkylsulphonyl, halo($C_1$-$C_6$)alkylsulphonyl, ($C_1$-$C_6$)alkoxy($C_1$-$C_6$)alkylsulphonyl, ($C_1$-$C_6$)alkylsulphonyl($C_1$-$C_6$)alkyl, ($C_1$-$C_6$)alkylsulphonyloxy, ($C_1$-$C_6$)alkylcarbonyl, halo($C_1$-$C_6$)alkylcarbonyl, carboxyl, ($C_1$-$C_6$)alkylcarbonyloxy, ($C_1$-$C_6$)alkoxycarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_6$)cycloalkylaminocarbonyl, ($C_1$-$C_6$)alkylsulphonylamino, aminosulphonyl, ($C_1$-$C_6$)alkylaminosulphonyl, di($C_1$-$C_6$)alkylaminosulphonyl, ($C_1$-$C_6$)alkylsulphoximino, aminothiocarbonyl, ($C_1$-$C_6$)alkylaminothiocarbonyl or di($C_1$-$C_6$)alkylaminothiocarbonyl, where all the aforementioned radicals may optionally be substituted by halogen; or are phenyl($C_1$-$C_3$)alkyl, phenoxy, phenyl($C_1$-$C_3$)alkyloxy, phenoxy($C_1$-$C_3$)alkyl, phenylthio, phenylthio($C_1$-$C_3$)alkyl, phenylsulphinyl, phenylsulphonyl, hetaryl($C_1$-$C_3$)alkyl, hetaryloxy, hetaryl($C_1$-$C_3$)alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are ($C_3$-$C_6$)cycloalkyl($C_1$-$C_3$)alkyl, ($C_3$-$C_6$)cycloalkyloxy, ($C_3$-$C_6$)cycloalkyl($C_1$-$C_3$)alkoxy, ($C_3$-$C_6$)cycloalkylthio, ($C_3$-$C_6$)cycloalkyl($C_1$-$C_3$)alkylthio, ($C_3$-$C_6$)cycloalkylsulphinyl, ($C_3$-$C_6$)cycloalkyl($C_1$-$C_3$)alkylsulphinyl, ($C_3$-$C_6$)cycloalkylsulphonyl, ($C_3$-$C_6$)cycloalkyl($C_1$-$C_3$)alkylsulphonyl or ($C_3$-$C_8$)cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"

where R' and R" each independently are hydrogen, cyano, ($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, ($C_1$-$C_6$)alkylthio($C_1$-$C_6$)alkyl, ($C_2$-$C_6$)alkenyl, halo($C_2$-$C_6$)alkenyl, cyano($C_2$-$C_6$)alkenyl, ($C_2$-$C_6$)alkynyl, halo($C_2$-$C_6$)alkynyl, cyano($C_2$-$C_6$)alkynyl, acyl or ($C_1$-$C_6$)alkoxycarbonyl; or R' and R" together with the nitrogen atom to which they are bonded may form an optionally identically or differently halogen-, cyano-, nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a ($C_3$-$C_6$)cycloalkyl, oxetanyl, oxolanyl, oxanyl, ($C_3$-$C_8$)cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

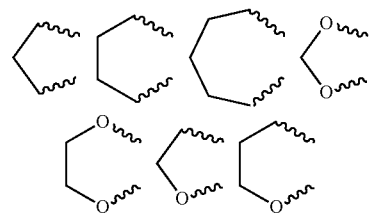

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

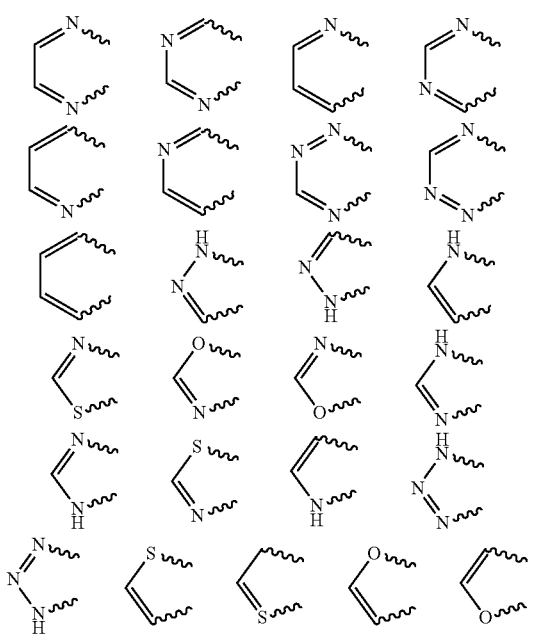

and
n is the number 0 or 1.

14. A compound according to claim 13 in which the substructure of formula (I-E) is a substructure of formula (I-E-1)

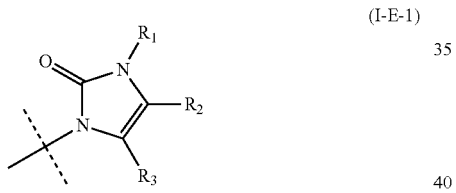
(I-E-1)

where
R¹ is hydrogen; or
is (C₁-C₆)alkyl, (C₃-C₆)cycloalkyl(C₁-C₃)alkyl, (C₂-C₆)alkenyl, (C₂-C₆)alkynyl, halo(C₂-C₆)alkyl, cyano(C₁-C₆)alkyl, (C₁-C₆)alkoxy(C₁-C₆)alkyl or phenyl(C₁-C₃)alkyl, where the aforementioned radicals may each optionally be mono- to trisubstituted by halogen, cyano, nitro, hydroxyl, amino, (C₁-C₆)alkyl, halo(C₁-C₆)alkyl, (C₁-C₆)alkoxy, halo(C₁-C₆)alkoxy, (C₁-C₆)alkylsulphinyl, (C₁-C₆)alkylsulphanyl, (C₁-C₆)alkylsulphonyl, halo(C₁-C₆)alkylsulphinyl, halo(C₁-C₆)alkylsulphanyl, halo(C₁-C₆)alkylsulphonyl or optionally methyl-, fluorine-, chlorine-, cyano-substituted cyclopropyl; or
is (C₃-C₆)cycloalkyl, (C₃-C₆)cycloalkenyl, oxetanyl, oxolanyl, oxanyl, phenyl, pyrimidyl, pyridazinyl, pyrazinyl, triazinyl, thiazolyl, thiazadiazolyl, oxazolyl, oxadiazolyl, pyrazolyl or triazolyl, where the aforementioned radicals may each be mono- to trisubstituted by halogen, cyano, nitro, hydroxyl, amino, (C₁-C₆)alkyl, halo(C₁-C₆)alkyl, (C₁-C₆)alkoxy, halo(C₁-C₆)alkoxy, (C₁-C₆)alkylsulphinyl, (C₁-C₆)alkylsulphanyl, (C₁-C₆)alkylsulphonyl, halo(C₁-C₆)alkyl s ulphinyl, halo(C₁-C₆)alkylsulphanyl, halo(C₁-C₆)alkylsulphonyl or optionally methyl-, fluorine-, chlorine-, cyano-substituted cyclopropyl;

$R^2$ and $R^3$ each independently are hydrogen; or
are (C₁-C₆)alkyl, (C₃-C₆)cycloalkyl(C₁-C₃)alkyl, (C₂-C₆)alkenyl, (C₂-C₆)alkynyl, halo(C₁-C₆)alkyl, cyano(C₁-C₆)alkyl, (C₁-C₆)alkoxy(C₁-C₆)alkyl or phenyl(C₁-C₃)alkyl, where the aforementioned radicals may each optionally be mono- to trisubstituted by halogen, cyano, nitro, hydroxyl, amino, (C₁-C₆)alkyl, halo(C₁-C₆)alkyl, (C₁-C₆)alkoxy, halo(C₁-C₆)alkoxy, (C₁-C₆)alkylsulphinyl, (C₁-C₆)alkylsulphanyl, (C₁-C₆)alkylsulphonyl, halo(C₁-C₆)alkylsulphinyl, halo(C₁-C₆)alkylsulphanyl, halo(C₁-C₆)alkylsulphonyl or optionally methyl-, fluorine-, chlorine-, cyano-substituted cyclopropyl; or
are (C₃-C₆)cycloalkyl, (C₃-C₆)cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, (C₁-C₆)alkyl, halo(C₁-C₆)alkyl, (C₁-C₆)alkoxy, halo(C₁-C₆)alkoxy, (C₁-C₆)alkylsulphinyl, (C₁-C₆)alkylsulphanyl, (C₁-C₆)alkylsulphonyl, halo(C₁-C₆)alkylsulphinyl, halo(C₁-C₆)alkylsulphanyl, halo(C₁-C₆)alkylsulphonyl or optionally methyl-, fluorine-, chlorine-, cyano-substituted cyclopropyl;
W is hydrogen or halogen, especially fluorine or chlorine;
X, Y and Z are each independently hydrogen, fluorine, chlorine, bromine, cyano, nitro, amino, hydroxyl, (C₁-C₄)alkyl, (C₁-C₄)haloalkyl, (C₂-C₄)alkenyl, (C₂-C₄)alkynyl, (C₁-C₄)alkoxy, (C₁-C₄)haloalkoxy or aminothiocarbonyl;
or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and
n is the number 0 or 1.
15. A compound according to claim 1, in which
A and B together with the atoms to which they are bonded are a substructure of formula (I-F)

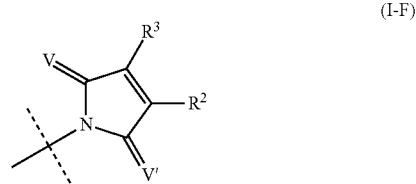
(I-F)

$R^2$ and $R^3$ each independently
- are hydrogen, cyano, halogen or nitro; or
- are $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulphanyl$(C_1-C_6)$alkyl, $(C_1-C_6)$alkylsulphinyl$(C_1-C_6)$alkyl, $(C_1-C_6)$alkylsulphonyl$(C_1-C_6)$alkyl, halo$(C_1-C_6)$alkylsulphanyl$(C_1-C_6)$alkyl, halo$(C_1-C_6)$alkylsulphinyl$(C_1-C_6)$alkyl, halo$(C_1-C_6)$alkylsulphonyl$(C_1-C_6)$alkyl, $(C_1-C_6)$alkoxy$(C_1-C_6)$alkylsulphanyl$(C_1-C_6)$alkyl, $(C_1-C_6)$alkoxy$(C_1-C_6)$alkylsulphinyl$(C_1-C_6)$alkyl, $(C_1-C_6)$alkoxy$(C_1-C_6)$alkylsulphonyl$(C_1-C_6)$alkyl, phenyl$(C_1-C_6)$alkyl, phenoxy$(C_1-C_6)$alkyl, phenylsulphanyl$(C_1-C_6)$alkyl, phenylsulphinyl$(C_1-C_6)$alkyl, phenylsulphonyl$(C_1-C_6)$alkyl, hetaryl$(C_1-C_6)$alkyl, hetaryloxy$(C_1-C_6)$alkyl, hetarylthio$(C_1-C_6)$alkyl, where the aforementioned radicals may each optionally be substituted and/or, under the condition that, in the case of an unsaturated radical, the defined minimum number of carbon atoms is 2, the radicals may be saturated or unsaturated; or
- are optionally substituted saturated or unsaturated $(C_3-C_6)$cycloalkyl which may optionally be interrupted by one or more heteroatoms; or
- are $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or are carbonyl or carboxyl; or
- are optionally substituted phenyl or optionally substituted hetaryl; or
- are $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or are hydroxyl; or
- are $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or are amino; or
- are $(C_1-C_6)$alkylsulphanyl, $(C_1-C_6)$alkylsulphinyl, $(C_1-C_6)$alkylsulphonyl, halo$(C_1-C_6)$alkylsulphanyl, halo$(C_1-C_6)$alkylsulphinyl, halo$(C_1-C_6)$alkylsulphonyl, $(C_3-C_6)$cycloalkylsulphanyl, $(C_3-C_6)$cycloalkylsulphinyl, $(C_3-C_6)$cycloalkylsulphonyl, $(C_3-C_6)$cycloalkyl$(C_1-C_6)$alkylsulphanyl, $(C_3-C_6)$cycloalkyl$(C_1-C_6)$alkylsulphinyl, $(C_3-C_6)$cycloalkyl$(C_1-C_6)$alkylsulphonyl, arylsulphanyl, arylsulphinyl, arylsulphonyl, aryl$(C_1-C_6)$alkylsulphanyl, aryl$(C_1-C_6)$alkylsulphinyl, aryl$(C_1-C_6)$alkylsulphonyl, aminosulphonyl, $(C_1-C_6)$alkylaminosulphonyl, di$(C_1-C_6)$alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or are sulphanyl; or
- are an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

W is hydrogen or halogen;

V and V' each independently
- are oxygen, sulphur or an optionally substituted nitrogen;

X, Y and Z each independently
- are hydrogen, halogen, hydroxyl, amino, cyano, nitro, OCN, SCN, $SF_5$; or
- are tri$(C_1-C_6)$alkylsilyl, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxycarbonyl$(C_1-C_6)$alkyl, $(C_1-C_6)$alkoxy$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, $(C_1-C_6)$alkoxy, halo$(C_1-C_6)$alkoxy, cyano$(C_1-C_6)$alkoxy, hydroxycarbonyl$(C_1-C_6)$alkoxy, $(C_1-C_6)$alkoxycarbonyl$(C_1-C_6)$alkoxy, $(C_1-C_6)$alkoxy$(C_1-C_6)$alkoxy, $(C_1-C_6)$alkylhydroxyimino, $(C_1-C_6)$alkoxyimino, $(C_1-C_6)$alkyl$(C_1-C_6)$alkoxyimino, halo$(C_1-C_6)$alkyl$(C_1-C_6)$alkoxyimino, $(C_1-C_6)$alkylthio, halo$(C_1-C_6)$alkylthio, $(C_1-C_6)$alkoxy$(C_1-C_6)$alkylthio, $(C_1-C_6)$alkylthio$(C_1-C_6)$alkyl, $(C_1-C_6)$alkylsulphinyl, halo$(C_1-C_6)$alkylsulphinyl, $(C_1-C_6)$alkoxy$(C_1-C_6)$alkylsulphinyl, $(C_1-C_6)$alkylsulphinyl$(C_1-C_6)$alkyl, $(C_1-C_6)$alkylsulphonyl, halo$(C_1-C_6)$alkylsulphonyl, $(C_1-C_6)$alkoxy$(C_1-C_6)$alkylsulphonyl, $(C_1-C_6)$alkylsulphonyl$(C_1-C_6)$alkyl, $(C_1-C_6)$alkylsulphonyloxy, $(C_1-C_6)$alkylcarbonyl, halo$(C_1-C_6)$alkylcarbonyl, carboxyl, $(C_1-C_6)$alkylcarbonyloxy, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_2-C_6)$alkenylaminocarbonyl, di$(C_2-C_6)$alkenylaminocarbonyl, $(C_3-C_6)$cyclo$(C_1-C_6)$alkylaminocarbonyl, $(C_1-C_6)$alkylsulphonylamino, aminosulphonyl, $(C_1-C_6)$alkylaminosulphonyl, di$(C_1-C_6)$alkylaminosulphonyl, $(C_1-C_6)$alkylsulphoximino, aminothiocarbonyl, (C$_1$-C$_6$)alkylaminothiocarbonyl or di(C$_1$-C$_6$)alkylaminothiocarbonyl, where all the aforementioned radicals may optionally be substituted by halogen; or are phenyl(C$_1$-C$_3$)alkyl, phenoxy, phenyl(C$_1$-C$_3$)alkyloxy, phenoxy(C$_1$-C$_3$)alkyl, phenylthio, phenylthio (C$_1$-C$_3$)alkyl, phenylsulphinyl, phenylsulphonyl, hetaryl(C$_1$-C$_3$)alkyl, hetaryloxy, hetaryl(C$_1$-C$_3$)alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are (C$_3$-C$_6$)cycloalkyl(C$_1$-C$_3$)alkyl, (C$_3$-C$_6$)cycloalkyloxy, (C$_3$-C$_6$)cycloalkyl(C$_1$-C$_3$)alkoxy, (C$_3$-C$_6$)cycloalkylthio, (C$_3$-C$_6$)cycloalkyl(C$_1$-C$_3$)alkylthio, (C$_3$-C$_6$)cycloalkylsulphinyl, (C$_3$-C$_6$)cycloalkyl(C$_1$-C$_3$)alkylsulphinyl, (C$_3$-C$_6$)cycloalkylsulphonyl, (C$_3$-C$_6$)cycloalkyl(C$_1$-C$_3$)alkylsulphonyl or (C$_3$-C$_8$)cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"
where R' and R" each independently
are hydrogen, cyano, (C$_1$-C$_6$)alkyl, halo(C$_1$-C$_6$)alkyl, cyano(C$_1$-C$_6$)alkyl, hydroxy(C$_1$-C$_6$)alkyl, (C$_1$-C$_6$)alkoxy(C$_1$-C$_6$)alkyl, (C$_1$-C$_6$)alkylthio(C$_1$-C$_6$)alkyl, (C$_2$-C$_6$)alkenyl, halo(C$_2$-C$_6$)alkenyl, cyano(C$_2$-C$_6$)alkenyl, (C$_2$-C$_6$)alkynyl, halo(C$_2$-C$_6$)alkynyl, cyano(C$_2$-C$_6$)alkynyl, acyl or (C$_1$-C$_6$)alkoxycarbonyl; or R' and R" together with the nitrogen atom to which they are bonded may form an optionally identically or differently halogen-, cyano-nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a (C$_3$-C$_6$)cycloalkyl, oxetanyl, oxolanyl, oxanyl, (C$_3$-C$_8$)cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent S1 which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

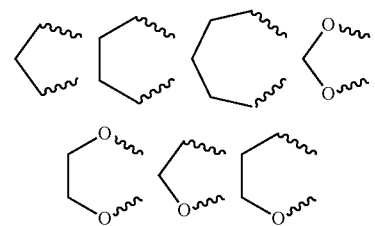

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

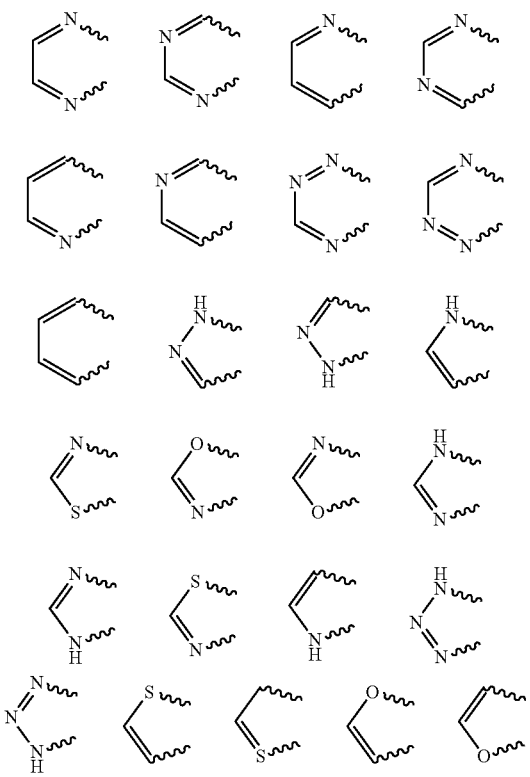

and n is the number 0 or 1.

16. An agrochemical composition, comprising at least one compound of formula (I) according to claim 1, and one or more extenders and/or surfactants.

17. A compound according to claim 15 in which the substructure of formula (I-F) is a substructure of the formula (I-F-1)

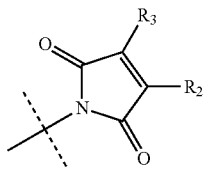

(I-F-1)

where

R² and R³ each independently are hydrogen or halogen; or
are (C₁-C₆)alkyl, (C₃-C₆)cycloalkyl(C₁-C₆)alkyl, (C₂-C₆)alkenyl, (C₂-C₆)alkynyl, halo(C₁-C₆)alkyl, cyano(C₁-C₆)alkyl, (C₁-C₆)alkoxy(C₁-C₆)alkyl or phenyl(C₁-C₃)alkyl, where the aforementioned radicals may each optionally be substituted; or
are (C₃-C₆)cycloalkyl, (C₃-C₆)cycloalkenyl or phenyl, where the aforementioned radicals may each be mono- to trisubstituted by halogen, cyano, nitro, hydroxyl, amino, methyl, ethyl, isopropyl, tert-butyl, trifluoromethyl, difluoromethyl, methoxy, trifluoromethoxy, difluoromethoxy, cyano, amino, hydroxyl, nitro, halo(C₁-C₃)alkylsulphanyl or optionally methyl-, fluorine-, chlorine-, cyano-substituted cyclopropyl;

W is hydrogen or halogen, optionally F or Cl;

X and Y are each independently hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z is hydrogen; and n is the number 0 or 1.

18. A compound according to claim 1, in which
A and B together with the atoms to which they are bonded are a substructure of the formula (I-G)

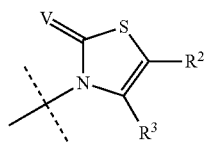

(I-G)

R² and R³ each independently
are hydrogen, cyano, halogen or nitro; or
are (C₁-C₆)alkyl, (C₃-C₆)cycloalkyl(C₁-C₆)alkyl, halo(C₁-C₆)alkyl, cyano(C₁-C₆)alkyl, hydroxy(C₁-C₆)alkyl, (C₁-C₆)alkoxy(C₁-C₆)alkyl, amino(C₁-C₆)alkyl, (C₁-C₆)alkoxycarbonyl(C₁-C₆)alkyl, (C₁-C₆)alkylsulphanyl(C₁-C₆)alkyl, (C₁-C₆)alkylsulphinyl(C₁-C₆)alkyl, (C₁-C₆)alkylsulphonyl(C₁-C₆)alkyl, halo(C₁-C₆)alkylsulphanyl(C₁-C₆)alkyl, halo(C₁-C₆)alkylsulphinyl(C₁-C₆)alkyl, halo(C₁-C₆)alkylsulphonyl(C₁-C₆)alkyl, (C₁-C₆)alkoxy(C₁-C₆)alkylsulphanyl(C₁-C₆)alkyl, (C₁-C₆)alkoxy(C₁-C₆)alkylsulphinyl(C₁-C₆)alkyl, (C₁-C₆)alkoxy(C₁-C₆)alkylsulphonyl(C₁-C₆)alkyl, phenyl(C₁-C₆)alkyl, phenoxy(C₁-C₆)alkyl, phenylsulphanyl(C₁-C₆)alkyl, phenylsulphinyl(C₁-C₆)alkyl, phenylsulphonyl(C₁-C₆)alkyl, hetaryl(C₁-C₆)alkyl, hetaryloxy(C₁-C₆)alkyl, hetarylthio(C₁-C₆)alkyl, where the aforementioned radicals may each optionally be substituted and/or, under the condition that, in the case of an unsaturated radical, the defined minimum number of carbon atoms is 2, the radicals may be saturated or unsaturated; or
are optionally substituted saturated or unsaturated (C₃-C₆)cycloalkyl which may optionally be interrupted by one or more heteroatoms; or
are (C₁-C₆)alkylcarbonyl, halo(C₁-C₆)alkylcarbonyl, hydroxy(C₁-C₆)alkylcarbonyl, (C₁-C₆)alkoxy(C₁-C₆)alkylcarbonyl, phenylcarbonyl, hetarylcarbonyl, (C₁-C₆)alkoxycarbonyl, halo(C₁-C₆)alkoxycarbonyl, aryloxycarbonyl, aminocarbonyl, (C₁-C₆)alkylaminocarbonyl, di(C₁-C₆)alkylaminocarbonyl, (C₃-C₆)cycloalkylaminocarbonyl, di(C₃-C₆)cycloalkylaminocarbonyl, (C₃-C₆)cycloalkyl((C₁-C₆)alkyl)aminocarbonyl, arylaminocarbonyl, diarylaminocarbonyl, (C₁-C₆)alkyl(aryl)aminocarbonyl, (C₃-C₆)cycloalkyl(aryl)aminocarbonyl, (C₁-C₆)alkylaminothiocarbonyl, di(C₁-C₆)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or are carbonyl or carboxyl; or
are optionally substituted phenyl or optionally substituted hetaryl; or
are (C₁-C₆)alkoxy, halo(C₁-C₆)alkoxy, (C₁-C₆)alkoxy(C₁-C₆)alkoxy, aryloxy, aryl(C₁-C₆)alkyloxy, (C₃-C₆)cycloalkyloxy, (C₃-C₆)cycloalkyl(C₁-C₆)alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or are hydroxyl; or
are (C₁-C₆)alkylamino, di(C₁-C₆)alkylamino, halo(C₁-C₆)alkylamino, dihalo(C₁-C₆)alkylamino, (C₃-C₆)cycloalkylamino, di(C₃-C₆)cycloalkylamino, (C₃-C₆)cycloalkyl((C₁-C₆)alkyl)amino, arylamino, diarylamino, hetarylamino, dihetarylamino, (C₁-C₆)alkyl(aryl)amino, (C₃-C₆)cycloalkyl(aryl)amino, (C₁-C₆)alkylcarbonylamino, arylcarbonylamino, (C₁-C₆)alkoxycarbonylamino, aryloxycarbonylamino, (C₁-C₆)alkylcarbamoylamino, arylcarbamoylamino, (C₁-C₆)alkylsulphonylamino, or arylsulphonylamino, where the aforementioned radicals may each optionally be substituted and/or, under the condition that, in the case of an unsaturated radical, the defined minimum number of carbon atoms is 2, the radicals may be saturated or unsaturated, or are amino; or
are (C₁-C₆)alkylsulphanyl, (C₁-C₆)alkylsulphinyl, (C₁-C₆)alkylsulphonyl, halo(C₁-C₆)alkylsulphanyl, halo(C₁-C₆)alkylsulphinyl, halo(C₁-C₆)alkylsulphonyl, (C₃-C₆)cycloalkylsulphanyl, (C₃-C₆)cycloalkylsulphinyl, (C₃-C₆)cycloalkylsulphonyl, (C₃-C₆)cycloalkyl(C₁-C₆)alkylsulphanyl, (C₃-C₆)cycloalkyl(C₁-C₆)alkylsulphinyl, (C₃-C₆)cycloalkyl(C₁-C₆)alkylsulphonyl, arylsulphanyl, arylsulphinyl, arylsulphonyl, aryl(C₁-C₆)alkylsulphanyl, aryl(C₁-C₆)alkylsulphinyl, aryl(C₁-C₆)alkylsulphonyl, aminosulphonyl, (C₁-C₆)alkylaminosulphonyl, di(C₁-C₆)alkylaminosulphonyl or arylaminosulphonyl, where the aforementioned radicals may each optionally be substituted and/or, under the condition that, in the case of an unsaturated radical, the defined minimum number of carbon atoms is 2, the radicals may be saturated or unsaturated, or are sulphanyl; or are an optionally singly or multiply, identically or differently halogen-, cyano-, nitro-, hydroxyl-, amino-, $(C_1-C_6)$alkyl-, halo$(C_1-C_6)$alkyl-, $(C_1-C_6)$alkoxy-, halo$(C_1-C_6)$alkoxy-, $(C_1-C_6)$alkylsulphinyl-, $(C_1-C_6)$alkylsulphanyl-, $(C_1-C_6)$alkylsulphonyl-, halo$(C_1-C_6)$alkylsulphinyl-, halo$(C_1-C_6)$alkylsulphanyl-, halo$(C_1-C_6)$alkylsulphonyl- or optionally substituted $(C_3-C_6)$cycloalkyl-substituted, saturated or unsaturated three- to six-membered ring optionally interrupted by heteroatoms from the group of O, S and N;

W is hydrogen or halogen;

V is oxygen, sulphur or an optionally substituted nitrogen;

X, Y and Z each independently are hydrogen, halogen, hydroxyl, amino, cyano, nitro, OCN, SCN, $SF_5$; or are tri$(C_1-C_6)$alkylsilyl, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxycarbonyl$(C_1-C_6)$alkyl, $(C_1-C_6)$alkoxy$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, $(C_1-C_6)$alkoxy, halo$(C_1-C_6)$alkoxy, cyano$(C_1-C_6)$alkoxy, hydroxycarbonyl$(C_1-C_6)$alkoxy, $(C_1-C_6)$alkoxycarbonyl$(C_1-C_6)$alkoxy, $(C_1-C_6)$alkoxy$(C_1-C_6)$alkoxy, $(C_1-C_6)$alkylhydroxyimino, $(C_1-C_6)$alkoxyimino, $(C_1-C_6)$alkyl$(C_1-C_6)$alkoxyimino, halo$(C_1-C_6)$alkyl$(C_1-C_6)$alkoxyimino, $(C_1-C_6)$alkylthio, halo$(C_1-C_6)$alkylthio, $(C_1-C_6)$alkoxy$(C_1-C_6)$alkylthio, $(C_1-C_6)$alkylthio$(C_1-C_6)$alkyl, $(C_1-C_6)$alkylsulphinyl, halo$(C_1-C_6)$alkylsulphinyl, $(C_1-C_6)$alkoxy$(C_1-C_6)$alkylsulphinyl, $(C_1-C_6)$alkylsulphinyl$(C_1-C_6)$alkyl, $(C_1-C_6)$alkylsulphonyl, halo$(C_1-C_6)$alkylsulphonyl, $(C_1-C_6)$alkoxy$(C_1-C_6)$alkylsulphonyl, $(C_1-C_6)$alkylsulphonyl$(C_1-C_6)$alkyl, $(C_1-C_6)$alkylsulphonyloxy, $(C_1-C_6)$alkylcarbonyl, halo$(C_1-C_6)$alkylcarbonyl, carboxyl, $(C_1-C_6)$alkylcarbonyloxy, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_2-C_6)$alkenylaminocarbonyl, di$(C_2-C_6)$alkenylaminocarbonyl, $(C_3-C_6)$cyclo$(C_1-C_6)$alkylaminocarbonyl, $(C_1-C_6)$alkylsulphonylamino, aminosulphonyl, $(C_1-C_6)$alkylaminosulphonyl, di$(C_1-C_6)$alkylaminosulphonyl, $(C_1-C_6)$alkylsulphoximino, aminothiocarbonyl, $(C_1-C_6)$alkylaminothiocarbonyl or di$(C_1-C_6)$alkylaminothiocarbonyl, where all the aforementioned radicals may optionally be substituted by halogen; or are phenyl$(C_1-C_3)$alkyl, phenoxy, phenyl$(C_1-C_3)$alkyloxy, phenoxy$(C_1-C_3)$alkyl, phenylthio, phenylthio$(C_1-C_3)$alkyl, phenylsulphinyl, phenylsulphonyl, hetaryl$(C_1-C_3)$alkyl, hetaryloxy, hetaryl$(C_1-C_3)$alkyloxy, hetarylthio, hetarylsulphinyl or hetarylsulphonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are $(C_3-C_6)$cycloalkyl$(C_1-C_3)$alkyl, $(C_3-C_6)$cycloalkyloxy, $(C_3-C_6)$cycloalkyl$(C_1-C_3)$alkoxy, $(C_3-C_6)$cycloalkylthio, $(C_3-C_6)$cycloalkyl$(C_1-C_3)$alkylthio, $(C_3-C_6)$cycloalkylsulphinyl, $(C_3-C_6)$cycloalkyl$(C_1-C_3)$alkylsulphinyl, $(C_3-C_6)$cycloalkylsulphonyl, $(C_3-C_6)$cycloalkyl$(C_1-C_3)$alkylsulphonyl or $(C_3-C_8)$cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or are NR'R"

where R' and R" each independently are hydrogen, cyano, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, $(C_1-C_6)$alkylthio$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, acyl or $(C_1-C_6)$alkoxycarbonyl; or R' and R" together with the nitrogen atom to which they are bonded may form an optionally identically or differently halogen-, cyano-nitro-, hydroxyl-, amino-, methyl-, ethyl-, trifluoromethyl-, difluoromethyl-, trifluoroethyl-, difluoroethyl-, methoxy-, ethoxy-, trifluoromethoxy-, trifluoroethoxy- or optionally methyl-, fluorine-, chlorine-, cyano-substituted cyclopropyl-substituted, saturated or unsaturated five- to seven-membered ring optionally interrupted by heteroatoms from the group of O, S and N; or are a $(C_3-C_6)$cycloalkyl, oxetanyl, oxolanyl, oxanyl, $(C_3-C_8)$cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be singly or multiply, identically or differently substituted by a substituent Si which is selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted identically or differently by hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl:

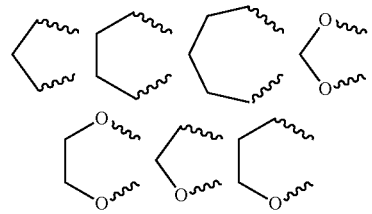

or X and Z, or Y and Z, may form the following fused rings which are optionally mono- or polysubstituted identically or differently, where the substituents may each independently be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

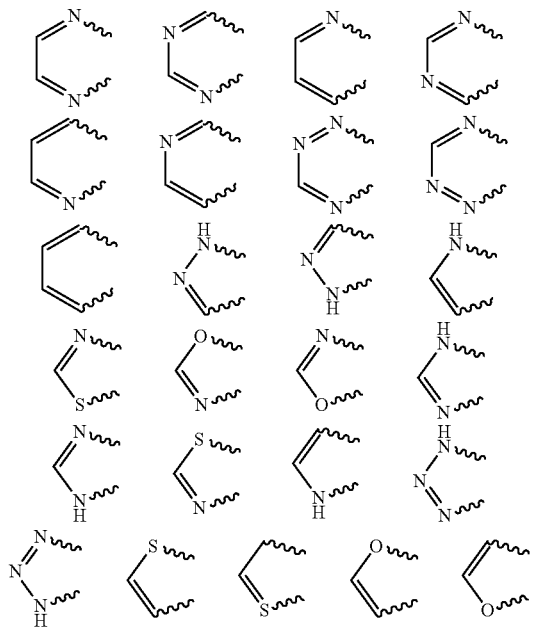

and
n is the number 0 or 1.

19. A compound according to claim 18 in which the substructure of formula (I-G) is a substructure (I-G-1)

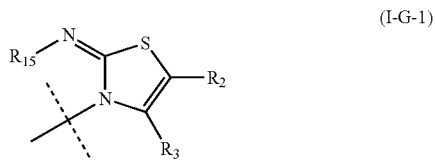

(I-G-1)

where
$R^2$ and $R^3$ each independently are hydrogen; or
are $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$alkyl, halo$(C_1-C_6)$alkyl, $(C_1-C_6)$ alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
are $(C_3-C_6)$cycloalkyl, $(C_3-C_6)$cycloalkenyl, azetidinyl, azolidinyl, azinanyl, oxetanyl, oxolanyl, oxanyl, thiethanyl, thiolanyl, thianyl, phenyl, pyrimidyl, pyridazinyl, pyrazinyl, triazinyl, thiazolyl, thiazadiazolyl, oxazolyl, oxadiazolyl, pyrazolyl, triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$ alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;

$R^{15}$ is hydrogen; or
is $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_2-C_6)$alkyl, cyano$(C_1-C_6)$alkyl, $(C_1-C_6)$alkoxy$(C_1-C_6)$alkyl or phenyl$(C_1-C_3)$alkyl, where the aforementioned radicals may each optionally be mono- to trisubstituted by halogen, cyano, nitro, hydroxyl, amino, $(C_1-C_6)$ alkyl, halo$(C_1-C_6)$alkyl, $(C_1-C_6)$ alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl; or
is $(C_3-C_6)$cycloalkyl, $(C_3-C_6)$cycloalkenyl, oxetanyl, oxolanyl, oxanyl, phenyl, pyrimidyl, pyridazinyl, pyrazinyl, triazinyl, thiazolyl, thiazadiazolyl, oxazolyl, oxadiazolyl, pyrazolyl or triazolyl, where the aforementioned radicals may each be mono- to trisubstituted by halogen, cyano, nitro, hydroxyl, amino, $(C_1-C_6)$alkyl, halo$(C_1-C_6)$alkyl, $(C_1-C_6)$ alkoxy, halo$(C_1-C_6)$alkoxy, $(C_1-C_6)$alkylsulphinyl, $(C_1-C_6)$alkylsulphanyl, $(C_1-C_6)$alkylsulphonyl, halo$(C_1-C_6)$alkylsulphinyl, halo$(C_1-C_6)$alkylsulphanyl, halo$(C_1-C_6)$alkylsulphonyl or optionally methyl-, fluorine-, chlorine-, cyano-substituted cyclopropyl;
W is hydrogen or halogen, optionally fluorine or chlorine;
X, Y and Z are each independently hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;
or are a benzyl, phenoxy, phenylthio, cyclopropylmethyl, cyclopropyloxy or cyclopropylthio, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl;
or are a cyclopropyl, cyclobutyl, cyclopentyl, cyclohexyl or phenyl, which is optionally mono- or polysubstituted identically or differently by fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; and
n is the number 0 or 1.

20. The compound of formula (I) according to claim 1 capable of being used for controlling one or more animal pests in crop protection, and/or in the protection of materials and/or in the veterinary sector.

21. An active ingredient composition comprising at least one compound of formula (I) according to claim 1 and at least one further insecticidally, acaricidally or nematicidally active ingredient.

22. A process for producing an agrochemical composition, comprising mixing a compound of formula (I) according to claim 1 with one or more extenders and/or surfactants.

23. A method for controlling one or more animal pests, comprising allowing a compound of formula (I) according to claim 1 to act on one or more animal pests and/or a habitat thereof.

* * * * *